US009797908B2

(12) United States Patent
Deiters et al.

(10) Patent No.: US 9,797,908 B2
(45) Date of Patent: *Oct. 24, 2017

(54) UNNATURAL REACTIVE AMINO ACID GENETIC CODE ADDITIONS

(71) Applicant: The Scripps Research Institute, La Jolla, CA (US)

(72) Inventors: Alexander Deiters, La Jolla, CA (US); T. Ashton Cropp, Richmond, VA (US); Jason W. Chin, Cambridge (GB); J. Christopher Anderson, San Francisco, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/338,113

(22) Filed: Jul. 22, 2014

(65) Prior Publication Data

US 2015/0018523 A1 Jan. 15, 2015

Related U.S. Application Data

(60) Division of application No. 13/787,400, filed on Mar. 6, 2013, now Pat. No. 8,815,542, which is a continuation of application No. 13/135,129, filed on Jun. 23, 2011, now Pat. No. 8,445,446, which is a continuation of application No. 10/561,121, filed as application No. PCT/US2004/011833 on Apr. 16, 2004, now Pat. No. 7,993,872.

(60) Provisional application No. 60/493,014, filed on Aug. 5, 2003, provisional application No. 60/496,548, filed on Aug. 19, 2003, provisional application No. 60/479,931, filed on Jun. 18, 2003.

(51) Int. Cl.
| | |
|---|---|
| C12P 21/00 | (2006.01) |
| G01N 33/58 | (2006.01) |
| C07C 227/22 | (2006.01) |
| C07C 229/36 | (2006.01) |
| C07C 269/06 | (2006.01) |
| C07C 311/41 | (2006.01) |
| C07K 1/107 | (2006.01) |
| C07K 1/13 | (2006.01) |
| C07K 14/00 | (2006.01) |
| C09B 11/08 | (2006.01) |
| C09B 57/00 | (2006.01) |
| C12N 9/00 | (2006.01) |
| C12N 15/67 | (2006.01) |
| C12P 17/04 | (2006.01) |
| C12P 21/02 | (2006.01) |
| G01N 33/532 | (2006.01) |
| C07K 16/18 | (2006.01) |

(52) U.S. Cl.
CPC ......... *G01N 33/583* (2013.01); *C07C 227/22* (2013.01); *C07C 229/36* (2013.01); *C07C 269/06* (2013.01); *C07C 311/41* (2013.01); *C07K 1/1072* (2013.01); *C07K 1/13* (2013.01); *C07K 14/001* (2013.01); *C07K 16/18* (2013.01); *C09B 11/08* (2013.01); *C09B 57/00* (2013.01); *C12N 9/93* (2013.01); *C12N 15/67* (2013.01); *C12P 17/04* (2013.01); *C12P 21/02* (2013.01); *G01N 33/532* (2013.01); *G01N 33/582* (2013.01); *C12N 2510/02* (2013.01)

(58) Field of Classification Search
USPC .... 435/69.1, 68.1, 7.1; 530/350, 323, 391.3, 530/391.9; 514/125; 424/178.1, 1.49; 506/18; 525/54.1; 552/1
See application file for complete search history.

(56) References Cited

U.S. PATENT DOCUMENTS

| | | |
|---|---|---|
| 6,927,042 B2 | 8/2005 | Schultz et al. |
| 7,045,337 B2 | 5/2006 | Schultz et al. |
| 7,083,970 B2 | 8/2006 | Schultz et al. |
| 7,183,082 B2 | 2/2007 | Schultz et al. |
| 7,199,222 B2 | 4/2007 | Shultz et al. |
| 7,217,809 B2 | 5/2007 | Schultz et al. |
| 7,238,510 B2 | 7/2007 | Schultz et al. |
| 7,262,040 B2 | 8/2007 | Schultz et al. |
| 2004/0198637 A1 | 10/2004 | Shultz et al. |
| 2004/0265952 A1 | 12/2004 | Deiters et al. |
| 2005/0009049 A1 | 1/2005 | Chin et al. |
| 2005/0136513 A1 | 6/2005 | Zhang et al. |
| 2005/0208536 A1 | 9/2005 | Schultz et al. |
| 2005/0227318 A1 | 10/2005 | Alfonta et al. |

(Continued)

FOREIGN PATENT DOCUMENTS

| | | |
|---|---|---|
| CN | 1379094 A | 11/2002 |
| EP | 1 424 395 A | 6/2004 |

(Continued)

OTHER PUBLICATIONS

Anderson, et al. (2002) "Exploring the Limits of Codon and Anticodon Size." *Chemistry and Biology*, 9:237-244.
Barker, et al. (1982) "The tyrosyl-tRNA synthetase from *Escherichia coli*: Complete Nucleotide Sequence of the Structural Gane." *FEBS Lett.*, 150:419-423.
Blake (2001) "Cellular screening assays using fluorescence microscopy." *Curr. Opin. Pharmacol.*, 1:533-539.
Bolletta, et al. (1996) "Synthesis and Photophysical Properties of Fluorescent Derivatives of Methylmercury." *Organometallics*, 15:2415-17.

(Continued)

*Primary Examiner* — Kagnew H Gebreyesus
(74) *Attorney, Agent, or Firm* — Quine Intellectual Property Law Group, PC

(57) ABSTRACT

This invention provides compositions and methods for producing translational components that expand the number of genetically encoded amino acids in eukaryotic cells. The components include orthogonal tRNAs, orthogonal aminoacyl-tRNA synthetases, orthogonal pairs of tRNAs/synthetases and unnatural amino acids. Proteins and methods of producing proteins with unnatural amino acids in eukaryotic cells are also provided.

9 Claims, 28 Drawing Sheets

(56) References Cited

U.S. PATENT DOCUMENTS

| | | |
|---|---|---|
| 2006/0063244 A1 | 3/2006 | Schultz et al. |
| 2006/0068478 A1 | 3/2006 | Schultz et al. |
| 2006/0160175 A1 | 7/2006 | Anderson et al. |
| 2006/0177900 A1 | 8/2006 | Anderson et al. |
| 2006/0234367 A1 | 10/2006 | Schultz et al. |
| 2007/0020634 A1 | 1/2007 | Anderson et al. |
| 2007/0042461 A1 | 2/2007 | Anderson et al. |
| 2007/0099990 A1 | 5/2007 | Alfonta et al. |
| 2007/0111193 A1 | 5/2007 | Zhang et al. |
| 2007/0154952 A1 | 7/2007 | Chin et al. |
| 2007/0166791 A1 | 7/2007 | Chin et al. |
| 2007/0172915 A1 | 7/2007 | Schultz et al. |
| 2007/0184517 A1 | 8/2007 | Schultz et al. |
| 2008/0227153 A1 | 9/2008 | Schultz et al. |

FOREIGN PATENT DOCUMENTS

| | | |
|---|---|---|
| WO | WO 99/61654 A1 | 12/1999 |
| WO | WO 02/085923 | 10/2002 |
| WO | WO 02/086075 | 10/2002 |
| WO | WO 03/014354 | 2/2003 |

OTHER PUBLICATIONS

Carboni, et al. (1993) "Aliphatic Amino Azides as Key Building Blocks for Efficient Polyamine Syntheses." *J. Org. Chem.*, 58:3736-3741.

Chin and Schultz, (2002) "In vivo Photocrosslinking with Unnatural Amino Acid Mutagenesis." *Chem. BioChem.*, 11:1135-1137.

Chin, et al. (2002) "Addition of p-Azido-L-phenylalanine to the Genetic code of *Escherichia coli*." *J. Am. Chem. Soc.*, 124:9026-9027.

Chin, et al. (2002) "Addition of a Photocrosslinker to the Genetic Code of *Escherichia coli*." *Proc. Natl. Acad. Sci. U. S. A.*, 99:11020-11024.

Chin, et al. (2003) "An expanded eukaryotic genetic code." *Science*, 301(5635):964-7.

Chin, et al. (2003) "Progress toward an expanded eukaryotic genetic code." *Chem. Biol.*, 10(6):511-519.

Cornish, et al. (1996) "Site-Specific Protein Modification Using a Ketone Handle." *J. Am. Chem. Soc.*, 118:8150-8151.

Crisp and Gore (1997) "Preparation of Biological Labels with Acetylenic Linker Arms." *Tetrahedron*, 53:1505-1522.

Cropp, et al. (2004) "An expanding genetic code." *Trends in Genetics*, 20(12):625-630.

Deiters and Schultz (2005) "In vivo incorporation of an alkyne into proteins in *Escherichia coli*." *Bioorg. Med. Chem. Lett.*, 15:1521-1524.

Deiters, et al. (2003) "Adding Amino Acids with Novel Reactivity to the Genetic Code of *Saccharomyces*." *J. Am. Chem. Soc.*, 125:11782-11783.

Deiters, et al. (2003) "Adding Amino Acids with Novel Reactivity to the Genetic Code of *Saccharomyces cerevisiae*." *J. Am. Chem. Soc.*, 125(39):11782-11783.

Dougerty, et al. (2000) "Unnatural Amino Acids as Probes of Protein Structure and Function." *Curr. Opin. Chem. Biol.*, 4:645-652.

Edwards, et al. (1990) "A Bacterial Amber Suppressor in *Saccharomyces cerevisiae* Is Selectively Recognized by a Bacterial Aminoacyl-tRNA Synthetase." *Mol. Cell Biol.*, 10(4):1633-1641.

Eriani, et al. (1990) "Partition of tRNA synthesys into two classes based on mutually exclusive sets of sequence motifs." *Nature*, 347(6289):203-206.

European Search Report for related EP Application No. 11165160.0, dated Sep. 13, 2012.

Feng, et al. (2003) "Expanding tRNA recognition of a tRNA synthetase by a single amino acid change." *Proc. Natl. Acad. Sci. U. S. A.*, 100(10):5676-5681.

Forster, et al. (2003) "Programming peptidomimetic synthetases by translating genetic codes designed de novo." *Proc. Natl. Acad. Sci. U. S. A.*, 100(11):6353-6357.

Francklyn, et al. (2002) "Aminoacyl-tRNA synthetases: Versatile players in the changing theater of translation." *RNA*, 8:1363-1372.

Fukunaga, et al. (2006) "Misacylation of yeast amber suppressor tRNATry by *E. coli*Lysyl-tRNA synthesys and its effective repression by genetic engineering of the tRNA sequence." *J. Biochem.*, 139(4):689-696.

Griffin, et al. (1998) "Specific covalent labeling of recombinant protein molecules inside live cells." *Science*, 281:269-272.

Hamano-Takaku, et al. (2000) "A mutant *Escherichia coli* Tyrosyl-tRNA Synthetase Utilizes the Unnatural Amino Acid Azatyrosine More Efficiently than Tyrosine." *J. Biol. Chem.*. 275(51):403234-40328.

Kiga, et al. (2002) "An engineered *Escherichia coli* tyrosyl-tRNA synthetase for site-specific incorporation of an unnatural amino acid into proteins in eukaryotic translation and its application in a wheat germ cell-free system." *Proc. Natl. Acad. Sci. U. S. A.*, 99(15):9715-9723.

Kiick, et al. (2002) "Incorporation of azides into recombinant proteins for chemoselective modification by the Staudinger ligation." *Proc. Natl. Acad. Sci. U. S. A.*, 99:19-24.

Köhrer el al. (2001) "Import of amber and ocher suppressor tRNAs into mammalian cells: a general approach to site-specific insertion of amino acid analogues into proteins." *Proc. Natl. Acad. Sci. U. S. A.*, 98(25):14310-14315.

Kolb, et al. (2001) "Click chemistry: diverse chemical function from a few good reactions." *Angew. Chem. Int. Ed.*, 40:1053-1057.

Lemineux and Bertozzi (1996) "Chemoselective ligation reactions with proteins, oligosaccharides and cells." *TIBTECH*, 16:506-513.

Lewis, et al. (2002) "Click chemistry in situ: acetylcholinesterase as a reaction vessel for the selective assembly for a femtomolar inhibitor from an array of building blocks." *Angew. Chem. Int. Ed.*, 41(6):1053-1057.

Liu and Schultz (1999) "Progress toward the evolution of an organism with an expanded genetic code." *Proc. Natl. Acad. Sci. U. S. A.*, 96:4780-4785.

Pasternak, et al. (2000) "A new orthogonal suppressor tRNA/aminoacyl-tRNA synthetase pair for evolving an organism with an expanded genetic code." *Helv. Chem. Acta.*, 83:2277.

Magliery, et al. (2001) "Expanding the Genetic Code: Selection of Efficient Suppressors of Four-base Codons and Identification of 'Shifty' Four-base Codons with a Library Approach in *Escherichia coli*." *J. Mol. Biol.*, 307: 755-769.

Mahal, et al. (1997) "Engineering chemical reactivity on cell surfaces through oligosaccharide biosynthesis." *Science*, 276:1125-1128.

Nowak, et al. (1995) "Nicotinic Receptor Binding Site Probed with Unnatural Amino Acid Incorporation in Intact Cells." *Science*, 268(5209): 439-442.

Padwa, A. (1991) "Intermolecular 1,3-Dipolar Cycloadditions." *Comprehensive Organic Synthesis*, vol. 4, Ed. Trost, B. M., Pergamon, Oxford, 1069-1109.

Reshetnyak, et al. (2001) "Decomposition of Protein Tryptophan Fluorescence Spectra into Log-Normal Components. II. The Statistical Proof of Discreteness of Tryptophan Classes in Proteins." *Biophys. J.*, 81(3):1710-1734.

Rostovtsev, et al. (2002) "A stepwise Huisgen cycloaddition process: copper(i)-catalyzed regioselective 'ligation' of azides and terminal alkynes." *Angew. Chem. Int. Ed.*, 41:2596-2599.

Sakamoto, et al. (2002) "Site Specific Incorporation of an Unnatural Amino Acid Into Proteins in Mammalian Cells." *Nucleic Acids Res.*, 30(21):4692-4699.

Speers, et al. (2003) "Activity-based protein profiling in vivo using a copper(i)-catalyzed azide-alkyne [3+2] cycloaddition." *J. Am. Chem. Soc.*, 125:4686-4687.

Tornøe, et al. (2002) "Peptidotriazoles on solid phase: [1,2,3]-triazoles by regiospecific copper(i)-catalyzed 1,3-dipolar cycloadditions of terminal alkynes to azides." *Org. Chem.*, 67:3057-3064.

Wang and Schultz (2002) "Expanding the Genetic Code." *Chem. Comm.*, (1):1-11.

(56) References Cited

OTHER PUBLICATIONS

Wang, et al. (2001) "Expanding the genetic code of *Escherichia coli.*" *Science*, 292:498-500.
Wang, et al. (2002) "Adding L-3-(2-naphthyl)alanine to the genetic code of *E-coli* ." *J. Am. Chem. Soc.*, 124:1836-1837.
Wang, et al. (2003) "Addition of the keto functional group to the genetic code of *Escherichia coli.*" *Proc. Natl. Acad. Sci. U.S.A.*, 100:56-61.
Wang, et al. (2003) "Bioconjugation by copper(i)-catalyzed azide-alkyne [3+2] cycloaddition." *J. Am. Chem. Soc.*, 125:3192-3193.
Wouters, et al. (2001) "Imaging biochemistry inside cells." *Trends Cell Biol.*, 11(5):203-211.
Zacharias, et al. (2000) "Recent advances in technology for measuring and manipulating cell signals." *Curr. Opin. Neurobiol.*, 10:416-421.
Zhang, et al. (2002) "The selective incorporation of alkenes into proteins in *Escherichia coli.*" *Angew. Chem. Int. Ed. Engl.*, 41:2840-2842.
Zhang, et al. (2003) "A new strategy for the site-specific modification of proteins in vivo." *Biochem.*, 42:6735-6746.
Gaur and Krupp (1993) "Enzymatic RNA synthesis with deoxynucleoside 5'-O-(1-thiotriphosphates)." *FEBS Lett.*, 315(1):56-60.

U.S. Appl. No. 13/443,800, filed Apr. 10, 2012 by Jason W. Chin, et al.
U.S. Appl. No. 11/978,121, filed Oct. 26, 2007 by Jason W. Chin, et al.
U.S. Appl. No. 11/978,223, filed Oct. 26, 2007 by Jason W. Chin, et al.
U.S. Appl. No. 11/978,172, filed Oct. 26, 2007 by Jason W. Chin, et al.
U.S. Appl. No. 11/710,672, filed Feb. 22, 2007 by Jason W. Chin, et al.
U.S. Appl. No. 11/710,655, filed Feb. 22, 2007 by Jason W. Chin, et al.
U.S. Appl. No. 10/825,867, filed Apr. 16, 2004 by Jason W. Chin, et al.
U.S. Appl. No. 10/826,919, filed Apr. 16, 2004 by Alexander Deiters, et al.
U.S. Appl. No. 12/583,558, filed Aug. 20, 2009 by Jason W. Chin, et al.
U.S. Appl. No. 10/561,121, filed May 23, 2006 by Alexander Deiters, et al.
U.S. Appl. No. 13/329,202, filed Dec. 16, 2011 by Jason W. Chin, et al.
U.S. Appl. No. 13/135,129, filed Jun. 23, 2011 by Alexander Deiters, et al.

SEQUENCE LISTING

<160> NUMBER OF SEQ ID NOS: 105

<210> SEQ ID NO 1
<211> LENGTH: 1275
<212> TYPE: DNA
<213> ORGANISM: Escherichia coli

<400> SEQUENCE: 1

```
atggcaagca gtaacttgat taaacaattg caagagcggg gctggtagc ccaggtgacg      60 gacgaggaag cgttagcaga gcgactggcg caaggcccga tcgcgctcta ttgcggcttc     120
gatcctaccg ctgacagctt gcatttgggg catcttgttc cattgttatg cctgaaacgc     180
ttccagcagg cgggccacaa gccggttgcg ctggtaggcg gcgcgacggg tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg cgaacaacta tgactggttc ggcaatatga atgtgctgac cttcctgcgc     420
gatattggca acacttctc cgttaaccag atgatcaaca agaagcggt taagcagcgt      480 ctcaaccgtg aagatcaggg gatttcgttc actgagtttt cctacaacct gttgcagggt     540
```

```
tatgacttcg cctgtctgaa caaacagtac ggtgtggtgc tgcaaattgg tggttctgac    600
cagtggggta acatcacttc tggtatcgac ctgacccgtc gtctgcatca gaatcaggtg    660
tttggcctga ccgttccgct gatcactaaa gcagatggca ccaaatttgg taaaactgaa    720
ggcggcgcag tctggttgga tccgaagaaa accagcccgt acaaattcta ccagttctgg    780
atcaacactg cggatgccga cgtttaccgc ttcctgaagt tcttcacctt tatgagcatt    840
gaagagatca cgccctgga agaagaagat aaaaacagcg gtaaagcacc gcgcgcccag    900
tatgtactgg cggagcaggt gactcgtctg gttcacggtg aagaaggttt acaggcggca    960
aaacgtatta ccgaatgcct gttcagcggt tctttgagtg cgctgagtga agcggacttc   1020
gaacagctgg cgcaggacgg cgtaccgatg gttgagatgg aaaagggcgc agacctgatg   1080
caggcactgg tcgattctga actgcaacct cccgtggtc aggcacgtaa aactatcgcc   1140
tccaatgcca tcaccattaa cggtgaaaaa cagtccgatc ctgaatactt ctttaaagaa   1200
gaagatcgtc tgtttggtcg ttttaccttac tgcgtcgcg gtaaaaagaa ttactgtctg   1260
atttgctgga aataa                                                    1275
```

<210> SEQ ID NO 2
<211> LENGTH: 424
<212> TYPE: PRT
<213> ORGANISM: Escherichia coli

<400> SEQUENCE: 2

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240
```

```
Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
        260                 265                 270

Lys Phe Phe Thr Phe Met Ser Ile Glu Glu Ile Asn Ala Leu Glu Glu
    275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 3
<211> LENGTH: 1275
<212> TYPE: DNA
<213> ORGANISM: Artificial Sequence
<220> FEATURE:
<223> OTHER INFORMATION: artificial synthetase

<400> SEQUENCE: 3
atggcaagca gtaacttgat taaacaattg caagagcggg ggctggtagc ccaggtgacg      60
gacgaggaag cgttagcaga gcgactggcg caaggcccga tcgcactcgt gtgtggcttc     120
gatcctaccg ctgacagctt gcatttgggg catcttgttc cattgttatg cctgaaacgc     180
ttccagcagg cgggccacaa gccggttgcg ctggtaggcg cgcgacgggg tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca acacttctc cgttaaccag atgatcaaca agaagcggt taagcagcgt      480 ctcaaccgtg aagatcaggg gatttcgttc actgagtttt cctacaacct gctgcagggt     540
tatagtatgg cctgttttga aacaacagtac ggtgtggtgc tgcaaattgg tggttctgac    600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa ccagcccgt acaaattcta ccagttctgg      780
atcaacactg cggatgccga cgtttaccgc ttcctgaagt tcttcacctt tatgagcatt     840
gaagagatca acgccctgga agaagaagat aaaaacagcg gtaaagcacc gcgcgcccag     900
tatgtactgg cggagcaggt gactcgtctg gttcacggtg aagaaggttt acaggcggca     960
aaacgtatta ccgaatgcct gttcagcggt tctttgagtg cgctgagtga agcggacttc    1020
```

```
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc ctgaatactt ctttaaagaa    1200
gaagatcgtc tgtttggtcg ttttaccttg ctgcgtcgcg taaaaagaa ttactgtctg    1260 atttgctgga aataa                                                    1275
```

```
<210> SEQ ID NO 4
<211> LENGTH: 1275
<212> TYPE: DNA
<213> ORGANISM: Artificial Sequence
<220> FEATURE:
<223> OTHER INFORMATION: artificial synthetase

<400> SEQUENCE: 4
atggcaagca gtaacttgat taaacaattg caagagcggg ggctggtagc ccaggtgacg     60
gacgaggaag cgttagcaga gcgactggcg caaggcccga tcgcactcac ttgtggcttc    120
gatcctaccg ctgacagctt gcatttgggg catcttgttc cattgttatg cctgaaacgc    180
ttccagcagg cgggccacaa gccggttgcg ctggtaggcg gcgcgacggg tctgattggc    240 gaccccgagct tcaaagctgc cgagcgtaag ctgaacaccg aagaaactgt tcaggagtgg    300
gtggacaaaa tccgtaagca ggttgccccg ttcctcgatt tcgactgtgg agaaaactct    360
gctatcgcgg ccaataatta tgactggttc agcaatatga atgtgctgac cttcctgcgc    420
gatattggca acacttctc cgttaaccag atgatcaaca aagaagcggt taagcagcgt    480
ctcaaccgtg aagatcaggg gatttcgttc actgagtttt cctacaacct gctgcagggt    540
tatacgtatg cctgtctgaa caaacagtac ggtgtggtgc tgcaaattgg tggttctgac    600
cagtggggta acatcacttc tggtatcgac ctgacccgtc gtctgcatca gaatcaggtg    660
tttggcctga ccgttccgct gatcactaaa gcagatggca ccaaatttgg taaaactgaa    720
ggcggcgcag tctggttgga tccgaagaaa accagcccgt acaaattcta ccagttctgg    780
atcaacactg cggatgccga cgtttaccgc ttcctgaagt tcttcacctt tatgagcatt    840
gaagagatca acgccctgga agaagaagat aaaaacagcg gtaaagcacc gcgcgcccag    900
tatgtactgg cggagcaggt gactcgtctg gttcacggtg aagaaggttt acaggcggca    960
aaacgtatta ccgaatgcct gttcagcggt tctttgagtg cgctgagtga gcggacttc    1020 gaacagctgg cgcaggacgg cgtaccgatg gttgagatgg aaaagggcgc agacctgatg   1080
caggcactgg tcgattctga actgcaacct tcccgtggtc aggcacgtaa aactatcgcc   1140
tccaatgcca tcaccattaa cggtgaaaaa cagtccgatc ctgaatactt ctttaaagaa   1200
gaagatcgtc tgtttggtcg ttttaccttg ctgcgtcgcg taaaaagaa ttactgtctg   1260 atttgctgga aataa                                                   1275
```

```
<210> SEQ ID NO 5
<211> LENGTH: 1275
<212> TYPE: DNA
<213> ORGANISM: Artificial Sequence
<220> FEATURE:
<223> OTHER INFORMATION: artificial synthetase

<400> SEQUENCE: 5
atggcaagca gtaacttgat taaacaattg caagagcggg ggctggtagc ccaggtgacg     60
gacgaggaag cgttagcaga gcgactggcg caaggcccga tcgcactcgt gtgtggcttc    120
```

```
gatcctaccg ctgacagctt gcatttgggg catcttgttc cattgttatg cctgaaacgc      180
ttccagcagg cgggccacaa gccggttgcg ctggtaggcg gcgcgacggg tctgattggc      240
gaccccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct      360
gctatcgcgg ccaataatta tgactggttc ggcaatatga atgtgctgac cttcctgcgc     420
gatattggca aacacttctc cgttaaccag atgatcaaca agaagcggt taagcagcgt       480
ctcaaccgtg aagatcaggg gatttcgttc actgagtttt cctacaacct gctgcagggt     540
tatagtatgg cctgtttgaa caaacagtac ggtgtggtgc tgcaaattgg tggttctgac    600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa accagcccgt acaaattcta ccagttctgg    780
atcaacactg cggatgccga cgtttaccgc ttcctgaagt tcttcacctt tatgagcatt     840
gaagagatca acgccctgga agaagaagat aaaaacagcg gtaaagcacc gcgcgcccag    900
tatgtactgg cggagcaggt gactcgtctg gttcacggtg aagaaggttt acaggcggca    960
aaacgtatta ccgaatgcct gttcagcggt tctttgagtg cgctgagtga agcggacttc   1020
gaacagctgg cgcaggacgg cgtaccgatg gttgagatgg aaaagggcgc agacctgatg    1080
caggcactgt cgattctga actgcaacct tcccgtggtc aggcacgtaa aactatcgcc     1140
tccaatgcca tcaccattaa cggtgaaaaa cagtccgatc ctgaatactt ctttaaagaa   1200
gaagatcgtc tgtttggtcg ttttaccta ctgcgtcgcg gtaaaaagaa ttactgtctg     1260
atttgctgga aataa                                                       1275

<210> SEQ ID NO 6
<211> LENGTH: 1275
<212> TYPE: DNA
<213> ORGANISM: Artificial Sequence
<220> FEATURE:
<223> OTHER INFORMATION: artificial synthetase

<400> SEQUENCE: 6
atggcaagca gtaacttgat taaacaattg caagagcggg ggctggtagc ccaggtgacg      60
gacgaggaag cgttagcaga gcgactggcg caaggcccga tcgcactcgt gtgtggcttc    120
gatcctaccg ctgacagctt gcatttgggg catcttgttc cattgttatg cctgaaacgc      180
ttccagcagg cgggccacaa gccggttgcg ctggtaggcg gcgcgacggg tctgattggc      240
gaccccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct      360
gctatcgcgg ccaataatta tgactggttc ggcaatatga atgtgctgac cttcctgcgc     420
gatattggca aacacttctc cgttaaccag atgatcaaca agaagcggt taagcagcgt       480
ctcaaccgtg aagatcaggg gatttcgttc actgagtttt cctacaacct gctgcagggt     540
tatagtatgg cctgtttgaa caaacagtac ggtgtggtgc tgcaaattgg tggttctgac    600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa accagcccgt acaaattcta ccagttctgg    780
atcaacactg cggatgccga cgtttaccgc ttcctgaagt tcttcacctt tatgagcatt     840
gaagagatca acgccctgga agaagaagat aaaaacagcg gtaaagcacc gcgcgcccag    900
```

-continued

| | |
|---|---|
| tatgtactgg cggagcaggt gactcgtctg gttcacggtg aagaaggttt acaggcggca | 960 |
| aaacgtatta ccgaatgcct gttcagcggt tctttgagtg cgctgagtga agcggacttc | 1020 |
| gaacagctgg cgcaggacgg cgtaccgatg gttgagatgg aaaagggcgc agacctgatg | 1080 |
| caggcactgg tcgattctga actgcaacct tcccgtggtc aggcacgtaa aactatcgcc | 1140 |
| tccaatgcca tcaccattaa cggtgaaaaa cagtccgatc ctgaatactt ctttaaagaa | 1200 |
| gaagatcgtc tgtttggtcg ttttacctta ctgcgtcgcg gtaaaaagaa ttactgtctg | 1260 |
| atttgctgga aataa | 1275 |

<210> SEQ ID NO 7
<211> LENGTH: 1275
<212> TYPE: DNA
<213> ORGANISM: Artificial Sequence
<220> FEATURE:
<223> OTHER INFORMATION: artificial synthetase

<400> SEQUENCE: 7

| | |
|---|---|
| atggcaagca gtaacttgat taaacaattg caagagcggg ggctggtagc ccaggtgacg | 60 |
| gacgaggaag cgttagcaga gcgactggcg caaggcccga tcgcactcac gtgtggcttc | 120 |
| gatcctaccg ctgacagctt gcatttgggg catcttgttc cattgttatg cctgaaacgc | 180 |
| ttccagcagg cgggccacaa gccggttgcg ctggtaggcg cgcgacggg tctgattggc | 240 |
| gacccgagct tcaaagctgc cgagcgtaag ctgaacaccg aagaaactgt tcaggagtgg | 300 |
| gtggacaaaa tccgtaagca ggttgccccg ttcctcgatt tcgactgtgg agaaaactct | 360 |
| gctatcgcgg ccaataatta tgactggttc ggcaatatga atgtgctgac cttcctgcgc | 420 |
| gatattggca acacttctc cgttaaccag atgatcaaca agaagcggt taagcagcgt | 480 |
| ctcaaccgtg aagatcaggg gatttcgttc actgagtttt cctacagcct gctgcagggt | 540 |
| tatacgatgg cctgtctgaa caaacagtac ggtgtggtgc tgcaaattgg tggttctgac | 600 |
| cagtggggta acatcacttc tggtatcgac ctgacccgtc gtctgcatca gaatcaggtg | 660 |
| tttggcctga ccgttccgct gatcactaaa gcagatggca ccaaatttgg taaaactgaa | 720 |
| ggcggcgcag tctggttgga tccgaagaaa accagcccgt acaaattcta ccagttctgg | 780 |
| atcaacactg cggatgccga cgtttaccgc ttcctgaagt tcttcacctt tatgagcatt | 840 |
| gaagagatca acgccctgga agaagaagat aaaaacagcg gtaaagcacc gcgcgcccag | 900 |
| tatgtactgg cggagcaggt gactcgtctg gttcacggtg aagaaggttt acaggcggca | 960 |
| aaacgtatta ccgaatgcct gttcagcggt tctttgagtg cgctgagtga agcggacttc | 1020 |
| gaacagctgg cgcaggacgg cgtaccgatg gttgagatgg aaaagggcgc agacctgatg | 1080 |
| caggcactgg tcgattctga actgcaacct tcccgtggtc aggcacgtaa aactatcgcc | 1140 |
| tccaatgcca tcaccattaa cggtgaaaaa cagtccgatc ctgaatactt ctttaaagaa | 1200 |
| gaagatcgtc tgtttggtcg ttttacctta ctgcgtcgcg gtaaaaagaa ttactgtctg | 1260 |
| atttgctgga aataa | 1275 |

<210> SEQ ID NO 8
<211> LENGTH: 540
<212> TYPE: DNA
<213> ORGANISM: Artificial Sequence
<220> FEATURE:
<223> OTHER INFORMATION: artificial synthetase

<400> SEQUENCE: 8

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcagcaat   360
atgaatgtgc tgaccttcct gcgcgatatt ggcaaacact ctccgttaa ccagatgatc    420 aacaaagaag cggttaagca gcgtctcaac cgtgaagatc aggggatttc gttcactgag   480
ttttcctaca acctgctgca gggttatacg tatgcctgtc tgaacaaaca gtacggtgtg   540
```

<210> SEQ ID NO 9
<211> LENGTH: 540
<212> TYPE: DNA
<213> ORGANISM: Artificial Sequence
<220> FEATURE:
<223> OTHER INFORMATION: artificial synthetase

<400> SEQUENCE: 9

```
cgggggctgg tacccaggt gacggacgag gaagcgttag cagagcgact ggcgcaaggc     60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcagcaat   360
atgaatgtgc tgaccttcct gcgcgatatt ggcaaacact ctccgttaa ccagatgatc    420 aacaaagaag cggttaagca gcgtctcaac cgtgaagatc aggggatttc gttcactgag   480
ttttcctaca acctgctgca gggttatacg tatgcctgtc tgaacaaaca gtacggtgtg   540
```

<210> SEQ ID NO 10
<211> LENGTH: 540
<212> TYPE: DNA
<213> ORGANISM: Artificial Sequence
<220> FEATURE:
<223> OTHER INFORMATION: artificial synthetase

<400> SEQUENCE: 10

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcagcaat   360
atgaatgtgc tgaccttcct gcgcgatatt ggcaaacact ctccgttaa ccagatgatc    420 aacaaagaag cggttaagca gcgtctcaac cgtgaagatc aggggatttc gttcactgag   480
ttttcctaca acctgctgca gggttatacg tatgcctgtc tgaacaaaca gtacggtgtg   540
```

<210> SEQ ID NO 11
<211> LENGTH: 540
<212> TYPE: DNA
<213> ORGANISM: Artificial Sequence
<220> FEATURE:
<223> OTHER INFORMATION: artificial synthetase

<400> SEQUENCE: 11

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttattcg tatgcctgtg cgaacaaaca gtacggtgtg   540
```

<210> SEQ ID NO 12
<211> LENGTH: 540
<212> TYPE: DNA
<213> ORGANISM: Artificial Sequence
<220> FEATURE:
<223> OTHER INFORMATION: artificial synthetase

<400> SEQUENCE: 12

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcagcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttatacg tatgcctgtc tgaacaaaca gtacggtgtg   540
```

<210> SEQ ID NO 13
<211> LENGTH: 540
<212> TYPE: DNA
<213> ORGANISM: Artificial Sequence
<220> FEATURE:
<223> OTHER INFORMATION: artificial synthetase

<400> SEQUENCE: 13

```
cgggggctgg tacccaggt gacggacgag gaagcgttag cagagcgact ggcgcaaggc    60
ccgatcgcac tcctttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttattct attgcctgtt cgaacaaaca gtacggtgtg   540
```

<210> SEQ ID NO 14
<211> LENGTH: 540
<212> TYPE: DNA
<213> ORGANISM: Artificial Sequence
<220> FEATURE:
<223> OTHER INFORMATION: artificial synthetase

<400> SEQUENCE: 14

```
cgggggctgg tagcccaggt gacggacgag gaagcgttag cagagcgact ggcgcaaggc    60
ccgatcgcac tcgtgtgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact ctccgttaa ccagatgatc    420
aacaaagaag cggttaagca gcgtctcaac cgtgaagatc aggggatttc gttcactgag   480
ttttcctaca acctgctgca gggttatagt attgcctgtt tgaacaaaca gtacggtgtg   540
```

<210> SEQ ID NO 15
<211> LENGTH: 540
<212> TYPE: DNA
<213> ORGANISM: Artificial Sequence
<220> FEATURE:
<223> OTHER INFORMATION: artificial synthetase

<400> SEQUENCE: 15

```
cgggggctgg tacccaggt gacggacgag gaagcgttag cagagcgact ggcgcaaggc     60
ccgatcgcac tcgtgtgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact ctccgttaa ccagatgatc    420
aacaaagaag cggttaagca gcgtctcaac cgtgaagatc aggggatttc gttcactgag   480
ttttcctaca acctgctgca gggttatagt attgcctgtt tgaacaaaca gtacggtgtg   540
```

<210> SEQ ID NO 16
<211> LENGTH: 540
<212> TYPE: DNA
<213> ORGANISM: Artificial Sequence
<220> FEATURE:
<223> OTHER INFORMATION: artificial synthetase

<400> SEQUENCE: 16

```
cgggggctgg tagcccaggt gacggacgag gaagcgttag cagagcgact ggcgcaaggc    60
ccgatcgcac tctggtgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaagg ctgccgagcg taagctgaac   240
accgaagaaa ctgttcagga gtgggtggac aaaatccgta agcaggttgc cccgttcctc   300
gatttcgact gtggagaaaa ctctgctatc gcggccaatt gttatgactg gttcggcaat   360
atgaatgtgc tgaccttcct gcgcgatatt ggcaaacact ctccgttaa ccagatgatc    420
```

```
aacaaagaag cggttaagca gcgtctcaac cgtgaagatc aggggatttc gttcactgag    480
ttttcctaca acctgctgca gggttatatg cgtgcctgtg agaacaaaca gtacggtgtg    540
```

<210> SEQ ID NO 17
<211> LENGTH: 624
<212> TYPE: DNA
<213> ORGANISM: Artificial Sequence
<220> FEATURE:
<223> OTHER INFORMATION: artificial synthetase

<400> SEQUENCE: 17

```
cgggggctgg tagcccaggt gacggacgag gaagcgttag cagagcgact ggcgcaaggc     60
ccgatcgcac tcatttgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact tctccgttaa ccagatgatc    420
aacaaagaag cggttaagca gcgtctcaac cgtgaaggtc aggggatttc gttcactgag    480
ttttcctaca acctgctgca gggttatggt atggcctgtg ctaacaaaca gtacggtgtg    540
gtgctgcaaa ttggtggttc tgaccaatgg ggtaacatca cttctggtat cgacctgacc    600
cgtcgtctgc atcagaatca ggtg                                           624
```

<210> SEQ ID NO 18
<211> LENGTH: 609
<212> TYPE: DNA
<213> ORGANISM: Artificial Sequence
<220> FEATURE:
<223> OTHER INFORMATION: artificial synthetase

<400> SEQUENCE: 18

```
caggtgacgg acgaggaagc gttagcagag cgactggcgc aaggcccgat cgcactcggt     60
tgtggcttcg atcctaccgc tgacagcttg catttggggc atcttgttcc attgttatgc    120
ctgaaacgct tccagcaggc gggccacaag ccggttgcgc tggtaggcgg cgcgacgggt    180
ctgattggcg acccgagctt caaagctgcc gagcgtaagc tgaacaccga agaaactgtt    240
caggagtggg tggacaaaat ccgtaagcag gttgccccgt tcctcgattt cgactgtgga    300
gaaaactctg ctatcgcggc caataattat gactggttcg gcaatatgaa tgtgctgacc    360
ttcctgcgcg atattggcaa acacttctcc gttaaccaga tgatcaacaa agaagcggtt    420
aagcagcgtc tcaaccgtga agatcagggg atttcgttca ctgagttttc ctacaacctg    480
ctgcagggtt atggttttgc ctgtttgaac aaacagtacg gtgtggtgct gcaaattggt    540
ggttctgacc agtggggtaa catcacttct ggtatcgacc tgacccgtcg tctgcatcag    600
aatcaggtg                                                            609
```

<210> SEQ ID NO 19
<211> LENGTH: 591
<212> TYPE: DNA
<213> ORGANISM: Artificial Sequence
<220> FEATURE:
<223> OTHER INFORMATION: artificial synthetase

<400> SEQUENCE: 19

| | |
|---|---|
| gcgttagcag agcgactggc gcaaggcccg atcgcactcg ggtgtggctt cgatcctacc | 60 |
| gctgacagct tgcatttggg gcatcttgtt ccattgttat gcctgaaacg cttccagcag | 120 |
| gcgggccaca agccggttgc gctggtaggc ggcgcgacgg gtctgattgg cgacccgagc | 180 |
| ttcaaagctg ccgagcgtaa gctgaacacc gaagaaactg ttcaggagtg ggtggacaaa | 240 |
| atccgtaagc aggttgcccc gttcctcgat ttcgactgtg agaaaactc tgctatcgcg | 300 |
| gccaataatt atgactggtt cggcaatatg aatgtgctga ccttcctgcg cgatattggc | 360 |
| aaacacttct ccgttaacca gatgatcaac aaagaagcgg ttaagcagcg tctcaaccgt | 420 |
| gaagatcagg ggatttcgtt cactgagttt tcctacaacc tgctgcaggg ttatggttat | 480 |
| gcctgtatga acaaacagta cggtgtggtg ctgcaaattg gtggttctga ccagtggggt | 540 |
| aacatcactt ctggtatcga cctgacccgt cgtctgcatc agaatcaggt g | 591 |

<210> SEQ ID NO 20
<211> LENGTH: 621
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t

<400> SEQUENCE: 20

| | |
|---|---|
| gggctggtag cccaggtgac ggacgnagaa gcgttagcag agcgactggc gcaaggcccg | 60 |
| atcgcactcc tttgtggctt cgatcctacc gctgacagct tgcatttggg gcatcttgtt | 120 |
| ccattgttat gcctgaaacg cttccagcag gcgggccaca agccggttgc gctggtaggc | 180 |
| ggcgcgacgg gtctgattgg cgacccgagc ttcaaagctg ccgagcgtaa gctgaacacc | 240 |
| gaagaaactg ttcaggagtg ggtggacaaa atccgtaagc aggttgcccc gttcctcgat | 300 |
| ttcgactgtg agaaaaactc tgctatcgcg gccaataatt atgactggtt cggcaatatg | 360 |
| aatgtgctga ccttcctgcg cgatattggc aaacacttct ccgttaacca gatgatcaac | 420 |
| aaagaagcgg ttaagcagcg tctcaaccgt gaagatcagg ggatttcgtt cactgagttt | 480 |
| tcctacaacc tgctgcaggg ttattctatg gcctgtgcga acaaacagta cggtgtggtg | 540 |
| ctgcaaattg gtggttctga ccagtggggt aacatcactt ctggtatcga cctgacccgt | 600 |
| cgtctgcatc anaatcangt g | 621 |

<210> SEQ ID NO 21
<211> LENGTH: 588
<212> TYPE: DNA
<213> ORGANISM: Artificial Sequence
<220> FEATURE:
<223> OTHER INFORMATION: artificial synthetase

<400> SEQUENCE: 21

| | |
|---|---|
| ttagcagagc gactggcgca aggcccgatc gcactcgttt gtggcttcga tcctaccgct | 60 |
| gacagcttgc atttggggca tcttgttcca ttgttatgcc tgaaacgctt ccagcaggcg | 120 |
| ggccacaagc cggttgcgct ggtaggcggc gcgacgggtc tgattggcga cccgagcttc | 180 |

```
aaagctgccg agcgtaagct gaacaccgaa gaaactgttc aggagtgggt ggacaaaatc    240
cgtaagcagg ttgccccgtt cctcgatttc gactgtggag aaaactctgc tatcgcggcc    300
aataattatg actggttcgg caatatgaat gtgctgacct tcctgcgcga tattggcaaa    360
cacttctccg ttaaccagat gatcaacaaa gaagcggtta agcagcgtct caaccgtgaa    420
gatcagggga tttcgttcac tgagttttcc tacaacctgc tgcagggtta ttctgcggcc    480
tgtgcgaaca aacagtacgg tgtggtgctg caaattggtg ttctgacca gtggggtaac    540 atcacttctg gtatcgacct gacccgtcgt ctgcatcaga atcaggtg                 588
```

```
<210> SEQ ID NO 22
<211> LENGTH: 600
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t

<400> SEQUENCE: 22
gacgaggaag cgttagcaga gcgactggcg caaggcccga tcgcactcct gtgtggcttc     60
gatcctaccg ctgacagctt gcatttgggg catcttgttc cattgttatg cctgaaacgc    120
ttccagcagg cgggccacaa gccggttgcg ctggtaggcg gcgcgacggg tctgattggc    180
gacccgagct tcaaagctgc cgagcgtaag ctgaacaccg aagaaactgt tcaggagtgg    240
gtggacaaaa tccgtaagca ggttgccccg ttcctcgatt tcgactgtgg agaaaactct    300
gctatcgcgg ccaataatta tgactggttc ggcaatatga atgtgctgac cttcctgcgc    360
gatattggca acacttctct cgttaaccag atgatcaaca anaagcggt taagcagcgt    420 ctcaaccgtg aagatcaggg gatttcgttc actgagtttt cctacaacct gctgcagggt    480
tattcggctg cctgtgcgaa caaacagtac ggngngngnc tgcaaattgg nggttctgac    540 cagggggta acatcacttc tggtatcgac ctgacccgtc gtctgcatca aaatcaggtg    600
```

```
<210> SEQ ID NO 23
<211> LENGTH: 591
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (588)..(588)
<223> OTHER INFORMATION: n is a, c, g, or t

<400> SEQUENCE: 23
```

```
gcgttagcag agcgactggc gcaaggcccg atcgcactcg tttgtggctt cgatcctacc    60
gctgacagct tgcatttggg gcatcttgtt ccattgttgt gcctgaaacg cttccagcag   120
gcgggccaca agccggttgc gctggtaggc ggcgcgacgg gtctgattgg cgacccgagc   180
ttcaaagctg ccgagcgtaa gctgaacacc gaagaaactg ttcaggagtg gtggacaaaa   240
atccgtaagc aggttgcccc gttcctcgat ttcgactgtg agaaaactc tgctatcgcg    300
gccaataatt atgactggtt cggcaatatg aatgtgctga ccttcctgcg cgatattggc   360
aaacacttct ccgttaacca gatgatcaac aagaagcgg ttaagcagcg tctcaaccgt    420
gaagatcagg ggatttcgtt cactgagttt cctacaacc tgctgcaggg ttatagtgcg    480
gcctgtgtta acaaacagta cggtgtggtg ctgcaaattg gtggttctga ccagtggggt   540
aacatcactt ctggtatcga cctgacccgt cgtctgcatc agaatcangt g             591
```

<210> SEQ ID NO 24
<211> LENGTH: 600
<212> TYPE: DNA
<213> ORGANISM: Artificial Sequence
<220> FEATURE:
<223> OTHER INFORMATION: artificial synthetase

<400> SEQUENCE: 24

```
gacgaggaag cgttagcaga gcgactggcg caaggcccga tcgcactcat tgtggcttc    60
gatcctaccg ctgacagctt gcatttgggg catcttgttc cattgttatg cctgaaacgc   120
ttccagcagg cgggccacaa gccggttgcg ctggtaggcg cgcgacggg tctgattggc    180
gacccgagct tcaaagctgc cgagcgtaag ctgaacaccg aagaaactgt tcaggagtgg   240
gtggacaaaa tccgtaagca ggttgccccg ttcctcgatt tcgactgtgg agaaaactct   300
gctatcgcgg ccaatgatta tgactggttc ggcaatatga atgtgctgac cttcctgcgc   360
gatattggca aacacttctc cgttaaccag atgatcaaca agaagcggt taagcagcgt    420
ctcaaccgtg aagatcaggg gatttcgttc actgagtttt cctacaacct gctgcagggt   480
tataattttg cctgtgtgaa caaacagtac ggtgtggtgc tgcaaattgg tggttctgac   540
cagtggggta acatcacttc tggtatcgac ctgacccgtc gtctgcatca gaatcaggtg   600
```

<210> SEQ ID NO 25
<211> LENGTH: 579
<212> TYPE: DNA
<213> ORGANISM: Artificial Sequence
<220> FEATURE:
<223> OTHER INFORMATION: artificial synthetase

<400> SEQUENCE: 25

```
cgactggcgc aaggcccgat cgcactcacg tgtggcttcg atcctaccgc tgacagcttg    60
catttggggc atcttgttcc attgttatgc ctgaaacgct tccagcaggc gggccacaag   120
ccggttgcgc tggtaggcgg cgcgacgggt ctgattggcg acccgagctt caaagctgcc   180
gagcgtaagc tgaacaccga agaaactgtt caggagtggg tggacaaaat ccgtaagcag   240
gttgccccgt tcctcgattt cgactgtgga gaaaactctg ctatcgcggc caataattat   300
gactggttcg gcaatatgaa tgtgctgacc ttcctgcgcg atattggcaa acacttctcc   360
gttaaccaga tgatcaacaa agaagcggtt aagcagcgtc tcaaccgtga agatcagggg   420
atttcgttca ctgagttttc ctacaatctg ctgcagggtt attcggctgc ctgtcttaac   480
aaacagtacg gtgtggtgct gcaaattggt ggttctgacc agtggggtaa catcacttct   540
ggtatcgacc tgacccgtcg tctgcatcag aatcaggtg                          579
```

<210> SEQ ID NO 26
<211> LENGTH: 624
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t

<400> SEQUENCE: 26

```
cgggggctgg tancccaggt gacggacgag gaagcgttag cagagcgact ggcgcaaggc    60
ccgatcgcac tcgggtgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttattct atggcctgtt tgaacaaaca gtacggtgtg   540
gtgctgcaaa ttggtggttc tgaccagtgg ggtaacatca cttctggtat cgacctganc   600
cgtcgtctgc atcagaatca ggtg                                          624
```

<210> SEQ ID NO 27
<211> LENGTH: 625
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (600)..(600)
<223> OTHER INFORMATION: n is a, c, g, or t

<400> SEQUENCE: 27

```
cgggggctgg tagcccaggt gacggacgag gaagcgttag cagagcgact ggcgcaaggc    60
ccgatcgcac tcacgtgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca atctgctgca gggttattcg gctgcctgtc ttaacaaaca gtacggtgtg   540
gtgctgcaaa ttggtggttc tgaccagtgg ggtaacatca cttctggtat cgaacctgan   600
ccgtcgtctg catcaaaatc aagtg                                         625
```

<210> SEQ ID NO 28

| <211> LENGTH: 624 |
| <212> TYPE: DNA |
| <213> ORGANISM: Artificial Sequence |
| <220> FEATURE: |
| <223> OTHER INFORMATION: artificial synthetase |

<400> SEQUENCE: 28

| cgggggctgg tacccaagt gacggacgag gaaacgttag cagagcgact ggcgcaaggc | 60 |
| ccgatcgcac tctcttgtgg cttcgatcct accgctgaca gcttgcattt ggggcatctt | 120 |
| gttccattgt tatgcctgaa acgcttccag caggcaggcc acaagccggt tgcgctggta | 180 |
| ggcggcgcga cgggtctgat tggcgacccg agcttcaaag ctgccgagcg taagctgaac | 240 |
| accgaagaaa ctgttcagga gtgggtggac aaaatccgta agcaggttgc cccgttcctc | 300 |
| gatttcgact gtggagaaaa ctctgctatc gcggccaata attatgactg gttcggcaat | 360 |
| atgaatgtgc tgaccttcct gcgcgatatt ggcaaacact tctccgttaa ccagatgatc | 420 |
| aacaaagaag cggttaagca gcgtctcaac cgtgaagatc aggggatttc gttcactgag | 480 |
| ttttcctaca acctgctgca gggttatacg atggcctgtg tgaacaaaca gtacggtgtg | 540 |
| gtgctgcaaa ttggtggttc tgaccagtgg ggtaacatca cttctggtat cgacctgacc | 600 |
| cgtcgtctgc atcagaatca ggtg | 624 |

| <210> SEQ ID NO 29 |
| <211> LENGTH: 624 |
| <212> TYPE: DNA |
| <213> ORGANISM: Artificial Sequence |
| <220> FEATURE: |
| <223> OTHER INFORMATION: artificial synthetase |

<400> SEQUENCE: 29

| cgggggctgg tagcccaggt gacggacgag gaagcgttag cagagcgact ggcgcaaggc | 60 |
| ccgatcgcac tcgcgtgcgg cttcgatcct accgctgaca gcttgcattt ggggcatctt | 120 |
| gttccattgt tatgcctgaa acgcttccag caggcgggcc acaagccggt tgcgctggta | 180 |
| ggcggcgcga cgggtctgat tggcgacccg agcttcaagg ctgccgagcg taagctgaac | 240 |
| accgaagaaa ctgttcagga gtgggtggac aaaatccgta agcaggttgc cccgttcctc | 300 |
| gatttcgact gtggagaaaa ctctgctatc gcggccaata attatgactg gttcggcaat | 360 |
| atgaatgtgc tgaccttcct gcgcgatatt ggcaaacact tctccgttaa ccagatgatc | 420 |
| aacaaagaag cggttaagca gcgtctcaac cgtgaagatc aggggatttc gttcactgag | 480 |
| ttttcctaca acctgctgca gggttattct tatgcctgtc ttaacaaaca gtacggtgtg | 540 |
| gtgctgcaaa ttggtggttc tgaccagtgg ggtaacatca cttctggtat cgacctgacc | 600 |
| cgtcgtctgc atcagaatca ggtg | 624 |

| <210> SEQ ID NO 30 |
| <211> LENGTH: 624 |
| <212> TYPE: DNA |
| <213> ORGANISM: Artificial Sequence |
| <220> FEATURE: |
| <223> OTHER INFORMATION: artificial synthetase |

<400> SEQUENCE: 30

| cgggggctgg tagcccaggt gacggacgag gaagcgttag cagagcgact ggcgcaaggc | 60 |
| ccgatcgcac tcgcgtgtgg cttcgatcct accgctgaca gcttgcattt ggggcatctt | 120 |
| gttccattgt tatgcctgaa acgcttccag caggcgggcc acaagccggt tgcgctggta | 180 |
| ggcggcgcga cgggtctgat tggcgacccg agcttcaaag ctgccgagcg taagctgaac | 240 |

```
accgaagaaa ctgttcagga gtgggtggac aaaatccgta agcaggttgc cccgttcctc      300
gatttcgact gtggagaaaa ctctgctatc gcggccaata attatgactg gttcggcaat      360
atgaatgtgc tgaccttcct gcgcgatatt ggcaaacact tctccgttaa ccagatgatc      420
aacaaagaag cggttaagca gcgtctcaac cgtgaagatc aggggatttc gttcactgag      480
ttttcctaca acctgctgca gggttatacg atggcctgtt gtaacaaaca gtacggtgtg      540
gtgctgcaaa ttggtggttc tgaccagtgg ggtaacatca cttctggtat cgacctgacc      600
cgtcgtctgc atcagaatca ggtg                                            624

<210> SEQ ID NO 31
<211> LENGTH: 624
<212> TYPE: DNA
<213> ORGANISM: Artificial Sequence
<220> FEATURE:
<223> OTHER INFORMATION: artificial synthetase

<400> SEQUENCE: 31
cgggggctgg taccccaagt gacggacgag gaagcgttag cagagcgact ggcgcaaggc       60
ccgatcgcac tcacgtgtgg cttcgatcct accgctgaca gcttgcattt ggggcatctt      120
gttccattgt tatgcctgaa acgcttccag caggcgggcc acaagccggt tgcgctggta      180
ggcggcgcga cgggtctgat tggcgacccg agcttcaaag ctgccgagcg taagctgaac      240
accgaagaaa ctgttcagga gtgggtggac aaaatccgta agcaggttgc cccgttcctc      300
gatttcgact gtggagaaaa ctctgctatc gcggccaata attatgactg gttcggcaat      360
atgaatgtgc tgaccttcct gcgcgatatt ggcaaacact tctccgttaa ccagatgatc      420
aacaaagaag cggttaagca gcgtctcaac cgtgaagatc aggggatttc gttcgctgag      480
ttttcctaca acctgctgca gggttatacg tttgcctgta tgaacaaaca gtacggtgtg      540
gtgctgcaaa ttggtggttc tgaccagtgg ggtaacatca cttctggtat cgacctgacc      600
cgtcgtctgc atcagaatca ggtg                                            624

<210> SEQ ID NO 32
<211> LENGTH: 606
<212> TYPE: DNA
<213> ORGANISM: Artificial Sequence
<220> FEATURE:
<223> OTHER INFORMATION: artificial synthetase

<400> SEQUENCE: 32
gtgacggacg aggaagcgtt agcagagcga ctggcgcaag gcccgatcgc actcacgtgt       60
ggcttcgatc ctaccgctga cagcttgcat ttggggcatc ttgttccatt gttatgcctg      120
aaacgcttcc agcaggcggg ccacaagccg gttgcgctgg taggcggcgc gacgggtctg      180
attggcgacc cgagcttcaa agctgccgag cgtaagctga acaccgaaga aactgttcag      240
gagtgggtgg acaaaatccg taagcaggtt gccccgttcc tcgatttcga ctgtggagaa      300
aactctgcta tcgcggccaa taattatgac tggttcggca atatgaatgt gctgaccttc      360
ctgcgcgata ttggcaaaca cttctccgtt aaccagatga tcaacaaaga agcggttaag      420
cagcgtctca accgtgaaga tcaggggatt tcgttcactg agttttccta caatctgctg      480
cagggttatt cggctgcctg tcttaacaaa cagtacggtg tggtgctgca aattggtggt      540
tctgaccagt ggggtaacat cacttctggt atcgacctga cccgtcgtct gcatcagaat      600
caggtg                                                                606
```

<210> SEQ ID NO 33
<211> LENGTH: 624
<212> TYPE: DNA
<213> ORGANISM: Artificial Sequence
<220> FEATURE:
<223> OTHER INFORMATION: artificial synthetase

<400> SEQUENCE: 33

```
cgggggctgg tagcccaggt gacggacgag gaagcgttag cagagcgact ggcgcaaggc    60
ccgatcgcac tcgtttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttattcg atggcctgta cgaacaaaca gtacggtgtg   540
gtgctgcaaa ttggtggttc tgaccagtgg ggtaacatca cttctggtat cgacctgacc   600
cgtcgtctgc atcagaatca ggtg                                         624
```

<210> SEQ ID NO 34
<211> LENGTH: 624
<212> TYPE: DNA
<213> ORGANISM: Artificial Sequence
<220> FEATURE:
<223> OTHER INFORMATION: artificial synthetase
<220> FEATURE:
<221> NAME/KEY: misc_feature
<222> LOCATION: (13)..(13)
<223> OTHER INFORMATION: n is a, c, g, or t

<400> SEQUENCE: 34

```
cgggggctgg tancccaagt gacggacggg gaagcgttag cagagcgact ggcgcaaggc    60
ccgatcgcac tcagttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatctcgact gtggagaaaa ctctgctatc gcggccaata attatgactg gttcggcaat   360
atgaatgtgc tgaccttcct gcgcgatatt ggcaaacact tctccgttaa ccagatgatc   420
aacaaagaag cggttaagca gcgtctcaac cgtgaagatc aggggatttc gttcactgag   480
ttttcctaca acctgctgca gggttatagt tttgcctgtc tgaacaaaca gtacggtgtg   540
gtgctgcaaa ttggtggttc tgaccagtgg ggtaacatca cttctggtat cgacctgacc   600
cgtcgtctgc atcagaatca ggtg                                         624
```

<210> SEQ ID NO 35
<211> LENGTH: 624
<212> TYPE: DNA
<213> ORGANISM: Artificial Sequence
<220> FEATURE:
<223> OTHER INFORMATION: artificial synthetase

<400> SEQUENCE: 35

```
cgggggctgg tagcccaggt gacggacgag gaagcgttag cagagcgact ggcgcaaggc    60
```

```
ccgatcgcac tcacgtgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttatacg tttgcctgta ctaacaaaca gtacggtgtg    540
gtgctgcaaa ttggtggttc tgaccagtgg ggtaacatca cttctggtat cgacctgacc    600
cgtcgtctgc atcagaatca ggtg                                           624
```

```
<210> SEQ ID NO 36
<211> LENGTH: 424
<212> TYPE: PRT
<213> ORGANISM: Artificial Sequence
<220> FEATURE:
<223> OTHER INFORMATION: artificial synthetase

<400> SEQUENCE: 36
```

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Tyr Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255
```

```
Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 37
<211> LENGTH: 424
<212> TYPE: PRT
<213> ORGANISM: Artificial Sequence
<220> FEATURE:
<223> OTHER INFORMATION: artificial synthetase

<400> SEQUENCE: 37

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190
```

-continued

```
Val Leu Gln Ile Gly Gly Ser Asp Gln Trp Gly Asn Ile Thr Ser Gly
            195                 200                 205

Ile Asp Leu Thr Arg Arg Leu His Gln Asn Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 38
<211> LENGTH: 424
<212> TYPE: PRT
<213> ORGANISM: Artificial Sequence
<220> FEATURE:
<223> OTHER INFORMATION: artificial synthetase

<400> SEQUENCE: 38

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125
```

```
Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420
```

<210> SEQ ID NO 39
<211> LENGTH: 424
<212> TYPE: PRT
<213> ORGANISM: Artificial Sequence
<220> FEATURE:
<223> OTHER INFORMATION: artificial synthetase

<400> SEQUENCE: 39

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Val Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60
```

Gly His Lys Pro Val Ala Leu Val Gly Gly Ala Thr Gly Leu Ile Gly
 65                  70                  75                  80

Asp Pro Ser Phe Lys Ala Ala Glu Arg Lys Leu Asn Thr Glu Glu Thr
                 85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 40
<211> LENGTH: 424
<212> TYPE: PRT
<213> ORGANISM: Artificial Sequence
<220> FEATURE:
<223> OTHER INFORMATION: artificial synthetase

<400> SEQUENCE: 40

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
                100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
```

```
                420

<210> SEQ ID NO 41
<211> LENGTH: 424
<212> TYPE: PRT
<213> ORGANISM: Artificial Sequence
<220> FEATURE:
<223> OTHER INFORMATION: artificial synthetase

<400> SEQUENCE: 41

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Tyr Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
```

-continued

```
                355                 360                 365
Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Arg Arg Gly Lys Lys
                405                 410                 415

Asn Tyr Cys Leu Ile Cys Trp Lys
            420

<210> SEQ ID NO 42
<211> LENGTH: 424
<212> TYPE: PRT
<213> ORGANISM: Artificial Sequence
<220> FEATURE:
<223> OTHER INFORMATION: artificial synthetase

<400> SEQUENCE: 42

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Leu Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ser Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
```

```
                    290                 295                 300
Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420
```

<210> SEQ ID NO 43
<211> LENGTH: 424
<212> TYPE: PRT
<213> ORGANISM: Artificial Sequence
<220> FEATURE:
<223> OTHER INFORMATION: artificial synthetase

<400> SEQUENCE: 43

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Leu Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
```

```
225                 230                 235                 240
Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 44
<211> LENGTH: 424
<212> TYPE: PRT
<213> ORGANISM: Artificial Sequence
<220> FEATURE:
<223> OTHER INFORMATION: artificial synthetase

<400> SEQUENCE: 44

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Thr Cys Gly Phe Asp Pro Thr Ala Asp Ser Leu His
                35                  40                  45

Leu Gly His Leu Val Pro Leu Leu Cys Leu Lys Arg Phe Gln Gln Ala
            50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
                100                 105                 110

Asp Phe Asp Cys Gly Glu Asn Ser Ala Ile Ala Ala Asn Asn Tyr Asp
                115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
```

```
                165                 170                 175

Leu Leu Gln Gly Tyr Arg Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Thr Ser Pro Tyr Lys Phe
            245                 250                 255

Tyr Gln Phe Trp Ile Asn Thr Ala Asp Ala Asp Val Tyr Arg Phe Leu
        260                 265                 270

Lys Phe Phe Thr Phe Met Ser Ile Glu Glu Ile Asn Ala Leu Glu Glu
    275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
        340                 345                 350

Met Glu Lys Gly Ala Asp Leu Met Gln Ala Leu Val Asp Ser Glu Leu
    355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420

<210> SEQ ID NO 45
<211> LENGTH: 424
<212> TYPE: PRT
<213> ORGANISM: Artificial Sequence
<220> FEATURE:
<223> OTHER INFORMATION: artificial synthetase

<400> SEQUENCE: 45

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
            85                  90                  95

Val Gln Glu Trp Val Asp Lys Ile Arg Lys Gln Val Ala Pro Phe Leu
```

```
            100                 105                 110
Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175

Leu Leu Gln Gly Tyr Gly Met Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 46
<211> LENGTH: 424
<212> TYPE: PRT
<213> ORGANISM: Artificial Sequence
<220> FEATURE:
<223> OTHER INFORMATION: artificial synthetase

<400> SEQUENCE: 46

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
```

```
                    35                  40                  45
Leu Gly His Leu Val Pro Leu Leu Cys Leu Lys Arg Phe Gln Gln Ala
 50                  55                  60
Gly His Lys Pro Val Ala Leu Val Gly Gly Ala Thr Gly Leu Ile Gly
 65                  70                  75                  80
Asp Pro Ser Phe Lys Ala Ala Glu Arg Lys Leu Asn Thr Glu Glu Thr
                 85                  90                  95
Val Gln Glu Trp Val Asp Lys Ile Arg Lys Gln Val Ala Pro Phe Leu
                100                 105                 110
Asp Phe Asp Cys Gly Glu Asn Ser Ala Ile Ala Ala Asn Asn Tyr Asp
                115                 120                 125
Trp Phe Gly Asn Met Asn Val Leu Thr Phe Leu Arg Asp Ile Gly Lys
                130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Gly Phe Ala Cys Ala Asn Lys Gln Tyr Gly Val
                180                 185                 190
Val Leu Gln Ile Gly Gly Ser Asp Gln Trp Gly Asn Ile Thr Ser Gly
                195                 200                 205
Ile Asp Leu Thr Arg Arg Leu His Gln Asn Gln Val Phe Gly Leu Thr
                210                 215                 220
Val Pro Leu Ile Thr Lys Ala Asp Gly Thr Lys Phe Gly Lys Thr Glu
225                 230                 235                 240
Gly Gly Ala Val Trp Leu Asp Pro Lys Lys Thr Ser Pro Tyr Lys Phe
                245                 250                 255
Tyr Gln Phe Trp Ile Asn Thr Ala Asp Ala Asp Val Tyr Arg Phe Leu
                260                 265                 270
Lys Phe Phe Thr Phe Met Ser Ile Glu Glu Ile Asn Ala Leu Glu Glu
                275                 280                 285
Glu Asp Lys Asn Ser Gly Lys Ala Pro Arg Ala Gln Tyr Val Leu Ala
                290                 295                 300
Glu Gln Val Thr Arg Leu Val His Gly Glu Glu Gly Leu Gln Ala Ala
305                 310                 315                 320
Lys Arg Ile Thr Glu Cys Leu Phe Ser Gly Ser Leu Ser Ala Leu Ser
                325                 330                 335
Glu Ala Asp Phe Glu Gln Leu Ala Gln Asp Gly Val Pro Met Val Glu
                340                 345                 350
Met Glu Lys Gly Ala Asp Leu Met Gln Ala Leu Val Asp Ser Glu Leu
                355                 360                 365
Gln Pro Ser Arg Gly Gln Ala Arg Lys Thr Ile Ala Ser Asn Ala Ile
                370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
                405                 410                 415
Asn Tyr Cys Leu Ile Cys Trp Lys
                420

<210> SEQ ID NO 47
<211> LENGTH: 424
<212> TYPE: PRT
<213> ORGANISM: Artificial Sequence
```

```
<220> FEATURE:
<223> OTHER INFORMATION: artificial synthetase

<400> SEQUENCE: 47

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Gly Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Gly Tyr Ala Cys Met Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400
```

```
Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 48
<211> LENGTH: 424
<212> TYPE: PRT
<213> ORGANISM: Artificial Sequence
<220> FEATURE:
<223> OTHER INFORMATION: artificial synthetase

<400> SEQUENCE: 48

Met Ala Ser Ser Asn Leu Ile Lys Gln Leu Gln Glu Arg Gly Leu Val
1               5                   10                  15

Ala Gln Val Thr Asp Glu Glu Ala Leu Ala Arg Leu Ala Gln Gly
            20                  25                  30

Pro Ile Ala Leu Leu Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335
```

```
Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 49
<211> LENGTH: 424
<212> TYPE: PRT
<213> ORGANISM: Artificial Sequence
<220> FEATURE:
<223> OTHER INFORMATION: artificial synthetase

<400> SEQUENCE: 49

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
            35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270
```

```
Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Arg Arg Gly Lys Lys
                405                 410                 415

Asn Tyr Cys Leu Ile Cys Trp Lys
            420

<210> SEQ ID NO 50
<211> LENGTH: 424
<212> TYPE: PRT
<213> ORGANISM: Artificial Sequence
<220> FEATURE:
<223> OTHER INFORMATION: artificial synthetase

<400> SEQUENCE: 50

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Leu Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205
```

-continued

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 51
<211> LENGTH: 424
<212> TYPE: PRT
<213> ORGANISM: Artificial Sequence
<220> FEATURE:
<223> OTHER INFORMATION: artificial synthetase

<400> SEQUENCE: 51

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

```
His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175

Leu Leu Gln Gly Tyr Ser Ala Ala Cys Val Asn Lys Gln Tyr Gly Val
        180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 52
<211> LENGTH: 424
<212> TYPE: PRT
<213> ORGANISM: Artificial Sequence
<220> FEATURE:
<223> OTHER INFORMATION: artificial synthetase

<400> SEQUENCE: 52

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80
```

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asp Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asn Phe Ala Cys Val Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 53
<211> LENGTH: 424
<212> TYPE: PRT
<213> ORGANISM: Artificial Sequence
<220> FEATURE:
<223> OTHER INFORMATION: artificial synthetase

<400> SEQUENCE: 53

Met Ala Ser Ser Asn Leu Ile Lys Gln Leu Gln Glu Arg Gly Leu Val
1               5                   10                  15

-continued

```
Ala Gln Val Thr Asp Glu Ala Leu Ala Glu Arg Leu Ala Gln Gly
            20                  25                  30

Pro Ile Ala Leu Thr Cys Gly Phe Asp Pro Thr Ala Asp Ser Leu His
            35                  40                  45

Leu Gly His Leu Val Pro Leu Leu Cys Leu Lys Arg Phe Gln Gln Ala
 50                  55                  60

Gly His Lys Pro Val Ala Leu Val Gly Gly Ala Thr Gly Leu Ile Gly
 65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Leu Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420
```

<210> SEQ ID NO 54
<211> LENGTH: 424
<212> TYPE: PRT
<213> ORGANISM: Artificial Sequence
<220> FEATURE:
<223> OTHER INFORMATION: artificial synthetase

<400> SEQUENCE: 54

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365
```

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420

<210> SEQ ID NO 55
<211> LENGTH: 424
<212> TYPE: PRT
<213> ORGANISM: Artificial Sequence
<220> FEATURE:
<223> OTHER INFORMATION: artificial synthetase

<400> SEQUENCE: 55

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

```
Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 56
<211> LENGTH: 424
<212> TYPE: PRT
<213> ORGANISM: Artificial Sequence
<220> FEATURE:
<223> OTHER INFORMATION: artificial synthetase

<400> SEQUENCE: 56

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Ser Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Met Ala Cys Val Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240
```

```
Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 57
<211> LENGTH: 424
<212> TYPE: PRT
<213> ORGANISM: Artificial Sequence
<220> FEATURE:
<223> OTHER INFORMATION: artificial synthetase

<400> SEQUENCE: 57

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Ala Cys Gly Phe Asp Pro Thr Ala Asp Ser Leu His
            35                  40                  45

Leu Gly His Leu Val Pro Leu Leu Cys Leu Lys Arg Phe Gln Gln Ala
            50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175
```

Leu Leu Gln Gly Tyr Ser Tyr Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 58
<211> LENGTH: 424
<212> TYPE: PRT
<213> ORGANISM: Artificial Sequence
<220> FEATURE:
<223> OTHER INFORMATION: artificial synthetase

<400> SEQUENCE: 58

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ala Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Met Ala Cys Cys Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 59
<211> LENGTH: 424
<212> TYPE: PRT
<213> ORGANISM: Artificial Sequence
<220> FEATURE:
<223> OTHER INFORMATION: artificial synthetase

<400> SEQUENCE: 59

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

```
Leu Gly His Leu Val Pro Leu Leu Cys Leu Lys Arg Phe Gln Gln Ala
 50                  55                  60
Gly His Lys Pro Val Ala Leu Val Gly Gly Ala Thr Gly Leu Ile Gly
 65                  70                  75                  80
Asp Pro Ser Phe Lys Ala Ala Glu Arg Lys Leu Asn Thr Glu Thr
                 85                  90                  95
Val Gln Glu Trp Val Asp Lys Ile Arg Lys Gln Val Ala Pro Phe Leu
                100                 105                 110
Asp Phe Asp Cys Gly Glu Asn Ser Ala Ile Ala Ala Asn Asn Tyr Asp
                115                 120                 125
Trp Phe Gly Asn Met Asn Val Leu Thr Phe Leu Arg Asp Ile Gly Lys
130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Thr Phe Ala Cys Met Asn Lys Gly Tyr Gly Val
                180                 185                 190
Val Leu Gln Ile Gly Gly Ser Asp Gln Trp Gly Asn Ile Thr Ser Gly
                195                 200                 205
Ile Asp Leu Thr Arg Arg Leu His Gln Asn Gln Val Phe Gly Leu Thr
210                 215                 220
Val Pro Leu Ile Thr Lys Ala Asp Gly Thr Lys Phe Gly Lys Thr Glu
225                 230                 235                 240
Gly Gly Ala Val Trp Leu Asp Pro Lys Lys Thr Ser Pro Tyr Lys Phe
                245                 250                 255
Tyr Gln Phe Trp Ile Asn Thr Ala Asp Ala Asp Val Tyr Arg Phe Leu
                260                 265                 270
Lys Phe Phe Thr Phe Met Ser Ile Glu Glu Ile Asn Ala Leu Glu Glu
                275                 280                 285
Glu Asp Lys Asn Ser Gly Lys Ala Pro Arg Ala Gln Tyr Val Leu Ala
                290                 295                 300
Glu Gln Val Thr Arg Leu Val His Gly Glu Glu Gly Leu Gln Ala Ala
305                 310                 315                 320
Lys Arg Ile Thr Glu Cys Leu Phe Ser Gly Ser Leu Ser Ala Leu Ser
                325                 330                 335
Glu Ala Asp Phe Glu Gln Leu Ala Gln Asp Gly Val Pro Met Val Glu
                340                 345                 350
Met Glu Lys Gly Ala Asp Leu Met Gln Ala Leu Val Asp Ser Glu Leu
                355                 360                 365
Gln Pro Ser Arg Gly Gln Ala Arg Lys Thr Ile Ala Ser Asn Ala Ile
                370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
                405                 410                 415
Asn Tyr Cys Leu Ile Cys Trp Lys
                420

<210> SEQ ID NO 60
<211> LENGTH: 424
<212> TYPE: PRT
<213> ORGANISM: Artificial Sequence
<220> FEATURE:
<223> OTHER INFORMATION: artificial synthetase
```

<400> SEQUENCE: 60

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Val Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
```

Asn Tyr Cys Leu Ile Cys Trp Lys
            420

<210> SEQ ID NO 61
<211> LENGTH: 424
<212> TYPE: PRT
<213> ORGANISM: Artificial Sequence
<220> FEATURE:
<223> OTHER INFORMATION: artificial synthetase

<400> SEQUENCE: 61

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Thr Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu

```
                340             345             350
Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                    405                 410                 415

Asn Tyr Cys Leu Ile Cys Trp Lys
                420

<210> SEQ ID NO 62
<211> LENGTH: 424
<212> TYPE: PRT
<213> ORGANISM: Artificial Sequence
<220> FEATURE:
<223> OTHER INFORMATION: artificial synthetase

<400> SEQUENCE: 62

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Ser Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
```

```
                    275                 280                 285
Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 63
<211> LENGTH: 424
<212> TYPE: PRT
<213> ORGANISM: Artificial Sequence
<220> FEATURE:
<223> OTHER INFORMATION: artificial synthetase

<400> SEQUENCE: 63

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Thr Cys Gly Phe Asp Pro Thr Ala Asp Ser Leu His
            35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Phe Ala Cys Thr Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
```

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420

<210> SEQ ID NO 64
<211> LENGTH: 129
<212> TYPE: DNA
<213> ORGANISM: Escherichia coli

<400> SEQUENCE: 64
agcttcccga taagggagca ggccagtaaa aagcattacc ccgtggtggg gttcccgagc      60
ggccaaaggg agcagactct aaatctgccg tcatcgacct cgaaggttcg aatccttccc    120
ccaccacca                                                            129

<210> SEQ ID NO 65
<211> LENGTH: 129
<212> TYPE: RNA
<213> ORGANISM: Escherichia coli

<400> SEQUENCE: 65
agcuucccga uaagggagca ggccaguaaa aagcauuacc ccguggnggg guucccgagc      60
ggccaaaggg agcagacucu aaaucugccg ucaucgaccu cgaagguucg aauccuuccc    120
ccaccacca                                                            129

<210> SEQ ID NO 66
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 66

```
atgaagtagc tgtcttctat cgaacaagca tgcg                                   34

<210> SEQ ID NO 67
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 67
cgaacaagca tgcgattagt gccgacttaa aaag                                   34

<210> SEQ ID NO 68
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 68
cgctactctc ccaaatagaa aaggtctccg ctg                                    33

<210> SEQ ID NO 69
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 69
ctggaacagc tatagctact gattttcct cg                                      32

<210> SEQ ID NO 70
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 70
gccgtcacag attagttggc ttcagtggag actg                                   34

<210> SEQ ID NO 71
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 71
gattggcttc ataggagact gatatgctct aac                                    33

<210> SEQ ID NO 72
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 72
gcctctatag ttgagacagc atagaataat gcg                                    33

<210> SEQ ID NO 73
<211> LENGTH: 35
<212> TYPE: DNA
<213> ORGANISM: Artificial Sequence
```

<220> FEATURE:
<223> OTHER INFORMATION: oligonucleotide primer

<400> SEQUENCE: 73
gagacagcat agatagagtg cgacatcatc atcgg                               35

<210> SEQ ID NO 74
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 74
gaataagtgc gacatagtca tcggaagaga gtagtag                             37

<210> SEQ ID NO 75
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 75
ggtcaaagac agttgtaggt atcgattgac tcggc                               35

<210> SEQ ID NO 76
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 76
cgctactctc cccaaattta aaggtctcc gctg                                 34

<210> SEQ ID NO 77
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 77
cgctactctc cccaaatata aaggtctcc gctg                                 34

<210> SEQ ID NO 78
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 78
cgctactctc cccaaatgga aaggtctcc gctg                                 34

<210> SEQ ID NO 79
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 79
cgctactctc cccaaagata aaggtctcc gctg                                 34

<210> SEQ ID NO 80
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 80
cgctactctc cccaaaaaaa aaaggtctcc gctg            34

<210> SEQ ID NO 81
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 81
gccgtcacag atttttggc ttcagtggag actg            34

<210> SEQ ID NO 82
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 82
gccgtcacag attatttggc ttcagtggag actg            34

<210> SEQ ID NO 83
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 83
gccgtcacag attggttggc ttcagtggag actg            34

<210> SEQ ID NO 84
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 84
gccgtcacag atgatttggc ttcagtggag actg            34

<210> SEQ ID NO 85
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 85
gccgtcacag ataaattggc ttcagtggag actg            34

<210> SEQ ID NO 86
<211> LENGTH: 424
<212> TYPE: PRT
<213> ORGANISM: Artificial Sequence
<220> FEATURE:
<223> OTHER INFORMATION: artificial synthetase

<400> SEQUENCE: 86

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Gly Gln Gly Ile Ser Phe Thr Glu Phe Ser Tyr Asn
                165                 170                 175

Leu Leu Gln Gly Tyr Gly Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
```

Asn Tyr Cys Leu Ile Cys Trp Lys
        420

<210> SEQ ID NO 87
<211> LENGTH: 6
<212> TYPE: PRT
<213> ORGANISM: Artificial Sequence
<220> FEATURE:
<223> OTHER INFORMATION: tryptic peptide including unnatural amino acids
<220> FEATURE:
<221> NAME/KEY: misc_feature
<222> LOCATION: (2)..(2)
<223> OTHER INFORMATION: X is an unnatural amino acid (p-acetyl-L-
      phenylalanine, p-benzoyl-L-phenylalanine, p-azido-L-phenylalanine,
      O-methyl-L-tyrosine, or p-iodo-L-phenylalanine) or trypotophan,
      tyrosine, or leucine

<400> SEQUENCE: 87

Val Xaa Gly Ser Ile Lys
1               5

<210> SEQ ID NO 88
<211> LENGTH: 11
<212> TYPE: DNA
<213> ORGANISM: Artificial Sequence
<220> FEATURE:
<223> OTHER INFORMATION: B box
<220> FEATURE:
<221> NAME/KEY: misc_feature
<222> LOCATION: (8)..(8)
<223> OTHER INFORMATION: n is a, c, g, or t

<400> SEQUENCE: 88
ggttcgantc c                                                          11

<210> SEQ ID NO 89
<211> LENGTH: 82
<212> TYPE: DNA
<213> ORGANISM: Artificial Sequence
<220> FEATURE:
<223> OTHER INFORMATION: oligonucleotide primer

<400> SEQUENCE: 89 gggggaccg gtgggggac cggtaagctt cccgataagg gagcaggcca gtaaaaagca      60
ttaccccgtg gtgggttccc ga                                              82

<210> SEQ ID NO 90
<211> LENGTH: 90
<212> TYPE: DNA
<213> ORGANISM: Artificial Sequence
<220> FEATURE:
<223> OTHER INFORMATION: oligonucleotide primer

<400> SEQUENCE: 90
ggcggcgcta gcaagcttcc cgataaggga gcaggccagt aaaagggaa gttcagggac      60 ttttgaaaaa aatggtggtg ggggaaggat                                      90

<210> SEQ ID NO 91
<211> LENGTH: 68
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)

```
<223> OTHER INFORMATION: n=I
<220> FEATURE:
<221> NAME/KEY: misc_feature
<222> LOCATION: (14)..(14)
<223> OTHER INFORMATION: n=I

<400> SEQUENCE: 91
nggggggacc ggtnggggg accggtcggg atcgaagaaa tgatggtaaa tgaaatagga      60
aatcaagg                                                              68

<210> SEQ ID NO 92
<211> LENGTH: 62
<212> TYPE: DNA
<213> ORGANISM: Artificial Sequence
<220> FEATURE:
<223> OTHER INFORMATION: oligonucleotide primer

<400> SEQUENCE: 92 ggggggaat tcagttgatt gtatgcttgg tatagcttga aatattgtgc agaaaaagaa     60
ac                                                                    62

<210> SEQ ID NO 93
<211> LENGTH: 86
<212> TYPE: DNA
<213> ORGANISM: Artificial Sequence
<220> FEATURE:
<223> OTHER INFORMATION: oligonucleotide primer

<400> SEQUENCE: 93
tcataacgag aattccggga tcgaagaaat gatggtaaat gaaataggaa atctcataac     60
gagaattcat ggcaagcagt aacttg                                          86

<210> SEQ ID NO 94
<211> LENGTH: 72
<212> TYPE: DNA
<213> ORGANISM: Artificial Sequence
<220> FEATURE:
<223> OTHER INFORMATION: oligonucleotide primer

<400> SEQUENCE: 94
ttactacgtg cggccgcatg gcaagcagta acttgttact acgtgcggcc gcttatttcc     60
agcaaatcag ac                                                         72

<210> SEQ ID NO 95
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 95
ccgatcgcgc tcgcttgcgg cttcgatc                                        28

<210> SEQ ID NO 96
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 96
atcgcggcga acgcctatga ctggttc                                         27
```

<210> SEQ ID NO 97
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 97
gttgcagggt tatgccgccg cctgtgcgaa caaacagtac                    40

<210> SEQ ID NO 98
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 98
gccgctttgc tatcaagtat aaatag                                  26

<210> SEQ ID NO 99
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 99
caagccgaca accttgattg g                                       21

<210> SEQ ID NO 100
<211> LENGTH: 60
<212> TYPE: DNA
<213> ORGANISM: Artificial Sequence
<220> FEATURE:
<223> OTHER INFORMATION: oligonucleotide primer

<400> SEQUENCE: 100
ggggacaagt ttgtacaaaa aagcaggcta cgccaatttt aatcaaagtg ggaatattgc    60

<210> SEQ ID NO 101
<211> LENGTH: 60
<212> TYPE: DNA
<213> ORGANISM: Artificial Sequence
<220> FEATURE:
<223> OTHER INFORMATION: oligonucleotide primer

<400> SEQUENCE: 101
ggggacaagt ttgtacaaaa aagcaggcta ggccaatttt aatcaaagtg ggaatattgc    60

<210> SEQ ID NO 102
<211> LENGTH: 58
<212> TYPE: DNA
<213> ORGANISM: Artificial Sequence
<220> FEATURE:
<223> OTHER INFORMATION: oligonucleotide primer

<400> SEQUENCE: 102
ggggaccact ttgtacaaga aagctgggtt actcttttt tgggtttggt ggggtatc      58

<210> SEQ ID NO 103
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 103
aagctatacc aagcatacaa tc                                              22

<210> SEQ ID NO 104
<211> LENGTH: 49
<212> TYPE: DNA
<213> ORGANISM: Artificial Sequence
<220> FEATURE:
<223> OTHER INFORMATION: oligonucleotide primer

<400> SEQUENCE: 104
acaaggcctt gctagcttac tcttttttg ggtttggtgg ggtatcttc                   49

<210> SEQ ID NO 105
<211> LENGTH: 424
<212> TYPE: PRT
<213> ORGANISM: Artificial Sequence
<220> FEATURE:
<223> OTHER INFORMATION: artificial synthetase
<220> FEATURE:
<221> NAME/KEY: misc_feature
<222> LOCATION: (37)..(37)
<223> OTHER INFORMATION: x = glycine, serine, or alanine
<220> FEATURE:
<221> NAME/KEY: misc_feature
<222> LOCATION: (126)..(126)
<223> OTHER INFORMATION: x = aspartate
<220> FEATURE:
<221> NAME/KEY: misc_feature
<222> LOCATION: (182)..(182)
<223> OTHER INFORMATION: x = asparagine
<220> FEATURE:
<221> NAME/KEY: misc_feature
<222> LOCATION: (183)..(183)
<223> OTHER INFORMATION: x = alanine or valine
<220> FEATURE:
<221> NAME/KEY: misc_feature
<222> LOCATION: (186)..(186)
<223> OTHER INFORMATION: x = methionine, valine, cysteine, or threonine

<400> SEQUENCE: 105

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Xaa Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Xaa Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175
```

```
Leu Leu Gln Gly Tyr Xaa Xaa Ala Cys Xaa Asn Lys Gln Tyr Gly Val
            180             185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420
```

UNNATURAL REACTIVE AMINO ACID GENETIC CODE ADDITIONS

CROSS-REFERENCE TO RELATED APPLICATIONS

This application is a divisional of U.S. Ser. No. 13/787,400 filed Mar. 6, 2013 (now allowed), which is a continuation of U.S. Ser. No. 13/135,129 filed Jun. 23, 2011 (now U.S. Pat. No. 8,445,446), which is a continuation of U.S. Ser. No. 10/561,121 filed May 23, 2006 (now U.S. Pat. No. 7,993,872), which is a 371, U.S. National Phase application of International Patent Application No. PCT/US004/011833 filed Apr. 16, 2004, which claims the priority to and the benefit of U.S. Ser. No. 60/479,931 entitled "Expanding the Eukaryotic Genetic Code" by Chin et al. filed Jun. 18, 2003; U.S. Ser. No. 60/493,014 entitled "Expanding the Eukaryotic Genetic Code" by Chin et al., filed Aug. 5, 2003; and U.S. Ser. No. 60/496,548 entitled "Expanding the Eukaryotic Genetic Code" by Chin et al., filed Aug. 19, 2003. Priority to and benefit of each of these prior applications is hereby claimed.

STATEMENT AS TO RIGHTS TO INVENTIONS MADE UNDER FEDERALLY SPONSORED RESEARCH AND DEVELOPMENT

This invention was made with government support under Grant No. GM 62159 from the National Institutes of Health and support under Grant DE-FG0300ER45812 from the Department of Energy. The government has certain rights to this invention.

FIELD OF THE INVENTION

The invention pertains to the field of translation biochemistry in eukaryotic cells. The invention relates to methods for producing and compositions of orthogonal tRNAs, orthogonal synthetases and pairs thereof, in eukaryotic cells. The invention also relates to compositions of unnatural amino acids, proteins and methods of producing proteins in eukaryotic cells that include unnatural amino acids.

BACKGROUND OF THE INVENTION

The genetic code of every known organism, from bacteria to humans, encodes the same twenty common amino acids. Different combinations of the same twenty natural amino acids form proteins that carry out virtually all the complex processes of life, from photosynthesis to signal transduction and the immune response. In order to study and modify protein structure and function, scientists have attempted to manipulate both the genetic code and the amino acid sequence of proteins. However, it has been difficult to remove the constraints imposed by the genetic code that limit proteins to twenty genetically encoded standard building blocks (with the rare exception of selenocysteine (see, e.g., A. Bock et al., (1991), *Molecular Microbiology* 5:515-20) and pyrrolysine (see, e.g., G. Srinivasan, et al., (2002), *Science* 296:1459-62).

Some progress has been made to remove these constraints, although this progress has been limited and the ability to rationally control protein structure and function is still in its infancy. For example, chemists have developed methods and strategies to synthesize and manipulate the structures of small molecules (see, e.g., E. J. Corey, & X.-M. Cheng, *The Logic of Chemical Synthesis* (Wiley-Interscience, New York, 1995)). Total synthesis (see, e.g., B. Merrifield, (1986), *Science* 232:341-7 (1986)), and semi-synthetic methodologies (see, e.g., D. Y. Jackson et al., (1994) Science 266:243-7; and, P. E. Dawson, & S. B. Kent, (2000), *Annual Review of Biochemistry* 69:923-60), have made it possible to synthesize peptides and small proteins, but these methodologies have limited utility with proteins over 10 kilo Daltons (kDa). Mutagenesis methods, though powerful, are restricted to a limited number of structural changes. In a number of cases, it has been possible to competitively incorporate close structural analogues of common amino acids throughout proteins. See, e.g., R. Furter, (1998), *Protein Science* 7:419-26; K. Kirshenbaum, et al., (2002), *ChemBioChem* 3:235-7; and, V. Doring et al., (2001), *Science* 292:501-4.

In an attempt to expand the ability to manipulate protein structure and function, in vitro methods using chemically acylated orthogonal tRNAs were developed that allowed unnatural amino acids to be selectively incorporated in response to a nonsense codon, in vitro (see, e.g., J. A. Ellman, et al., (1992), *Science* 255:197-200). Amino acids with novel structures and physical properties were selectively incorporated into proteins to study protein folding and stability and biomolecular recognition and catalysis. See, e.g., D. Mendel, et al., (1995), *Annual Review of Biophysics and Biomolecular Structure* 24:435-462; and, V. W. Cornish, et al. (Mar. 31, 1995), *Angewandte Chemie-International Edition in English* 34:621-633. However, the stoichiometric nature of this process severely limited the amount of protein that could be generated.

Unnatural amino acids have been microinjected into cells. For example, unnatural amino acids were introduced into the nicotinic acetylcholine receptor in *Xenopus* oocytes (e.g., M. W. Nowak, et al. (1998), *In vivo incorporation of unnatural amino acids into ion channels in Xenopus oocyte expression system, Method Enzymol.* 293:504-529) by microinjection of a chemically misacylated *Tetrahymena thermophila* tRNA (e.g., M. E. Saks, et al. (1996), *An engineered Tetrahymena tRNAGln for in vivo incorporation of unnatural amino acids into proteins by nonsense suppression, J. Biol. Chem.* 271: 23169-23175), and the relevant mRNA. This has allowed detailed biophysical studies of the receptor in oocytes by the introduction of amino acids containing side chains with unique physical or chemical properties. See, e.g., D. A. Dougherty (2000), *Unnatural amino acids as probes of protein structure and function, Curr. Opin. Chem. Biol.* 4:645-652. Unfortunately, this methodology is limited to proteins in cells that can be microinjected, and because the relevant tRNA is chemically acylated in vitro, and cannot be re-acylated, the yields of protein are very low.

To overcome these limitations, new components were added to the protein biosynthetic machinery of the prokaryote *Escherichia coli* (*E. coli*) (e.g., L. Wang, et al., (2001), *Science* 292:498-500), which allowed genetic encoding of unnatural amino acids in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 11:1135-1137; J. W. Chin, et al., (2002), *PNAS United States of America* 99:11020-11024: and, L. Wang, & P. G. Schultz, (2002), *Chem. Comm.*, 1-10. However, the translational machinery of prokaryotes and eukaryotes are not highly conserved; thus, components of the biosynthetic machinery added to *E. coli* cannot often be used to site-specifically incorporate unnatural amino acids into proteins in eukaryotic cells. For example, the *Methanococcus jannaschii* tyrosyl-tRNA synthetase/tRNA pair that was used in *E. coli* is not orthogonal in eukaryotic cells. In addition, the transcription of tRNA in eukaryotes, but not in prokaryotes, is carried out by RNA Polymerase III and this places restrictions on the primary sequence of the tRNA structural genes that can be transcribed in eukaryotic cells. Moreover, in contrast to prokaryotic cells, tRNAs in eukaryotic cells need to be exported from the nucleus, where they are transcribed, to the cytoplasm, to function in translation. Finally, the eukaryotic 80S ribosome is distinct from the 70S prokaryotic ribosome. Thus, there is a need to develop improved components of the biosynthetic machinery to expand the eukaryotic genetic code. This invention fulfills these and other needs, as will be apparent upon review of the following disclosure.

SUMMARY OF THE INVENTION

The invention provides eukaryotic cells with translation components, e.g., pairs of orthogonal aminoacyl-tRNA synthetases (O-RSs) and orthogonal tRNAs (O-tRNAs) and individual components thereof, that are used in eukaryotic protein biosynthetic machinery to incorporate an unnatural amino acid in a growing polypeptide chain, in a eukaryotic cell.

Compositions of the invention include a eukaryotic cell (e.g., a yeast cell (such as a *Saccharomyces cerevisiae* cell), a mammalian cell, a plant cell, an algae cell, a fungal cell, an insect cell, etc.) comprising an orthogonal aminoacyl-tRNA synthetase (O-RS) (e.g., derived from a non-eukaryotic organism, such as *Escherichia coli, Bacillus stearothermophilus*, etc.), where the O-RS preferentially aminoacylates an orthogonal tRNA (O-tRNA) with at least one unnatural amino acid in the eukaryotic cell. Optionally, two or more OtRNAs can be aminoacylated in a given eukaryotic cell. In one aspect, an O-RS aminoacylates an O-tRNA with the unnatural amino acid, e.g., at least 40%, at least 45%, at least 50%, at least 60%, at least 75%, at least 80%, or even 90% or more as efficiently as does an O-RS having an amino acid sequence, e.g., as set forth in SEQ ID NO.: 86 or 45. In one embodiment, an O-RS of the invention aminoacylates the O-tRNA with the unnatural amino acid, e.g., at least 10-fold, at least 20-fold, at least 30-fold, etc., more efficiently than the O-RS aminoacylates the O-tRNA with a natural amino acid.

In one embodiment, the O-RS or a portion thereof is encoded by a polynucleotide sequence as set forth in any one of SEQ ID NO.: 3-35 (e.g., 3-19, 20-35, or any other subset of sequences 3-35), or a complementary polynucleotide sequence thereof. In another embodiment, the O-RS comprises an amino acid sequence as set forth in any one of SEQ ID NO.: 36-63 (e.g., 36-47, 48-63, or any other subset of 36-63), and/or 86, or a conservative variation thereof. In yet another embodiment, the O-RS comprises an amino acid sequence that is, e.g., at least 90%, at least 95%, at least 98%, at least 99%, or at least 99.5% or more, identical to that of a naturally occurring tyrosyl aminoacyl-tRNA synthetase (TyrRS) and comprises two or more amino acids from groups A-E. Group A includes valine, isoleucine, leucine, glycine, serine, alanine, or threonine at a position corresponding to Tyr37 of an *E. coli* TyrRS. Group B includes aspartate at a position corresponding to Asn126 of an *E. coli* TyrRS. Group C includes threonine, serine, arginine, asparagine or glycine at a position corresponding to Asp182 of an *E. coli* TyrRS. Group D includes methionine, alanine, valine, or tyrosine at a position corresponding to Phe183 of an *E. coli* TyrRS; and, group E includes serine, methionine, valine, cysteine, threonine, or alanine at a position corresponding to Leu186 of an *E. coli* TyrRS.

Any subset of combinations of these groups are a feature of the invention. For example, in one embodiment, the O-RS has two or more amino acids selected from valine, isoleucine, leucine, or threonine occurs at a position corresponding to Tyr37 of *E. coli* TyrRS; threonine, serine, arginine, or glycine at a position corresponding to Asp182 of *E. coli* TyrRS; methionine, or tyrosine at a position corresponding to Phe183 of *E. coli* TyrRS; and, serine, or alanine at a position corresponding to Leu186 of *E. coli* TyrRS. In another embodiment, the O-RS includes two more amino acids selected from glycine, serine, or alanine at a position corresponding to Tyr37 of *E. coli* TyrRS, aspartate at a position corresponding to Asn126 of *E. coli* TyrRS, asparagine at a position corresponding to Asp182 of *E. coli* TyrRS, alanine, or valine, at a position corresponding to Phe183 of *E. coli* TyrRS, and/or methionine, valine, cysteine, or threonine, at a position corresponding to Leu186 of *E. coli* TyrRS.

In another embodiment, the O-RS has one or more improved or enhanced enzymatic properties for the unnatural amino acid as compared to a natural amino acid. For example, the improved or enhanced properties for the unnatural amino acid as compared to a natural amino acid include any of, e.g., a higher Km, a lower Km, a higher kcat, a lower kcat, a lower kcat/km, a higher kcat/km, etc.

The eukaryotic cell also optionally includes an unnatural amino acid(s). The eukaryotic cell optionally includes an orthogonal tRNA (O-tRNA) (e.g., derived from a non-eukaryotic organism, such as *Escherichia coli, Bacillus stearothermophilus*, and/or the like), where the O-tRNA recognizes a selector codon and is preferentially aminoacylated with the unnatural amino acid by the O-RS. In one aspect, the O-tRNA mediates the incorporation of the unnatural amino acid into a protein with, e.g., at least 45%, at least 50%, at least 60%, at least 75%, at least 80%, at least 90%, at least 95%, or 99% or the efficiency of a tRNA that comprises or is processed in a cell from a polynucleotide sequence as set forth in SEQ ID NO.: 65. In another aspect, the O-tRNA comprises the sequence of SEQ ID NO.:65, and the O-RS comprises a polypeptide sequence selected from an amino acid sequence set forth in any one of SEQ ID NO.: 36-63 (e.g., 36-47, 48-63, or any other subset of 36-63), and/or 86, and/or a conservative variation thereof.

In another embodiment, the eukaryotic cell comprises a nucleic acid that comprises a polynucleotide that encodes a polypeptide of interest, where the polynucleotide comprises a selector codon that is recognized by the O-tRNA. In one aspect, the yield of the polypeptide of interest comprising the unnatural amino acid is, e.g., at least 2.5%, at least 5%, at least 10%, at least 25%, at least 30%, at least 40%, 50% or more, of that obtained for the naturally occurring polypeptide of interest from a cell in which the polynucleotide lacks the selector codon. In another aspect, the cell produces the polypeptide of interest in the absence of the unnatural amino acid, with a yield that is, e.g., less than 35%, less than 30%, less than 20%, less than 15%, less than 10%, less than 5%, less than 2.5%, etc., of the yield of the polypeptide in the presence of the unnatural amino acid.

The invention also provides a eukaryotic cell comprising an orthogonal aminoacyl-tRNA synthetase (O-RS), an orthogonal tRNA (O-tRNA), an unnatural amino acid, and a nucleic acid that comprises a polynucleotide that encodes a polypeptide of interest. The polynucleotide comprises a selector codon that is recognized by the O-tRNA. In addition, the O-RS preferentially aminoacylates the orthogonal tRNA (O-tRNA) with the unnatural amino acid in the eukaryotic cell, and the cell produces the polypeptide of interest in the absence of the unnatural amino acid, with a yield that is, e.g., less than 30%, less than 20%, less than 15%, less than 10%, less than 5%, less than 2.5%, etc., of the yield of the polypeptide in the presence of the unnatural amino acid.

Compositions that include a eukaryotic cell comprising an orthogonal tRNA (O-tRNA) are also a feature of the invention. Typically, the O-tRNA mediates incorporation of an unnatural amino acid into a protein that is encoded by a polynucleotide that comprises a selection codon that is recognized by the O-tRNA in vivo. In one embodiment, the O-tRNA mediates the incorporation of the unnatural amino acid into the protein with, e.g., at least 45%, at least 50%, at least 60%, at least 75%, at least 80%, at least 90%, at least 95%, or even 99% or more the efficiency of a tRNA that comprises or is processed in a cell from a polynucleotide sequence as set forth in SEQ ID NO.: 65. In another embodiment, the O-tRNA comprises or is processed from a polynucleotide sequence as set forth in SEQ ID NO.: 65, or a conservative variation thereof. In yet another embodiment, the O-tRNA comprises a recyclable O-tRNA.

In one aspect of the invention, the O-tRNA is post-transcriptionally modified. The invention also provides a nucleic acid that encodes an O-tRNA in a eukaryotic cell, or a complementary polynucleotide thereof. In one embodiment, the nucleic acid comprises an A box and a B box.

The invention also features methods of producing translational components, e.g., O-RSs or O-tRNA/O-RS pairs (and translational components produced by these methods). For example, the invention provides methods of producing an orthogonal aminoacyl-tRNA synthetase (O-RS) that preferentially aminoacylates an orthogonal tRNA with an unnatural amino acid in a eukaryotic cell. The method includes, e.g., (a) subjecting to positive selection, in the presence of an unnatural amino acid, a population of eukaryotic cells of a first species, where the eukaryotic cells each comprise: i) a member of a library of aminoacyl-tRNA synthetases (RSs), ii) an orthogonal tRNA (O-tRNA), iii) a polynucleotide that encodes a positive selection marker, and iv) a polynucleotide that encodes a negative selection marker; where cells that survive the positive selection comprise an active RS that aminoacylates the orthogonal tRNA (O-tRNA) in the presence of an unnatural amino acid. The cells that survive the positive selection are subjected to negative selection in the absence of the unnatural amino acid to eliminate active RSs that aminoacylate the O-tRNA with a natural amino acid. This provides the O-RS that preferentially aminoacylates the O-tRNA with the unnatural amino acid.

In certain embodiments, the polynucleotide that encodes the positive selection marker is operably linked to a response element and the cells further comprise a polynucleotide that: a) encodes a transcriptional modulator protein (e.g., a eukaryotic transcriptional modulator protein, etc.) that modulates transcription from the response element, and b) comprises at least one selector codon. The incorporation of the unnatural amino acid into the transcriptional modulator protein by the O-tRNA aminoacylated with the unnatural amino acid results in transcription of the positive selection marker. In one embodiment, the transcriptional modulator protein is a transcriptional activator protein (e.g., GAL4, etc.), and the selector codon is an amber stop codon, e.g., where the amber stop codon is located in or substantially near a portion of the polynucleotide that encodes a DNA binding domain of the transcriptional activator protein.

The positive selection marker can be any of a variety of molecules. In one embodiment, the positive selection marker comprises a nutritional supplement for growth and the selection is performed on a medium that lacks the nutritional supplement. In another embodiment, the polynucleotide that encodes the positive selection marker is, e.g., an ura3, leu2, lys2, lacZ gene, his3 (e.g., where the his3 gene encodes an imidazole glycerol phosphate dehydratase, detected by providing 3-aminotriazole (3-AT)), and/or the like. In yet another embodiment, the polynucleotide that encodes the positive selection marker comprises a selector codon.

As with the positive selection marker, the negative selection marker can also be any of a variety of molecules. In certain embodiments, the polynucleotide that encodes the negative selection marker is operably linked to a response element from which transcription is mediated by the transcriptional modulator protein. The incorporation of a natural amino acid into the transcriptional modulator protein by the O-tRNA aminoacylated with a natural amino acid results in transcription of the negative selection marker. In one embodiment, the polynucleotide that encodes the negative selection marker is, e.g., an ura3 gene and the negative selection is accomplished on a medium that comprises 5-fluoroorotic acid (5-FOA). In another embodiment, the medium used for negative selection comprises a selecting or screening agent that is converted to a detectable substance by the negative selection marker. In one aspect of the invention, the detectable substance is a toxic substance. In one embodiment, the polynucleotide that encodes the negative selection marker comprises a selector codon.

In certain embodiments, the positive selection marker and/or the negative selection marker comprises a polypeptide that fluoresces or catalyzes a luminescent reaction in the presence of a suitable reactant. In one aspect of the invention, the positive selection marker and/or the negative selection marker is detected by fluorescence-activated cell sorting (FACS), or by luminescence. In certain embodiments, the positive selection marker and/or negative selection marker comprises an affinity based screening marker, or a transcriptional modulator protein. In one embodiment, the same polynucleotide encodes both the positive selection marker and the negative selection marker.

In one embodiment, the polynucleotide that encodes the positive selection marker and/or negative selection marker of the invention can comprises at least two selector codons, which each or both can comprise at least two different selector codons or at least two of the same selector codons.

Additional levels of selection/screening stringency can also be used in the methods of the invention. In one embodiment, the methods can comprise, e.g., providing a varying amount of an inactive synthetase in step (a), (b) or both (a) and (b), where the varying amount of the inactive synthetase provides an additional level of selection or screening stringency. In one embodiment, step (a), (b) or both steps (a) and (b) of the method for producing an O-RS includes varying a selection or screening stringency, e.g., of the positive and/or negative selection marker. The method optionally includes subjecting the O-RS that preferentially aminoacylates the O-tRNA with the unnatural amino acid to an additional selection round, e.g., an additional positive selection round(s), an additional negative selection round(s) or combinations of both additional positive and negative selection rounds.

In one embodiment, the selecting/screening comprises one or more positive or negative selection/screening chosen from, e.g., a change in amino acid permeability, a change in translation efficiency, a change in translational fidelity, etc. The one or more change is based upon a mutation in one or more polynucleotide that encodes a component of orthogonal tRNA-tRNA synthetase pair is used to produce protein.

Typically, the library of RSs (e.g., a library of mutant RSs) comprises RSs derived from at least one aminoacyl-tRNA synthetase (RS), e.g., from a non-eukaryotic organism. In one embodiment, the library of RSs is derived from an inactive RS, e.g., where the inactive RS is generated by mutating an active RS. In another embodiment, the inactive RS comprises an amino acid binding pocket and one or more amino acids that comprise the binding pocket are substituted with one or more different amino acids, e.g., the substituted amino acids are substituted with alanines.

In certain embodiments, the method of producing an O-RS further includes performing random mutation, site-specific mutation, recombination, chimeric construction, or any combination thereof, on a nucleic acid that encodes an RS, thereby producing the library of mutant RSs. In certain embodiments, the method further includes, e.g., (c) isolating a nucleic acid that encodes the O-RS; (d) generating from the nucleic acid a set of polynucleotides that encode mutated O-RSs (e.g., by random mutagenesis, site-specific mutagenesis, chimeric construction, recombination or any combination thereof); and, (e) repeating steps (a) and/or (b) until a mutated O-RS is obtained that preferentially aminoacylates the O-tRNA with the unnatural amino acid. In one aspect of the invention, steps (c)-(e) are performed at least two times.

Methods of producing O-tRNA/O-RS pairs are also a feature of the invention. In one embodiment, the O-RS is obtained as described above and the O-tRNA is obtained by subjecting to negative selection a population of eukaryotic cells of a first species, where the eukaryotic cells comprise a member of a library of tRNAs, to eliminate cells that comprise a member of the library of tRNAs that is aminoacylated by an aminoacyl-tRNA synthetase (RS) that is endogenous to the eukaryotic cells. This provides a pool of tRNAs that are orthogonal to the eukaryotic cell of the first species. In one aspect of the invention, the library of tRNAs comprises tRNAs derived from at least one tRNA, e.g., from a non-eukaryotic organism. In another aspect of the invention, the library of aminoacyl-tRNA synthetases (RSs) comprises RSs derived from at least one aminoacyl-tRNA synthetase (RS), e.g., from a non-eukaryotic organism. In yet another aspect of the invention, the library of tRNAs comprises tRNAs derived from at least one tRNA from a first non-eukaryotic organism. The library of aminoacyl-tRNA synthetases (RSs) optionally comprises RSs derived from at least one aminoacyl-tRNA synthetase (RS) from a second non-eukaryotic organism. In one embodiment, the first and second non-eukaryotic organisms are the same. Alternatively, the first and second non-eukaryotic organisms can be different. Specific O-tRNA/O-RS pairs produced by the methods of the invention are also a feature of the invention.

Another feature of the invention is a method for producing translational components in one species and introducing the selected/screened translational components into a second species. For example, the method of producing a O-tRNA/ O-RS pair in a first species (e.g., a eukaryotic species, such as a yeast and the like) further includes introducing a nucleic acid that encodes the O-tRNA and a nucleic acid that encodes the O-RS into a eukaryotic cell of a second species (e.g., a mammal, an insect, a fungus, an algae, a plant and the like). The second species can use the introduced translational components to incorporate an unnatural amino acid into a growing polypeptide chain in vivo, e.g., during translation.

In another example, a method of producing an orthogonal aminoacyl-tRNA synthetase (O-RS) that preferentially aminoacylates an orthogonal tRNA with an unnatural amino acid in a eukaryotic cell includes: (a) subjecting to positive selection, in the presence of an unnatural amino acid, a population of eukaryotic cells of a first species (e.g., a eukaryotic species, such as a yeast or the like). The eukaryotic cells of the first species each comprise: i) a member of a library of aminoacyl-tRNA synthetases (RSs), ii) an orthogonal tRNA (O-tRNA), iii) a polynucleotide that encodes a positive selection marker, and iv) a polynucleotide that encodes a negative selection marker. The cells that survive the positive selection comprise an active RS that aminoacylates the orthogonal tRNA (O-tRNA) in the presence of an unnatural amino acid. The cells that survive the positive selection are subjected to negative selection in the absence of the unnatural amino acid to eliminate active RSs that aminoacylate the O-tRNA with a natural amino acid, thereby providing an O-RS that preferentially aminoacylates the O-tRNA with the unnatural amino acid. A nucleic acid that encodes the O-tRNA and a nucleic acid that encodes the O-RS are introduced into a eukaryotic cell of a second species (e.g., mammal, an insect, a fungus, an algae, a plant and/or the like). These components, when translated in the second species, can be used to incorporate unnatural amino acids into a protein or polypeptide of interest in the second species. In one embodiment, the O-tRNA and/or the O-RS are introduced into a eukaryotic cell of a second species.

In certain embodiments, the O-tRNA is obtained by subjecting to negative selection a population of eukaryotic cells of a first species, where the eukaryotic cells comprise a member of a library of tRNAs, to eliminate cells that comprise a member of the library of tRNAs that is aminoacylated by an aminoacyl-tRNA synthetase (RS) that is endogenous to the eukaryotic cells. This provides a pool of tRNAs that are orthogonal to the eukaryotic cell of the first species and the second species.

In one aspect, the invention comprises a composition comprising a protein, wherein the protein comprises at least one unnatural amino acid and at least one post-translational modification, wherein the at least one post-translational modification comprises attachment of a molecule comprising a second reactive group by a [3+2] cycloaddition to the at least one unnatural amino acid comprising a first reactive group.

Thus, proteins (or polypeptides of interest) with at least one unnatural amino acid are also a feature of the invention. In certain embodiments of the invention, a protein with at least one unnatural amino acid includes at least one post-translational modification. In one embodiment, the at least one post-translational modification comprises attachment of a molecule (e.g., a dye, a polymer, e.g., a derivative of polyethylene glycol, a photocrosslinker, a cytotoxic compound, an affinity label, a derivative of biotin, a resin, a second protein or polypeptide, a metal chelator, a cofactor, a fatty acid, a carbohydrate, a polynucleotide (e.g., DNA, RNA, etc.), etc.) comprising a second reactive group by a [3+2] cycloaddition to the at least one unnatural amino acid comprising a first reactive group. For example, the first reactive group is an alkynyl moiety (e.g., in the unnatural amino acid p-propargyloxyphenylalanine) (this group is also sometimes refer to as an acetylene moiety) and the second reactive group is an azido moiety. In another example, the first reactive group is the azido moiety (e.g., in the unnatural amino acid p-azido-L-phenylalanine) and the second reactive group is the alkynyl moiety. In certain embodiments, a protein of the invention includes at least one unnatural amino acid (e.g., a keto unnatural amino acid) comprising at least one post-translational modification, where the at least one post-translational modification comprises a saccharide moiety. In certain embodiments, the post-translational modification is made in vivo in a eukaryotic cell.

In certain embodiments, the protein includes at least one post-translational modification that is made in vivo by a eukaryotic cell, where the post-translational modification is not made by a prokaryotic cell. Examples of post-translational modifications include, but are not limited to, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (e.g., where the oligosaccharide comprises (GlcNAc-Man)$_2$-Man-GlcNAc-GlcNAc, and the like). In another embodiment, the post-translational modification comprises attachment of an oligosaccharide (e.g., Gal-Gal-NAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like.

Typically, the proteins are, e.g., at least 60%, at least 70%, at least 75%, at least 80%, at least 90%, at least 95%, or even at least 99% or more identical to any available protein (e.g., a therapeutic protein, a diagnostic protein, an industrial enzyme, or portion thereof, and/or the like), and they comprise one or more unnatural amino acid. In one embodiment, a composition of the invention includes a protein or polypeptide of interest and an excipient (e.g., a buffer, a pharmaceutically acceptable excipient, etc.).

The protein or polypeptide of interest can contain at least one, at least two, at least three, at least four, at least five, at least six, at least seven, at least eight, at least nine, or ten or more unnatural amino acids. The unnatural amino acids can be the same or different, e.g., there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

Examples of a protein (or polypeptide of interest) include, but are not limited to, e.g., a cytokine, a growth factor, a growth factor receptor, an interferon, an interleukin, an inflammatory molecule, an oncogene product, a peptide hormone, a signal transduction molecule, a steroid hormone receptor, erythropoietin (EPO), insulin, human growth hormone, an Alpha-1 antitrypsin, an Angiostatin, an Antihemolytic factor, an antibody, an Apolipoprotein, an Apoprotein, an Atrial natriuretic factor, an Atrial natriuretic polypeptide, an Atrial peptide, a C—X—C chemokine, T39765, NAP-2, ENA-78, a Gro-a, a Gro-b, a Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, I309, R83915, R91733, HCC1, T58847, D31065, T64262, a CD40, a CD40 ligand, a C-kit Ligand, a Collagen, a Colony stimulating factor (CSF), a Complement factor 5a, a Complement inhibitor, a Complement receptor 1, a cytokine, DHFR, an epithelial Neutrophil Activating Peptide-78, a GROα/MGSA, a GROβ, a GROγ a MIP-1α, a MIP-1δ, a MCP-1, an Epidermal Growth Factor (EGF), an epithelial Neutrophil Activating Peptide, an Erythropoietin (EPO), an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a Staphylococcal enterotoxins, an SEA, an SEB, an SEC1, an SEC2, an SEC3, an SED, an SEE, a steroid hormone receptor, a Superoxide dismutase (SOD), a Toxic shock syndrome toxin, a Thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGEF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, a SCF/c-Kit, a CD40L/CD40, a VLA-4/VCAM-1, an ICAM-1/LFA-1, a hyalurin/CD44, a corticosterone, a protein present in Genebank or other available databases, and the like, and/or a portion thereof. In one embodiment, the polypeptide of interest includes a transcriptional modulator protein (e.g., a transcriptional activator protein (such as GAL4), or a transcriptional repressor protein, etc.) or a portion thereof.

Compositions of a GAL4 protein, or portion thereof, in a eukaryotic cell are also a feature of the invention. Typically, the GAL4 protein or portion thereof comprises at least one unnatural amino acid.

A eukaryotic cell of the invention provides the ability to synthesize proteins that comprise unnatural amino acids in large useful quantities. For example, proteins comprising an unnatural amino acid can be produced at a concentration of, e.g., at least 10 μg/liter, at least 50 μg/liter, at least 75 μg/liter, at least 100 μg/liter, at least 200 μg/liter, at least 250 μg/liter, or at least 500 μg/liter or more of protein in a cell extract, a buffer, a pharmaceutically acceptable excipient, and/or the like. In certain embodiments, a composition of the invention includes, e.g., at least 10 μg, at least 50 μg, at least 75 μg, at least 100 μg, at least 200 μg, at least 250 μg, or at least 500 μg or more of protein that comprises a unnatural amino acid.

In certain embodiments, the protein or polypeptide of interest (or portion thereof) is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, or even ten or more selector codons.

The invention also provides methods for producing, in a eukaryotic cell, at least one protein comprising at least one unnatural amino acid (as well as proteins produced by such methods). The methods include, e.g., growing, in an appropriate medium, a eukaryotic cell that comprises a nucleic acid that comprises at least one selector codon and encodes the protein. The eukaryotic cell also comprises an orthogonal tRNA (O-tRNA) that functions in the cell and recognizes the selector codon and an orthogonal aminoacyl tRNA synthetase (O-RS) that preferentially aminoacylates the O-tRNA with the unnatural amino acid, and the medium comprises an unnatural amino acid. In one embodiment, the O-RS aminoacylates the O-tRNA with the unnatural amino acid e.g., at least 45%, at least 50%, at least 60%, at least 75%, at least 80%, at least 90%, at least 95%, or even 99% or more as efficiently as does an O-RS having an amino acid sequence, e.g., as set forth in SEQ ID NO.: 86 or 45. In another embodiment, the O-tRNA comprises, is processed from, or is encoded by SEQ ID NO.: 64 or 65, or a complementary polynucleotide sequence thereof. In yet another embodiment, the O-RS comprises an amino acid sequence as set forth in any one of SEQ ID NO.: 36-63 (e.g., 36-47, 48-63, or any other subset of 36-63), and/or 86.

In one embodiment, the method further includes incorporating into the protein the unnatural amino acid, where the unnatural amino acid comprises a first reactive group; and contacting the protein with a molecule (e.g., a dye, a polymer, e.g., a derivative of polyethylene glycol, a photocrosslinker, a cytotoxic compound, an affinity label, a derivative of biotin, a resin, a second protein or polypeptide, a metal chelator, a cofactor, a fatty acid, a carbohydrate, a polynucleotide (e.g., DNA, RNA, etc.), etc.) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (e.g., in unnatural amino acid p-propargyloxyphenylalanine) and the second reactive group is the azido moiety. In another example, the first reactive group is the azido moiety (e.g., in the unnatural amino acid p-azido-L-phenylalanine) and the second reactive group is the alkynyl moiety.

In certain embodiments, the encoded protein comprises a therapeutic protein, a diagnostic protein, an industrial enzyme, or portion thereof. In one embodiment, the protein that is produced by the method is further modified through the unnatural amino acid. For example, the unnatural amino acid is modified through, e.g., a nucleophilic-electrophilic reaction, through a [3+2] cycloaddition, etc. In another embodiment, the protein produced by the method is modified by at least one post-translational modification (e.g., N-glycosylation, O-glycosylation, acetylation, acylation, lipid-modification, palmitoylation, palmitate addition, phosphorylation, glycolipid-linkage modification, and the like) in vivo.

Methods of producing a screening or selecting transcriptional modulator protein are also provided (as are screening or selecting transcriptional modulator proteins produced by such methods). The methods include, e.g., selecting a first polynucleotide sequence, where the polynucleotide sequence encodes a nucleic acid binding domain; and mutating the first polynucleotide sequence to include at least one selector codon. This provides a screening or selecting polynucleotide sequence. The methods also include, e.g., selecting a second polynucleotide sequence, where the second polynucleotide sequence encodes a transcriptional activation domain; providing a construct that comprises the screening or selecting polynucleotide sequence operably linked to the second polynucleotide sequence; and, introducing the construct, an unnatural amino acid, an orthogonal tRNA synthetase (O-RS) and an orthogonal tRNA (O-tRNA), into a cell. With these components, the O-RS preferentially aminoacylates the O-tRNA with the unnatural amino acid and the O-tRNA recognizes the selector codon and incorporates the unnatural amino acid into the nucleic acid binding domain, in response to the selector codon in the screening or selecting polynucleotide sequence. This provides the screening or selecting transcriptional modulator protein.

In certain embodiments, the compositions and the methods of the invention include eukaryotic cells. A eukaryotic cell of the invention includes any of, e.g., a mammalian cell, a yeast cell, a fungus cell, a plant cell, an insect cell, etc. The translation components of the invention can be derived from a variety of organisms, e.g., non-eukaryotic organisms, such as a prokaryotic organism (e.g., *E. coli*, *Bacillus stearothermophilus*, or the like), or an archaebacterium, or e.g., a eukaryotic organism.

A selector codon of the invention expands the genetic codon framework of eukaryotic protein biosynthetic machinery. Any of a variety of selector codons can be used in the invention, including stop codons (e.g., an amber codon, an ochre codon, or an opal stop codon), nonsense codons, rare codons, four (or more) base codons, and/or the like.

Examples of unnatural amino acids that can be used in the compositions and methods described herein include (but are not limited to): a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a cyclic amino acid other than proline or histidine, an aromatic amino acid other than phenylalanine, tyrosine or tryptophan, and/or the like.

The invention also provides polypeptides (O-RSs) and polynucleotides, e.g., O-tRNAs, polynucleotides that encode O-RSs or portions thereof (e.g., the active site of the synthetase), oligonucleotides used to construct aminoacyl-tRNA synthetase mutants, polynucleotides that encode a protein or polypeptide of interest that comprise one or more selector codon, etc. For example, a polypeptide of the invention includes a polypeptide that comprises an amino acid sequence as set forth in any one of SEQ ID NO.: 36-63 (e.g., 36-47, 48-63, or any other subset of 36-63), and/or 86, a polypeptide that comprises an amino acid sequence encoded by a polynucleotide sequence as set forth in any one of SEQ ID NO.: 3-35 (e.g., 3-19, 20-35, or any other subset of sequences 3-35), and a polypeptide that is specifically immunoreactive with an antibody specific for a polypeptide that comprises an amino acid sequence as shown in any one of SEQ ID NO.: 36-63 (e.g., 36-47, 48-63, or any other subset of 36-63), and/or 86, or a polypeptide that comprises an amino acid sequence encoded by a polynucleotide sequence as shown in any one of SEQ ID NO.: 3-35 (e.g., 3-19, 20-35, or any other subset of sequences 3-35).

Also included among the polypeptides of the invention is a polypeptide that comprises an amino acid sequence that is at least 90% identical to that of a naturally occurring tyrosyl aminoacyl-tRNA synthetase (TyrRS) (e.g., SEQ ID NO.:2) and comprises two or more amino acids of groups A-E (noted above). Similarly, polypeptides of the invention also optionally include a polypeptide that comprises at least 20 contiguous amino acids of any one of SEQ ID NO.: 36-63 (e.g., 36-47, 48-63, or any other subset of 36-63), and/or 86, and two or more amino acid substitutions as indicated above in groups A-E. An amino acid sequence comprising a conservative variation of any of the above polypeptides is also included as a polypeptide of the invention.

In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention.

Polynucleotides are also provided in the invention. Polynucleotides of the invention include those that encode proteins or polypeptides of interests of the invention with one or more selector codon. In addition, polynucleotides of the invention include, e.g., a polynucleotide comprising a nucleotide sequence as set forth in any one of SEQ ID NO.: 3-35 (e.g., 3-19, 20-35, or any other subset of sequences 3-35), 64-85; a polynucleotide that is complementary to or that encodes a polynucleotide sequence thereof; and/or a polynucleotide encoding a polypeptide that comprises an amino acid sequence as set forth in any one of SEQ ID NO.: 36-63 (e.g., 36-47, 48-63, or any other subset of 36-63), and/or 86, or a conservative variation thereof. A polynucleotide of the invention also includes a polynucleotide that encodes a polypeptide of the invention. Similarly, a nucleic acid that hybridizes to a polynucleotide indicated above under highly stringent conditions over substantially the entire length of the nucleic acid is a polynucleotide of the invention.

A polynucleotide of the invention also includes a polynucleotide that encodes a polypeptide that comprises an amino acid sequence that is at least 90% identical to that of a naturally occurring tyrosyl aminoacyl-tRNA synthetase (TyrRS) (e.g., SEQ ID NO.: 2) and comprises two or more mutations as indicated above in groups A-E (noted above). A polynucleotide that is that is at least 70%, (or at least 75%, at least 80%, at least 85%, at least 90%, at least 95%, at least 98%, or least 99% or more) identical to a polynucleotide indicated above and/or a polynucleotide comprising a conservative variation of any of the polynucleotides indicated above are also included among the polynucleotides of the invention.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

In another aspect, the invention provides compositions of compounds and methods of producing such compounds. For example, compounds include, e.g., an unnatural amino acid (such as p-(propargyloxy)-phenylalanine (e.g., 1 in FIG. 11), azido dyes (such as shown in chemical structure 4 and chemical structure 6), an alkynyl polyethylene glycol (e.g., as shown in chemical structure 7), where n is an integer between, e.g., 50 and 10,000, 75 and 5,000, 100 and 2,000, 100 and 1,000, etc., and the like. In embodiment of the invention, the alkynyl polyethylene glycol has a molecular weight of, e.g., about 5,000 to about 100,000 Da, about 20,000 to about 50,000 Da, about 20,000 to about 10,000 Da (e.g., 20,000 Da).

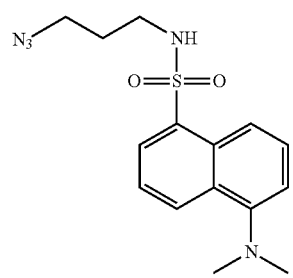

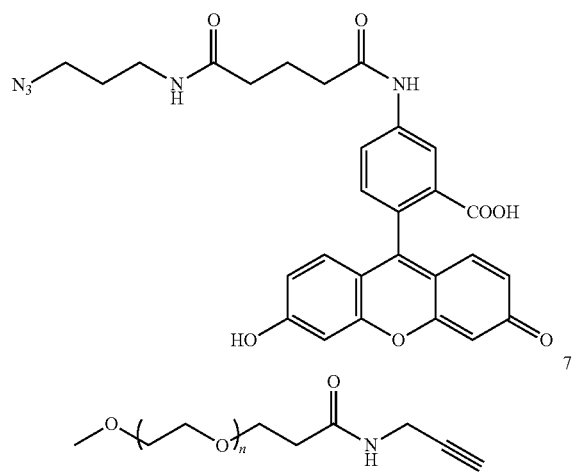

Various compositions comprising these compounds, e.g., with proteins and cells, are also provided. In one aspect, the composition that includes the p-(propargyloxy)-phenylanine unnatural amino acid, further includes an orthogonal tRNA. The unnatural amino acid can be bonded (e.g., covalently) to the orthogonal tRNA, e.g., covalently bonded to the orthogonal tRNA though an amino-acyl bond, covalently bonded to a 3'OH or a 2'OH of a terminal ribose sugar of the orthogonal tRNA, etc.

In one aspect of the invention, a protein comprising an azido dye (e.g., of chemical structure 4 or chemical structure 6), further includes at least one unnatural amino acid (e.g., an alkynyl amino acid), where the azido dye is attached to the unnatural amino acid through a [3+2] cycloaddition.

In one embodiment, a protein comprises the alkynyl polyethylene glycol of chemical structure 7. In another embodiment, the composition further includes at least one unnatural amino acid (e.g., an azido amino acid), wherein the alkynyl polyethylene glycol is attached to an unnatural amino acid through a [3+2] cycloaddition.

Methods for synthesizing various compounds are included in the invention. For example, a method for synthesizing a p-(propargyloxy)phenyalanine compound is provided. For example, the method comprises (a) suspending N-tert-butoxycarbonyl-tyrosine and $K_2CO_3$ in anhydrous DMF; (b) adding propargyl bromide to the reaction mixture of (a) and alkylating the hydroxyl and the carboxyl group, resulting in an protected intermediate compound having the structure:

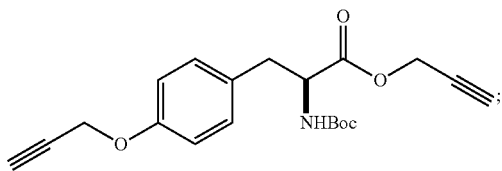 [SMILES: C#CCOC(=O)[C@H](Cc1ccc(OCC#C)cc1)NC(=O)OC(C)(C)C]

and (c) mixing the protected intermediate compound with anhydrous HCl in MeOH and deprotecting the amine moiety, thereby synthesizing the p-(propargyloxy)phenyalanine compound. In one embodiment, the method further comprises (d) dissolving the p-(propargyloxy)phenyalanine HCl in aqueous NaOH and MeOH and stirring it at room temperature; (e) adjusting the pH of to pH 7; and (f) precipitating the p-(propargyloxy)phenyalanine compound.

Methods for synthesizing azido dyes are also provided. For example, a method comprises: (a) providing a dye compound comprising a sulfonyl halide moiety; (b) warming the dye compound to room temperature in the presence of 3-azidopropylamine and triethylamine and coupling an amine moiety of the 3-azidopropylamine to the halide position of the dye compound, thereby synthesizing the azido dye. In one embodiment, the dye compound comprises dansyl chloride, and the azido dye comprises the composition of chemical structure 4. In one aspect, the method further comprises purifying the azido dye from the reaction mixture.

In another example, a method for synthesizing an azido dye comprises (a) providing an amine-containing dye compound; (b) combining the amine-containing dye compound with a carbodiimide and 4-(3-azidopropylcarbamoyl)-butyric acid in a suitable solvent, and coupling a carbonyl group of the acid to the amine moiety of the dye compound, thereby synthesizing the azido dye. In one embodiment, the carbodiimide comprises 1-ethyl-3-(3-dimethylaminopropyl)carbodiimide hydrochloride (EDCI). In one aspect, the amine-containing dye comprises fluoresceinamine, and suitable solvent comprises pyridine. For example, the amine-containing dye comprises fluoresceinamine and the azido dye comprises the composition of chemical structure 6. In one embodiment, the method further comprises (c) precipitating the azido dye; (d) washing the precipitate with HCl; (e) dissolving the washed precipitate in EtOAc; and (f) precipitating the azido dye in hexanes.

Methods for synthesizing a propargyl amide polyethylene glycol are also provided. For example, the method comprises reacting propargylamine with polyethylene glycol (PEG)-hydroxysuccinimide ester in an organic solvent (e.g., $CH_2Cl_2$) at room temperature, resulting in the propargyl amide polyethylene glycol of chemical structure 7. In one embodiment, the method further comprises precipitating the propargylamide polyethylene glycol using ethyl acetate. In one aspect, the method further includes recrystallizing the propargylamide polyethylene glycol in methanol; and drying the product under a vacuum.

Kits are also a feature of the invention. For example, a kit for producing a protein that comprises at least one unnatural amino acid in a cell is provided, where the kit includes a container containing a polynucleotide sequence encoding an O-tRNA or an O-tRNA, and a polynucleotide sequence encoding an O-RS or an O-RS. In one embodiment, the kit further includes at least one unnatural amino acid. In another embodiment, the kit further comprises instructional materials for producing the protein.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Unless otherwise defined herein or below in the remainder of the specification, all technical and scientific terms used herein have the same meaning as commonly understood by those of ordinary skill in the art to which the invention belongs.

Homologous: Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein, as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficient, less than 10% efficient, less than 5% efficient, or less than 1% efficient, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA in a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 50% efficiency, 60% efficiency, 70% efficiency, 75% efficiency, 80% efficiency, 90% efficiency, 95% efficiency, or 99% or more efficiency) to that of a corresponding tRNA/RS endogenous pair.

Complementary: The term "complementary" refers to components of an orthogonal pair, O-tRNA and O-RS that can function together, e.g., where the O-RS aminoacylates the O-tRNA.

Preferentially aminoacylates: The term "preferentially aminoacylates" refers to an efficiency, e.g., 70% efficient, 75% efficient, 85% efficient, 90% efficient, 95% efficient, or 99% or more efficient, at which an O-RS aminoacylates an O-tRNA with an unnatural amino acid as compared to the O-RS aminoacylating a naturally occurring tRNA or a starting material used to generate the O-tRNA. The unnatural amino acid is incorporated into a growing polypeptide chain with high fidelity, e.g., at greater than 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, and/or the like.

Recyclable tRNA: The term "recyclable tRNA" refers to a tRNA that is aminoacylated and can be repeatedly reaminoacylated with an amino acid (e.g., an unnatural amino acid) for the incorporation of the amino acid (e.g., the unnatural amino acid) into one or more polypeptide chains during translation.

Translation system: The term "translation system" refers to the collective set of components that incorporate a naturally occurring amino acid into a growing polypeptide chain (protein). Components of a translation system can include, e.g., ribosomes, tRNAs, synthetases, mRNA, amino acids, and the like. The components of the invention (e.g., ORS, OtRNAs, unnatural amino acids, etc.) can be added to an in vitro or in vivo translation system, e.g., a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue that is not one of the 20 common naturally occurring amino acids, seleno cysteine or pyrrolysine.

Derived from: As used herein, the term "derived from" refers to a component that is isolated from or made using information from a specified molecule or organism.

Inactive RS: As used herein, the term "inactive RS" refers to a synthetase that has been mutated so that it no longer can aminoacylate its natural cognate tRNA with an amino acid.

Positive selection or screening marker: As used herein, the term "positive selection or screening marker" refers to a marker that when present, e.g., expressed, activated or the like, results in identification of a cell with the positive selection marker from those without the positive selection marker.

Negative selection or screening marker: As used herein, the term "negative selection or screening marker" refers to a marker that when present, e.g., expressed, activated or the like, allows identification of a cell that does not possess the desired property (e.g., as compared to a cell that does possess the desired property).

Reporter: As used herein, the term "reporter" refers to a component that can be used to select target components of a system of interest. For example, a reporter can include a fluorescent screening marker (e.g., green fluorescent protein), a luminescent marker (e.g., a firefly luciferase protein), an affinity based screening marker, or selectable marker genes such as his3, ura3, leu2, lys2, lacZ, β-gal/lacZ (β-galactosidase), Adh (alcohol dehydrogenase), or the like.

Eukaryote: As used herein, the term "eukaryote" refers to organisms belonging to the phylogenetic domain Eucarya such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g., *Methanococcus jannaschii, Methanobacterium thermoautotrophicum, Halobacterium* such as *Haloferax volcanii* and *Halobacterium* species NRC-1, *Archaeoglobus fulgi-* dus, *Pyrococcus furiosus, Pyrococcus horikoshii, Aeuropyrum pernix*, etc.) phylogenetic domain.

Antibody: The term "antibody," as used herein, includes, but is not limited to a polypeptide substantially encoded by an immunoglobulin gene or immunoglobulin genes, or fragments thereof, which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

Conservative variant: The term "conservative variant" refers to a translation component, e.g., a conservative variant O-tRNA or a conservative variant O-RS, that functionally performs like the component from which the conservative variant is based, e.g., an O-tRNA or O-RS, but has variations in the sequence. For example, an O-RS will aminoacylate a complementary O-tRNA or a conservative variant O-tRNA with an unnatural amino acid, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for a selection/screening of certain components from a population. For example, a selection or screening agent includes, but is not limited to, e.g., a nutrient, an antibiotic, a wavelength of light, an antibody, an expressed polynucleotide (e.g., a transcriptional modulator protein), or the like. The selection agent can be varied, e.g., by concentration, intensity, etc.

Detectable substance: The term "detectable substance," as used herein, refers to an agent that, when activated, altered, expressed or the like, allows for the selection/screening of certain components from a population. For example, the detectable substance can be a chemical agent, e.g., 5-fluoroorotic acid (5-FOA), which under certain conditions, e.g., expression of a URA3 reporter, becomes detectable, e.g., a toxic product that kills cells that express the URA3 reporter.

BRIEF DESCRIPTION OF THE DRAWINGS

FIG. 1, Panel A schematically illustrates the activated transcription of reporter genes, which are is driven by amber suppression of TAG codons in GAL4. The DNA binding domain is indicated by the striped box and the major and cryptic activation domains are indicated in the hatched box. FIG. 1, Panel B illustrates examples of reporter genes, e.g., HIS3, LacZ, URA3 in MaV203. FIG. 1, Panel C schematically illustrates plasmids that can be used in the selection scheme, e.g., pEcTyrRS/tRNA$_{CUA}$ and pGADGAL4xxTAG.

FIG. 3, Panel A illustrates constructs each with single amino acid mutation in GAL4. FIG. 3, Panel B illustrates constructs each with two amino acid mutations in GAL4.

FIG. 4, Panel A shows the results in the presence of X-gal, –Ura, or –Leu, –Trp. FIG. 4, Panel B shows the results in the presence of varying concentrations of 3-AT. FIG. 4, Panel C shows the results in the present of varying percentages of 5-FOA.

FIG. 5, Panel A illustrates the ONPG hydrolysis measurement with various types of mutations at the T44 site. FIG. 5, Panel B illustrates the ONPG hydrolysis measurement with various types of mutations at the R110 site. 'GAL4' is MaV203 transformed with pCL1 and was offscale ~600 ONPG hydrolysis units. 'None' is MaV203 transformed with plasmids encoding the GAL4 DB and GAL4 AD separately.

FIG. 7, Panel A illustrates a stereoview of the active site of *B. Stearothermophilus* tyrosyl-tRNA synthetase with bound tyrosine. The mutated residues are shown and correspond to residues from *E. coli* tyrosyl-tRNA synthetase Tyr$^{37}$ (*B. Stearothermophilus* TyrRS residue Tyr$^{34}$), Asn$^{126}$ (Asn123), Asp$^{182}$ (Asp$^{176}$), Phe$^{183}$ (Phe$^{177}$), and Leu$^{186}$ (Leu$^{180}$). FIG. 7, Panel B illustrates the structural formulae of examples of unnatural amino acids (from left to right) p-acetyl-L-phenylalanine (1), p-benzoyl-L-phenylalanine (2), p-azido-L-phenylalanine (3), O-methyl-L-tyrosine (4), and p-iodo-L-tyrosine (5).

FIG. 8, Panel A illustrates vectors and reporter constructs that can be used in selection/screening for orthogonal tRNAs, orthogonal aminoacyl synthetases or pairs of orthogonal tRNA/RS in eukaryotic cells. FIG. 8, Panel B illustrates phenotypes of yeast harboring GAL4 responsive HIS3, URA3 and lacZ responsive reporters in response to active (TyrRS) or inactive (A5RS) aminoacyl-tRNA synthetases on selective media. FIG. 8, Panel C illustrates an example of a selection scheme used to select mutant synthetases that encode additional amino acids in a eukaryotic cell, e.g., *S. cerevisiae*, where UAA is an unnatural amino acid. FIG. 8, Panel D illustrates phenotypes of yeast isolated from a selection with p-acetyl-L-phenylalanine.

FIG. 10, Panel A illustrates tandem mass spectrum of tryptic peptide with unnatural amino acid p-acetyl-L-phenylalanine (1). FIG. 10, Panel B illustrates tandem mass spectrum of tryptic peptide with unnatural amino acid p-benzoyl-L-phenylalanine (2). FIG. 10, Panel C illustrates tandem mass spectrum of tryptic peptide with unnatural amino acid p-azido-L-phenylalanine (3). FIG. 10, Panel D illustrates tandem mass spectrum of tryptic peptide with unnatural amino acid O-methyl-L-tyrosine (4). FIG. 10, Panel E illustrates tandem mass spectrum of tryptic peptide with unnatural amino acid p-iodo-L-tyrosine (5). FIG. 10, Panel F illustrates tandem mass spectrum of tryptic peptide with amino acid trytophan (W) at position Y*. FIG. 10, Panel G illustrates tandem mass spectrum of tryptic peptide with amino acid tyrosine (Y) at position Y*. FIG. 10, Panel H illustrates tandem mass spectrum of tryptic peptide with amino acid leucine (L) at position Y*.

FIG. 12, Panel A illustrates Gelcode Blue stain experiment. FIG. 12, Panel B illustrates a western blot with an anti-SOD antibody. FIG. 12, Panel C illustrates a western blot with anti-6×His antibody.

FIG. 13, Panel A illustrates synthesized dye labels 3-6. FIG. 13, Panel B illustrates the reaction between the SOD and the dye. FIG. 13, Panel C illustrates in-gel fluorescence scanning and Gelcode Blue staining.

FIG. 17, Panel A illustrates the reaction of a propargyl amide PEG with a protein comprising an azido amino acid (e.g., $N_3$-SOD) in the presence of Cu(I) and phosphate buffer (PB). FIG. 17, Panel B illustrates the PEGylation of the protein by gel analysis. FIG. 17, Panel C illustrates the synthesis of the propargyl amide PEG.

DETAILED DESCRIPTION

Figure 1A:
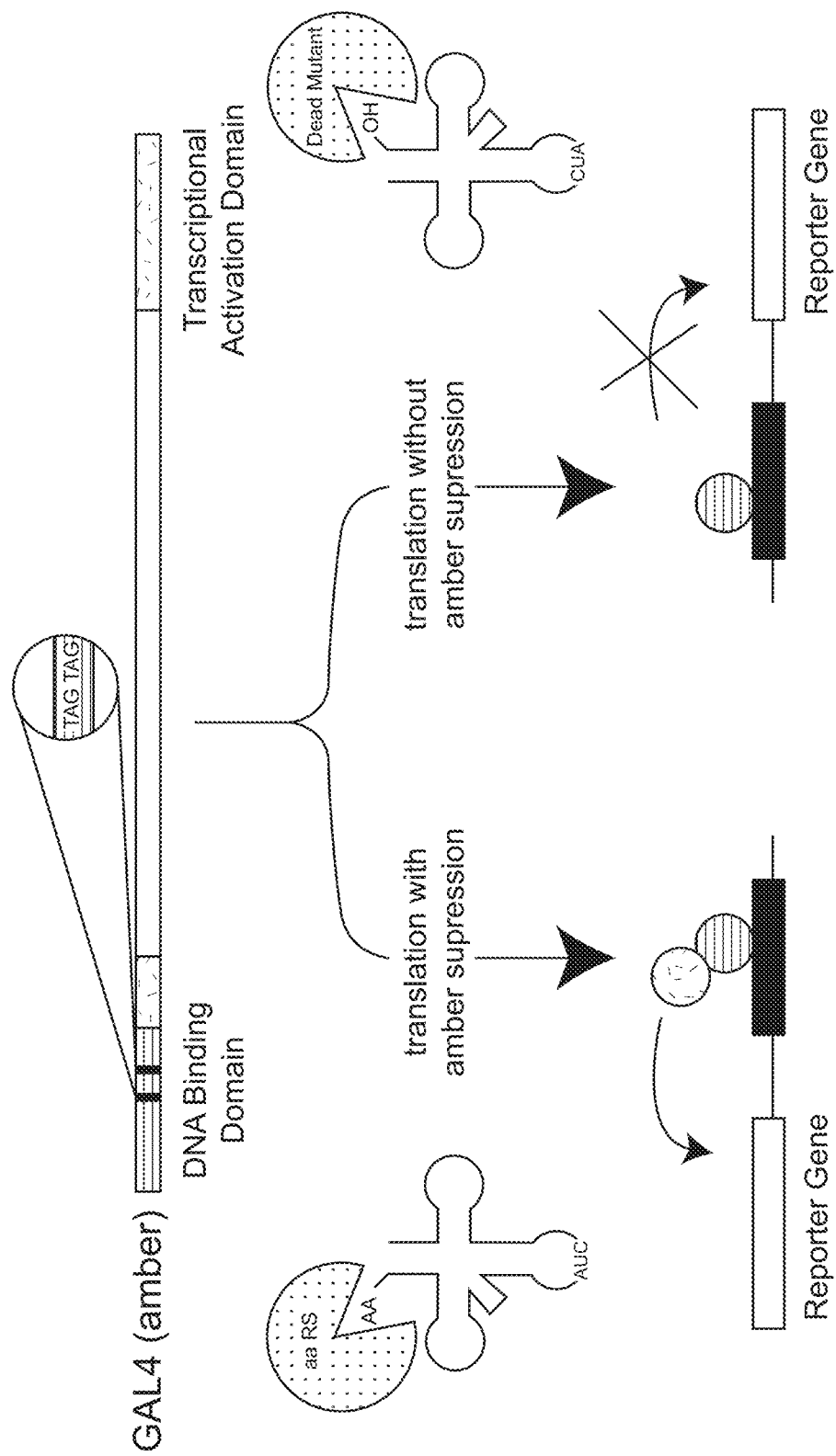
FIG. 1, Panels A, B and C schematically illustrates a general positive and negative selection scheme for expanding the genetic code of a eukaryotic cell, e.g., *S. cerevisiae*.

The ability to genetically modify the structures of proteins directly in eukaryotic cells, beyond the chemical constraints imposed by the genetic code, would provides a powerful molecular tool to both probe and manipulate cellular processes. The invention provides translational components that expand the number of genetically encoded amino acids in eukaryotic cells. These include tRNAs (e.g., orthogonal tRNAs (O-tRNAs)), aminoacyl-tRNA synthetases (e.g., orthogonal synthetase (O-RS)), pairs of O-tRNA/O-RSs, and unnatural amino acids.

Typically, O-tRNAs of the invention are expressed and processed efficiently, and function in translation in a eukaryotic cell, but are not significantly aminoacylated by the host's aminoacyl-tRNA synthetases. In response to a selector codon, an O-tRNA of the invention delivers an unnatural amino acid, which does not encode any of the common twenty amino acids, to a growing polypeptide chain during mRNA translation.

An O-RS of the invention preferentially aminoacylates an O-tRNA of the invention with an unnatural amino acid in a eukaryotic cell, but does not aminoacylate any of the cytoplasmic host's tRNAs. Moreover, the specificity of an aminoacyl-tRNA synthetase of the invention provides acceptance of an unnatural amino acid while excluding any endogenous amino acids. Polypeptides that include amino acid sequences of example O-RSs, or portions thereof, are also a feature of the invention. In addition, polynucleotides that encode translational components, O-tRNAs, O-RSs and portions thereof, are features of the invention.

The invention also provides methods of producing the desired translational components, e.g., O-RS, and or an orthogonal pair (orthogonal tRNA and orthogonal aminoacyl-tRNA synthetase), that utilizes an unnatural amino acid for use in a eukaryotic cell (and translational components produced by such methods). For example, a tyrosyl-tRNA synthetase/tRNA$_{CUA}$ pair from *E. coli* is an O-tRNA/O-RS pair of the invention. In addition, the invention also features methods of selecting/screening translational components in one eukaryotic cell, and once selected/screened, using those components in a different eukaryotic cell (a eukaryotic cell that was not used for selection/screening). For example, the selection/screening methods to produce the translation components for eukaryotic cells can be done in yeast, e.g., *Saccharomyces cerevisiae*, and then those selected components can be used in another eukaryotic cell, e.g., another yeast cell, a mammalian cell, an insect cell, a plant cell, a fungus cell, etc.

The invention further provides methods for producing a protein in a eukaryotic cell, where the protein comprises an unnatural amino acid. The protein is produced using the translation components of the invention. The invention also provides proteins (and proteins produced by the methods of the invention), which include unnatural amino acids. The protein or polypeptide of interest can also include a post-translational modification, e.g., that is added through a [3+2] cycloaddition, or a nucleophilic-electrophilic reaction, that is not made by a prokaryotic cell, etc. In certain embodiments, methods of producing a transcriptional modulator protein with an unnatural amino acid (and proteins produced by such methods) are also included in the invention. Compositions, which include proteins that include an unnatural amino acid is also a feature of the invention.

Kits for producing a protein or polypeptide with an unnatural amino acid are also a feature of the invention.

Orthogonal Aminoacyl-tRNA Synthetases (O-RS)

In order to specifically incorporate an unnatural amino acid in to a protein or polypeptide of interest, in a eukaryotic cell, the substrate specificity of the synthetase is altered so that only the desired unnatural amino acid, but not any of the common 20 amino acids are charged to the tRNA. If the orthogonal synthetase is promiscuous, it will result in mutant proteins with a mixture of natural and unnatural amino acids at the target position. The invention provides compositions of, and methods of, producing orthogonal aminoacyl-tRNA synthetases that have modified substrate specificity for a specific unnatural amino acid.

A eukaryotic cell that includes an orthogonal aminoacyl-tRNA synthetase (O-RS) is a feature of the invention. The O-RS preferentially aminoacylates an orthogonal tRNA (O-tRNA) with an unnatural amino acid in the eukaryotic cell. In certain embodiments, the O-RS utilizes more than one unnatural amino acid, e.g., two or more, three or more, etc. Thus, an O-RS of the invention can have the capability to preferentially aminoacylate an O-tRNA with different unnatural amino acids. This allows an additional level of control by selecting which unnatural amino acid or combination of unnatural amino acids are put with the cell and/or by selecting the different amounts of unnatural amino acids that are put with the cell for their incorporation.

An O-RS of the invention optionally has one or more improved or enhanced enzymatic properties for the unnatural amino acid as compared to a natural amino acid. These properties include, e.g., higher Km, lower Km, higher kcat, lower kcat, lower kcat/km, higher kcat/km, etc., for the unnatural amino acid, as compared to a naturally occurring amino acid, e.g., one of the 20 known common amino acids.

Optionally, the O-RS can be provided to the eukaryotic cell by a polypeptide that includes an O-RS and/or by a polynucleotide that encodes an O-RS or a portion thereof. For example, an O-RS, or a portion thereof, is encoded by a polynucleotide sequence as set forth in any one of SEQ ID NO.: 3-35 (e.g., 3-19, 20-35, or any other subset of sequences 3-35), or a complementary polynucleotide sequence thereof. In another example, an O-RS comprises an amino acid sequence as set forth in any one of SEQ ID NO.: 36-63 (e.g., 36-47, 48-63, or any other subset of 36-63), and/or 86, or a conservative variation thereof. See, e.g., Tables 5, 6 and 8, and Example 6 herein for sequences of exemplary O-RS molecules.

An O-RS can also comprise an amino acid sequence that is, e.g., at least 90%, at least 95%, at least 98%, at least 99%, or even at least 99.5% identical to that of a naturally occurring tyrosyl aminoacyl-tRNA synthetase (TyrRS) (e.g., as set forth in SEQ ID NO.:2) and comprises two or more amino acids of group A-E. Group A includes valine, isoleucine, leucine, glycine, serine, alanine, or threonine at a position corresponding to Tyr37 of E. coli TyrRS; group B includes aspartate at a position corresponding to Asn126 of E. coli TyrRS; group C includes threonine, serine, arginine, asparagine or glycine at a position corresponding to Asp182 of E. coli TyrRS; group D includes methionine, alanine, valine, or tyrosine at a position corresponding to Phe183 of E. coli TyrRS; and, group E includes serine, methionine, valine, cysteine, threonine, or alanine at a position corresponding to Leu186 of E. coli TyrRS. Any subset of combinations of these groups are a feature of the invention. For example, in one embodiment, the O-RS has two or more amino acids selected from valine, isoleucine, leucine, or threonine occurs at a position corresponding to Tyr37 of E. coli TyrRS; threonine, serine, arginine, or glycine at a position corresponding to Asp182 of E. coli TyrRS; methionine, or tyrosine at a position corresponding to Phe183 of E. coli TyrRS; and, serine, or alanine at a position corresponding to Leu186 of E. coli TyrRS. In another embodiment, the O-RS includes two more amino acids selected from glycine, serine, or alanine at a position corresponding to Tyr37 of E. coli TyrRS, aspartate at a position corresponding to Asn126 of E. coli TyrRS, asparagine at a position corresponding to Asp182 of E. coli TyrRS, alanine, or valine, at a position corresponding to Phe183 of E. coli TyrRS, and/or methionine, valine, cysteine, or threonine, at a position corresponding to Leu186 of E. coli TyrRS. See also, e.g., Table 4, Table 6 and Table 8, herein.

Besides the O-RS, a eukaryotic cell of the invention can include additional components, e.g., an unnatural amino acid(s). The eukaryotic cell also includes an orthogonal tRNA (O-tRNA) (e.g., derived from a non-eukaryotic organism, such as Escherichia coli, Bacillus stearothermophilus, and/or the like), where the O-tRNA recognizes a selector codon and is preferentially aminoacylated with the unnatural amino acid by the O-RS. A nucleic acid that comprises a polynucleotide that encodes a polypeptide of interest, wherein the polynucleotide comprises a selector codon that is recognized by the O-tRNA, or a combination of one or more of these, can also be present in the cell.

In one aspect, the O-tRNA mediates the incorporation of the unnatural amino acid into a protein with, e.g., at least 45%, at least 50%, at least 60%, at least 75%, at least 80%, at least 90%, at least 95%, or 99% or the efficiency of as a tRNA that comprises or is processed from a polynucleotide sequence as set forth in SEQ ID NO.: 65. In another aspect, the O-tRNA comprises SEQ ID NO.:65, and the O-RS comprises a polypeptide sequence set forth in any one of SEQ ID NO.: 36-63 (e.g., 36-47, 48-63, or any other subset of 36-63), and/or 86, and/or a conservative variation thereof. See also, e.g., Table 5 and Example 6, herein, for sequences of exemplary O-RS and O-tRNA molecules.

In one example, a eukaryotic cell comprises an orthogonal aminoacyl-tRNA synthetase (O-RS), an orthogonal tRNA (O-tRNA), an unnatural amino acid, and a nucleic acid that comprises a polynucleotide that encodes a polypeptide of interest, which polynucleotide comprises a selector codon that is recognized by the O-tRNA. The O-RS preferentially aminoacylates the orthogonal tRNA (O-tRNA) with the unnatural amino acid in the eukaryotic cell, and the cell produces the polypeptide of interest in the absence of the unnatural amino acid with a yield that is, e.g., less than 30%, less than 20%, less than 15%, less than 10%, less than 5%, less than 2.5%, etc., of the yield of the polypeptide in the presence of the unnatural amino acid.

Methods for producing an O-RS, which are a feature of the invention, optionally include generating a pool of mutant synthetases from the framework of a wild-type synthetase, and then selecting for mutated RSs based on their specificity for an unnatural amino acid relative to the common twenty amino acids. To isolate such a synthetase, the selection methods of the are: (i) sensitive, as the activity of desired synthetases from the initial rounds can be low and the population small; (ii) "tunable", since it is desirable to vary the selection stringency at different selection rounds; and, (iii) general, so that the methods can be used for different unnatural amino acids.

Methods of producing an orthogonal aminoacyl-tRNA synthetase (O-RS) that preferentially aminoacylates an orthogonal tRNA with an unnatural amino acid in a eukaryotic cell typically include applying a combination of a positive selection followed by a negative selection. In the positive selection, suppression of the selector codon introduced at nonessential position(s) of a positive marker allows the eukaryotic cells to survive under positive selection pressure. In the presence of unnatural amino acids, survivors thus encode active synthetases charging the orthogonal suppressor tRNA with an unnatural amino acid. In the negative selection, suppression of a selector codon introduced at nonessential position(s) of a negative marker removes synthetases with natural amino acid specificities. Survivors of the negative and positive selection encode synthetases that aminoacylate (charge) the orthogonal suppressor tRNA with unnatural amino acids only (or at least preferentially).

For example, the method includes: (a) subjecting to positive selection, in the presence of an unnatural amino acid, a population of eukaryotic cells of a first species, where the eukaryotic cells each comprise: i) a member of a library of aminoacyl-tRNA synthetases (RSs), ii) an orthogonal tRNA (O-tRNA), iii) a polynucleotide that encodes a positive selection marker, and iv) a polynucleotide that encodes a negative selection marker; wherein cells that survive the positive selection comprise an active RS that aminoacylates the orthogonal tRNA (O-tRNA) in the presence of an unnatural amino acid; and, (b) subjecting the cells that survive the positive selection to negative selection in the absence of the unnatural amino acid to eliminate active RSs that aminoacylate the O-tRNA with a natural amino acid, thereby providing the O-RS that preferentially aminoacylates the O-tRNA with the unnatural amino acid.

The positive selection marker can be any of a variety of molecules. In one embodiment, the positive selection marker is a product that provides a nutritional supplement for growth and the selection is performed on a medium that lacks the nutritional supplement. Examples of polynucleotides that encode positive selection markers include, but are not limited to, e.g., a reporter gene based on complementing the amino acid auxotrophy of a cell, a his3 gene (e.g., where the his3 gene encodes an imidazole glycerol phosphate dehydratase, detected by providing 3-aminotriazole (3-AT)), ura3 gene, leu2 gene, lys2 gene, lacZ gene, adh gene, etc. See, e.g., G. M. Kishore, & D. M. Shah, (1988), *Amino acid biosynthesis inhibitors as herbicides, Annual Review of Biochemistry* 57:627-663. In one embodiment, lacZ production is detected by ortho-nitrophenyl-β-D-galactopyranoside (ONPG) hydrolysis. See, e.g., I. G. Serebriiskii, & E. A. Golemis, (2000), *Uses of lacZ to study gene function: evaluation of beta-galactosidase assays employed in the yeast two-hybrid system, Analytical Biochemistry* 285:1-15. Additional positive selection markers include, e.g., luciferase, green fluorescent protein (GFP), YFP, EGFP, RFP, the product of an antibiotic resistant gene (e.g., chloramphenicol acetyltransferase (CAT)), a transcriptional modulator protein (e.g., GAL4), etc. Optionally, a polynucleotide that encodes a positive selection marker comprises a selector codon.

A polynucleotide that encodes the positive selection marker can be operably linked to a response element. An additional polynucleotide that encodes a transcriptional modulator protein that modulates transcription from the response element, and comprises at least one selector codon, can also be present. The incorporation of the unnatural amino acid into the transcriptional modulator protein by the O-tRNA aminoacylated with the unnatural amino acid results in transcription of the polynucleotide (e.g., reporter gene) encoding the positive selection marker. For example, see FIG. 1A. Optionally, the selector codon is located in or substantially near a portion of the polynucleotide that encodes a DNA binding domain of the transcriptional modulator protein.

A polynucleotide that encodes the negative selection marker can also be operably linked to a response element from which transcription is mediated by the transcriptional modulator protein. See, e.g., A. J. DeMaggio, et al., (2000), *The yeast split-hybrid system, Method Enzymol.* 328:128-137; H. M. Shih, et al., (1996), *A positive genetic selection for disrupting protein protein interactions: identification of CREB mutations that prevent association with the coactivator CBP, Proc. Natl. Acad. Sci. U.S.A.* 93:13896-13901; M. Vidal, et al., (1996), *Genetic characterization of a mammalian protein-protein interaction domain by using a yeast reverse two-hybrid system. [comment], Proc. Natl. Acad. Sci. U.S.A.* 93:10321-10326; and, M. Vidal, et al., (1996), *Reverse two-hybrid and one-hybrid systems to detect dissociation of protein-protein and DNA-protein interactions. [comment], Proc. Natl. Acad. Sci. U.S.A.* 93:10315-10320. The incorporation of a natural amino acid into the transcriptional modulator protein by the O-tRNA aminoacylated with a natural amino acid results in transcription of the negative selection marker. Optionally, the negative selection marker comprises a selector codon. In one embodiment, the positive selection marker and/or negative selection marker of the invention can comprise at least two selector codons, which each or both can comprise at least two different selector codons or at least two of the same selector codons.

The transcriptional modulator protein is a molecule that binds (directly or indirectly) to a nucleic acid sequence (e.g., a response element) and modulates transcription of a sequence that is operably linked to the response element. A transcriptional modulator protein can be a transcriptional activator protein (e.g., GAL4, nuclear hormone receptors, AP1, CREB, LEF/tcf family members, SMADs, VP16, SP1, etc.), a transcriptional repressor protein (e.g., nuclear hormone receptors, Groucho/tle family, Engrailed family, etc), or a protein that can have both activities depending on the environment (e.g., LEF/tcf, homobox proteins, etc.). A response element is typically a nucleic acid sequence that is recognized by the transcriptional modulator protein or an additional agent that acts in concert with the transcriptional modulator protein.

Figure 1B:
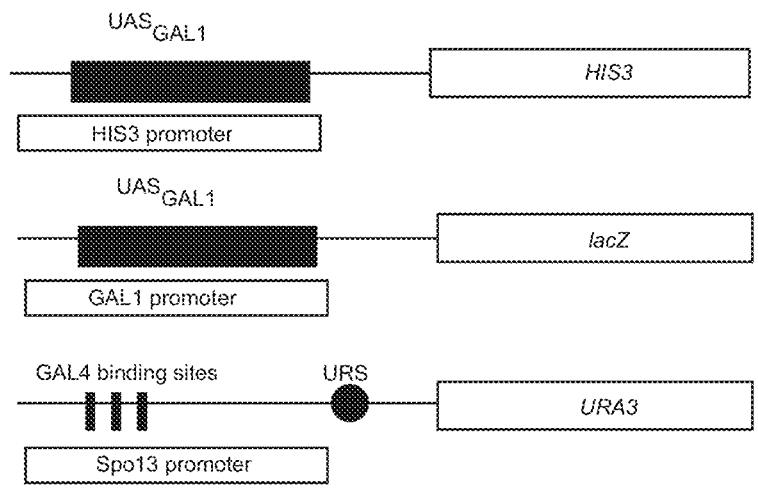
Figure 1C:
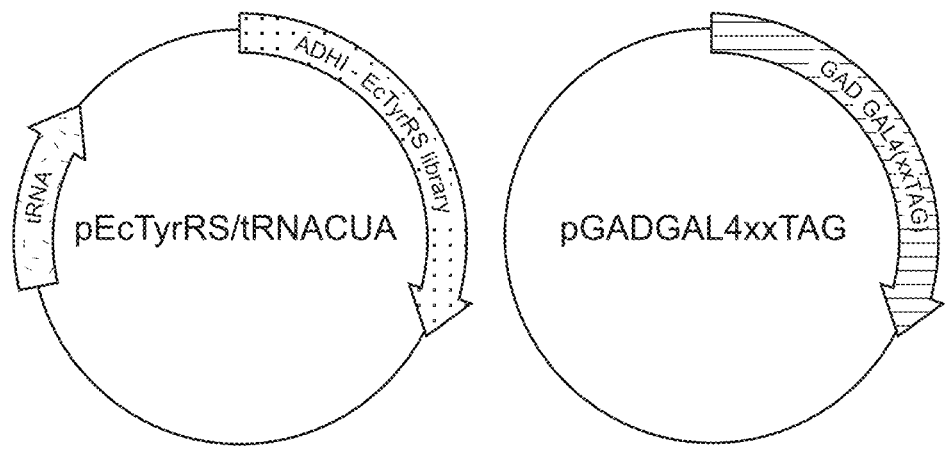

Another example of a transcriptional modulator protein is the transcriptional activator protein, GAL4 (see e.g., FIG. 1A). See, e.g., A. Laughon, et al., (1984), *Identification of two proteins encoded by the Saccharomyces cerevisiae GAL4 gene, Molecular & Cellular Biology* 4:268-275; A. Laughon, & R. F. Gesteland, (1984), *Primary structure of the Saccharomyces cerevisiae GAL4 gene, Molecular & Cellular Biology* 4:260-267; L. Keegan, et al., (1986), *Separation of DNA binding from the transcription-activating function of a eukaryotic regulatory protein, Science* 231:699-704; and, M. Ptashne, (1988), *How eukaryotic transcriptional activators work, Nature* 335:683-689. The N-terminal 147 amino acids of this 881 amino acid protein form a DNA binding domain (DBD) that binds DNA sequence specifically. See, e.g., M. Carey, et al., (1989), *An amino-terminal fragment of GAL4 binds DNA as a dimer, J. Mol. Biol.* 209:423-432; and, E. Giniger, et al., (1985), *Specific DNA binding of GAL4, a positive regulatory protein of yeast, Cell* 40:767-774. The DBD is linked, by an intervening protein sequence, to a C-terminal 113 amino acid activation domain (AD) that can activate transcription when bound to DNA. See, e.g., J. Ma, & M. Ptashne, (1987), *Deletion analysis of GAL4 defines two transcriptional activating segments, Cell* 48:847-853: and, J. Ma, & M. Ptashne, (1987), *The carboxy-terminal* 30 *amino acids of GAL4 are recognized by GAL80, Cell* 50:137-142. By placing amber codons towards, e.g., the N-terminal DBD of a single polypeptide that contains both the N-terminal DBD of GAL4 and its C-terminal AD, amber suppression by the O-tRNA/O-RS pair can be linked to transcriptional activation by GAL4 (FIG. 1, Panel A). GAL4 activated reporter genes can be used to perform both positive and negative selections with the gene (FIG. 1, Panel B).

Figure 8A:
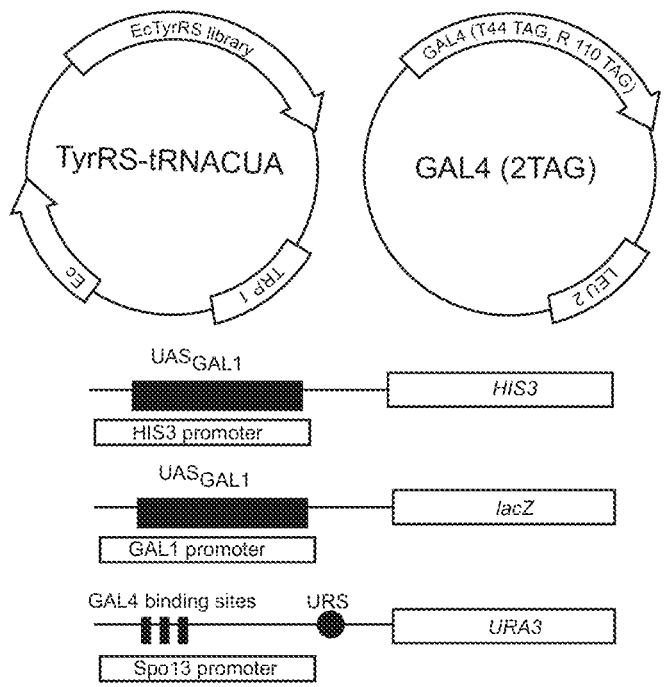
FIG. 8, Panels A, B, C and D.
Figure 8B:
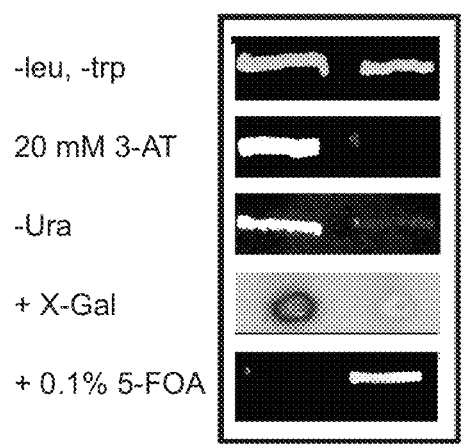
Figure 8C:
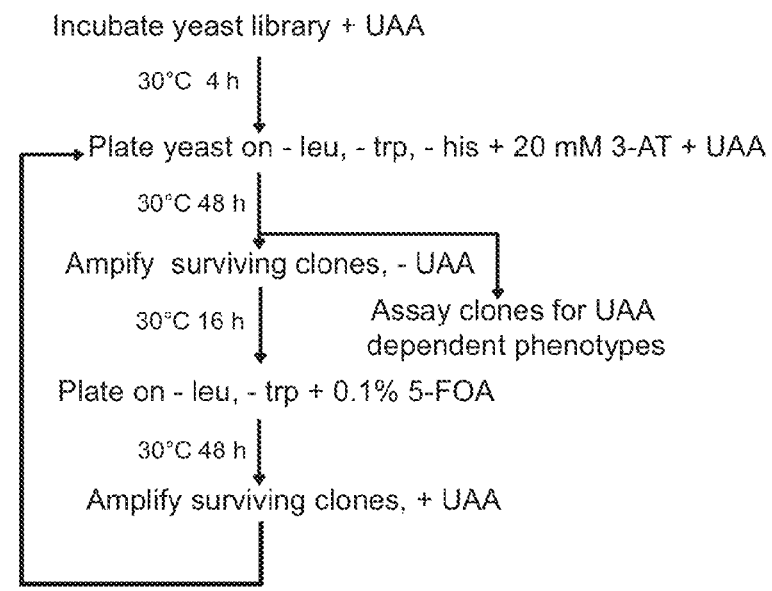
Figure 8D:
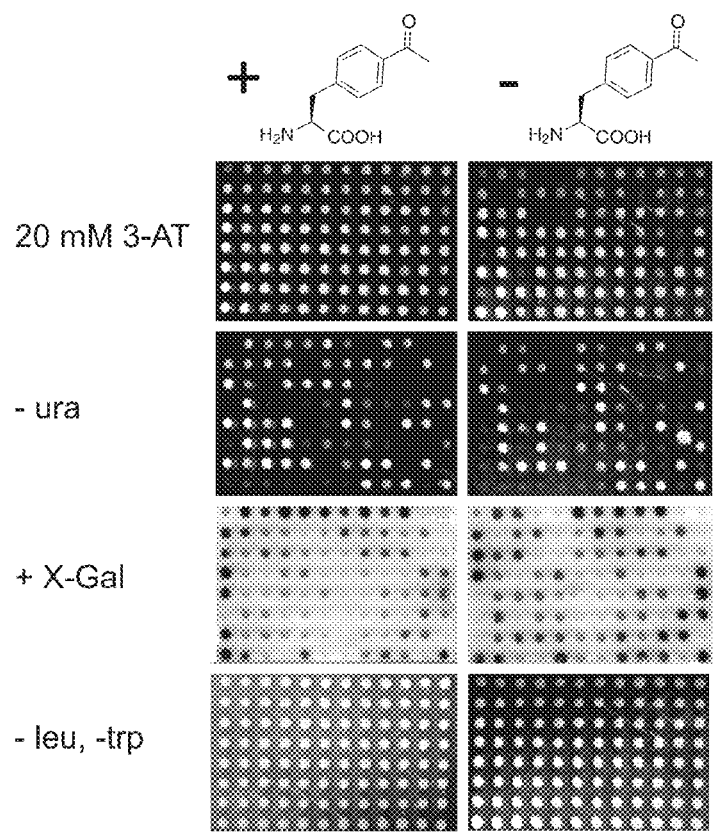

The medium used for negative selection can comprise a selecting or screening agent that is converted to a detectable substance by the negative selection marker. In one aspect of the invention, the detectable substance is a toxic substance. A polynucleotide that encodes a negative selection marker can be, e.g., an ura3 gene. For example, the URA3 reporter can be placed under control of a promoter that contains GAL4 DNA binding sites. When the negative selection marker is produced, e.g., by translation of a polynucleotide encoding the GAL4 with selector codons, GAL4 activates transcription of URA3. The negative selection is accomplished on a medium that comprises 5-fluoroorotic acid (5-FOA), which is converted into a detectable substance (e.g., a toxic substance which kills the cell) by the gene product of the ura3 gene. See, e.g., J. D. Boeke, et al., (1984), *A positive selection for mutants lacking orotidine-5'-phosphate decarboxylase activity in yeast: 5-fluoroorotic acid resistance, Molecular & General Genetics* 197:345-346); M. Vidal, et al., (1996), *Genetic characterization of a mammalian protein-protein interaction domain by using a yeast reverse two-hybrid system. [comment]*, Proc. Natl. Acad. Sci. U.S.A. 93:10321-10326; and, M. Vidal, et al., (1996), *Reverse two-hybrid and one-hybrid systems to detect dissociation of protein-protein and DNA-protein interactions. [comment]*, Proc. Natl. Acad. Sci. U.S.A. 93:10315-10320. See also, FIG. 8C.

As with the positive selection marker, the negative selection marker can also be any of a variety of molecules. In one embodiment, the positive selection marker and/or the negative selection marker is a polypeptide that fluoresces or catalyzes a luminescent reaction in the presence of a suitable reactant. For example, negative selection markers include, but are not limited to, e.g., luciferase, green fluorescent protein (GFP), YFP, EGFP, RFP, the product of an antibiotic resistant gene (e.g., chloramphenicol acetyltransferase (CAT)), the product of a lacZ gene, transcriptional modulator protein, etc. In one aspect of the invention, the positive selection marker and/or the negative selection marker is detected by fluorescence-activated cell sorting (FACS) or by luminescence. In another example, the positive selection marker and/or negative selection marker comprise an affinity based screening marker. The same polynucleotide can encode both the positive selection marker and the negative selection marker.

Additional levels of selection/screening stringency can also be used in the methods of the invention. The selection or screening stringency can be varied on one or both steps of the method to produce an O-RS. This could include, e.g., varying the amount of response elements in a polynucleotide that encodes the positive and/or negative selection marker, adding a varying amount of an inactive synthetase to one or both of the steps, varying the amount of selection/screening agent that is used, etc. Additional rounds of positive and/or negative selections can also be performed.

Selecting or screening can also comprise one or more positive or negative selection or screening that includes, e.g., a change in amino acid permeability, a change in translation efficiency, a change in translational fidelity, etc. Typically, the one or more change is based upon a mutation in one or more polynucleotides that comprise or encode components of an orthogonal tRNA-tRNA synthetase pair that are used to produce protein.

Model enrichment studies can also be used to rapidly select an active synthetase from an excess of inactive synthetases. Positive and/or negative model selection studies can be done. For example, eukaryotic cells that comprise potential active aminoacyl-tRNA synthetases are mixed with a varying fold excess of inactive aminoacyl-tRNA synthetases. A ratio comparison is made between cells grown in a nonselective media and assayed by, e.g., X-GAL overlay, and those grown and able to survive in a selective media (e.g., in the absence of histidine and/or uracil) and assayed by, e.g., an X-GAL assay. For a negative model selection, potential active aminoacyl-tRNA synthetases are mixed with a varying fold excess of inactive aminoacyl-tRNA synthetases and selection is performed with a negative selection substance, e.g., 5-FOA.

Typically, the library of RSs (e.g., a library of mutant RSs) comprises RSs derived from at least one aminoacyl-tRNA synthetase (RS), e.g., from a non-eukaryotic organism. In one embodiment, the library of RSs is derived from an inactive RS, e.g., where the inactive RS is generated by mutating an active RS, e.g., at the active site in the synthetase, at the editing mechanism site in the synthetase, at different sites by combining different domains of synthetases, or the like. For example, residues in the active site of the RS are mutated to, e.g., alanine residues. The polynucleotide that encodes the alanine mutated RS is used as a template to mutagenize the alanine residues to all 20 amino acids. The library of mutant RSs is selected/screened to produce the O-RS. In another embodiment, the inactive RS comprises an amino acid binding pocket and one or more amino acids that comprise the binding pocket are substituted with one or more different amino acids. In one example, the substituted amino acids are substituted with alanines. Optionally, the polynucleotide that encodes the alanine mutated RS is used as a template to mutagenize the alanine residues to all 20 amino acids and screened/selected.

The method of producing an O-RS can further include producing the library of RSs by using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In one aspect of the invention, the steps are performed at least two times.

Additional details for producing O-RS can be found in WO 2002/086075 entitled "Methods and compositions for the production of orthogonal tRNA-aminoacyltRNA synthetase pairs." See also, Hamano-Takaku et al., (2000) *A mutant Escherichia coli Tyrosyl-tRNA Synthetase Utilizes the Unnatural Amino Acid Azatyrosine More Efficiently than Tyrosine, Journal of Biological Chemistry*, 275(51):40324-40328; Kiga et al. (2002), *An engineered Escherichia coli tyrosyl-tRNA synthetase for site-specific incorporation of an unnatural amino acid into proteins in eukaryotic translation and its application in a wheat germ cell-free system, PNAS* 99(15): 9715-9723; and, Francklyn et al., (2002), *Aminoacyl-tRNA synthetases: Versatile players in the changing theater of translation; RNA,* 8:1363-1372.

Orthogonal tRNAs

Eukaryotic cells that include an orthogonal tRNA (O-tRNA) are provided by the invention. The orthogonal tRNA mediates incorporation of an unnatural amino acid into a protein that is encoded by a polynucleotide that comprises a selector codon that is recognized by the O-tRNA, in vivo. In certain embodiments, an O-tRNA of the invention mediates the incorporation of an unnatural amino acid into a protein with, e.g., at least 40%, at least 45%, at least 50%, at least 60%, at least 75%, at least 80%, or even 90% or more as efficiently as tRNA that comprises or is processed in a cell from a polynucleotide sequence as set forth in SEQ ID NO.: 65. See, Table 5, herein.

An example of an O-tRNA of the invention is SEQ ID NO.: 65. (See Example 6 and Table 5, herein). SEQ ID NO.: 65 is a pre-splicing/processing transcript that is optionally processed in the cell, e.g., using the cell's endogenous splicing and processing machinery, and modified to form an active O-tRNA. Typically, a population of such pre-splicing transcripts form a population of active tRNAs in the cell (the active tRNAs can be in one or more active forms). The invention also includes conservative variations of the O-tRNA and its processed cellular products. For example, conservative variations of O-tRNA include those molecules that function like the O-tRNA of SEQ ID NO.:65 and maintain the tRNA L-shaped structure, e.g., in processed form, but do not have the same sequence (and are other than wild type tRNA molecules). Typically, an O-tRNA of the invention is a recyclable O-tRNA, because the O-tRNA can be reaminoacylated in vivo to again mediate the incorporation of the unnatural amino acid into a protein that is encoded by a polynucleotide in response to a selector codon.

The transcription of the tRNA in eukaryotes, but not in prokaryotes, is carried out by RNA Polymerase III, which places restrictions on the primary sequence of the tRNA structural genes that can be transcribed in eukaryotic cells. In addition, in eukaryotic cells, tRNAs need to be exported from the nucleus, where they are transcribed, to the cytoplasm, to function in translation. Nucleic acids that encode an O-tRNA of the invention or a complementary polynucleotide thereof are also a feature of the invention. In one aspect of the invention, a nucleic acid that encodes an O-tRNA of the invention includes an internal promoter sequence, e.g., an A box (e.g., TRGCNNAGY) and a B box (e.g., GGTTCGANTCC, SEQ ID NO:88). The O-tRNA of the invention can also be post-transcriptionally modified. For example, post-transcriptional modification of tRNA genes in eukaryotes include removal of the 5'- and 3'-flanking sequences by Rnase P and a 3'-endonuclease, respectively. The addition of a 3'-CCA sequence is also a post-transcriptional modification of a tRNA gene in eukaryotes.

In one embodiment, an O-tRNA is obtained by subjecting to negative selection a population of eukaryotic cells of a first species, where the eukaryotic cells comprise a member of a library of tRNAs. The negative selection eliminates cells that comprise a member of the library of tRNAs that is aminoacylated by an aminoacyl-tRNA synthetase (RS) that is endogenous to the eukaryotic cells. This provides a pool of tRNAs that are orthogonal to the eukaryotic cell of the first species.

Alternatively, or in combination with others methods described above to incorporate an unnatural amino acid into a polypeptide, a trans-translation system can be used. This system involves a molecule called tmRNA present in *Escherichia coli*. This RNA molecule is structurally related to an alanyl tRNA and is aminoacylated by the alanyl synthetase. The difference between tmRNA and tRNA is that the anticodon loop is replaced with a special large sequence. This sequence allows the ribosome to resume translation on sequences that have stalled using an open reading frame encoded within the tmRNA as template. In the invention, an orthogonal tmRNA can be generated that is preferentially aminoacylated with an orthogonal synthetase and loaded with an unnatural amino acid. By transcribing a gene by the system, the ribosome stalls at a specific site; the unnatural amino acid is introduced at that site, and translation resumes using the sequence encoded within the orthogonal tmRNA.

Additional methods for producing a recombinant orthogonal tRNAs can be found, e.g., in International patent applications WO 2002/086075, entitled "Methods and compositions for the production of orthogonal tRNA-aminoacyltRNA synthetase pairs." See also, Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100(10): 5676-5681.

Orthogonal tRNA and Orthogonal Aminoacyl-tRNA Synthetase PAIRS

An orthogonal pair is composed of an O-tRNA, e.g., a suppressor tRNA, a frameshift tRNA, or the like, and an O-RS. The O-tRNA is not acylated by endogenous synthetases and is capable of mediating incorporation of an unnatural amino acid into a protein that is encoded by a polynucleotide that comprises a selector codon that is recognized by the O-tRNA in vivo. The O-RS recognizes the O-tRNA and preferentially aminoacylates the O-tRNA with an unnatural amino acid in a eukaryotic cell. Methods for producing orthogonal pairs along with orthogonal pairs produced by such methods and compositions of orthogonal pairs for use in eukaryotic cells are included in the invention. The development of multiple orthogonal tRNA/synthetase pairs can allow the simultaneous incorporation of multiple unnatural amino acids using different codons in a eukaryotic cell.

An orthogonal O-tRNA/O-RS pair in a eukaryotic cell can be produced by importing a pair, e.g., a nonsense suppressor pair, from a different organism with inefficient cross species aminoacylation. The O-tRNA and O-RS are efficiently expressed and processed in the eukaryotic cell and the O-tRNA is efficiently exported from the nucleus to the cytoplasm. For example, one such pair is the tyrosyl-tRNA synthetase/tRNA$_{CUA}$ pair from *E. coli* (see, e.g., H. M. Goodman, et al., (1968), *Nature* 217:1019-24; and, D. G. Barker, et al., (1982), *FEBS Letters* 150:419-23). *E. coli* tyrosyl-tRNA synthetase efficiently aminoacylates its cognate *E. coli* tRNA$_{CUA}$ when both are expressed in the cytoplasm of *S. cerevisiae*, but does not aminoacylate *S. cerevisiae* tRNAs. See, e.g., H. Edwards, & P. Schimmel, (1990), *Molecular & Cellular Biology* 10:1633-41; and, H. Edwards, et al., (1991), *PNAS United States of America* 88:1153-6. In addition, *E. coli* tyrosyl tRNA$_{CUA}$ is a poor substrate for *S. cerevisiae* aminoacyl-tRNA synthetases (see, e.g., V. Trezeguet, et al., (1991), *Molecular & Cellular Biology* 11:2744-51), but functions efficiently in protein translation in *S. cerevisiae*. See, e.g., H. Edwards, & P. Schimmel, (1990) *Molecular & Cellular Biology* 10:1633-41; H. Edwards, et al., (1991), *PNAS United States of America* 88:1153-6; and, V. Trezeguet, et al., (1991), *Molecular & Cellular Biology* 11:2744-51. Moreover, *E. coli* TyrRS does not have an editing mechanism to proofread an unnatural amino acid ligated to the tRNA.

The O-tRNA and O-RS can be naturally occurring or can be derived by mutation of a naturally occurring tRNA and/or RS, which generates libraries of tRNAs and/or libraries of RSs, from a variety of organism. See the section entitled "Sources and Hosts" herein. In various embodiments, the O-tRNA and O-RS are derived from at least one organism. In another embodiment, the O-tRNA is derived from a naturally occurring or mutated naturally occurring tRNA from a first organism and the O-RS is derived from naturally occurring or mutated naturally occurring RS from a second organism. In one embodiment, the first and second non-eukaryotic organisms are the same. Alternatively, the first and second non-eukaryotic organisms can be different.

See sections herein entitled "Orthogonal aminoacyl-tRNA synthetases" and "O-tRNA" for methods of producing O-RSs and O-tRNAs. See also, International patent application WO 2002/086075, entitled "Methods and compositions for the production of orthogonal tRNA-aminoacyl-tRNA synthetase pairs."

Fidelity, Efficiency, and Yield

Fidelity refers to the accuracy with which a desired molecule, e.g., an unnatural amino acid or amino acid, is incorporated into a growing polypeptide at a desired position. The translational components of the invention incorporate unnatural amino acids, with high fidelity, into proteins in response to a selector codon. For example, using the components of the invention, the efficiency of incorporation of a desired unnatural amino acid into a growing polypeptide chain at a desired position (e.g., in response to a selector codon) is, e.g., greater than 75%, greater than 85%, greater than 95%, or even greater than 99% or more as efficient as compared to unwanted incorporation a specific natural amino acid being incorporated into the growing polypeptide chain the desired position.

Efficiency can also refer to the degree with which the O-RS aminoacylates the O-tRNA with the unnatural amino acid as compared to a relevant control. O-RSs of the invention can be defined by their efficiency. In certain embodiments of the invention, an O-RS is compared to another O-RS. For example, a O-RS of the invention aminoacylates a O-tRNA with an unnatural amino acid, e.g., at least 40%, at least 50%, at least 60%, at least 75%, at least 80%, at least 90%, at least 95%, or even 99% or more as efficiently as an O-RS having an amino acid sequence, e.g., as set forth in SEQ ID NO.: 86 or 45) or another specific RS in Table 5) aminoacylates an O-tRNA. In another embodiment, an O-RS of the invention aminoacylates the O-tRNA with the unnatural amino acid at least 10-fold, at least 20-fold, at least 30-fold, etc., more efficiently than the O-RS aminoacylates the O-tRNA with a natural amino acid.

Using the translational components of the invention, the yield of the polypeptide of interest comprising the unnatural amino acid is, e.g., at least 5%, at least 10%, at least 20%, at least 30%, at least 40%, 50% or more, of that obtained for the naturally occurring polypeptide of interest from a cell in which the polynucleotide lacks the selector codon. In another aspect, the cell produces the polypeptide of interest in the absence of the unnatural amino acid with a yield that is, e.g., less than 30%, less than 20%, less than 15%, less than 10%, less than 5%, less than 2.5%, etc., of the yield of the polypeptide in the presence of the unnatural amino acid.

Source and Host Organisms

The orthogonal translational components of the invention are typically derived from non-eukaryotic organisms for use in eukaryotic cells or translation systems. For example, the orthogonal O-tRNA can be derived from a non-eukaryotic organism, e.g., a eubacterium, such as *Escherichia coli, Thermus thermophilus, Bacillus stearothermphilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, or the like, while the orthogonal O-RS can be derived from a non-eukaryotic organism, e.g., a eubacterium, such as *Escherichia coli, Thermus thermophilus, Bacillus stearothermphilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, or the like. Alternately, eukaryotic sources can also be used, e.g., plants, algae, protists, fungi, yeasts, animals (e.g., mammals, insects, arthropods, etc.), or the like, e.g., where the components are orthogonal to a cell or translation system of interest, or where they are modified (e.g., mutated) to be orthogonal to the cell or translation system.

The individual components of an O-tRNA/O-RS pair can be derived from the same organism or different organisms. In one embodiment, the O-tRNA/O-RS pair is from the same organism. For example, the O-tRNA/O-RS pair can be derived from a tyrosyl-tRNA synthetase/tRNA$_{CUA}$ pair from *E. coli*. Alternatively, the O-tRNA and the O-RS of the O-tRNA/O-RS pair are optionally from different organisms.

The orthogonal O-tRNA, O-RS or O-tRNA/O-RS pair can be selected or screened and/or used in a eukaryotic cell to produce a polypeptide with an unnatural amino acid. A eukaryotic cell can be from an of a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of eukaryotic cells with translational components of the invention are also a feature of the invention.

The invention also provides for the efficient screening in one species for optional use in that species and/or a second species (optionally, without additional selection/screening). For example, the components of the O-tRNA/O-RS are selected or screened in one species, e.g., an easily manipulated species (such as a yeast cell, etc.) and introduced into a second eukaryotic species, e.g., a plant (e.g., complex plant such as monocots, or dicots), an algae, a protist, a fungus, a yeast, an animal (e.g., a mammal, an insect, an arthropod, etc.), or the like, for use in the in vivo incorporation of an unnatural amino acid in the second species.

For example, *Saccharomyces cerevisiae* (*S. cerevisiae*) can be chosen as the eukaryotic first species, as it is unicellular, has a rapid generation time, and relatively well-characterized genetics. See, e.g., D. Burke, et al., (2000) *Methods in Yeast Genetics*. Cold Spring Harbor Laboratory Press, Cold Spring Harbor, N.Y. Moreover, since the translational machinery of eukaryotes is highly conserved (see, e.g., (1996) *Translational Control*. Cold Spring Harbor Laboratory, Cold Spring Harbor, N.Y.; Y. Kwok, & J. T. Wong, (1980), *Evolutionary relationship between Halobacterium cutirubrum and eukaryotes determined by use of aminoacyl-tRNA synthetases as phylogenetic probes*, Canadian Journal of Biochemistry 58:213-218; and, (2001) *The Ribosome*. Cold Spring Harbor Laboratory Press, Cold Spring Harbor, N.Y.), aaRSs genes for the incorporation of unnatural amino acids discovered in *S. cerevisiae* can be introduced into higher eukaryotic organisms and used, in partnership with cognate tRNAs (see, e.g., K. Sakamoto, et al., (2002) *Site-specific incorporation of an unnatural amino acid into proteins in mammalian cells*, Nucleic Acids Res. 30:4692-4699; and, C. Kohrer, et al., (2001), *Import of amber and ochre suppressor tRNAs into mammalian cells: a general approach to site-specific insertion of amino acid analogues into proteins*, Proc. Natl. Acad. Sci. U.S.A. 98:14310-14315) to incorporate unnatural amino acids.

In one example, the method of producing O-tRNA/O-RS in a first species as described herein further includes introducing a nucleic acid that encodes the O-tRNA and a nucleic acid that encodes the O-RS into a eukaryotic cell of a second species (e.g., a mammal, an insect, a fungus, an algae, a plant and the like). In another example, a method of producing an orthogonal aminoacyl-tRNA synthetase (O-RS) that preferentially aminoacylates an orthogonal tRNA with an unnatural amino acid in a eukaryotic cell includes: (a) subjecting to positive selection, in the presence of an unnatural amino acid, a population of eukaryotic cells of a first species (e.g., yeast and the like). Each of the eukaryotic cells comprise: i) a member of a library of aminoacyl-tRNA synthetases (RSs), ii) an orthogonal tRNA (O-tRNA), iii) a polynucleotide that encodes a positive selection marker, and iv) a polynucleotide that encodes a negative selection marker. The cells that survive the positive selection comprise an active RS that aminoacylates the orthogonal tRNA (O-tRNA) in the presence of an unnatural amino acid. The cells that survive the positive selection are subjected to negative selection in the absence of the unnatural amino acid to eliminate active RSs that aminoacylate the O-tRNA with a natural amino acid. This provides an O-RS that preferentially aminoacylates the O-tRNA with the unnatural amino acid. A nucleic acid that encodes the O-tRNA and a nucleic acid that encodes the O-RS (or the components O-tRNA and/or O-RS) are introduced into a eukaryotic cell of a second species e.g., a mammal, an insect, a fungus, an algae, a plant and/or the like. Typically, the O-tRNA is obtained by subjecting to negative selection a population of eukaryotic cells of a first species, where the eukaryotic cells comprise a member of a library of tRNAs. The negative selection eliminates cells that comprise a member of the library of tRNAs that is aminoacylated by an aminoacyl-tRNA synthetase (RS) that is endogenous to the eukaryotic cells, which provides a pool of tRNAs that are orthogonal to the eukaryotic cell of the first species and the second species.

Selector Codons

Selector codons of the invention expand the genetic codon framework of the protein biosynthetic machinery. For example, a selector codon includes, e.g., a unique three base codon, a nonsense codon, such as a stop codon, e.g., an amber codon (UAG), an opal codon (UGA), an unnatural codon, at least a four base codon, a rare codon, or the like. A number of selector codons can be introduced into a desired gene, e.g., one or more, two or more, more than three, etc. Once gene can include multiple copies of a given selector codon, or can include multiple different selector codons, or any combination thereof.

In one embodiment, the methods involve the use of a selector codon that is a stop codon for the incorporation of unnatural amino acids in vivo in a eukaryotic cell. For example, an O-tRNA is produced that recognizes the stop codon, e.g., UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, e.g., TAG, at the site of interest in a polypeptide of interest. See, e.g., Sayers, J. R., et al. (1988), 5',3' *Exonuclease in phosphorothioate-based oligonucleotide-directed mutagenesis. Nucleic Acids Res*, 791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA.

Selector codons also comprise extended codons, e.g., four or more base codons, such as, four, five, six or more base codons. Examples of four base codons include, e.g., AGGA, CUAG, UAGA, CCCU and the like. Examples of five base codons include, e.g., AGGAC, CCCCU, CCCUC, CUAGA, CUACU, UAGGC and the like. A feature of the invention includes using extended codons based on frameshift suppression. Four or more base codons can insert, e.g., one or multiple unnatural amino acids into the same protein. For example, in the presence of mutated O-tRNAs, e.g., a special frameshift suppressor tRNAs, with anticodon loops, e.g., with at least 8-10 nt anticodon loops, the four or more base codon is read as single amino acid. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology,* 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.,* 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid ana-* logues into protein, *Nature Biotechnology*, 20:177-182. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.* 121:11586; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

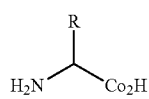

I

An unnatural amino acid is typically any structure having Formula I wherein the R group is any substituent other than one used in the twenty natural amino acids. See, e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, acyl-, keto-, azido-, hydroxyl-, hydrazine, cyano-, halo-, hydrazide, alkenyl, alkynyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radio-active amino acids, amino acids with novel functional groups, amino acids that covalently or noncovalently interact with other molecules, photocaged and/or photoisomerizable amino acids, biotin or biotin-analogue containing amino acids, keto containing amino acids, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, redox-active amino acids, amino thioacid containing amino acids, and amino acids containing one or more toxic moiety. In some embodiments, the unnatural amino acids have a photoactivatable cross-linker that is used, e.g., to link a protein to a solid support. In one embodiment, the unnatural amino acids have a saccharide moiety attached to the amino acid side chain (e.g., glycosylated amino acids) and/or other carbohydrate modification.

In addition to unnatural amino acids that contain novel side chains, unnatural amino acids also optionally comprise modified backbone structures, e.g., as illustrated by the structures of Formula II and III:

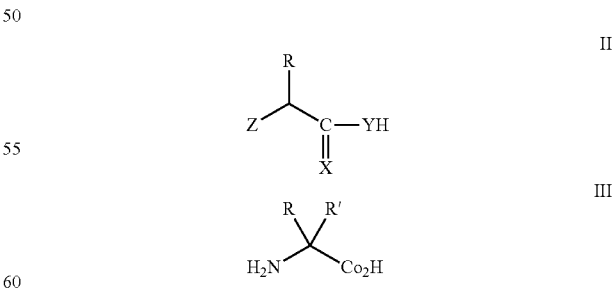

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Figure 7A:
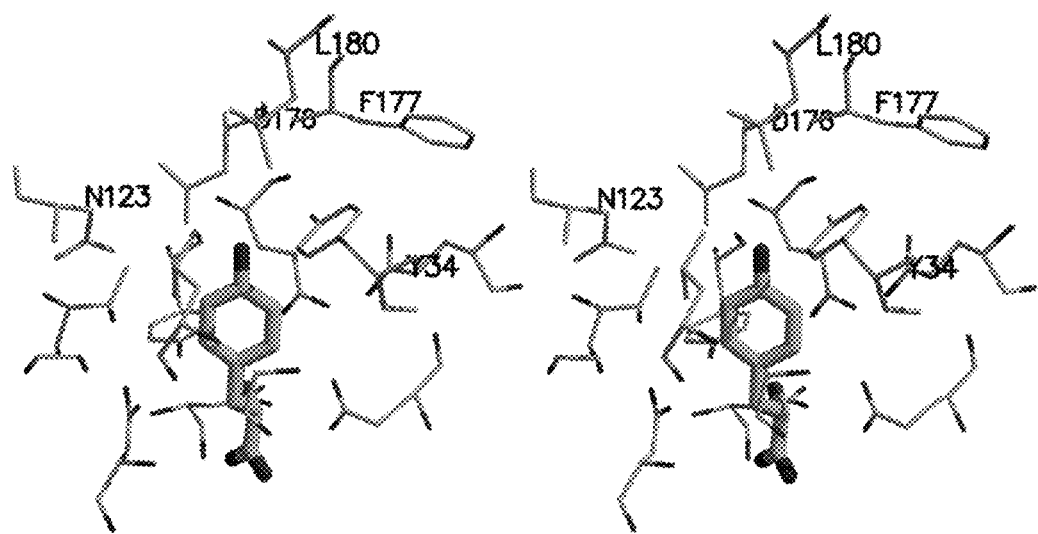
FIG. 7, Panels A and B.
Figure 7B:
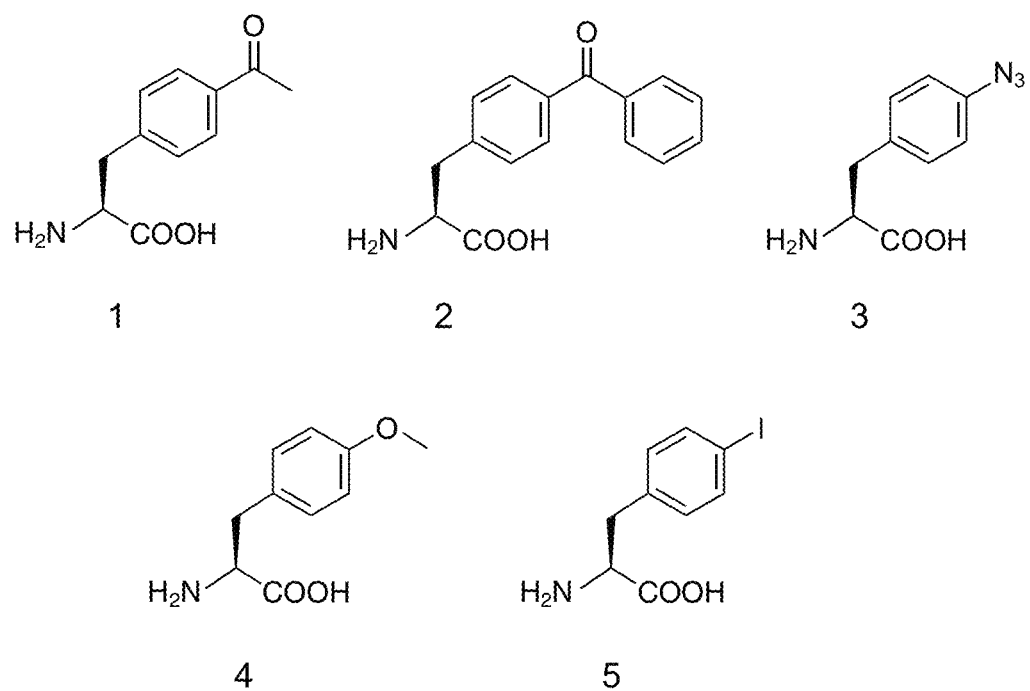

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, where the substituted tyrosine comprises, e.g., a keto group (e.g., an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, where the substituent comprises, e.g., a hydroxy group, a methoxy group, a methyl group, an allyl group, an aldehyde, an azido, an iodo, a bromo, a keto group (e.g., an acetyl group), a benzoyl, an alkynyl group, or the like. Specific examples of unnatural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. Examples of structures of unnatural amino acids are illustrated in FIG. 7, Panel B and FIG. 11. Additional structures of a variety of unnatural amino acids are provided in, for example, FIGS. 16, 17, 18, 19, 26, and 29 of WO 2002/085923 entitled "In vivo incorporation of unnatural amino acids." See also, FIG. 1 structures 2-5 of Kiick et al., (2002) *Incorporation of azides into recombinant proteins for chemoselective modification by the Staudinger ligtation*, PNAS 99:19-24, for additional methionine analogs.

In one embodiment, compositions that include an unnatural amino acid (such as p-(propargyloxy)-phenylalanine) are provided. Various compositions comprising p-(propargyloxy)-phenylalanine and, e.g., proteins and/or cells, are also provided. In one aspect, a composition that includes the p-(propargyloxy)-phenylalanine unnatural amino acid further includes an orthogonal tRNA. The unnatural amino acid can be bonded (e.g., covalently) to the orthogonal tRNA, e.g., covalently bonded to the orthogonal tRNA though an aminoacyl bond, covalently bonded to a 3'OH or a 2'OH of a terminal ribose sugar of the orthogonal tRNA, etc.

The chemical moieties via an unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing x-ray structure data. The site-specific introduction of heavy atoms using unnatural amino acids also provides selectivity and flexibility in choosing positions for heavy atoms. Photoreactive unnatural amino acids (e.g., amino acids with benzophenone and arylazides (e.g., phenylazide) side chains), for example, allow for efficient in vivo and in vitro photocrosslinking of proteins. Examples of photoreactive unnatural amino acids include, but are not limited to, e.g., p-azido-phenylalanine and p-benzoyl-phenylalanine. The protein with the photoreactive unnatural amino acids can then be crosslinked at will by excitation of the photoreactive group-providing temporal (and/or spatial) control. In one example, the methyl group of an unnatural amino can be substituted with an isotopically labeled, e.g., methyl group, as a probe of local structure and dynamics, e.g., with the use of nuclear magnetic resonance and vibrational spectroscopy. Alkynyl or azido functional groups, for example, allow the selective modification of proteins with molecules through a [3+2] cycloaddition reaction.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials,. Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic*

*acid derivatives and their activity at a novel quisqualate-sensitized site. J. Med. Chem.* 35:4602-7. See also, Provisional Patent Application Ser. No. 60/435,821 entitled "Protein Arrays," filed on Dec. 22, 2002.

In one aspect of the invention, a method for synthesizing a p-(propargyloxy)phenyalanine compound is provided. A method comprises, e.g., (a) suspending N-tert-butoxycarbonyl-tyrosine and K$_2$CO$_3$ in anhydrous DMF; (b) adding propargyl bromide to the reaction mixture of (a) and alkylating the hydroxyl and the carboxyl group, resulting in an protected intermediate compound having the structure:

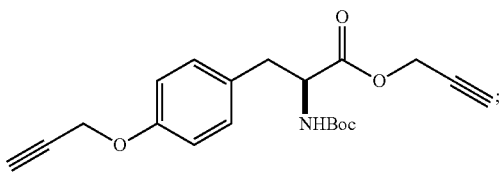 [SMILES: C#CCOC(=O)[C@H](Cc1ccc(OCC#C)cc1)NC(=O)OC(C)(C)C]

and (c) mixing the protected intermediate compound with anhydrous HCl in MeOH and deprotecting the amine moiety, thereby synthesizing the p-(propargyloxy)phenyalanine compound. In one embodiment, the method further comprises (d) dissolving the p-(propargyloxy)phenylalanine HCl in aqueous NaOH and MeOH and stirring it at room temperature; (e) adjusting the pH of to pH 7; and (f) precipitating the p-(propargyloxy)phenylalanine compound. See e.g., synthesis of propargyloxyphenylalanine in Example 4, herein.

Cellular Uptake Of Unnatural Amino Acids

Unnatural amino acid uptake by a eukaryotic cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., Provisional Patent Application Ser. No. 60/435,821 entitled "Protein Arrays," filed on Dec. 22, 2002; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a eukaryotic cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc., is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly DesignPath™, developed by Genencor is optionally used for metabolic pathway engineering, e.g., to engineer a pathway to create O-methyl-L-tyrosine in a cell. This technology reconstructs existing pathways in host organisms using a combination of new genes, e.g., identified through functional genomics, and molecular evolution and design. Diversa Corporation also provides technology for rapidly screening libraries of genes and gene pathways, e.g., to create new pathways.

Typically, the unnatural amino acid produced with an engineered biosynthetic pathway of the invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

Proteins or polypeptides of interest with at least one unnatural amino acid are a feature of the invention. The invention also includes polypeptides or proteins with at least one unnatural amino acid produced using the compositions and methods of the invention. An excipient (e.g., a pharmaceutically acceptable excipient) can also be present with the protein.

By producing proteins or polypeptides of interest with at least one unnatural amino acid in eukaryotic cells, proteins or polypeptides will typically include eukaryotic posttranslational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, e.g., acetylation, acylation, lipid-modification, palmitoylation, palmitate addition, phosphorylation, glycolipid-linkage modification, glycosylation, and the like. In one aspect, the post-translational modification includes attachment of an oligosaccharide (e.g., (GlcNAc-Man)$_2$-Man-GlcNAc-GlcNAc)) to an asparagine by a GlcNAc-asparagine linkage. See also, Table 7, which lists some examples of N-linked oligosaccharides of eukaryotic proteins (additional residues can also be present, which are not shown). In another aspect, the post-translational modification includes attachment of an oligosaccharide (e.g., Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 7

EXAMPLES OF OLIGOSACCHARIDES THROUGH GlcNAc-LINKAGE

| Type | Base Structure |
|---|---|
| High-mannose | Manα1-6\>Manα1-6\>Manβ1-4GlcNAcβ1-4GlcNAcβ1-Asn<br>Manα1-3/ Manα1-3/ |
| Hybrid | Manα1-6\>Manβ1-4GlcNAcβ1-4GlcNAcβ1-Asn<br>GlcNAcβ1-2——Manα1-3/ |
| Complex | GlcNAcβ1-2——Manα1-6\>Manβ1-4GlcNAcβ1-4GlcNAcβ1-Asn<br>GlcNAcβ1-2——Manα1-3/ |
| Xylose | Manα1-6\>Manβ1-4GlcNAcβ1-4GlcNAcβ1-Asn<br>Xylβ1-2/ |

In yet another aspect, the post-translation modification includes proteolytic processing of precursors (e.g., calcitonin precursor, calcitonin gene-related peptide precursor, preproparathyroid hormone, preproinsulin, proinsulin, pre-pro-opiomelanocortin, pro-opiomelanocortin and the like), assembly into a multisubunit protein or macromolecular assembly, translation to another site in the cell (e.g., to organelles, such as the endoplasmic reticulum, the golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, e.g. the reaction of α-haloketones with histidine or cysteine side chains. Selectivity in these cases is determined by the number and accessibility of the nucleophilic residues in the protein. In proteins of the invention, other more selective reactions can be used, such as the reaction of an unnatural keto-amino acid with hydrazides or aminooxy compounds, in vitro and in vivo. See, e.g., Cornish, et al., (1996) *Am. Chem. Soc.,* 118:8150-8151; Mahal, et al., (1997) *Science,* 276:1125-1128; Wang, et al., (2001) *Science* 292:498-500; Chin, et al., (2002) *Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* in press. This allows the selective labeling of virtually any protein with a host of reagents including fluorophores, crosslinking agents, saccharide derivatives and cytotoxic molecules. See also, patent application U.S. Ser. No. 10/686,944 entitled "Glycoprotein synthesis" filed Oct. 15, 2003. Post-translational modifications, e.g., through an azido amino acid, can also made through the Staudinger ligation (e.g., with triarylphosphine reagents). See, e.g., Kiick et al., (2002) *Incorporation of azides into recombinant proteins for chemoselective modification by the Staudinger ligtation, PNAS* 99:19-24.

This invention provides another highly efficient method for the selective modification of proteins, which involves the genetic incorporation of unnatural amino acids, e.g., containing an azide or alkynyl moiety (see, e.g., 2 and 1 of FIG. 11), into proteins in response to a selector codon. These amino acid side chains can then be modified by, e.g., a Huisgen [3+2] cycloaddition reaction (see, e.g., Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry,* (1984) Ed. Padwa, A., Wiley, New York, p. 1-176) with, e.g., alkynyl or azide derivatives, respectively. See, e.g., FIG. 16. Because this method involves a cycloaddition rather than a nucleophilic substitution, proteins can be modified with extremely high selectivity. This reaction can be carried out at room temperature in aqueous conditions with excellent regio selectivity (1.4>1.5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

Figure 13A:
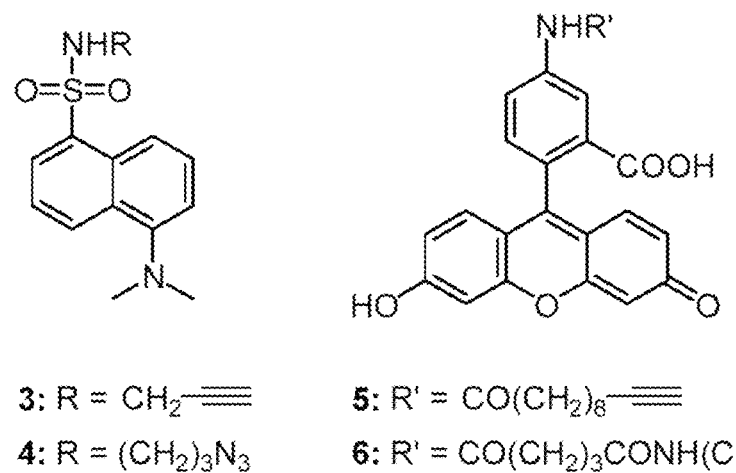
FIG. 13, Panels A, B and C illustrate protein labeling by [3+2] cycyloaddition.
Figure 13B:
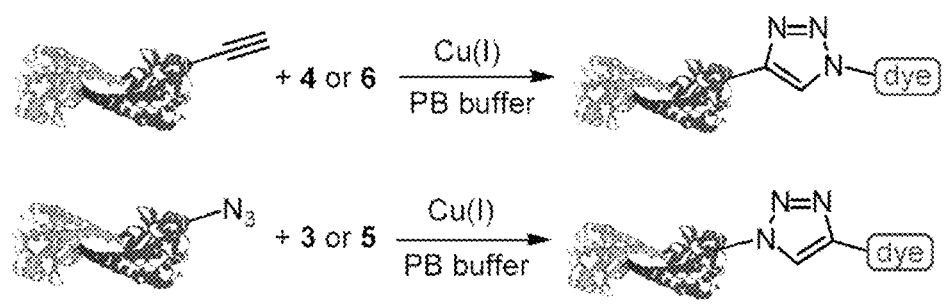

A molecule that can be added to a protein of the invention through a [3+2] cycloaddition includes virtually any molecule with an azido or alkynyl derivative. See, e.g., Example 3 and 5, herein. Such molecules include, but are not limited to, dyes, fluorophores, crosslinking agents, saccharide derivatives, polymers (e.g., derivatives of polyethylene glycol), photocrosslinkers, cytotoxic compounds, affinity labels, derivatives of biotin, resins, beads, a second protein or polypeptide (or more), polynucleotide(s) (e.g., DNA, RNA, etc.), metal chelators, cofactors, fatty acids, carbohydrates, and the like. See, e.g., FIG. 13A, and Example 3 and 5, herein. These molecules can be added to an unnatural amino acid with an alkynyl group, e.g., p-propargyloxyphenylalanine, or azido group, e.g., p-azido-phenylalanine, respectively. For example, see FIG. 13B and FIG. 17A.

In another aspect, the invention provides compositions including such molecules and methods of producing these molecules, e.g., azido dyes (such as shown in chemical structure 4 and chemical structure 6), an alkynyl polyethylene glycol (e.g., as shown in chemical structure 7), where n is an integer between, e.g., 50 and 10,000, 75 and 5,000, 100 and 2,000, 100 and 1,000, etc. In embodiment of the invention, the alkynyl polyethylene glycol has a molecular weight of, e.g., about 5,000 to about 100,000 Da, about 20,000 to about 50,000 Da, about 20,000 to about 10,000 Da (e.g., 20,000 Da), etc.

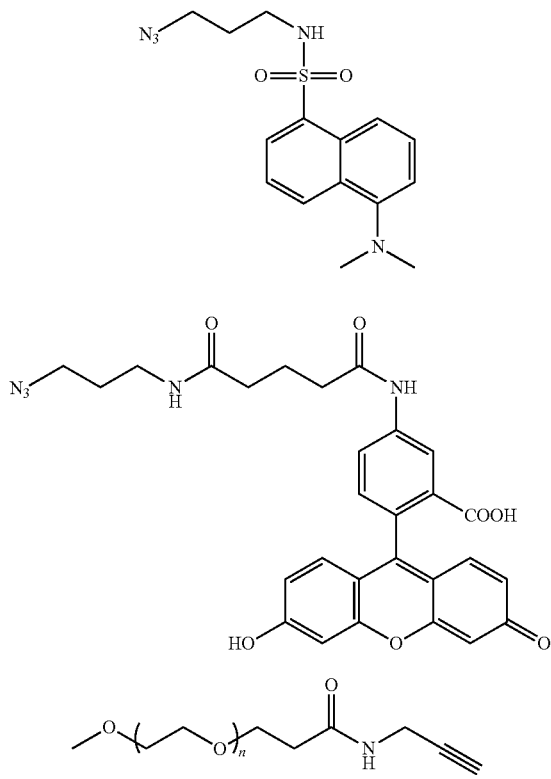

Various compositions comprising these compounds, e.g., with proteins and cells, are also provided. In one aspect of the invention, a protein comprising an azido dye (e.g., of chemical structure 4 or chemical structure 6), further includes at least one unnatural amino acid (e.g., an alkynyl amino acid), where the azido dye is attached to the unnatural amino acid through a [3+2] cycloaddition.

In one embodiment, a protein comprises the alkynyl polyethylene glycol of chemical structure 7. In another embodiment, the composition further includes at least one unnatural amino acid (e.g., an azido amino acid), wherein the alkynyl polyethylene glycol is attached to an unnatural amino acid through a [3+2] cycloaddition.

Methods for synthesizing azido dyes are also provided. For example, one such method comprises: (a) providing a dye compound comprising a sulfonyl halide moiety; (b) warming the dye compound to room temperature in the presence of 3-azidopropylamine and triethylamine and coupling an amine moiety of the 3-azidopropylamine to the halide position of the dye compound, thereby synthesizing the azido dye. In one example embodiment, the dye compound comprises dansyl chloride, and the azido dye comprises the composition of chemical structure 4. In one aspect, the method further comprises purifying the azido dye from the reaction mixture. See, e.g., Example 5, herein.

In another example, a method for synthesizing an azido dye comprises (a) providing an amine-containing dye compound; (b) combining the amine-containing dye compound with a carbodiimide and 4-(3-azidopropylcarbamoyl)-butyric acid in a suitable solvent, and coupling a carbonyl group of the acid to the amine moiety of the dye compound, thereby synthesizing the azido dye. In one embodiment, the carbodiimine comprises 1-ethyl-3-(3-dimethylaminopropyl) carbodiimide hydrochloride (EDCI). In one aspect, the amine-containing dye comprises fluoresceinamine, and the suitable solvent comprises pyridine. For example, the amine-containing dye optionally comprises fluoresceinamine and the azido dye optionally comprises the composition of chemical structure 6. In one embodiment, the method further comprises (c) precipitating the azido dye; (d) washing the precipitate with HCl; (e) dissolving the washed precipitate in EtOAc; and (f) precipitating the azido dye in hexanes. See, e.g., Example 5, herein.

Methods for synthesizing a propargyl amide polyethylene glycol are also provided. For example, the method comprises reacting propargylamine with polyethylene glycol (PEG)-hydroxysuccinimide ester in an organic solvent (e.g., $CH_2Cl_2$) at room temperature, resulting in the propargyl amide polyethylene glycol of chemical structure 7. In one embodiment, the method further comprises precipitating the propargylamide polyethylene glycol using ethyl acetate. In one aspect, the method further includes recrystallizing the propargylamide polyethylene glycol in methanol; and drying the product under a vacuum. See, e.g., Example 5, herein.

A eukaryotic cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an unnatural amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nl to about 100 L). The production of large quantities (e.g., greater that that typically possible with other methods, e.g., in vitro translation) of a protein in a eukaryotic cell including at least one unnatural amino acid is a feature of the invention.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like.

The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO", representing a preferred target for modification by the incorporation of one or more unnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase, and many others.

One class of proteins that can be made using the compositions and methods for in vivo incorporation of unnatural amino acids described herein includes transcriptional modulators or portions thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. For example, compositions of GAL4 protein or portion thereof in a eukaryotic cell are also a feature of the invention. Typically, the GAL4 protein or portion thereof comprises at least one unnatural amino acid. See also the section herein entitled "Orthogonal aminoacyl-tRNA synthetases."

One class of proteins of the invention (e.g., proteins with one or more unnatural amino acids) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes), or portions thereof with at least one unnatural amino acid, are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2002 catalogue and price list), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., *vaccinia*; Picornaviruses, e.g. *polio*; Togaviruses, e.g., *rubella*; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

The invention also provides methods for producing in a eukaryotic cell at least one protein comprising at least one unnatural amino acid (and proteins produced by such methods). For example, a method includes: growing, in an appropriate medium, a eukaryotic cell that comprises a nucleic acid that comprises at least one selector codon and encodes the protein. The eukaryotic cell also comprises: an orthogonal tRNA (O-tRNA) that functions in the cell and recognizes the selector codon; and an orthogonal aminoacyl tRNA synthetase (O-RS) that preferentially aminoacylates the O-tRNA with the unnatural amino acid, and the medium comprises an unnatural amino acid.

In one embodiment, the method further includes incorporating into the protein the unnatural amino acid, where the unnatural amino acid comprises a first reactive group; and contacting the protein with a molecule (e.g., a dye, a polymer, e.g., a derivative of polyethylene glycol, a photocrosslinker, a cytotoxic compound, an affinity label, a derivative of biotin, a resin, a second protein or polypeptide, a metal chelator, a cofactor, a fatty acid, a carbohydrate, a polynucleotide (e.g., DNA, RNA, etc.), and the like) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (e.g., in unnatural amino acid p-propargyloxyphenylalanine) and the second reactive group is the azido moiety. In another example, the first reactive group is the azido moiety (e.g., in the unnatural amino acid p-azido-L-phenylalanine) and the second reactive group is the alkynyl moiety.

In one embodiment, the O-RS aminoacylates the O-tRNA with the unnatural amino acid at least 50% as efficiently as does an O-RS having an amino acid sequence, e.g., as set forth in SEQ ID NO.: 86 or 45. In another embodiment, the O-tRNA comprises, is processed from, or is encoded by SEQ ID NO.: 65 or 64, or a complementary polynucleotide sequence thereof. In yet another embodiment, the O-RS comprises an amino acid set forth in any one of SEQ ID NO.: 36-63 (e.g., 36-47, 48-63, or any other subset of 36-63) and/or 86.

The encoded protein can comprise, e.g., a therapeutic protein, a diagnostic protein, an industrial enzyme, or portion thereof. Optionally, the protein that is produced by the method is further modified through the unnatural amino acid. For example, the protein produced by the method is optionally modified by at least one post-translational modification in vivo.

Methods of producing a screening or selecting transcriptional modulator protein are also provided (and screening or selecting transcriptional modulator proteins produced by such methods). For example, a method includes: selecting a first polynucleotide sequence, where the polynucleotide sequence encodes a nucleic acid binding domain; and mutating the first polynucleotide sequence to include at least one selector codon. This provides a screening or selecting polynucleotide sequence. The method also includes: selecting a second polynucleotide sequence, where the second polynucleotide sequence encodes a transcriptional activation domain; providing a construct that comprises the screening or selecting polynucleotide sequence operably linked to the second polynucleotide sequence; and, introducing the construct, an unnatural amino acid, an orthogonal tRNA synthetase (O-RS) and an orthogonal tRNA (O-tRNA) into a cell. With these components, the O-RS preferentially aminoacylates the O-tRNA with the unnatural amino acid and the O-tRNA recognizes the selector codon and incorporates the unnatural amino acid into the nucleic acid binding domain, in response to the selector codon in the screening or selecting polynucleotide sequence, thereby providing the screening or selecting transcriptional modulator protein.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

In one example embodiment, the invention provides compositions (& compositions produced by the methods of the invention) that include a Thr44, Arg110 TAG mutant of GAL4, where the GAL4 protein includes at least one unnatural amino acid. In another embodiment, the invention provides compositions that include a Trp33 TAG mutant of human Superoxide dimutase (hSOD), where the hSOD protein includes at least one unnatural amino.

Purifying Recombinant Proteins Comprising Unnatural Amino Acids

Proteins of the invention, e.g., proteins comprising unnatural amino acids, antibodies to proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, e.g., for affinity-based purification of proteins comprising one or more unnatural amino acid(s). Once purified, partially or to homogeneity, as desired, the polypeptides are optionally used e.g., as assay components, therapeutic reagents or as immunogens for antibody production.

In addition to other references noted herein, a variety of purification/protein folding methods are well known in the art, including, e.g., those set forth in R. Scopes, Protein Purification, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods,* 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

One advantage of producing a protein or polypeptide of interest with an unnatural amino acid in a eukaryotic cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished, e.g., by adding a chaperonin to the protein or polypeptide of interest, and/or by solubilizing the proteins in a chaotropic agent such as guanidine HCl, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.,* 268: 14065-14070; Kreitman and Pastan (1993) *Bioconjug. Chem.,* 4: 581-585; and Buchner, et al., (1992) *Anal. Biochem.,* 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

Antibodies

In one aspect, the invention provides antibodies to molecules of the invention, e.g., synthetases, tRNA, and proteins comprising unnatural amino acids. Antibodies to molecules of the invention are useful as purification reagents, e.g., for purifying the molecules of the invention. In addition, the antibodies can be used as indicator reagents to indicate the presence of a synthetase, a tRNA, or protein comprising an unnatural amino acid, e.g., to track the presence or location (e.g., in vivo or in situ) of the molecule.

An antibody of the invention can be a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain ($V_H$) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce $F(ab')_2$, a dimer of Fab which itself is a light chain joined to $V_H$-$C_H$1 by a disulfide bond. The F(ab)$_2$ may be reduced under mild conditions to break the disulfide linkage in the hinge region thereby converting the F(ab)$_2$dimer into an Fab' monomer. The Fab' monomer is essentially an Fab with part of the hinge region (see, *Fundamental Immunology*, 4$^{th}$ addition, W.E. Paul, ed., Raven Press, N.Y. (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein, also optionally includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide. Antibodies of the invention can be, e.g., polyclonal, monoclonal, chimeric, humanized, single chain, Fab fragments, fragments produced by an Fab expression library, or the like.

In general, antibodies of the invention are valuable, both as general reagents and as therapeutic reagents in a variety of molecular biological or pharmaceutical processes. Methods of producing polyclonal and monoclonal antibodies are available, and can be applied to making the antibodies of the invention. A number of basic texts describe standard antibody production processes, including, e.g., Borrebaeck (ed) (1995) *Antibody Engineering*, 2$^{nd}$ *Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul); Paul (ed.), (1999) *Fundamental Immunology, Fifth edition* Raven Press, N.Y.; Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

A variety of recombinant techniques for antibody preparation which do not rely on, e.g., injection of an antigen into an animal have been developed and can be used in the context of the present invention. For example, it is possible to generate and select libraries of recombinant antibodies in phage or similar vectors. See, e.g., Winter et al. (1994) *Making Antibodies by Phage Display Technology Annu. Rev. Immunol.* 12:433-55 and the references cited therein for a review. See also, Griffiths and Duncan (1998) *Strategies for selection of antibodies by phage display Curr Opin Biotechnol* 9: 102-8; Hoogenboom et al. (1998) *Antibody phage display technology and its applications Immunotechnology* 4: 1-20; Gram et al. (1992) *in vitro selection and affinity maturation of antibodies from a naïve combinatorial immunoglobulin library PNAS* 89:3576-3580; Huse et al. (1989) *Science* 246: 1275-1281; and Ward, et al. (1989) *Nature* 341: 544-546.

In one embodiment, antibody libraries can include repertoires of V genes (e.g., harvested from populations of lymphocytes or assembled in vitro) which are cloned for display of associated heavy and light chain variable domains on the surface of filamentous bacteriophage. Phage are selected by binding to an antigen. Soluble antibodies are expressed from phage infected bacteria and the antibody can be improved, e.g., via mutagenesis. See e.g., Balint and Larrick (1993) *Antibody Engineering by Parsimonious Mutagenesis Gene* 137:109-118; Stemmer et al. (1993) *Selection of an Active Single Chain Fv Antibody From a Protein Linker Library Prepared by Enzymatic Inverse PCR Biotechniques* 14(2):256-65; Crameri et al. (1996) *Construction and evolution of antibody-phage libraries by DNA shuffling Nature Medicine* 2:100-103; and Crameri and Stemmer (1995) *Combinatorial multiple cassette mutagenesis creates all the permutations of mutant and wildtype cassettes BioTechniques* 18:194-195.

Kits for cloning and expression of recombinant antibody phage systems are also known and available, e.g., the "recombinant phage antibody system, mouse ScFv module," from Amersham-Pharmacia Biotechnology (Uppsala, Sweden). Bacteriophage antibody libraries have also been produced for making high affinity human antibodies by chain shuffling (See, e.g., Marks et al. (1992) *By-Passing Immunization: Building High Affinity Human Antibodies by Chain Shuffling Biotechniques* 10:779-782. It will also be recognized that antibodies can be prepared by any of a number of commercial services (e.g., Bethyl Laboratories (Montgomery, Tex.), Anawa (Switzerland), Eurogentec (Belgium and in the US in Philadelphia, Pa., etc.) and many others.

In certain embodiments, it is useful to "humanize" antibodies of the invention, e.g., where the antibodies are to be administered therapeutically. The use of humanized antibodies tends to reduce the incidence of unwanted immune responses against the therapeutic antibodies (e.g., when the patient is a human). The antibody references above describe humanization strategies. In addition to humanized antibodies, human antibodies are also a feature of the invention. Human antibodies consist of characteristically human immunoglobulin sequences. Human antibodies can be produced in using a wide variety of methods (see, e.g., Larrick et al., U.S. Pat. No. 5,001,065, for a review). A general approach for producing human antibodies by trioma technology is described by Ostberg et al. (1983), *Hybridoma* 2: 361-367, Ostberg, U.S. Pat. No. 4,634,664, and Engelman et al., U.S. Pat. No. 4,634,666.

A variety of methods of using antibodies in the purification and detection of proteins are known and can be applied to detecting and purifying proteins comprising unnatural amino acids as noted herein. In general, antibodies are useful reagents for ELISA, western blotting, immunochemistry, affinity chromatograpy methods, SPR, and many other methods. The references noted above provide details on how to perform ELISA assays, western blots, surface plasmon resonance (SPR) and the like.

In one aspect of the invention, antibodies of the invention themselves include unnatural amino acids, providing the antibodies with properties of interest (e.g., improved half-life, stability, toxicity, or the like). See also, the section herein entitled "Polypeptides with unnatural amino acids." Antibodies account for nearly 50% of all compounds currently in clinical trials (Wittrup, (1999) *Phage on display Tibtech* 17: 423-424 and antibodies are used ubiquitously as diagnostic reagents. Accordingly, the ability to modify antibodies with unnatural amino acids provides an important tool for modifying these valuable reagents.

For example, there are many applications of MAbs to the field of diagnostics. Assays range from simple spot tests to more involved methods such as the radio-labeled NR-LU-10 MAb from DuPont Merck Co. used for tumor imaging (Rusch et al. (1993) *NR-LU-10 monoclonal antibody scanning. A helpful new adjunct to computed tomography in* evaluating non-small-cell lung cancer. *J Thorac Cardiovasc Surg* 106: 200-4). As noted, MAbs are central reagents for ELISA, western blotting, immunochemistry, affinity chromatograpy methods and the like. Any such diagnostic antibody can be modified to include one or more unnatural amino acid, altering, e.g., the specificity or avidity of the Ab for a target, or altering one or more detectable property, e.g., by including a detectable label (e.g., spectrographic, fluorescent, luminescent, etc.) in the unnatural amino acid.

One class of valuable antibody reagents are therapeutic Abs. For example, antibodies can be tumor-specific MAbs that arrest tumor growth by targeting tumor cells for destruction by antibody-dependent cell-mediated cytotoxicity (ADCC) or complement-mediated lysis (CML) (these general types of Abs are sometimes referred to as "magic bullets"). One example is Rituxan, an anti-CD20 MAb for the treatment of Non-Hodgkins lymphoma (Scott (1998) *Rituximab: a new therapeutic monoclonal antibody for non-Hodgkin's lymphoma Cancer Pract* 6: 195-7). A second example relates to antibodies which interfere with a critical component of tumor growth. Herceptin is an anti-HER-2 monoclonal antibody for treatment of metastatic breast cancer, and provides an example of an antibody with this mechanism of action (Baselga et al. (1998) *Recombinant humanized anti-HER2 antibody (Herceptin) enhances the antitumor activity of paclitaxel and doxorubicin against HER2/neu overexpressing human breast cancer xenografts* [published erratum appears in *Cancer Res* (1999) 59(8): 2020], *Cancer Res* 58: 2825-31). A third example relates to antibodies for delivery of cytotoxic compounds (toxins, radionuclides, etc.) directly to a tumor or other site of interest. For example, one application Mab is CYT-356, a 90Y-linked antibody that targets radiation directly to prostate tumor cells (Deb et al. (1996) *Treatment of hormone-refractory prostate cancer with 90Y-CYT-356 monoclonal antibody Clin Cancer Res* 2: 1289-97. A fourth application is antibody-directed enzyme prodrug therapy, where an enzyme co-localized to a tumor activates a systemically-administered pro-drug in the tumor vicinity. For example, an anti-Ep-CAM1 antibody linked to carboxypeptidase A is being developed for treatment of colorectal cancer (Wolfe et al. (1999) *Antibody-directed enzyme prodrug therapy with the T268G mutant of human carboxypeptidase Al: in vitro and in vivo studies with prodrugs of methotrexate and the thymidylate synthase inhibitors GW*1031 *and GW*1843 *Bioconjug Chem* 10: 38-48). Other Abs (e.g., antagonists) are designed to specifically inhibit normal cellular functions for therapeutic benefit. An example is Orthoclone OKT3, an anti-CD3 MAb offered by Johnson and Johnson for reducing acute organ transplant rejection (Strate et al. (1990) *Orthoclone OKT3 as first-line therapy in acute renal allograft rejection Transplant Proc* 22: 219-20. Another class of antibody products are agonists. These Mabs are designed to specifically enhance normal cellular functions for therapeutic benefit. For example, Mab-based agonists of acetylcholine receptors for neurotherapy are under development (Xie et al. (1997) *Direct demonstration of MuSK involvement in acetylcholine receptor clustering through identification of agonist ScFv Nat. Biotechnol.* 15: 768-71. Any of these antibodies can be modified to include one or more unnatural amino acid to enhance one or more therapeutic property (specificity, avidity, serum-half-life, etc.).

Another class of antibody products provide novel functions. The main antibodies in this group are catalytic antibodies such as Ig sequences that have been engineered to mimic the catalytic abilities of enzymes (Wentworth and Janda (1998) *Catalytic antibodies Curr Opin Chem Biol* 2: 138-44. For example, an interesting application involves using the catalytic antibody mAb-15A10 to hydrolyze cocaine in vivo for addiction therapy (Mets et al. (1998) *A catalytic antibody against cocaine prevents cocaine's reinforcing and toxic effects in rats Proc Natl Acad Sci USA* 95: 10176-81). Catalytic antibodies can also be modified to include one or more unnatural amino acid to improve one or more property of interest.

Defining Polypeptides by Immunoreactivity

Because the polypeptides of the invention provide a variety of new polypeptide sequences (e.g., comprising unnatural amino acids in the case of proteins synthesized in the translation systems herein, or, e.g., in the case of the novel synthetases herein, novel sequences of standard amino acids), the polypeptides also provide new structural features which can be recognized, e.g., in immunological assays. The generation of antibodies or antibodies which specifically bind the polypeptides of the invention, as well as the polypeptides which are bound by such antibodies or antisera, are a feature of the invention.

For example, the invention includes synthetase proteins that specifically bind to or that are specifically immunoreactive with an antibody or antisera generated against an immunogen comprising an amino acid sequence selected from one or more of (SEQ ID NO: 36-63 (e.g., 36-47, 48-63, or any other subset of 36-63), and/or 86). To eliminate cross-reactivity with other homologues, the antibody or antisera is subtracted with available control synthetase homologues, such as the wild-type *E. coli* tyrosyl synthetase (TyrRS) (e.g., SEQ ID NO.:2).

In one typical format, the immunoassay uses a polyclonal antiserum which was raised against one or more polypeptide comprising one or more of the sequences corresponding to one or more of SEQ ID NO: 36-63 (e.g., 36-47, 48-63, or any other subset of 36-63), and/or 86, or a substantial subsequence thereof (i.e., at least about 30% of the full length sequence provided). The set of potential polypeptide immunogens derived from SEQ ID NO: 36-63 and 86 are collectively referred to below as "the immunogenic polypeptides." The resulting antisera is optionally selected to have low cross-reactivity against the control synthetase homologues and any such cross-reactivity is removed, e.g., by immunoabsorbtion, with one or more control synthetase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional references and discussion of antibodies is also found herein and can be applied here to make antibodies that define/detect polypeptides by immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control synthetase polypeptides to produce subtracted pooled titered polyclonal antisera.

The subtracted pooled titered polyclonal antisera are tested for cross reactivity against the control homologues in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic synthetase as compared to binding to a control synthetase homologue. That is, the stringency of the binding/washing reaction(s) is/are adjusted by the addition of non-specific competitors such as albumin or non-fat dry milk, and/or by adjusting salt conditions, temperature, and/or the like. These binding/washing conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control synthetase homologue under discriminatory binding conditions, and at least about a ½ signal to noise ratio as compared to the immunogenic polypeptide(s), shares substantial structural similarity with the immunogenic polypeptide as compared to known synthetases, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Pharmaceutical Compositions

The polypeptides or proteins of the invention (e.g., synthetases, proteins comprising one or more unnatural amino acid, etc.) are optionally employed for therapeutic uses, e.g., in combination with a suitable pharmaceutical carrier. Such compositions, e.g., comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (e.g., comparison of an EPO modified to include one or more unnatural amino acids to a natural amino acid EPO), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to: oral, intravenous, intraperitoneal, intramuscular, transdermal, subcutaneous, topical, sublingual, or rectal means. Unnatural amino acid polypeptide compositions can also be administered via liposomes. Such administration routes and appropriate formulations are generally known to those of skill in the art.

The unnatural amino acid polypeptide, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (e.g., those typically used for EPO, GCSF, GMCSF, IFNs, interleukins, antibodies, and/or any other pharmaceutically delivered protein), along with formulations in current use, provide preferred routes of administration and formulation for the proteins that include unnatural amino acids of the invention (e.g., pegylated variants of current thereputic proteins, etc.).

The dose administered to a patient, in the context of the present invention, is sufficient to effect a beneficial therapeutic response in the patient over time, or, e.g., to inhibit infection by a pathogen, or other appropriate activity, depending on the application. The dose is determined by the efficacy of a particular composition/formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular composition/formulation, or the like in a particular patient.

In determining the effective amount of the composition/formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, e.g., to a 70 kilogram patient, is typically in the range equivalent to dosages of currently-used therapeutic proteins, adjusted for the altered activity or serum half-life of the relevant composition. The compositions/formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 of the relevant formulation, and/or observation of any side-effects of the unnatural amino acids at various concentrations, e.g., as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Nucleic Acid and Polypeptide Sequence and Variants

As described above and below, the invention provides for nucleic acid polynucleotide sequences and polypeptide amino acid sequences, e.g., O-tRNAs and O-RSs, and, e.g., compositions and methods comprising said sequences. Examples of said sequences, e.g., O-tRNAs and O-RSs are disclosed herein (see, Table 5, e.g., SEQ ID NO. 3-65, 86, and other than SEQ ID NO.: 1 and 2). However, one of skill in the art will appreciate that the invention is not limited to those sequences disclosed herein, e.g., the Examples and Table 5. One of skill will appreciate that the invention also provides many related and even unrelated sequences with the functions described herein, e.g., encoding an O-tRNA or an O-RS.

The invention also provides polypeptides (O-RSs) and polynucleotides, e.g., O-tRNA, polynucleotides that encode O-RSs or portions thereof (e.g., the active site of the synthetase), oligonucleotides used to construct aminoacyl-tRNA synthetase mutants, etc. For example, a polypeptide of the invention includes a polypeptide that comprises an amino acid sequence as shown in any one of SEQ ID NO.: 36-63 (e.g., 36-47, 48-63, or any other subset of 36-63), and/or 86, a polypeptide that comprises an amino acid sequence encoded by a polynucleotide sequence as shown in any one of SEQ ID NO.: 3-35 (e.g., 3-19, 20-35, or any other subset of sequences 3-35), and a polypeptide that is specifically immunoreactive with an antibody specific for a polypeptide that comprises an amino acid sequence as shown in any one of SEQ ID NO.: 36-63, and/or 86, or a polypeptide that comprises an amino acid sequence encoded by a polynucleotide sequence as shown in any one of SEQ ID NO.: 3-35 (e.g., 3-19, 20-35, or any other subset of sequences 3-35).

Also included among the polypeptides of the invention are polypeptides that comprise an amino acid sequence that is at least 90% identical to that of a naturally occurring tyrosyl aminoacyl-tRNA synthetase (TyrRS) (e.g., SEQ ID NO.:2) and comprises two or more amino acids of groups A-E. For example, group A includes valine, isoleucine, leucine, glycine, serine, alanine, or threonine at a position corresponding to Tyr37 of *E. coli* TyrRS; group B includes aspartate at a position corresponding to Asn126 of *E. coli* TyrRS; group C includes threonine, serine, arginine, asparagine or glycine at a position corresponding to Asp182 of *E. coli* TyrRS; group D includes methionine, alanine, valine, or tyrosine at a position corresponding to Phe183 of *E. coli* TyrRS; and, group E includes serine, methionine, valine, cysteine, threonine, or alanine at a position corresponding to Leu186 of *E. coli* TyrRS. Any subset of combinations of these groups are a feature of the invention. For example, in one embodiment, the O-RS has two or more amino acids selected from valine, isoleucine, leucine, or threonine occurs at a position corresponding to Tyr37 of *E. coli* TyrRS; threonine, serine, arginine, or glycine at a position corresponding to Asp182 of *E. coli* TyrRS; methionine, or tyrosine at a position corresponding to Phe183 of *E. coli* TyrRS; and, serine, or alanine at a position corresponding to Leu186 of *E. coli* TyrRS. In another embodiment, the O-RS includes two more more amino acids selected from glycine, serine, or alanine at a position corresponding to Tyr37 of *E. coli* TyrRS, aspartate at a position corresponding to Asn126 of *E. coli* TyrRS, asparagine at a position corresponding to Asp182 of *E. coli* TyrRS, alanine, or valine, at a position corresponding to Phe183 of *E. coli* TyrRS, and/or methionine, valine, cysteine, or threonine, at a position corresponding to Leu186 of *E. coli* TyrRS. Similarly, polypeptides of the invention also include a polypeptide that comprises at least 20 contiguous amino acids of SEQ ID NO.: 36-63 (e.g., 36-47, 48-63, or any other subset of 36-63), and/or 86, and two or more amino acid substitutions as indicated above in groups A-E. See also, Table 4, Table 6, and/or Table 8, herein. An amino acid sequence comprising a conservative variation of any of the above polypeptides is also included as a polypeptide of the invention.

In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention.

Polynucleotides are also provided in the invention. Polynucleotides of the invention include those that encode proteins or polypeptides of interest of the invention, or that include one or more selector codon, or both. For example, polynucleotides of the invention include, e.g., a polynucleotide comprising a nucleotide sequence as set forth in any one of SEQ ID NO.: 3-35 (e.g., 3-19, 20-35, or any other subset of sequences 3-35), 64-85; a polynucleotide that is complementary to or that encodes a polynucleotide sequence thereof; and/or a polynucleotide encoding a polypeptide that comprises an amino acid sequence as set forth in any one of SEQ ID NO.: 36-63, and/or 86, or a conservative variation thereof. A polynucleotide of the invention also includes a polynucleotide that encodes a polypeptide of the invention. Similarly, a nucleic acid that hybridizes to a polynucleotide indicated above under highly stringent conditions over substantially the entire length of the nucleic acid is a polynucleotide of the invention.

A polynucleotide of the invention also includes a polynucleotide that encodes a polypeptide that comprises an amino acid sequence that is at least 90% identical to that of a naturally occurring tyrosyl aminoacyl-tRNA synthetase (TyrRS) (e.g., SEQ ID NO.: 2) and comprises two or more mutations as indicated above in groups A-E (above). A polynucleotide that is that is at least 70%, (or at least 75%, at least 80%, at least 85%, at least 90%, at least 95%, at least 98%, or least 99% or more) identical to a polynucleotide indicated above and/or a polynucleotide comprising a conservative variation of any of the polynucleotides indicated above are also included among the polynucleotides of the invention. See also, Table 4, Table 6, and/or Table 8, herein.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences that do not alter the encoded activity of a nucleic acid molecule, such as the addition of a non-functional sequence, is a conservative variation of the basic nucleic acid.

Conservative substitution tables providing functionally similar amino acids are well known in the art. The following sets forth example groups which contain natural amino acids that include "conservative substitutions" for one another.

| | Conservative Substitution Groups | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) Valine (V) |
| 6 | Phenylalanine (F) | Tyrosine (Y) | Tryptophan (W) |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to the nucleic acids represented by SEQ ID NO: 3-35 (e.g., 3-19, 20-35, or any other subset of sequences 3-35), 64-85 under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at lest ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes part I* chapter 2, "Overview of principles of hybridization and the strategy of nucleic acid probe assays," (Elsevier, New York), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, preferably 80%, most preferably 90-95% nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual (2nd Ed.)*, Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the invention, e.g., to produce libraries of tRNAs, to produce libraries of synthetases, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis, in Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); *Methods in Enzymol.* 100: 468-500 (1983); *Methods in Enzymol.* 154: 329-350 (1987); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Point Mismatch Repair, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond. A* 317: 415-423 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shot-gun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA,* 83:7177-7181 (1986); Arnold, *Protein engineering for unusual environments, Current Opinion in Biotechnology* 4:450-455 (1993); Sieber, et al., Nature Biotechnology, 19:456-460 (2001). W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

The invention also relates to eukaryotic host cells and organisms for the in vivo incorporation of an unnatural amino acid via orthogonal tRNA/RS pairs. Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)).

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., Easy-Prep™, FlexiPrep™, both from Pharmacia Biotech; Strata-Clean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Ghema et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif.), ExpressGen Inc. (Chicago, Ill.), Operon Technologies Inc. (Alameda, Calif.) and many others.

Kits

Kits are also a feature of the invention. For example, a kit for producing a protein that comprises at least one unnatural amino acid in a cell is provided, where the kit includes a container containing a polynucleotide sequence encoding an O-tRNA, and/or an O-RS, and/or a polynucleotide sequence encoding an O-RS, and/or an O-RS. In one embodiment, the kit further includes at least one unnatural amino acid. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

Methods of Producing and Compositions of Aminoacyl-tRNA Synthetases that Incorporate Unnatural Amino Acids in Eukaryotic Cells The expansion of the eukaryotic genetic code to include unnatural amino acids with novel physical, chemical or biological properties would provide powerful tools for analyzing and controlling protein function in these cells. Towards this goal, a general approach for the isolation of aminoacyl-tRNA synthetases that incorporate unnatural amino acids with high fidelity into proteins in response to an amber codon in *Saccharomyces cerevisiae* (*S. cerevisiae*) is described. The method is based on the activation of GAL4 responsive reporter genes, HIS3, URA3 or LacZ, by suppression of amber codons between the DNA binding domain and transcriptional activation domain of GAL4. The optimization of a GAL4 reporter for positive selection of active *Escherichia coli* tyrosyl-tRNA synthetase (EcTyrRS) variants is described. A negative selection of inactive EcTyrRS variants has also been developed with the URA3 reporter by use of a small molecule (5-fluoroorotic acid (5-FOA)) added to the growth media as a 'toxic allele.' Importantly both positive and negative selections can be performed on a single cell and with a range of stringencies. This can facilitate the isolation of a range of aminoacyl-tRNA synthetase (aaRS) activities from large libraries of mutant synthetases. The power of the method for isolating desired aaRS phenotypes is demonstrated by model selections.

The recent addition of unnatural amino acids to the genetic code of *Escherichia coli* (*E. coli*) provides a powerful new approach for analyzing and manipulating protein structure and function both in vitro and in vivo Amino acids with photoaffinity labels, heavy atoms, keto and olefinic groups and chromophores have been incorporated into proteins in *E. coli* with an efficiency and fidelity rivaling that of the common twenty amino acids. See, e.g., Chin, et al., (2002), *Addition of a Photocrosslinker to the Genetic Code of Escherichia coli, Proc. Natl. Acad. Sci. U.S.A.* 99:11020-11024; Chin and Schultz, (2002), *In vivo Photocrosslinking with Unnatural Amino Acid Mutagenesis, Chem BioChem* 11:1135-1137; Chin et al., (2002), *Addition of p-Azido-L-phenylalanine to the Genetic code of Escherichia coli, J. Am. Chem. Soc.* 124:9026-9027; Zhang et al., (2002), *The selective incorporation of alkenes into proteins in Escherichia coli, Angewandte Chemie. International Ed. in English* 41:2840-2842; and, Wang and Schultz, (2002), *Expanding the Genetic Code, Chem. Comm* 1-10.

Unnatural amino acids have been introduced previously into the nicotinic acetylcholine receptor in *Xenopus oocytes* (e.g., M. W. Nowak, et al. (1998), *In vivo incorporation of unnatural amino acids into ion channels in Xenopus oocyte expression system, Method Enzymol.* 293:504-529) by microinjection of a chemically misacylated Tetrahymena thermophila tRNA (e.g., M. E. Saks, et al. (1996), *An engineered Tetrahymena tRNAGln for in vivo incorporation of unnatural amino acids into proteins by nonsense suppression, J. Biol. Chem.* 271:23169-23175, and the relevant mRNA. This has allowed detailed biophysical studies of the receptor in oocytes by the introduction of amino acids containing side chains with unique physical or chemical properties. See, e.g., D. A. Dougherty (2000), *Unnatural amino acids as probes of protein structure and function, Curr. Opin. Chem. Biol.* 4:645-652. Unfortunately, this methodology is limited to proteins in cells that can be microinjected, and because the tRNA is chemically acylated in vitro, and cannot be re-acylated, the yields of protein are very low. This in turn necessitates sensitive techniques to assay protein function.

There is interest in the genetic incorporation of unnatural amino acids into proteins in eukaryotic cells in response to an amber codon. See also, H. J. Drabkin et al., (1996), *Amber suppression in mammalian cells dependent upon expression of an Escherichia coli aminoacyl-tRNA synthetase gene, Molecular & Cellular Biology* 16:907-913; A. K. Kowal, et al., (2001), *Twenty-first aminoacyl-tRNA synthetase-suppressor tRNA pairs for possible use in site-specific incorporation of amino acid analogues into proteins in eukaryotes and in eubacteria.* [comment], *Proc. Natl. Acad. Sci. U.S.A.* 98:2268-2273; and, K. Sakamoto, et al., (2002), *Site-specific incorporation of an unnatural amino acid into proteins in mammalian cells, Nucleic Acids Res.* 30:4692-4699. This would have significant technical and practical advantages, since tRNAs would be re-acylated by their cognate synthetases-leading to large amounts of mutant protein. Moreover, genetically encoded aminoacyl-tRNA synthetases and tRNAs are, in principle, heritable, allowing the unnatural amino acid to be incorporated into proteins through many cell divisions without exponential dilution.

The steps necessary to add new amino acids to the genetic code of *E. coli* have been described (see, e.g., D. R. Liu, & P. G. Schultz, (1999), *Progress toward the evolution of an organism with an expanded genetic code, Proc. Natl. Acad. Sci. U.S.A.* 96:4780-4785; and similar principles can be useful for expanding the genetic code of eukaryotes. In the first step, an orthogonal aminoacyl-tRNA synthetase (aaRS)/ tRNA$_{CUA}$ pair is identified. This pair needs to function with the host cells translational machinery, but the aaRS should not charge any endogenous tRNAs with an amino acid and the tRNA$_{CUA}$ should not be aminoacylated by any endogenous synthetases. See, e.g., D. R. Liu, et al., *Engineering a tRNA and aminoacyl-tRNA synthetase for the site-specific incorporation of unnatural amino acids into proteins in vivo*, Proc. Natl. Acad. Sci. U.S.A. 94:10092-10097. In a second step, those aaRS/tRNA pairs that are capable of using only the unnatural amino acid are selected from a library of mutant aaRSs. In *E. coli* the selection of unnatural amino acid utilizing variants of MjTyrRS was carried out using two-step 'double sieve' selections. See, e.g., D. R. Liu, & P. G. Schultz, (1999), *Progress toward the evolution of an organism with an expanded genetic code*, Proc. Natl. Acad. Sci. U.S.A. 96:4780-4785. A modified selection method is used in eukaryotic cells.

Figure 2:
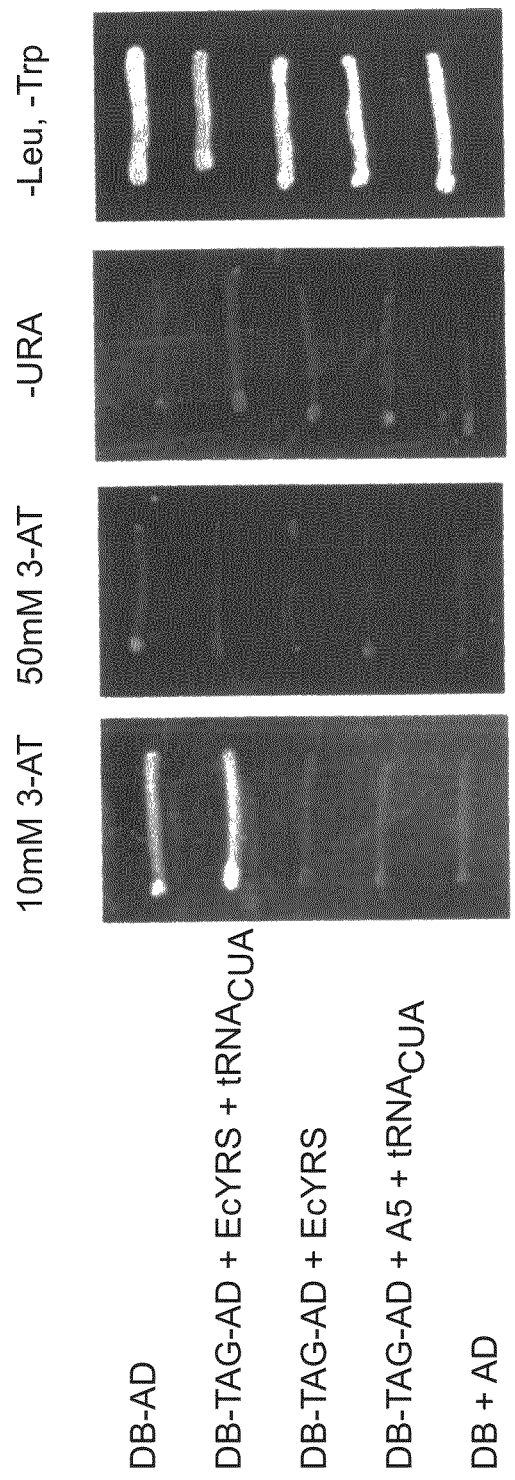
FIG. 2 illustrates the EcTyrRS and tRNA$_{CUA}$ dependent phenotypes of 1$^{st}$ generation GAL4 reporters on selective media. DB-AD is a fusion between the GAL4 DNA binding domain and activation domain. DB-TAG-AD has a TAG codon replacing a tyrosine codon in the synthetic linker between DB and AD. A5 is an inactive version of EcTyrRS in which 5 residues in the active site have been mutated to alanine.

Saccharomyces cerevisiae (*S. cerevisiae*) was chosen as the eukaryotic host organism, as it is unicellular, has a rapid generation time, as well as relatively well characterized genetics. See, e.g., D. Burke, et al., (2000) *Methods in Yeast Genetics*. Cold Spring Harbor Laboratory Press, Cold Spring Harbor, N.Y. Moreover, since the translational machinery of eukaryotes is highly conserved (see, e.g., (1996) *Translational Control*. Cold Spring Harbor Laboratory, Cold Spring Harbor, N.Y.; Y. Kwok, & J. T. Wong, (1980), *Evolutionary relationship between Halobacterium cutirubrum and eukaryotes determined by use of aminoacyl-tRNA synthetases as phylogenetic probes*, Canadian Journal of Biochemistry 58:213-218; and, (2001) *The Ribosome*. Cold Spring harbor Laboratory Press, Cold Spring Harbor, N.Y.), it is likely that aaRSs genes for the incorporation of unnatural amino acids discovered in *S. cerevisiae* can be 'cut and pasted' into higher eukaryotic organisms and used, in partnership with cognate tRNAs (see, e.g., K. Sakamoto, et al., (2002) *Site-specific incorporation of an unnatural amino acid into proteins in mammalian cells*, Nucleic Acids Res. 30:4692-4699; and, C. Kohrer, et al., (2001), *Import of amber and ochre suppressor tRNAs into mammalian cells: a general approach to site-specific insertion of amino acid analogues into proteins*, Proc. Natl. Acad. Sci. U.S.A. 98:14310-14315) to incorporate unnatural amino acids. The expansion of the genetic code of *S. cerevisiae* is therefore a gateway to expanding the genetic code of complex multicellular eukaryotic organisms. See, e.g., M. Buvoli, et al., (2000), *Suppression of nonsense mutations in cell culture and mice by multimerized suppressor tRNA genes*, Molecular & Cellular Biology 20:3116-3124. The tyrosyl pair derived from *Methanococcus jannaschii* TyrRS (MjTyrRS)/ tRNA (see e.g., L. Wang, & P. G. Schultz, (2002), *Expanding the Genetic Code*, Chem. Comm 1-10) which was previously used to expand the genetic code of *E. coli* is not orthogonal in eukaryotic organisms (e.g., P. Fechter, et al., (2001), *Major tyrosine identity determinants in Methanococcus jannaschii and Saccharomyces cerevisiae tRNA(Tyr) are conserved but expressed differently*, Eur. J. Biochem. 268:761-767) and a new orthogonal pair is required to expand the eukaryotic genetic code. Schimmel and coworkers have shown that the *E. coli* tyrosyl-tRNA synthetase (EcTyrRS)/ tRNA$_{CUA}$ pair suppresses amber codons in *S. cerevisiae*, and that *E. coli* tRNA$_{CUA}$ is not charged by endogenous aminoacyl tRNA synthetases in the yeast cytosol (FIG. 2). See also, e.g., H. Edwards, et al., (1991), *An Escherichia coli tyrosine transfer RNA is a leucine-specific transfer RNA in the yeast Saccharomyces cerevisiae*, Proc. Natl. Acad. Sci. U.S.A. 88:1153-1156; and, H. Edwards, & P. Schimmel (1990), *A bacterial amber suppressor in Saccharomyces cerevisiae is selectively recognized by a bacterial aminoacyl-tRNA synthetase*, Molecular & Cellular Biology 10:1633-1641. In addition, EcTyrRS has been shown not to charge yeast tRNA in vitro. See, e.g., Y. Kwok, & J. T. Wong, (1980), *Evolutionary relationship between Halobacterium cutirubrum and eukaryotes determined by use of aminoacyl-tRNA synthetases as phylogenetic probes*, Canadian Journal of Biochemistry 58:213-218; B. P. Doctor, et al., (1966), *Studies on the species specificity of yeast and E. coli tyrosine tRNAs*, Cold Spring Harbor Symp. Quant. Biol. 31:543-548; and, K. Wakasugi, et al., (1998), *Genetic code in evolution: switching species-specific aminoacylation with a peptide transplant*, EMBO Journal 17:297-305. Thus, the EcTyrRS/tRNA$_{CUA}$ pair is a candidate for an orthogonal pair in *S. cerevisiae*, as well as in higher eukaryotes (e.g., A. K. Kowal, et al., (2001), *Twenty-first aminoacyl-tRNA synthetase-suppressor tRNA pairs for possible use in site-specific incorporation of amino acid analogues into proteins in eukaryotes and in eubacteria*. [comment], Proc. Natl. Acad. Sci. U.S.A. 98 (2001) 2268-2273).

To broaden the substrate specificity of EcTyrRS in *E. coli*, Nishimura and coworkers screened an error prone PCR generated library of mutants of EcTyrRS and discovered a mutant with an improved ability to incorporate 3-azatyrosine. See, e.g., F. Hamano-Takaku, et al., (2000), *A mutant Escherichia coli tyrosyltRNA synthetase utilizes the unnatural amino acid azatyrosine more efficiently than tyrosine*, J. Biol. Chem. 275:40324-40328. However, this amino acid is incorporated throughout the proteome of *E. coli*, and the evolved enzyme still prefers tyrosine as a substrate. Yokoyama and coworkers screened a small collection of designed active site variants of EcTyrRS in a wheat germ translation system and discovered an EcTyrRS variant that utilizes 3-iodotyrosine more effectively than tyrosine. See, D. Kiga, et al., (2002), *An engineered Escherichia coli tyrosyl-tRNA synthetase for site-specific incorporation of an unnatural amino acid into proteins in eukaryotic translation and its application in a wheat germ cellfree system*, Proc. Natl. Acad. Sci. U.S.A. 99:9715-9720. In contrast to the enzymes we have evolved in *E. coli* (e.g., J. W. Chin, et al., (2002), *Addition of a Photocrosslinker to the Genetic Code of Escherichia coli*, Proc. Natl. Acad. Sci. U.S.A. 99:11020-11024; J. W. Chin, et al., (2002), *Addition of p-Azido-L-phenylalanine to the Genetic code of Escherichia coli*, J. Am. Chem. Soc. 124:9026-9027; L. Wang, et al., (2001), *Expanding the genetic code of Escherichia coli*, Science 292:498-500; and, L. Wang, et al., (2002), *Adding L-3-(2-naphthyl)alanine to the genetic code of E-coli*, J. Am. Chem. Soc. 124:1836-1837), this enzyme still incorporates tyrosine in the absence of the unnatural amino acid. See, e.g., D. Kiga, et al., (2002), *An engineered Escherichia coli tyrosyl-tRNA synthetase for site-specific incorporation of an unnatural amino acid into proteins in eukaryotic translation and its application in a wheat germ cellfree system*, Proc. Natl. Acad. Sci. U.S.A. 99:9715-9720. Recently, Yokoyama and coworkers have also demonstrated that this EcTyrRS mutant functions with a tRNA$_{CUA}$ from *Bacillus stearothermophilus* to suppress amber codons in mammalian cells. See, K. Sakamoto, et al., (2002), *Site-specific incorporation of an unnatural amino acid into proteins in mammalian cells*, Nucleic Acids Res. 30:4692-4699.

A requirement is that any amino acid added to the eukaryotic genetic code be incorporated with a fidelity similar to that of the common twenty amino acids. To accomplish this goal, a general, in vivo selection method has been used for the discovery of EcTyrRS/tRNA$_{CUA}$ variants that function in *S. cerevisiae* to incorporate unnatural amino acids, but none of the common amino acids, in response to the amber codon TAG. A major advantage of a selection is that enzymes which selectively incorporate unnatural amino acids can be rapidly selected and enriched from libraries of $10^8$ EcTyrRS active site variants, 6-7 orders of magnitude more diversity than has been screened in vitro. See, e.g., D. Kiga, et al., (2002), *An engineered Escherichia coli tyrosyl-tRNA synthetase for site-specific incorporation of an unnatural amino acid into proteins in eukaryotic translation and its application in a wheat germ cellfree system*, Proc. Natl. Acad. Sci. U.S.A. 99:9715-9720. This increase in diversity vastly increases the likelihood of isolating EcTyrRS variants for the incorporation of a diverse range of useful functionality with very high fidelity. See, e.g., L. Wang, & P. G. Schultz, (2002), *Expanding the Genetic Code*, Chem. Comm 1-10.

To extend the selection approach to *S. cerevisiae*, the transcriptional activator protein, GAL4 was used (see FIG. 1). See, e.g., A. Laughon, et al., (1984), *Identification of two proteins encoded by the Saccharomyces cerevisiae GAL4 gene*, Molecular & Cellular Biology 4:268-275; A. Laughon, & R. F. Gesteland, (1984), *Primary structure of the Saccharomyces cerevisiae GAL4 gene*, Molecular & Cellular Biology 4:260-267; L. Keegan, et al., (1986), *Separation of DNA binding from the transcription-activating function of a eukaryotic regulatory protein*, Science 231:699-704; and, M. Ptashne, (1988), *How eukaryotic transcriptional activators work*, Nature 335:683-689. The N-terminal 147 amino acids of this 881 amino acid protein form a DNA binding domain (DBD) that binds DNA sequence specifically. See, e.g., M. Carey, et al., (1989), *An amino-terminal fragment of GAL4 binds DNA as a dimer*, J. Mol. Biol. 209:423-432; and, E. Giniger, et al., (1985), *Specific DNA binding of GAL4, a positive regulatory protein of yeast*, Cell 40:767-774. The DBD is linked, by an intervening protein sequence, to a C-terminal 113 amino acid activation domain (AD) that can activate transcription when bound to DNA. See, e.g., J. Ma, & M. Ptashne, (1987), *Deletion analysis of GAL4 defines two transcriptional activating segments*, Cell 48:847-853: and, J. Ma, & M. Ptashne, (1987), *The carboxy-terminal 30 amino acids of GAL4 are recognized by GAL80*, Cell 50:137-142. We envisioned that by placing amber codons towards the N-terminal DBD of a single polypeptide that contained both the N-terminal DBD of GAL4 and its C-terminal AD, amber suppression by the EcTyrRS/tRNA$_{CUA}$ pair can be linked to transcriptional activation by GAL4 (FIG. 1, Panel A). By the choice of appropriate GAL4 activated reporter genes both positive and negative selections can be performed with the gene (FIG. 1, Panel B). While many reporter genes based on complementing the amino acid auxotrophy of a cell can be used for positive selections (eg: URA3, LEU2, HIS3, LYS2), the HIS3 gene is an attractive reporter gene, as the activity of the protein it encodes (imidazole glycerol phosphate dehydratase) can be modulated in a dose dependent manner by addition of 3-aminotriazole (3-AT). See, e.g., G. M. Kishore, & D. M. Shah, (1988), *Amino acid biosynthesis inhibitors as herbicides*, Annual Review of Biochemistry 57:627-663. In *S. cerevisiae*, fewer genes have been used for negative selections. One of several negative selection strategies (see, e.g., A. J. DeMaggio, et al., (2000), *The yeast split-hybrid system*, Method Enzymol. 328:128-137; H. M. Shih, et al., (1996), *A positive genetic selection for disrupting protein-protein interactions: identification of CREB mutations that prevent association with the coactivator CBP*, Proc. Natl. Acad. Sci. U.S.A. 93:13896-13901; M. Vidal, et al., (1996), *Genetic characterization of a mammalian protein-protein interaction domain by using a yeast reverse two-hybrid system*. [comment], Proc. Natl. Acad. Sci. U.S.A 93:10321-10326; and, M. Vidal, et al., (1996), *Reverse two-hybrid and one-hybrid systems to detect dissociation of protein-protein and DNA-protein interactions*. [comment], Proc. Natl. Acad. Sci. U.S.A. 93:10315-10320) that has been successfully used is the URA3/5-fluoroorotic acid (5-FOA) negative selection (e.g., J. D. Boeke, et al., (1984), *A positive selection for mutants lacking orotidine-5'-phosphate decarboxylase activity in yeast: 5-fluoroorotic acid resistance*, Molecular & General Genetics 197:345-346) system described in the 'reverse two-hybrid' system developed by Vidal and co-workers. See, M. Vidal, et al., (1996), *Genetic characterization of a mammalian protein-protein interaction domain by using a yeast reverse two-hybrid system*. [comment], Proc. Natl. Acad. Sci. U.S.A 93:10321-10326; and, M. Vidal, et al., (1996), *Reverse two-hybrid and one-hybrid systems to detect dissociation of protein-protein and DNA-protein interactions*. [comment], Proc. Natl. Acad. Sci. U.S.A. 93:10315-10320). In the reverse two-hybrid system, a genomically integrated URA3 reporter is placed under a tightly controlled promoter that contains GAL4 DNA binding sites. When two proteins that interact are produced as fusions to the GAL4 DBD and GAL4 AD they reconstitute the activity of GAL4 and activate transcription of URA3. In the presence of 5-FOA, the URA3 gene product converts 5-FOA to a toxic product, killing the cell. See, J. D. Boeke, et al., supra. This selection has been used to select for proteins that disrupt a protein-protein interaction and for mutations that disrupt a protein-protein interaction. A variant for screening small molecule inhibitors of protein-protein interactions has also been described. See, e.g., J. Huang, & S. L. Schreiber, (1997) *A yeast genetic system for selecting small molecule inhibitors of protein-protein interactions in nanodroplets*, Proc. Natl. Acad. Sci. U.S.A. 94:13396-13401.

The appropriate choice of amber codons in full length GAL4 allows efficient positive selections for active EcTyrRS variants using either a HIS3 or URA3 GAL4 activated reporters to complement histidine or uracil auxotrophy in yeast cells. Moreover, the URA3 reporter can be used in negative selections for inactive EcTyrRS variants in the presence of 5-FOA. In addition, colorometric assays using lacZ can be used to read out aminoacyl-tRNA synthetase activity in yeast cells.

Results and Discussion

The EcTyrRS gene was expressed under the control of the constitutive ADH1 promoter, and the tRNA$_{CUA}$ gene was expressed from the same high copy yeast plasmid (pEcTyrRStRNA$_{CUA}$, FIG. 1, Panel C). Upon co-transformation of pEcTyrRStRNA$_{CUA}$ and a low copy reporter that contains a single amber mutation between the DNA binding domain and activation domain of a chimericGAL4 construct into MaV203, cells grew on selective media lacking histidine and containing 10-20 mM 3-AT (FIG. 2). When MaV203 cells were transformed with the same GAL4 construct and either an inactive synthetase mutant (A5) or a construct lacking the EctRNA gene, no growth was observed on 10 mM 3-AT (FIG. 2). These experiments establish that EcTyrRS can be constitutively expressed in a functional form from the ADH1 promoter, that there is minimal endogenous amber suppression in MaV203, and that there is little charging of EctRNA$_{CUA}$ by yeast synthetases in this system. See, e.g., H. Edwards, et al., (1991), *An Escherichia coli tyrosine transfer RNA is a leucine-specific transfer RNA in the yeast Saccharomyces cerevisiae, Proc. Natl. Acad. Sci. U.S.A.* 88:1153-1156; and, H. Edwards, & P. Schimmel, (1990), *A bacterial amber suppressor in Saccharomyces cerevisiae is selectively recognized by a bacterial aminoacyl-tRNA synthetase, Molecular & Cellular Biology* 10:1633-1641. Since EcTyrRS does not charge *S. cerevisiae* tRNA (e.g., Y. Kwok, & J. T. Wong, (1980), *Evolutionary relationship between Halobacterium cutirubrum and eukaryotes determined by use of aminoacyl-tRNA synthetases as phylogenetic probes, Canadian Journal of Biochemistry* 58:213-218; B. P. Doctor, et al., (1966), *Studies on the species specificity of yeast and E. coli tyrosine tRNAs, Cold Spring Harbor Symp. Quant. Biol.* 31:543-548; and, K. Wakasugi, et al., (1998), *Genetic code in evolution: switching species-specific aminoacylation with a peptide transplant, EMBO Journal* 17:297-305), these experiments confirm that EcTyrRS/EctRNA$_{CUA}$ are an orthogonal pair in *S. cerevisiae*.

Figure 3:
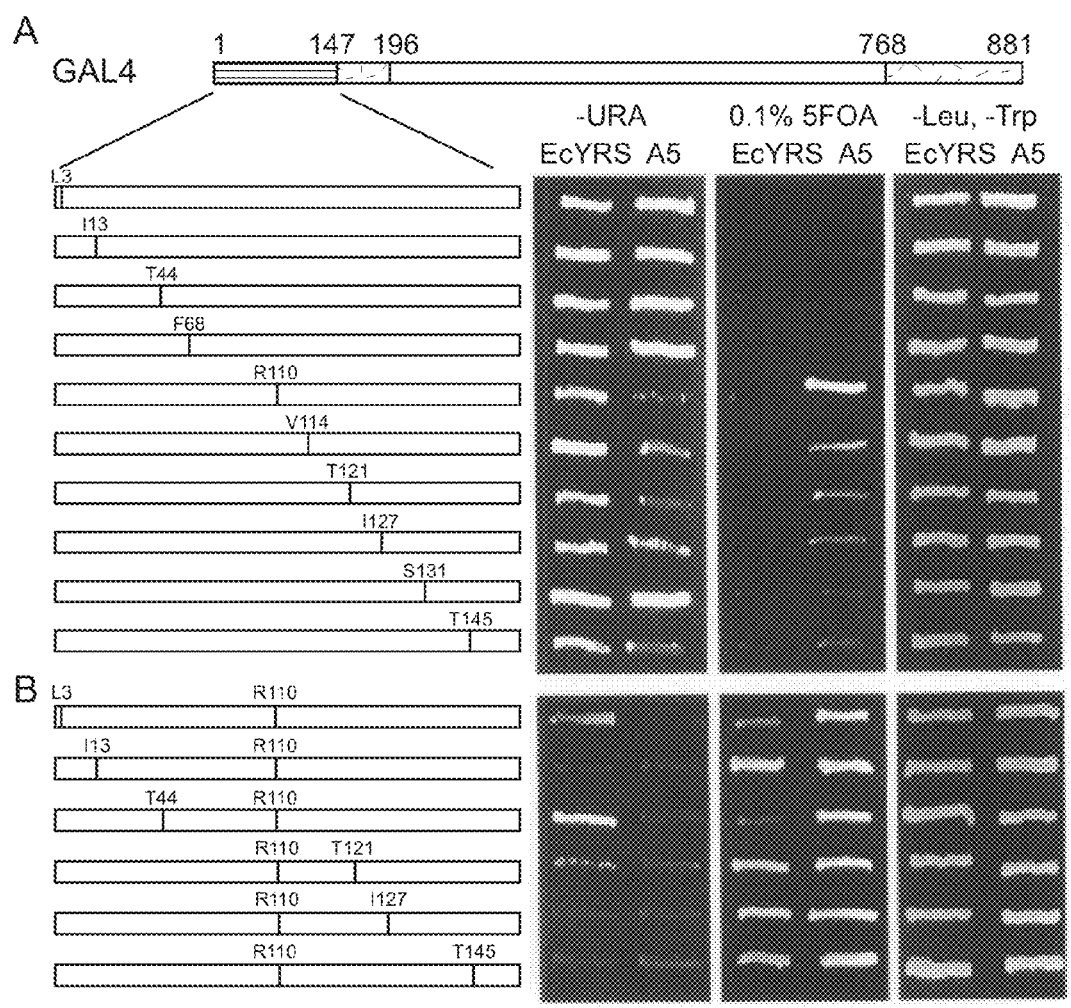
FIG. 3, Panel A and B illustrate EcTyrRS and tRNA$_{CUA}$ dependent phenotypes of 2nd generation GAL4 reporters on selective media. The DNA binding domain is indicated by the striped box and the major and cryptic activation domains are indicated in the hatched box.

While the first generation GAL4 chimera was able to activate transcription of the weak HIS3 reporter it was unable to activate transcription of the URA3 reporter in MaV203 sufficiently to allow significant growth on concentrations of 3-AT greater than 20 mM, or on −URA plates (FIG. 2). For the purposes of selection of EcTyrRS, variants a second generation GAL4 construct was made. This GAL4 reporter was designed to be more active, to have a greater dynamic range, and to avoid the accumulation of revertants. To increase the activity of the GAL4 reporters, full length GAL4 was used (which has a transcriptional activation activity twice that of a DBD-AD fusion (see, e.g., J. Ma, & M. Ptashne, (1987), *Deletion analysis of GAL4 defines two transcriptional activating segments, Cell* 48:847-853) under the control of a strong ADH1 promoter, and a high copy 2-µm plasmid (with a copy number 10-30 times that of the centromeric plasmid of the initial GAL4 chimera) was used. An increase in both the copy number of the plasmid and the activity of the protein it encodes should extend the dynamic range of the reporters. Amber mutations were targeted to the region of the GAL4 gene that encodes amino acid residues 2 and 147 (FIG. 3). This region is sufficient for sequence specific DNA binding (see, e.g., M. Carey, et al., (1989), *An amino-terminal fragment of GAL4 binds DNA as a dimer, J. Mol. Biol.* 209:423-432), and lies to the 5' side of the first cryptic activation domain in the GAL4gene (see, e.g., J. Ma, & M. Ptashne, (1987) *Deletion analysis of GAL4 defines two transcriptional activating segments, Cell* 48:847-853), such that the truncated products produced in the absence of amber suppression are not anticipated to activate transcription. The choice of amino acid codons to mutate was guided by previous saturation mutagenesis selections on GAL4 (see, e.g., M. Johnston, & J. Dover, (1988), *Mutational analysis of the GAL4-encoded transcriptional activator protein of Saccharomyces cerevisiae, Genetics* 120:63-74), as well as the X-ray structures of the N-terminal DNA binding domain of GAL4 (see, e.g., R. Marmorstein, et al., (1992), *DNA recognition by GAL4: structure of a protein-DNA complex.* [comment], *Nature* 356:408-414; and, J. D. Baleja, et al., (1992), *Solution structure of the DNA-binding domain of Cd2-GAL4 from S. cerevisiae.* [comment], *Nature* 356:450-453) and the NMR structure of its dimerization region. See, e.g., P. Hidalgo, et al., (2001), *Recruitment of the transcriptional machinery through GAL11P: structure and interactions of the GAL4 dimerization domain, Genes & Development* 15:1007-1020.

Full length GAL4 was cloned into a small pUC based vector to allow the rapid construction of 10 single amber mutants (at the codons for amino acids L3, I13, T44, F68, R110, V114, T121, I127, S131, T145) by site directed mutageneisis. GAL 4 and the resulting amber mutants were then subcloned into a 2-µm yeast vector under the control of the full length ADH1 promoter to create pGADGAL4 and a series of amber mutants denoted pGADGAL4 (xxTAG) (FIG. 1, Panel C), where xx denotes the amino acid codon in the GAL4 gene that was mutated to the amber codon. Each GAL4 mutant was co-transformed with either EcTyrRS/tRNA$_{CUA}$ or A5/tRNA$_{CUA}$ into MaV203 cells, converting transformants to leucine and tryptophan protrophy. pGADGAL4 itself transformed with very low efficiency (<10-3 times that of the GAL4 amber mutants) and is presumably deleterious to MaV203 cells at such high copy; no such effect was observed with the amber mutants of GAL4.

Figure 4A:
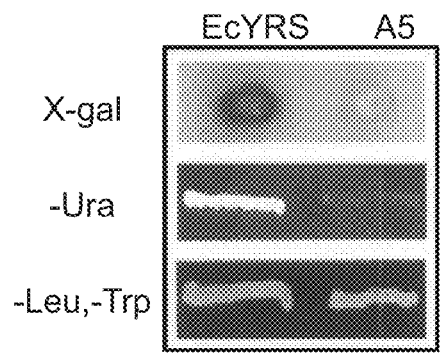
FIG. 4 Panels A, B and C illustrate pGADGAL4 (T44TAG, R110TAG) with and without EcTyrRS and various reporters in MaV203.
Figure 4B:
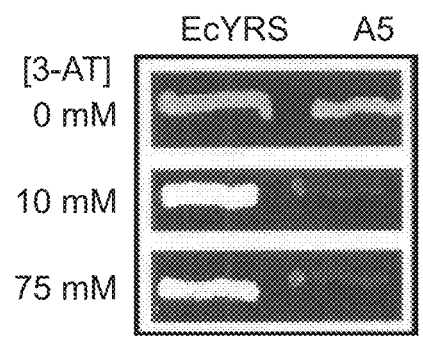
Figure 4C:
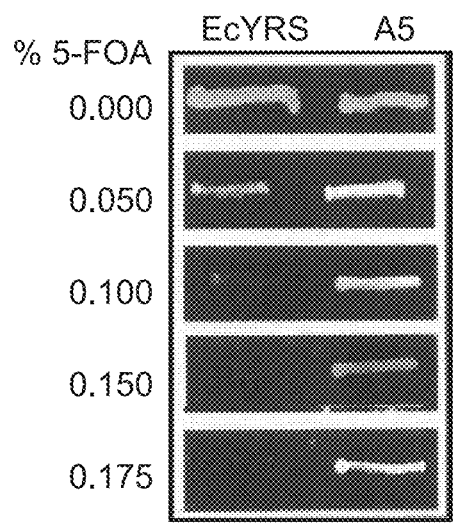

The phenotypes of GAL4 reporters, in the presence of an active or dead synthetase, were assayed on −URA plates, and 0.1% 5-FOA plates (FIG. 3, Panel A). Five GAL4 mutants (L3TAG, I13TAG, T44TAG, F68TAG, S131TAG) grew on −URA plates and failed to grow on 0.1% 5-FOA in the presence of either a wild type or inactive EcTyrRS. In these amber mutants, endogenous suppression is apparently sufficient to push the EcTyrRS/tRNA$_{CUA}$ mediated suppression beyond the dynamic range of the URA3 reporter in MaV203. Five GAL4 single amber mutants (R110TAG, V114TAG, T121TAG, I127TAG, T145TAG) grew in the absence of uracil and in the presence EcTyrRS/tRNA$_{CUA}$, (but not A5/tRNA$_{CUA}$) and showed the reverse phenotype on 5-FOA. These mutants show EcTyrRS dependent phenotypes that fall within the dynamic range of the URA3 reporter in MaV203. The cleanest EcTyrRS dependent phenotype on both −URA and 0.1% 5-FOA was observed with the R110TAG mutant of GAL4. However, this mutant showed some blue color in X-GAL assays when cotransformed with A5. To further improve the dynamic range, a series of six double amber mutants of GAL4 were made containing R110TAG (FIG. 3, Panel B), (L3TAG, R110TAG; I13TAG, R110TAG; T44TAG, R110TAG; R110TAG, T121TAG; R110TAG, I127TAG; R110TAG, T145TAG). Four of these double mutants (I13TAG, R110TAG; R110TAG, T121TAG; R110TAG, I127TAG and T145TAG, R110TAG) were unable to grow in the absence of uracil and grew on 0.1% 5-FOA. These double mutants have activities outside (below) the dynamic range of the plate assays. Two of the double mutants (L3TAG, R110TAG and T44TAG, R110TAG) grew in the presence of wild type EcTyrRS/tRNA$_{CUA}$, but not with A5/tRNA$_{CUA}$ on −URA plates; these mutants also showed the expected reciprocal phenotypes on 5-FOA. pGADGAL4 (T44TAG, R110TAG), the more active of these two GAL4 mutants, was selected for a more detailed characterization (FIG. 4). MaV203 containing pGADGAL4(T44TAG, R110TAG)/pEcTyrRS-tRNA$_{CUA}$ were blue on X-GAL but the corresponding strain containing pA5/tRNA$_{CUA}$ was not. Similarly MaV203 containing pGADGAL4(T44TAG, R110TAG)/pEcTyrRS/tRNA$_{CUA}$ grew robustly on plates with 3-AT concentrations up to 75 mM, and on −URA plates but the corresponding strain containing pA5/tRNA$_{CUA}$ failed to grow on 10 mM 3AT or in the absence of uracil. Taken together, the EcTyrRS dependent phenotypes of pGADGAL4(T44TAG, R110TAG) can span the dynamic range of the URA3, HIS3 and lacZ reporters in MaV203.

Figure 5A:
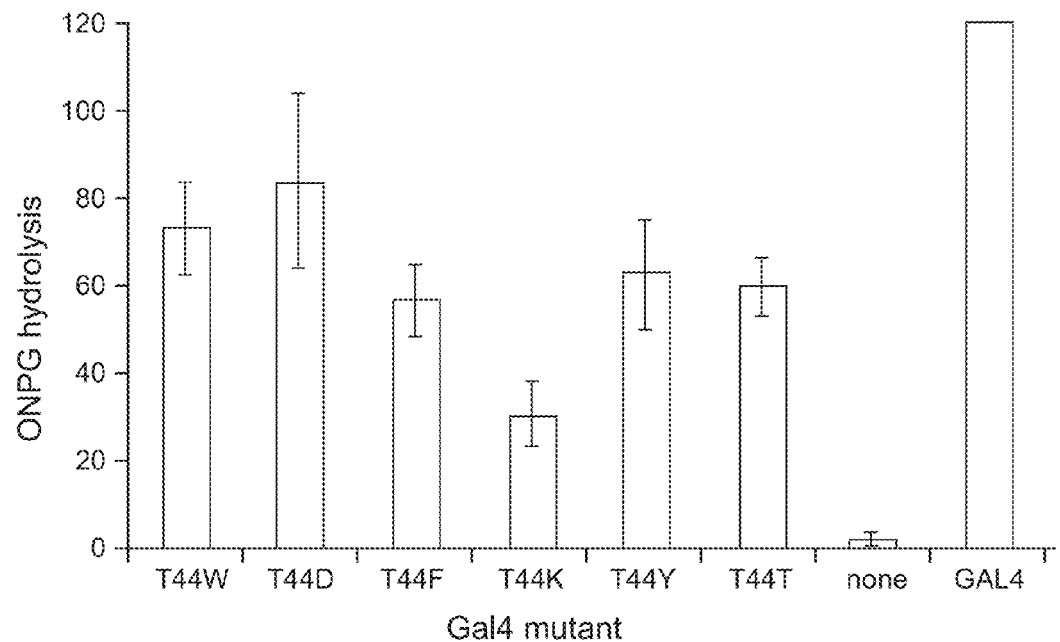
FIG. 5 Panels A and B illustrate ONPG hydrolysis with various GAL4 mutants, e.g., where residues T44 (A) and R110 (B) are permissive sites.
Figure 5B:
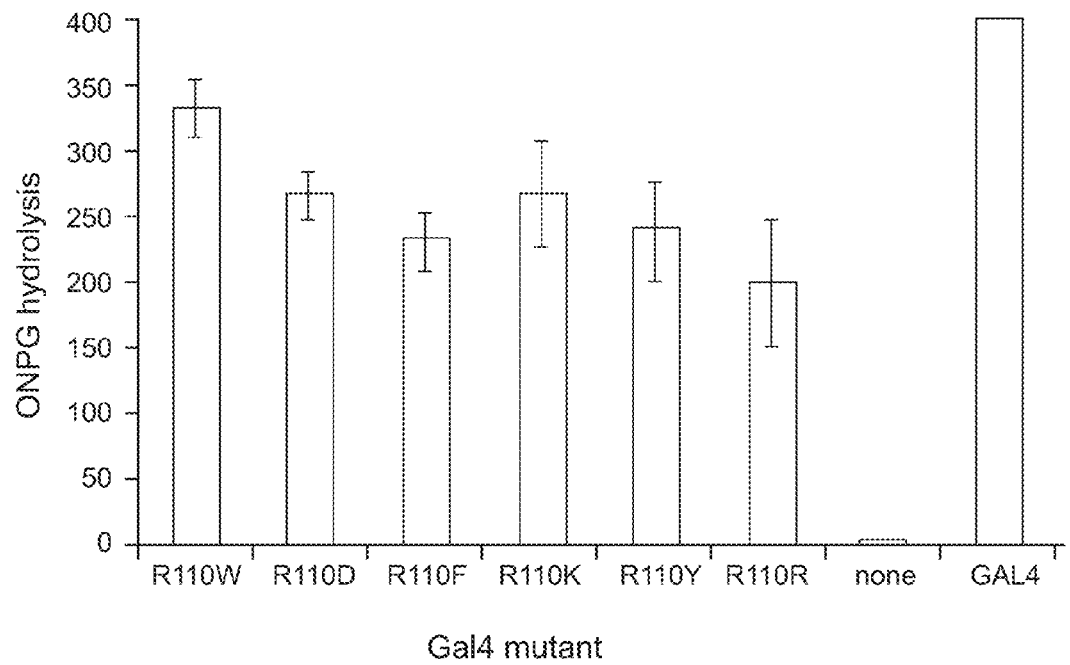

It was of interest to determine the activity of GAL4 mutants in which T44 or R110 were substituted with amino acids other than tyrosine, since the ability to substitute varied amino acids without altering the activity of GAL4 is likely to be useful for selection of mutant aminoacyl-tRNA synthetases that can incorporate unnatural amino acids into proteins. See, e.g., M. Pasternak, et al., (2000), *A new orthogonal suppressor tRNA/aminoacyl-tRNA synthetase pair for evolving an organism with an expanded genetic code, Helvetica Chemica Acta* 83:2277. A series of five mutants of residue T44 in GAL4, (T44Y, T44W, T44F, T44D, T44K) were constructed in pGADGAL4 (R110TAG), since pGADGAL4 is itself toxic. A similar series of mutants at position R110 in GAL4, (R110Y, R110W, R110F, R110D, R110K) in pGADGAL4(T44TAG) was constructed. These mutants are biased towards the large hydrophobic amino acid side chains that we are interested in incorporating into proteins, but also contain a positively and negatively charged residue as a stringent test of permissiveness. Each mutant was co-transformed with pEcTyrRS/tRNA$_{CUA}$ into MaV203 cells and leu+ trp+ isolates assayed for lacZ production by ortho-nitrophenyl-β-D-galactopyranoside (ONPG) hydrolysis (FIG. 5). The variation in activity between cells containing GAL4 with different amino acids substituted for either T44 or R110 was less than 3 fold in all cases. This minimal variability demonstrates the permissiveness of these sites to amino acid substitution without altering the transcriptional activity of GAL4. As expected from the activity of the single amber mutants assayed on selective plates, mutants of T44 made in the GAL4 (R110TAG) background lead to slower hydrolysis of ONPG than mutants of R110 made in the GAL4(T44TAG) background.

Figure 6:
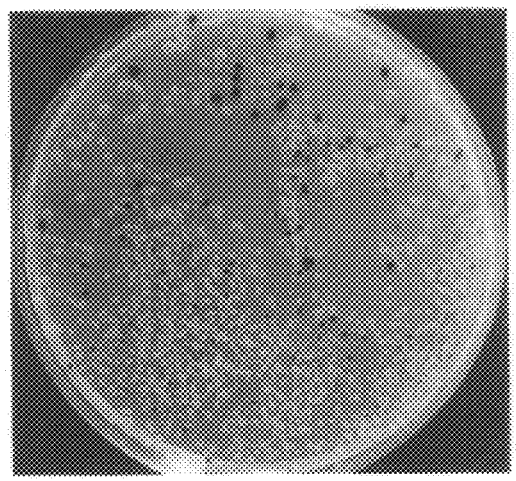
FIG. 6 shows the selection of active EcTyrRS clones. MaV203 containing a 1:10 mixture of pEcTyrRS-tRNA$_{CUA}$: pA5-tRNA$_{CUA}$ were plated at a 10$^3$ dilution on (–Leu, –Trp) plates (left) or (–Leu, –Trp, –His+50 mM 3-AT) plates (right) and processed using XGAL overlay.
Figure 6:
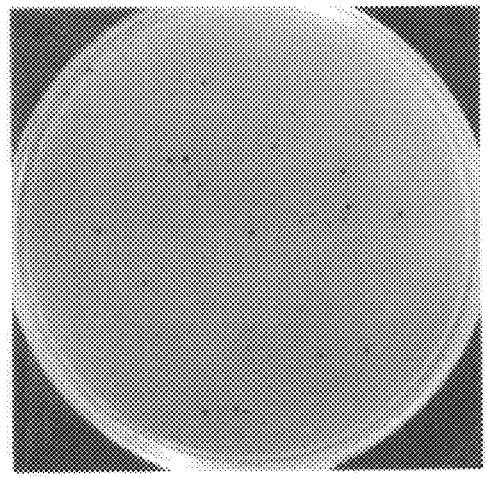

Model enrichment studies were performed to examine the ability of the system to select an active synthetase from a large excess of inactive synthetases (Table 1, Table 2, FIG. 6). This selection models the ability to select active synthetases from a library of variants in the presence of an unnatural amino acid. MaV203 cells containing the GAL4 (T44, R110) and EcTyrRS/tRNA$_{CUA}$ were mixed with a 10 to $10^6$ fold excess of GAL4(T44TAG, R110TAG) and A5/tRNA$_{CUA}$ as judged by both OD$_{660}$, and the fraction of colonies that turned blue when plated on nonselective –leu, –trp media and assayed by X-GAL overlay. Those cells able to survive on 50 mM 3-AT or in the absence of uracil were selected. The ratio of cells surviving on 3-AT or –URA that were blue in the X-GAL assay to those that were white, when compared to the same ratio in the absence of selection, clearly demonstrates that the positive selections can enrich active synthetases from dead synthetases by a factor >$10^5$ (Table 1). Measurement of accurate enrichments for starting ratios greater than 1:$10^5$ was generally not possible, because no more than $10^6$ cells can be conveniently plated without significant crosstalk between cells leading to unreliable phenotypes.

TABLE 2

MODEL NEGATIVE SELECTIONS FOR NON-FUNCTIONAL EcTyrRS (A5).

| StartingRatio, A5:EcYRS[a] | 1:10 | 1:$10^2$ | 1:$10^3$ | 1:$10^4$ |
|---|---|---|---|---|
| Cell Dilution | $10^3$ | $10^2$ | $10^2$ | $10^2$ 10 |
| -Leu,Trp (#white[b]) | 353 (22) | 1401 (31) | 1336 (2) | 1375 (0) >$10^4$ |
| 0.1% 5-FOA (#white[b]) | 16 (16) | 41 (41) | 4 (4) | 0 (—) 2 (2) |
| Enrichment factor | >10 | >45 | >600 | >0.67 × $10^4$ |

[a]Determined by OD$_{660}$
[b]On X-GAL

After a positive selection in the presence of unnatural amino acid, the selected cells will contain synthetases able to use natural amino acids and those able to use an added unnatural amino acid. To isolate those synthetases capable of using only the unnatural amino acid, cells encoding synthetases that use natural amino acids must be deleted from the selected clones. This can be accomplished with a negative selection in which the unnatural amino acid is withheld and those synthetases that function with a natural amino acid are removed. A model negative selection was performed in an analogous manner to the model positive selection. EcTyrRS/tRNA$_{CUA}$ was mixed with a 10 to $10^5$ fold excess of A5/tRNA$_{CUA}$ and selection was performed on 0.1% 5-FOA. Comparison of the ratio of cells surviving on 0.1% 5-FOA that were white in the X-GAL assay to those that were blue, to the same ratio under non-selective conditions (see Table 2) makes it clear that the negative selections can enrich dead synthetases from active synthetases by a factor of at least 0.6×$10^4$. Measurement of accurate enrichments for starting ratios greater than 1:$10^4$ was generally not possible, because no more than $10^5$ cells could be conveniently plated without significant crosstalk between cells leading to unreliable phenotypes.

A general approach was developed that allows both positive selection of aaRSs that recognize unnatural amino acids and negative selection of aaRSs that recognize natural amino acids. By varying the stringencies of the selection, a variety of synthetase activities can be isolated. Application of this method to a model selection using variants of EcTyrRS showed enrichments of greater than $10^5$ in a single round of either positive selection and greater than 0.6×$10^4$ in a single round of negative selection. These observations suggest that this method can provide rapid access to orthogonal aminoacyl-tRNA synthetases that function to site-specifically incorporation unnatural amino acids with a diversity of side chains into proteins in *S. cerevisiae*. Moreover, enzymes evolved in *S. cerevisiae* can be used in higher eukaryotes.

TABLE 1

MODEL POSITIVE SELECTIONS FOR FUNCTIONAL EcTyrRS.

| StartingRatio, EcYRS:A5[a] | 1:10 | 1:$10^2$ | 1:$10^3$ | 1:$10^4$ | 1:$10^5$ |
|---|---|---|---|---|---|
| Cell Dilution | $10^3$ | $10^3$ | $10^2$ $10^3$ | 10 $10^3$ | 1 $10^3$ |
| -Leu,Trp (#blue[b]) | 1360 (81) | 1262 (0) | >$10^3$ (1) 1774 (0) | >$10^4$ (—) 1092 (0) | >$10^4$ (—) 1472 (0) |
| -Ura (#blue[b]) | 152 (152) | 9 (9) | 8 (8) 0 (—) | 5 (5) 0 (—) | 16 (14) 0 (—) |
| -His + 50 mM3AT (#blue[b]) | 135 (135) | 7 (7) | 0 (—) 0 (—) | 3 (3) 0 (—) | 10 (10) 0 (—) |
| Enrichment factor | >10 | >$10^2$ | >$10^3$ | >$10^4$ | >$10^5$ |

[a]Determined by OD$_{660}$
[b]On X-GAL

Materials and Methods

Vector Construction

The tRNA$_{CUA}$ gene was amplified by PCR using the primers tRNA5'GGGGGGACCGGTGGGGGACCG-GTAAGCTTCCCGATAAGGGAGCAGG CCAG-TAAAAAGCATTACCCCGTGGTGGGTTCCCGA (SEQ ID NO:89), and tRNA3':GGCGGCGCTAGCAAGCTTC-CCGATAAGGGAGCAGGCCAGTAAAAAGGG AAGT-TCAGGGACTTTTGAAAAAAATGGTG-GTGGGGGAAGGAT (SEQ ID NO:90) from pESCSU3URA. This, and all other PCR reactions were preformed using the Expand PCR kit from Roche, according to the manufacturers instructions. After restriction endonuclease digestion with NheI and AgeI this tRNA gene was inserted between the same sites in the 2 μm vector pESCTrp (Stratagene) to yield ptRNA$_{CUA}$. The full length ADH1 promoter was amplified by PCR from pDBLeu (Invitrogen) with the primers PADHf: IGGGGGGACCG-GTIGGGGGGACCGGTCGGGATCGAAGAAATGATG-GTAAATGA AATAGGAAATCAAGG (SEQ ID NO:91) and pADHR: GGGGGGGAATTCAGTTGATTGTATGCT-TGGTATAGCTTGAAATATTGTCAGAA AAAGAAAC (SEQ ID NO:92), digested with AgeI and EcoRI. EcTyrRS was amplified with the primers pESCTrp1:TCATAACGA-GAATTCCGGGATCGAAGAAATGATGGTAAAT-GAAATA GGAAATCTCATAACGAGAATTCATG-GCAAGCAGTAACTTG (SEQ ID NO:93) and pESCTrp2: TTACTACGTGCGGCCGCATGGCAAGCAGTAACTT-GTTACTACGTGCG GCCGCTTATTTCCAGCAAATCA-GAC(SEQ ID NO:94). The EcTyrRS PCR product were digested with EcoRI and Not I. ptRNA$_{CUA}$ was then digested with Age I and Not I. A triple ligation of these three DNAs yielded pEcTyrRS-tRNA$_{CUA}$. Plasmid pA5-tRNA$_{CUA}$ in which amino acid residues (37, 126, 182, 183 and 186 in the active site are mutated to alanine) was created by overlap PCR using the oligonucleotides F37Afwd: CCGATCGCGCTCGCTTGCGGCTTCGATC (SEQ ID NO:95), N126Afwd: ATCGCGGCGAACGCCTAT-GACTGGTTC (SEQ ID NO:96), 182, 183, 186A, GTT-GCAGGGTTATGCCGCCGCCTGTGCGAACAAACAG-TAC (SEQ ID NO:97) and their reverse complements, as well as the flanking oligonucleotides, 4783: GCCGCTTT-GCTATCAAGTATAAATAG (SEQ ID NO:98), 3256: CAAGCCGACAACCTTGATTGG (SEQ ID NO:99) and pEcTyrRS-tRNA$_{CUA}$ as a template. The PCR product was digested with EcoRI and Not I and ligated into the large fragment of pEcTyrRS-tRNA$_{CUA}$ released upon digestion with the same enzymes. To construct 1st generation DB-AD reporters, the GAL4 DNA binding domain was PCR amplified from pGADT7 (Clontech) using the forward primer pADfwd: GGGGACAAGTTTGTACAAAAAAGCAGGC-TACGCCAATTTTAATCAAAGTGG GAATATTGC (SEQ ID NO:100) or pADfwd(TAG) GGGGACAAGTTTGTA-CAAAAAAGCAGGCTAGGCCAATTTTAAT-CAAAGTGG GAATATTGC (SEQ ID NO:101) and ADrev: GGGGACCACTTTGTACAAGAAAGCTGGGT-TACTCTTTTTTTGGGTTTGGTGG GGTATC (SEQ ID NO:102). These PCR products were cloned into the vector pDEST3-2 (invitrogen) using the Clonase procedure, according to the manufacturer's instructions, yielding pDB-AD and pDB-(TAG)-AD. To construct PGADGAL4 and variants, the GAL4 gene was amplified from pCL1 (Clontech) by PCR using the primers ADH1428-1429 AAGC-TATACCAAGCATACAATC (SEQ ID NO:103), and GAL4C: ACAAGGCCTTGCTAGCT-TACTCTTTTTTTGGGTTTGGTGGGGTATCTTC (SEQ ID NO:104). This fragment was cloned into the vector pCR2.1 TOPO (Invitrogen) according to the manufacturer's instructions. A clone containing the GAL4 gene (pCR2.1 TOPOGAL4) was digested with Hind III and the 2.7 kb GAL4 fragment gel purified and ligated to the large fragment of pGADT7 that had been digested with Hind III, treated with calf intestinal phosphotase and gel purified. Variants of the GAL4 gene were created by Quikchange reactions (Stratagene), carried out according to the manufacturers instructions, on pCR2.1 using primers listed in the supplementary information. GAL4 mutants were cloned into pGADT7 in the same manner as the wildtype GAL4 gene. All final constructs were confirmed by DNA sequencing.

Yeast Media and Manipulations

S. cerevisiae strain MaV203, (Invitrogen) is MATα; leu2-3,112; trp1 109; his3 Δ200; ade2-101; cyh2$^R$; cyh1$^R$; GAL4 Δ; gal80 Δ; GAL1::lacZ; HIS3UASGAL1::HIS3@LYS2; SPAL10UASGAL1::URA3. Yeast media were purchased from Clontech, 5-FOA and X-GAL were from Invitrogen and 3-AT was from BIO 101. YPER (Yeast Protein Extraction Reagent) and ONPG were purchased from Pierce Chemicals. Plasmid transformations were performed by the PEG/Lithium actetate method (see, e.g., D. Burke, et al., (2000) *Methods in Yeast Genetics*. Cold Spring Harbor Laboratory Press, Cold Spring Harbor, N.Y.) and transformants selected on the appropriate synthetic complete dropout media. To test the phenotypes conferred by various plasmid combinations on MaV203 yeast colonies from synthetic complete dropout plates of each transformation were resuspended in 15 μL of sterile water and streaked on the selective media of interest. Each phenotype was confirmed with at least five independent colonies. X-GAL assays were performed by the agarose overlay method. See, I. G. Serebriiskii, & E. A. Golemis, (2000), *Uses of lacZ to study gene function: evaluation of beta-galactosidase assays employed in the yeast two-hybrid system, Analytical Biochemistry* 285:1-15. Briefly, colonies or cell patches were lysed on agar plates by several additions of neatchlorofom. After chloroform evaporation 1 agarose containing 0.25 g/L of XGAL and buffered with 0.1 M Na$_2$PO$_4$ was applied to the plate surface. Once the agarose was set, plates were incubated at 37° C. for 12 h. ONPG assays were carried out by inoculation of 1 mL of SD –leu, –trp in a 96 well block with a single colony and incubated at 30° C. with shaking. The OD$_{660}$ of 100 μL of cells, and several dilutions of cells were recorded in parallel in a 96 well microtiter plate. Cells (100 μL) were mixed with a 100 μL of YPER:ONPG (1×PBS, 50% v/v YPER, 20 mM MgCl$_2$, 0.25% v/v β-mercaptoethanol, and 3 mM ONPG) and incubated with shaking at 37° C. Upon color development, cells were pelleted by centrifugation, the supernatant transferred to a clean 96 well microtiter plate (Nunclon, cat. #167008), and the A420 recorded. All data shown are the mean of trials from at least 4 independent clones and the error bars shown represent the standard deviation. ONPG hydrolysis was calculated using the equation: beta-galactosidase units=1000. A420/(V.t.OD$_{660}$), where V is the volume of cells in milliliters, t is the time of incubation in minutes. See, e.g., I. G. Serebriiskii, & E. A. Golemis, (2000), *Uses of lacZ to study gene function: evaluation of beta-galactosidase assays employed in the yeast two-hybrid system, Analytical Biochemistry* 285:1-15. One beta-galactosidase unit corresponds to the hydrolysis of 1 μmol of ONPG per minute per cell. See, Serebriiskii and Golemis, supra. Spectrophotometric readings were performed on a SPECTRAmax190 plate reader.

Model Selections

Positive selections: Two overnight cultures were grown in SD –Leu, –Trp. One contained MaV203 harboring pEc-TyrRS-tRNA$_{CUA}$/pGADGAL4(T44, R110TAG) and the other pA5-tRNASU3/pGADGAL4(T44, R110TAG). These cells were harvested by centrifugation and resuspended in 0.9% NaCl by vortexing. The two cell solutions were then diluted to identical OD$_{660}$s. MaV203 harboring pEcTyrRS-tRNA$_{CUA}$/pGADGAL4(T44, R110TAG) were serially diluted over 7 orders of magnitude and each dilution was then mixed 1:1 vol:vol with undiluted MaV203 harboring pA5-tRNA$_{CUA}$/pGADGAL4(T44, R110TAG) to afford defined ratios of cells containing active and inactive tyrosyl-tRNA synthetase. For each ratio a second serial dilution was performed in which the number of cells was decreased but the ratio of cells harboring pEcTyrRS-tRNA$_{CUA}$/pGAD-GAL4(T44, R110TAG) and pA5-tRNA$_{CUA}$/pGADGAL4 (T44, R110TAG) was maintained. These dilutions were plated on SD –Leu, -trp, SD –Leu, –Trp, –URA and SD –Leu, –Trp, –His+50 mM 3-AT. After 60 h the number of colonies on each plate was counted, using an Eagle Eye CCD camera (Stratagene), and the phenotype of survivors were confirmed with a X-GAL beta-galactosidase assay. Cells from several individual blue or white colonies were isolated and grown to saturation in SD –leu, –trp and the plasmid DNA isolated by standard methods. The identity of the EcTyrRS variant was confirmed by DNA sequencing.

Negative selection: The model negative selection was performed in an analogous manner to the positive selection except that MaV203 harboring pA5-tRNA$_{CUA}$/pGADGAL4 (T44, R110TAG) were serially diluted and mixed with a fixed density of MaV203 harboring pEcTyrRS-tRNA$_{CUA}$/pGADGAL4(T44, R110TAG). Cells were plated on SD –leu, –trp+0.1% 5-FOA, the number of colonies counted after 48 hours and the plates processed as described above.

The following oligonucleotides (Table 3) were used in combination with their reverse complements to construct site-directed mutants by Quikchange mutagenesis. The position of the mutation is denoted by bold text.

TABLE 3

OLIGONUCLEOTIDES USED TO
CONSTRUCT SITE-DIRECTED MUTANTS.

Amber
Mutants Oligo Sequence

L3TAG
(SEQ ID NO: 66)
5'-ATGAAGTAGCTGTCTTCTATCGAACAAGCATGCG-3'

I13TAG
(SEQ ID NO: 67)
5'-CGAACAAGCATGCGATTAGTGCCGACTTAAAAAG-3'

T44TAG
(SEQ ID NO: 68)
5'-CGCTACTCTCCCCAAATAGAAAAGGTCTCCGCTG-3'

F68TAG
(SEQ ID NO: 69)
5'-CTGGAACAGCTATAGCTACTGATTTTTCCTCG-3'

R110TAG
(SEQ ID NO: 70)
5'-GCCGTCACAGATTAGTTGGCTTCAGTGGAGACTG-3'

V114TAG
(SEQ ID NO: 71)
5'-GATTGGCTTCATAGGAGACTGATATGCTCTAAC-3'

T121TAG
(SEQ ID NO: 72)
5'-GCCTCTATAGTTGAGACAGCATAGAATAATGCG-3'

I127TAG
(SEQ ID NO: 73)
5'-GAGACAGCATAGATAGAGTGCGACATCATCATCGG-3'

S131TAG
(SEQ ID NO: 74)
5'-GAATAAGTGCGACATAGTCATCGGAAGAGAGTAGTAG-3'

TABLE 3-continued

OLIGONUCLEOTIDES USED TO
CONSTRUCT SITE-DIRECTED MUTANTS.

T145TAG
(SEQ ID NO: 75)
5'-GGTCAAAGACAGTTGTAGGTATCGATTGACTCGGC-3'

Permissive
Site Mutants Oligo Sequence

T44F
(SEQ ID NO: 76)
5'-CGCTACTCTCCCCAAATTTAAAAGGTCTCCGCTG-3'

T44Y
(SEQ ID NO: 77)
5'-CGCTACTCTCCCCAAATATAAAAGGTCTCCGCTG-3'

T44W
(SEQ ID NO: 78)
5'-CGCTACTCTCCCCAAATGGAAAAGGTCTCCGCTG-3'

T44D
(SEQ ID NO: 79)
5'-CGCTACTCTCCCCAAAGATAAAAGGTCTCCGCTG-3'

T44K
(SEQ ID NO: 80)
5'-CGCTACTCTCCCCAAAAAAAAAAGGTCTCCGCTG-3'

R110F
(SEQ ID NO: 81)
5'-GCCGTCACAGATTTTTTGGCTTCAGTGGAGACTG-3'

R110Y
(SEQ ID NO: 82)
5'-GCCGTCACAGATTATTTGGCTTCAGTGGAGACTG-3'

R110W
(SEQ ID NO: 83)
5'-GCCGTCACAGATTGGTTGGCTTCAGTGGAGACTG-3'

R110D
(SEQ ID NO: 84)
5'-GCCGTCACAGATGATTTGGCTTCAGTGGAGACTG-3'

R110K
(SEQ ID NO: 85)
5'-GCCGTCACAGATAAATTGGCTTCAGTGGAGACTG-3'

Example 2

An Expanded Eukaryotic Genetic Code

A general and rapid route for the addition of unnatural amino acids to the genetic code of *Saccharomyces cerevisiae* is described. Five amino acids have been incorporated into proteins efficiently, with high fidelity, in response to the nonsense codon TAG. The side chains of these amino acids contain a keto group, which can be uniquely modified in vitro and in vivo with a wide range of chemical probes and reagents; a heavy atom-containing amino acid for structural studies; and photocrosslinkers for cellular studies of protein interactions. This methodology not only removes the constraints imposed by the genetic code on our ability to manipulate protein structure and function in yeast, it provides a gateway to the systematic expansion of the genetic codes of multicellular eukaryotes.

Although chemists have developed a powerful array of methods and strategies to synthesize and manipulate the structures of small molecules (see, e.g., E. J. Corey, & X.-M. Cheng, *The Logic of Chemical Synthesis* (Wiley-Interscience, New York, 1995)), the ability to rationally control protein structure and function is still in its infancy. Mutagenesis methods are limited to the common 20 amino acid building blocks, although in a number of cases it has been possible to competitively incorporate close structural analogues of common amino acids throughout the proteome. See, e.g., K. Kirshenbaum, et al., (2002), *ChemBioChem* 3:235-7; and, V. Doring et al., (2001), *Science* 292:501-4. Total synthesis (see, e.g., B. Merrifield, (1986), *Science* 232:341-7 (1986)), and semi-synthetic methodologies (see, e.g., D. Y. Jackson et al., (1994) Science 266:243-7; and, P. E. Dawson, & S. B. Kent, (2000), *Annual Review of Biochemistry* 69:923-60, have made it possible to synthesize peptides and small proteins, but have more limited utility with proteins over 10 kilodaltons (kDa). Biosynthetic methods that involve chemically acylated orthogonal tRNAs (see, e.g., D. Mendel, et al., (1995), *Annual Review of Biophysics and Biomolecular Structure* 24:435-462; and, V. W. Cornish, et al. (Mar. 31, 1995), Angewandte Chemie-International Edition in English 34:621-633) have allowed unnatural amino acids to be incorporated into larger proteins, both in vitro (see, e.g., J. A. Ellman, et al., (1992), *Science* 255: 197-200) and in microinjected cells (see, e.g., see, e.g., D. A. Dougherty, (2000), *Current Opinion in Chemical Biology* 4:645-52). However, the stoichiometric nature of chemical acylation severely limits the amount of protein that can be generated. Thus, despite considerable efforts the properties of proteins, and possibly entire organisms, have been limited throughout evolution by the twenty genetically encoded amino acids (with the rare exceptions of pyrrolysine and selenocysteine (see, e.g., A. Bock et al., (1991), *Molecular Microbiology* 5:515-20; and, G. Srinivasan, et al., (2002), *Science* 296:1459-62)).

To overcome this limitation, new components were added to the protein biosynthetic machinery of the prokaryote *Escherichia coli* (*E. coli*) (e.g., L. Wang, et al., (2001), *Science* 292:498-500), which make it possible to genetically encode unnatural amino acids in vivo. A number of new amino acids with novel chemical, physical or biological properties have been incorporated efficiently and selectively into proteins in response to the amber codon, TAG. See, e.g., J. W. Chin et al., (2002), *Journal of the American Chemical Society* 124:9026-9027; J. W. Chin, & P. G. Schultz, (2002), ChemBioChem 11:1135-1137; J. W. Chin, et al., (2002), *PNAS United States of America* 99:11020-11024: and, L. Wang, & P. G. Schultz, (2002), *Chem. Comm.*, 1:1-10. However, because the translational machinery is not well conserved between prokaryotes and eukaryotes, components of the biosynthetic machinery added to *E. coli* cannot generally be used to site-specifically incorporate unnatural amino acids into proteins to study or manipulate cellular processes in eukaryotic cells.

Thus, translational components were created that would expand the number of genetically encoded amino acids in eukaryotic cells. *Saccharomyces cerevisiae* was chosen as the initial eukaryotic host organism, because it is a useful model eukaryote, genetic manipulations are facile (see, e.g., D. Burke, et al., (2000), *Methods in Yeast Genetics* (Cold Spring Harbor Laboratory Press, Cold Spring Harbor, N.Y.), and its translational machinery is highly homologous to that of higher eukaryotes (see, e.g., T. R. Hughes, (2002), *Funct. Integr. Genomics* 2:199-211). The addition of new building blocks to the *S. cerevisiae* genetic code requires a unique codon, tRNA, and aminoacyl-tRNA synthetase ('aaRS') that do not cross-react with any components of the yeast translational machinery (see, e.g., Noren et al., (1989) *Science* 244:182; Furter (1998) *Protein Sci.* 7:419; and, Liu et al., (1999) *PNAS USA* 96:4780). One candidate orthogonal pair is the amber suppressor tyrosyl-tRNA synthetase-tRNA$_{CUA}$ pair from *E. coli* (see, e.g., H. M. Goodman, et al., (1968), *Nature* 217:1019-24; and, D. G. Barker, et al., (1982), *FEBS Letters* 150:419-23). *E. coli* tyrosyl-tRNA synthetase (TyrRS) efficiently aminoacylates *E. coli* tRNA$_{CUA}$ when both are genetically encoded in *S. cerevisiae* but does not aminoacylate *S. cerevisiae* cytoplasmic tRNAs. See, e.g., H. Edwards, & P. Schimmel, (1990), *Molecular & Cellular Biology* 10:1633-41; and, H. Edwards, et al., (1991), *PNAS United States of America* 88:1153-6. In addition, *E. coli* tyrosyl tRNA$_{CUA}$ is a poor substrate for *S. cerevisiae* aminoacyl-tRNA synthetases (see, e.g., V. Trezeguet, et al., (1991), *Molecular & Cellular Biology* 11:2744-51.) but is processed and exported from the nucleus to the cytoplasm (see, e.g., S. L. Wolin, & A. G. Matera, (1999) *Genes & Development* 13:1-10) and functions efficiently in protein translation in *S. cerevisiae*. See, e.g., H. Edwards, & P. Schimmel, (1990) Molecular & Cellular Biology 10:1633-41; H. Edwards, et al., (1991), *PNAS United States of America* 88:1153-6; and, V. Trezeguet, et al., (1991), *Molecular & Cellular Biology* 11:2744-51. Moreover, *E. coli* TyrRS does not have an editing mechanism and therefore should not proofread an unnatural amino acid ligated to the tRNA.

To alter the amino acid specificity of the orthogonal TyrRS so that it aminoacylates tRNA$_{CUA}$ with a desired unnatural amino acid and none of the endogenous amino acids, a large library of TyrRS mutants was generated and subject to a genetic selection. On the basis of the crystal structure of the homologous TyrRS from *Bacillus stearothermophilus* (see, e.g., P. Brick, et al., (1989), *Journal of Molecular Biology* 208:83) five residues ((*B. stearothermophilus*, FIG. 7, Panel A)) in the active site of *E coli*. TyrRS that are within 6.5 Å of the para position of the aryl ring of bound tyrosine were mutated. For example, to create the EcTyrRS library of mutants the five positions targeted for mutation were first converted to alanine codons to produce the A5RS gene. This was split between two plasmids at a unique Pst I site in the gene. The library was created essentially as described by techniques known in the art (see, e.g., Stemmer et al., (1993) *Biotechniques* 14:256-265). One plasmid contains the 5' half of the A5RS gene, the other plasmid contains the 3' half of the A5RS gene. Mutagenesis was performed on each fragment by PCR with oligonucleotide primers for the amplification of the whole plasmid. The primers are doped, containing NNK (N=A+G+T+C and K=G+T) and Bsa I restriction endonuclease recognition sites. Digestion with Bsa I and ligation yielded two circular plasmids, each containing mutant copies of one half of the EcTyrRS gene. The two plasmids were then digested with Pst I and assembled into a single plasmid by ligation, leading to assembly of the full-length mutant genes. The mutant EcTyrRS genes were excised from this plasmid and ligated into pA5RS/tRNA$_{CUA}$ between EcoR I and Not I sites. The library was transformed into *S. cerevisiae* May 203: pGAD-GAL4 (2TAG) using the PEG-lithium acetate method yielding ~10$^8$ independent transformants.

A selection strain of *S. cerevisiae* NaV203: pGADGAL4 (2 TAG) (see, e.g., M. Vidal, et al., (1996), *PNAS United States of America* 93:10321-6; M. Vidal, et al., (1996), *PNAS United States of America* 93:10315-201 and, Chin et al., (2003) *Chem. Biol.* 10:511)] was transformed with the library to afford 10$^8$ independent transformants and grown in the presence of 1 mM unnatural amino acid (FIG. 8, Panel C). Suppression of two permissive amber codons in the transcriptional activator GAL4 leads to the production of full-length GAL4 and the transcriptional activation of the GAL4-responsive HIS3, URA3, and lacZ reporter genes (FIG. 8, Panel A). For example, the permissive codons are for T44 and R110 of Ga14. Expression of HIS3 and URA3 in media lacking uracil (−ura), or containing 20 mM 3-aminotriazole (see, e.g., G. M. Kishore, & D. M. Shah, (1988), *Annual Review of Biochemistry* 57, 627-63) (3-AT, a competitive inhibitor of the His3 protein) and lacking histidine (−his), allows clones expressing active aaRS-tRNA$_{CUA}$ pairs to be positively selected. If a mutant TyrRS charges the tRNA$_{CUA}$ with an amino acid, then the cell biosynthesizes histidine and uracil and survives. Surviving cells were amplified in the absence of 3-AT and unnatural amino acid to remove full-length GAL4 from cells that selectively incorporate the unnatural amino acid. To remove clones that incorporate endogenous amino acids in response to the amber codon, cells were grown on media containing 0.1% 5-fluoroorotic acid (5-FOA) but lacking the unnatural amino acid. Those cells expressing URA3, as a result of suppression of the GAL4 amber mutations with natural amino acids, convert 5-FOA to a toxic product, killing the cell. See, e.g., J. D. Boeke, et al., (1984), *Molecular & General Genetics* 197:345-6. Surviving clones were amplified in the presence of unnatural amino acid and reapplied to the positive selection. The lacZ reporter allows active and inactive synthetase-tRNA pairs to be discriminated colorometrically (FIG. 8, Panel B).

With the use of this approach, five novel amino acids with distinct steric and electronic properties (FIG. 7, Panel B) were independently added to the genetic code of *S. cerevisiae*. These amino acids include p-acetyl-L-phenylalanine (1), p-benzoyl-L-phenylalanine (2), p-azido-L-phenylalanine (3), O-methyl-L-tyrosine (4), and p-iodo-L-phenylalanine (5) (indicated by the numbers in FIG. 7, Panel B). The unique reactivity of the keto functional group of p-acetyl-L-phenylalanine allows selective modification of proteins with an array of hydrazine- or hydroxylamine-containing reagents in vitro and in vivo (See, e.g., V. W. Cornish, et al., (Aug. 28, 1996), Journal of the American Chemical Society 118:8150-8151; and, Zhang, Smith, Wang, Brock, Schultz, in preparation). The heavy atom of p-iodo-L-phenylalanine can prove useful for phasing x-ray structure data (with the use of multiwavelength anomalous diffraction). The benzophenone and phenylazide side chains of p-benzoyl-L-phenylalanine and p-azido-L-phenylalanine allow efficient in vivo and in vitro photocrosslinking of proteins (see e.g., Chin et al., (2002) *J. Am. Chem. Soc.*, 124:9026; Chin and Schultz, (2002) *Chem. Bio. Chem.* 11:1135; and, Chin et al., (2002) PNAS, USA 99:11020). The methyl group of O-methyl-L-tyrosine can be readily substituted with an isotopically labeled methyl group as a probe of local structure and dynamics with the use of nuclear magnetic resonance and vibrational spectroscopy. After three rounds of selection (positive-negative-positive), several colonies were isolated whose survival on −ura or on 20 mM 3-AT −his media was strictly dependent on the addition of the selected unnatural amino acid. See, FIG. 8, Panel D. The same clones were blue on x-gal only in the presence of 1 mM unnatural amino acid. These experiments demonstrate that the observed phenotypes result from the combination of the evolved aminoacyl-tRNA synthetase-tRNA$_{CUA}$ pairs and their cognate amino acids (see, Table 4).

For example, to select mutant synthetases, cells (~$10^9$) were grown for 4 hours in liquid SD −leu, −trp+1 mM amino acid. Cells were then harvested by centrifugation, resuspended in 0.9% NaCl, and plated on SD −leu, −trp, −his+20 mM 3-AT, +1 mM unnatural amino acid or SD −leu, −trp, −ura, +1 mM unnatural amino acid. After 48 to 60 hours at 30° C. the cells were scraped from the plates into liquid SD −leu, −trp and grown for 15 hours at 30° C. Cells were harvested by centrifugation, resuspended in 0.9% NaCl and plated on SD −leu, −trp+0.1% 5-FOA. After 48 hours at 30° C. cells were scraped into liquid SD −leu, −trp+1 mM unnatural amino acid and grown for 15 hours. Cells were then harvested by centrifugation, resuspended in 0.9% NaCl, and plated on SD −leu, −trp, −his+20 mM 3-AT, +1 mM unnatural amino acid or SD −leu, −trp, −ura, +1 mM unnatural amino acid. To screen phenotypes of selected cells, colonies (192) from each selection were transferred to wells of 96 well blocks containing 0.5 mL of SD −leu, −trp and grown at 30° C. for 24 hours. Glycerol (50% v/v; 0.5 mL) was added to each well, and the cells replica plated onto agar (SD −leu, −trp; SD −leu, −trp, −his, +20 mM 3-AT; SD −leu, −trp, −ura) in the presence or absence of 1 mM unnatural amino acid. X-Gal assays were performed on SD −leu, −trp plates using the agarose overlay method.

To further demonstrate that the observed phenotypes are due to site-specific incorporation of the unnatural amino acids by the orthogonal mutant TyrRS/tRNA pairs, mutants of human superoxide dismutase 1 (hSOD) (see, e.g., H. E. Parge, et al., (1992), *PNAS United States of America* 89:6109-13) containing each unnatural amino acid were generated and characterized.

For example, the addition of DNA encoding a C-terminal hexahistidine tag, and mutation of the codon for Trp 33 to an amber codon in the human superoxide dismutase gene was performed by overlap PCR using PS356 (ATCC) as a template. hSOD (Trp 33 TAG) HIS was cloned between the GAL1 promoter and CYC1 terminator from pYES2.1 (Invitrogen, Carlsbad, Calif. USA). Mutant synthetase and tRNA genes on pECTyrRS-tRNA$_{CUA}$ derived plasmids were co-transformed with pYES2.1 hSOD (Trp 33 TAG) HIS into the strain InvSc (Invitrogen). For protein expression, cells were grown in SD −trp, −ura+raffinose and expression induced at an OD$_{660}$ of 0.5 by the addition of galactose. HSOD mutants were purified by Ni-NTA chromatography (Qiagen, Valencia, Calif., USA).

Production of hexa-histidine-tagged hSOD from a gene containing an amber codon at position 33 was strictly dependent on p-acetylPheRS-1-tRNA$_{CUA}$ and 1 mM p-acetyl-L-phenylalanine (<0.1% by densitometry, in the absence of either component) (See FIG. 9). p-Acetyl-L-phenylalanine containing full-length hSOD was purified (e.g., by Ni-NTA affinity chromatography) with a yield of 50 ng/mL, comparable to that purified from cells containing *E. coli* TyrRStRNA$_{CUA}$. For comparison, wild type hSODHIS could be purified with a yield of 250 ng/mL under identical conditions.

Figure 9:
FIG. 9 illustrates protein expression of human superoxide dismutase (hSOD) (33TAG)HIS in *S. cerevisiae* genetically encoding unnatural amino acids as indicated in FIG. 7, Panel B.
Figure 10A:
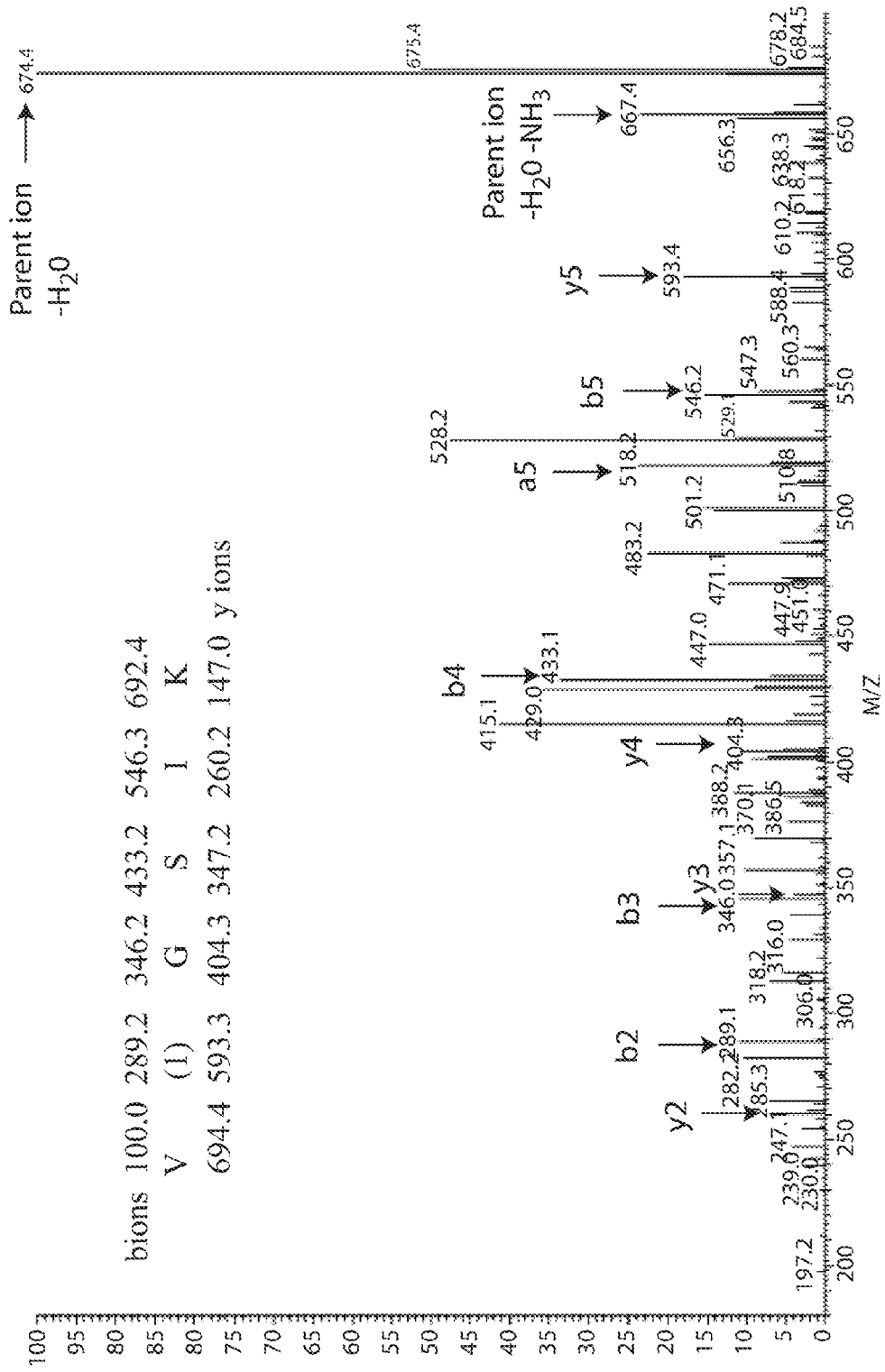
FIG. 10, Panels A-H illustrate tandem mass spectrum of the tryptic peptide VY*GSIK (SEQ ID NO:87) containing the unnatural amino acids (denoted Y*) as indicated in FIG. 7, Panel B.
Figure 10B:
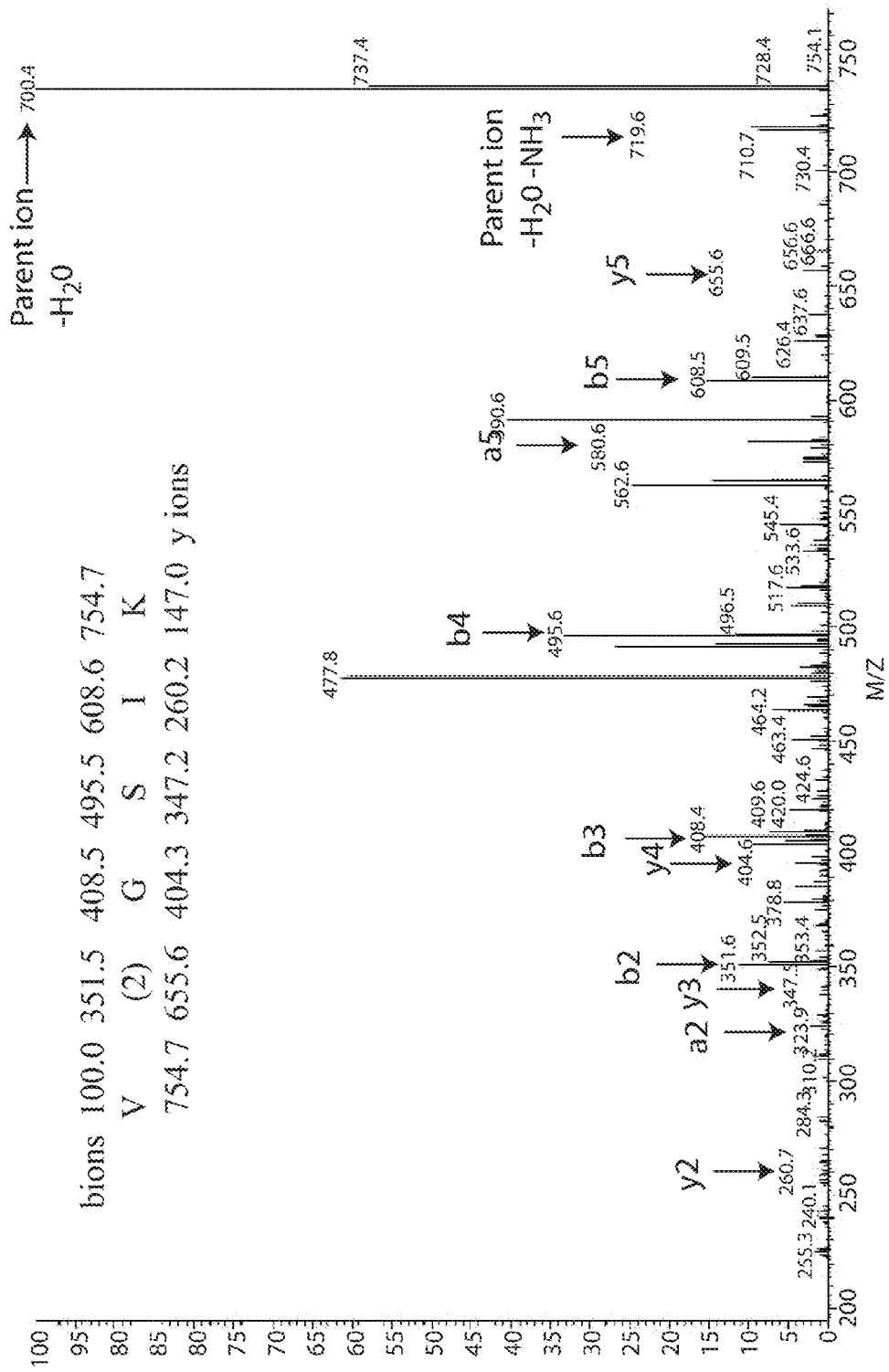
Figure 10C:
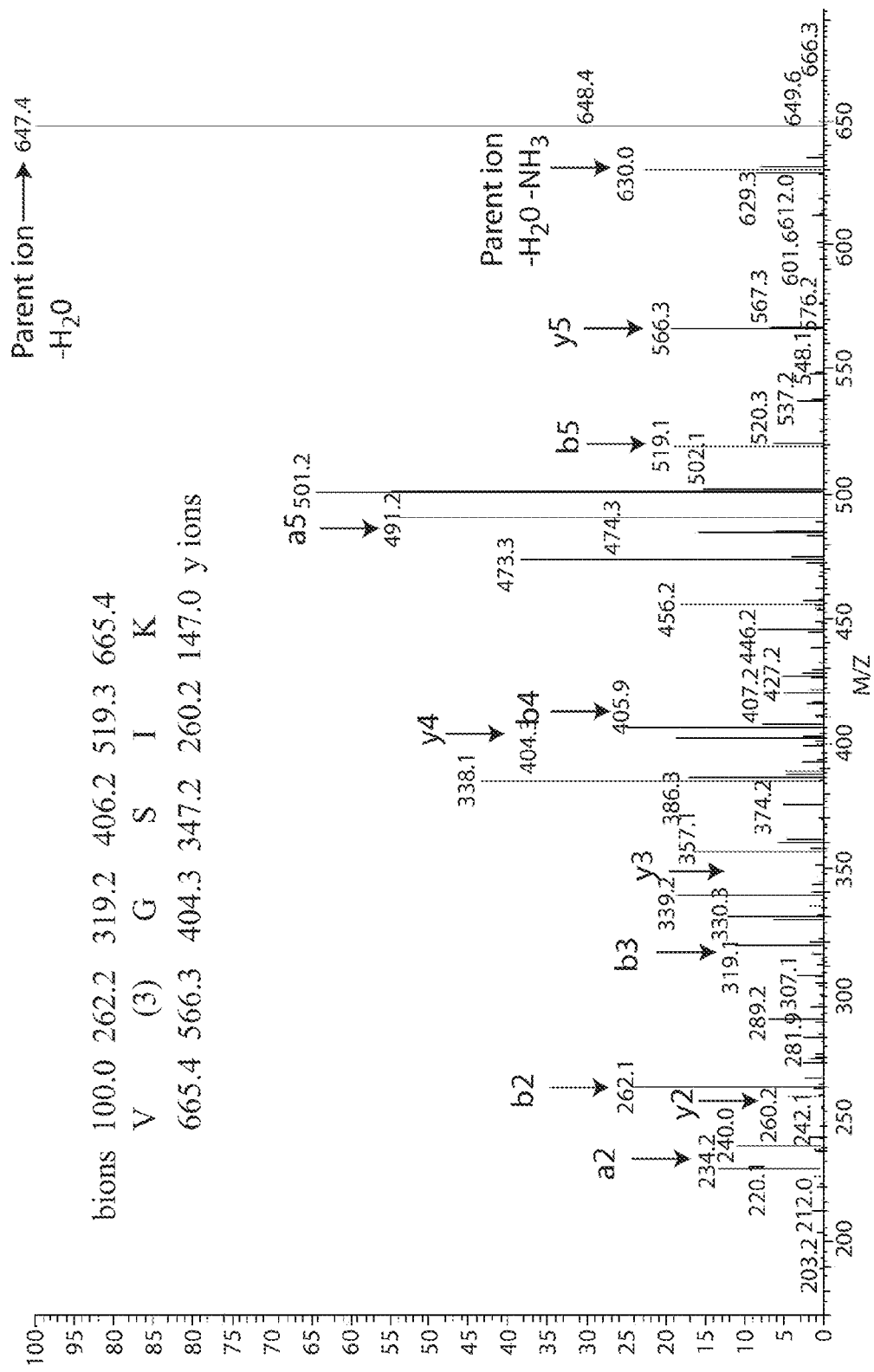
Figure 10D:
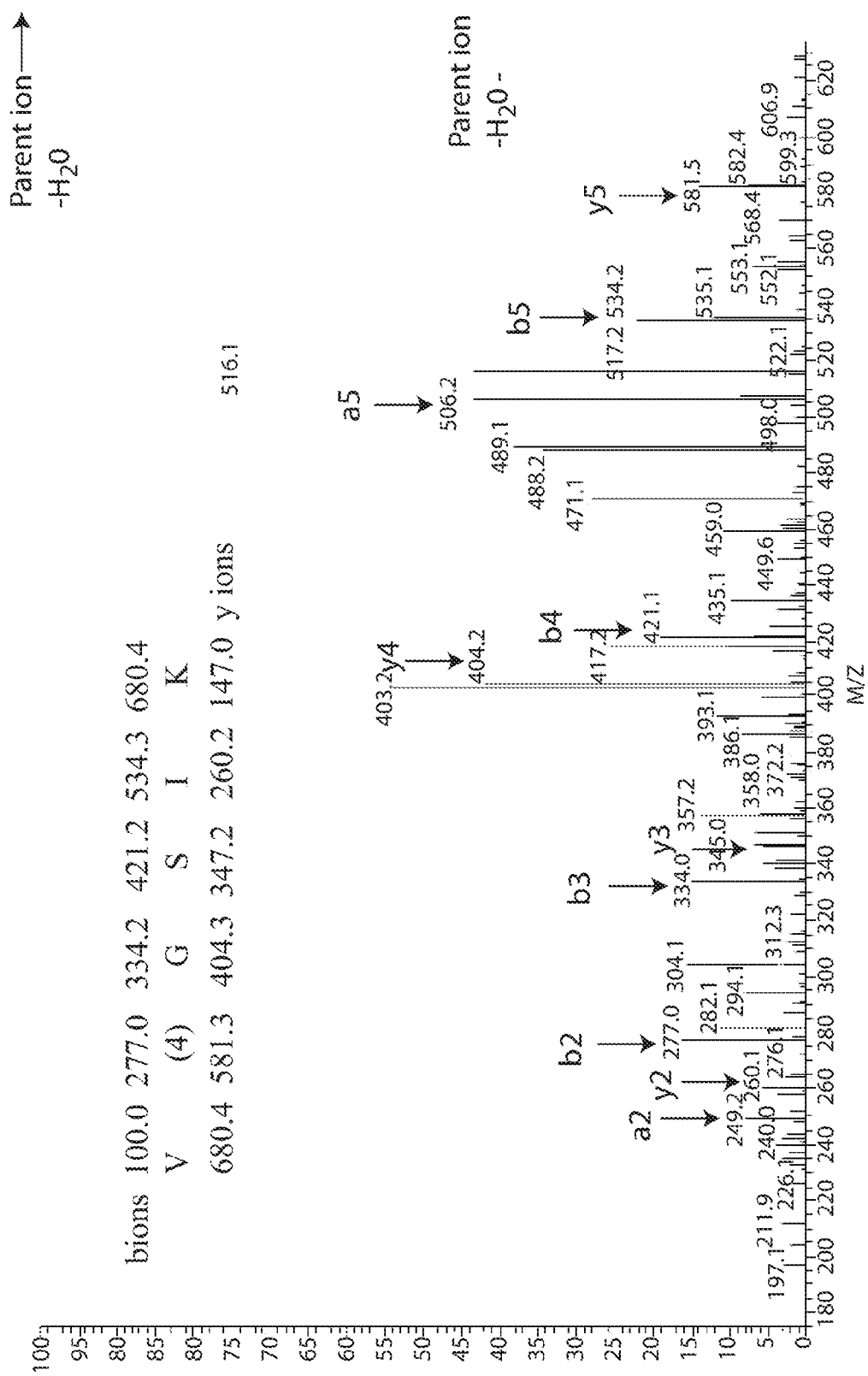
Figure 10E:
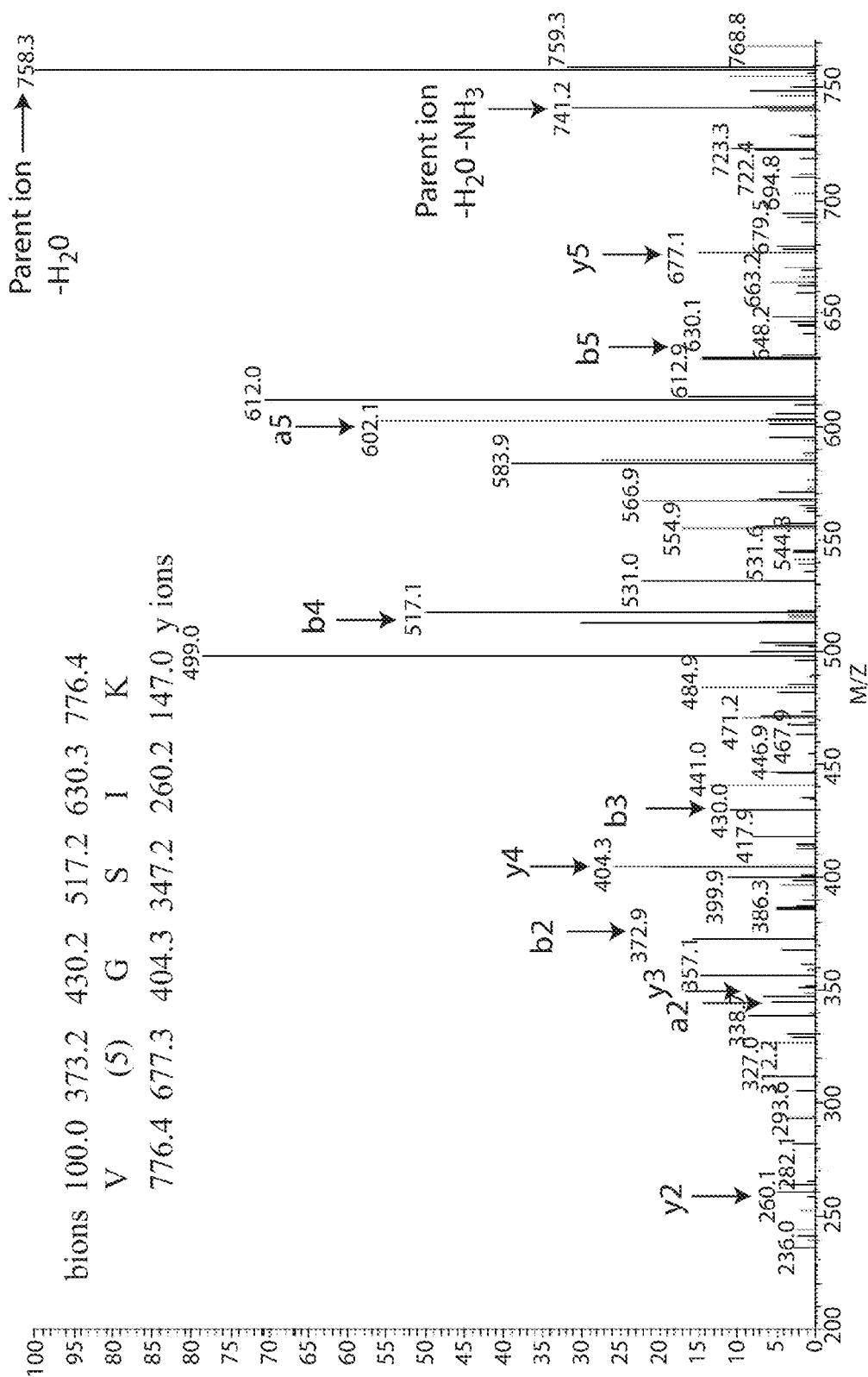
Figure 10F:
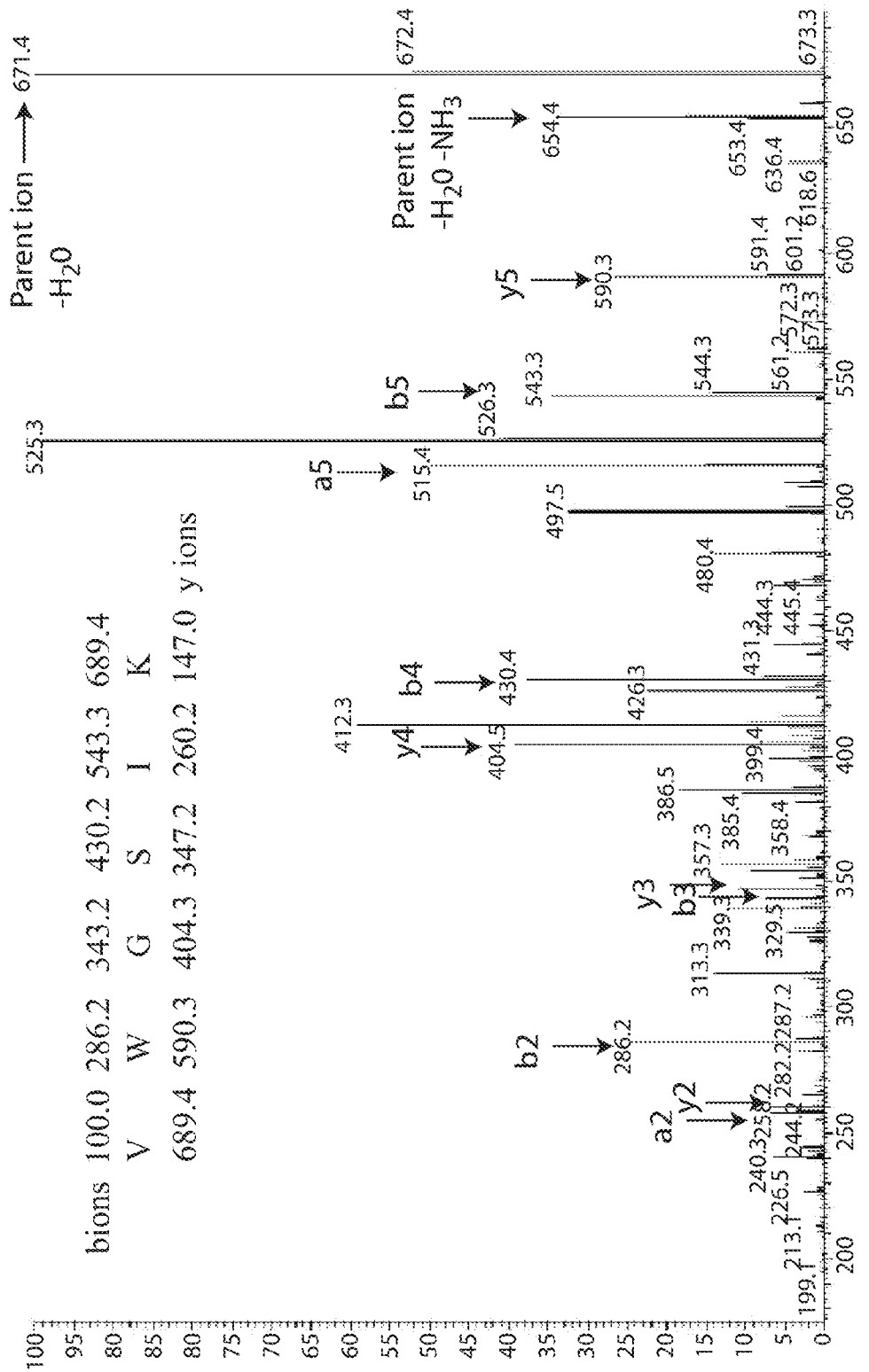
Figure 10G:
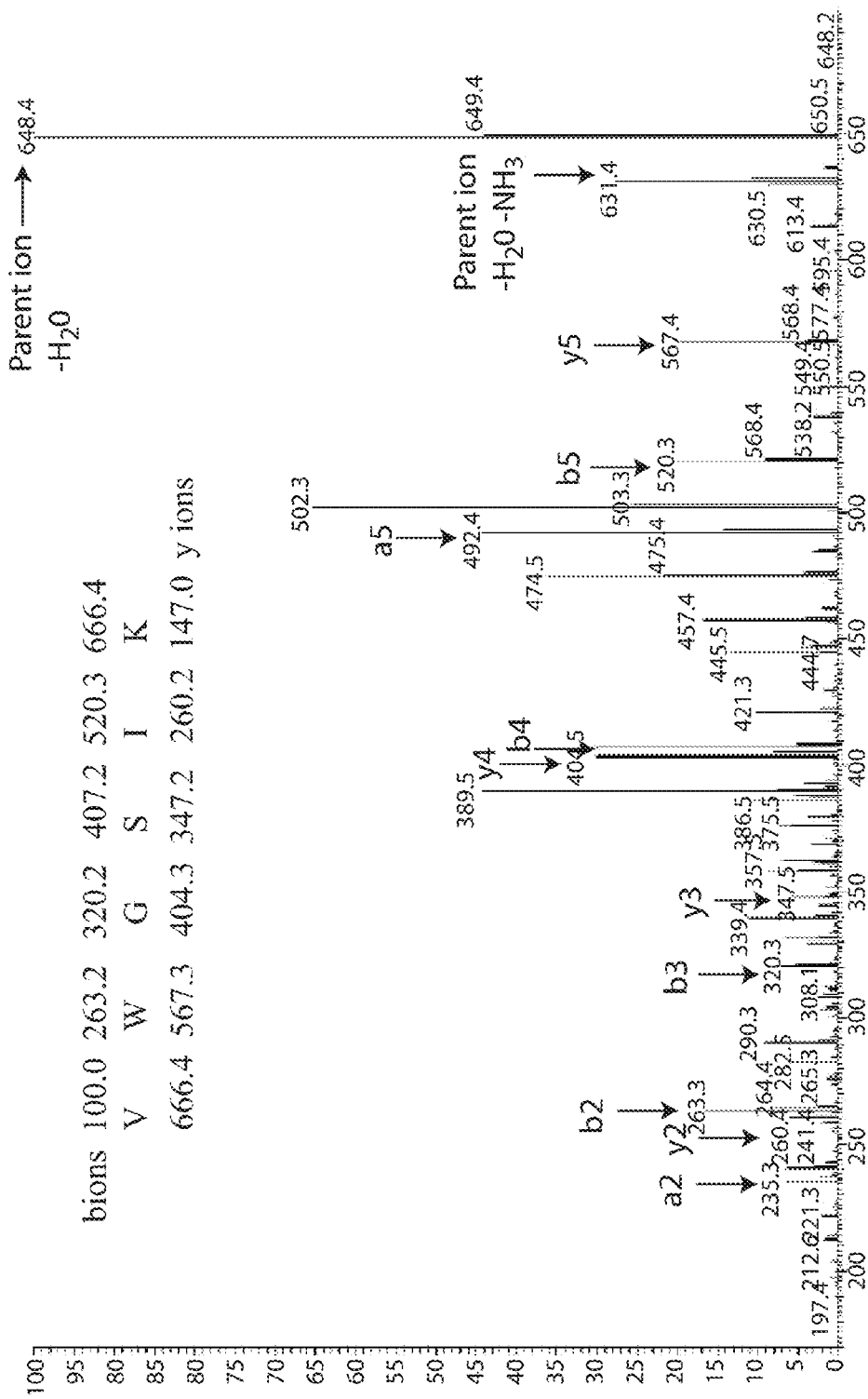
Figure 10H:
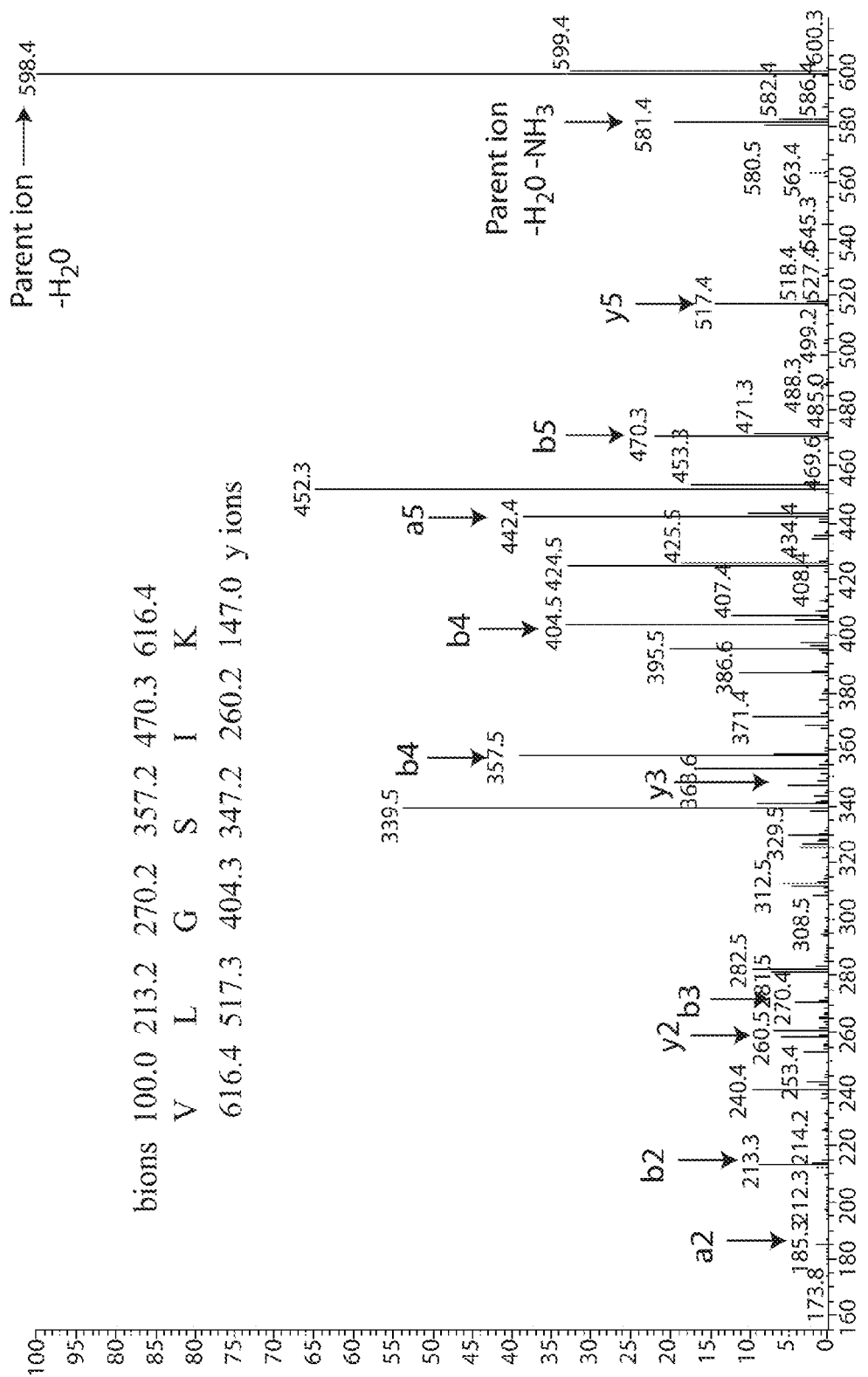

FIG. 9 illustrates protein expression of hSOD (33TAG) HIS in *S. cerevisiae* genetically encoding unnatural amino acids (as illustrated in FIG. 7, Panel B and indicated in FIG. 9 by their numbering in FIG. 7, Panel B). The top portion of FIG. 9 illustrates SDS-polyacrylamide gel electrophoresis of hSOD purified from yeast in the presence (+) and absence (−) of the unnatural amino acid indicated by the number, which corresponds to unnatural amino illustrated in FIG. 7, Panel B stain with Coomassie. Cells contain the mutant synthetase-tRNA pair selected for the amino acid indicated. The center portion of FIG. 9 illustrates a western blot probed with an antibody against hSOD. The bottom portion of FIG. 9 illustrates a western blot probed with an antibody against the C-terminal His6 tag.

The identity of the amino acid incorporated was determined by subjecting a tryptic digest of the mutant protein to liquid chromatography and tandem mass spectrometry. For example, for mass spectrometry protein bands were visualized by colloidal Coomassie stain. Gel bands corresponding to wild-type and mutant SOD were excised from polyacrylamide gels, sliced into 1.5-mm cubes, reduced and alkylated, then subjected to trypsin hydrolysis essentially as described. See, e.g., A. Shevchenko, et al., (1996), *Analytical Chemistry* 68, 850-858. Tryptic peptides containing the unnatural amino acid were analyzed by nanoflow reversed-phase HPLC/µESI/MS with an LCQ ion trap mass spectrometer. Liquid chromatography tandem mass spectrometry (LC-MS/MS) analysis was performed on a Finnigan LCQ Deca ion trap mass spectrometer (Thermo Finnigan) fitted with a Nanospray HPLC (Agilent 1100 series). See, e.g., FIG. 10, Panels A-H.

The precursor ions corresponding to the singly and doubly charged ions of the peptide Val-Y*-Gly-Ser-Ile-Lys (SEQ ID NO:87) containing the unnatural amino acids (denoted Y*) were separated and fragmented with an ion trap mass spectrometer. The fragment ion masses could be unambiguously assigned, confirming the site-specific incorporation of p-acetyl-L-phenylalanine (see, FIG. 10, Panel A). No indication of tyrosine or other amino acids in place of p-acetyl-L-phenylalanine was observed, and a minimum of 99.8% incorporation purity was obtained from the signal-to-noise ratio of the peptide spectra. Similar fidelity and efficiency in protein expression were observed when p-benzoylPheRS-1, p-azidoPheRS-1, O-meTyrRS-1, or p-iodoPheRS-1 was used to incorporate p-benzoyl-L-phenylalanine, p-azido-L-phenylalanine, O-methyl-L-tyrosine, or p-iodo-L-phenylalanine into hSOD (See, FIG. 9, and FIG. 10, Panels A-H). In the experiments, p-Azido-L-phenylalanine is reduced to p-amino-L-phenylalanine in sample preparation, and the latter is observed in mass spectra. The reduction does not occur in vivo by chemical deriviatation of purified SOD containing p-azido-L-phenylalanine. In control experiments, hexa-histidine-tagged hSOD containing trypotophan, tyrosine, and leucine at position 33 was prepared and subject to mass spectrometry (See, FIG. 10, Panels F, G and H). Ions containing amino acid 33 were clearly visible in the mass spectra of these samples.

The independent addition of five unnatural amino acids to the genetic code of *S. cerevisiae* demonstrates the generality of our method and suggests that it can be applicable to other unnatural amino acids including spin-labeled, metal-binding, or photoisomerizable amino acids. This methodology can allow the generation of proteins with new or enhanced properties as well as facilitate control of protein function in yeast. Moreover, in mammalian cells the *E. coli* tyrosyl-tRNA synthetase forms an orthogonal pair with the *B. stearothermophilus* tRNA$_{CUA}$. See, e.g., Sakamoto et al., (2002) *Nucleic Acids Res.* 30:4692. Therefore one can use the aminoacyl-tRNA synthethases that have been evolved in yeast to add unnatural amino acids to the genetic codes of higher eukaryotes.

TABLE 4

SEQUENCES OF SELECTED AMINOACYL-TRNA SYNTHETASES.

| | Residue # | | | | |
|---|---|---|---|---|---|
| | 37 | 126 | 182 | 183 | 186 | # clones |
| Ec TyrRS | Tyr | Asn | Asp | Phe | Leu | |
| p-IodoPheRS-1 | Val | Asn | Ser | Tyr | Leu | 1/8 |
| p-IodoPheRS-2 | Ile | Asn | Ser | Met | Leu | 1/8 |
| p-IodoPheRS-3 | Val | Asn | Ser | Met | Ala | 6/8 |
| p-OMePheRS-1 | Val | Asn | Ser | Met | Leu | 5/13 |

TABLE 4-continued

SEQUENCES OF SELECTED AMINOACYL-TRNA SYNTHETASES.

| | Residue # | | | | |
|---|---|---|---|---|---|
| | 37 | 126 | 182 | 183 | 186 | # clones |
| p-OMePheRS-2 | Thr | Asn | Thr | Met | Leu | 1/13 |
| p-OMePheRS-3 | Thr | Asn | Thr | Tyr | Leu | 1/13 |
| p-OMePheRS-4 | Leu | Asn | Ser | Met | Ser | 1/13 |
| p-OMePheRS-5 | Leu | Asn | Ser | Met | Ala | 1/13 |
| p-OMePheRS-6 | Thr | Asn | Arg | Met | Leu | 4/13 |
| p-acetylPheRS-1[a] | Ile | Asn | Gly | Met | Ala | 10/10 |
| p-benzoylPheRS-1 | Gly | Asn | Gly | Phe | Ala | 1/2 |
| p-benzoylPheRS-2 | Gly | Asn | Gly | Tyr | Met | 1/2 |
| p-azidoPheRS-1 | Leu | Asn | Ser | Met | Ala | 1/6 |
| p-azidoPheRS-2 | Val | Asn | Ser | Ala | Ala | 1/6 |
| p-azidoPheRS-3 | Leu | Asn | Ser | Ala | Ala | 1/6 |
| p-azidoPheRS-4 | Val | Asn | Ser | Ala | Val | 1/6 |
| p-azidoPheRS-5 | Ile | Asp | Asn | Phe | Val | 1/6 |
| p-azidoPheRS-6 | Thr | Asn | Ser | Ala | Leu | 1/6 |

[a]These clones also contain a Asp165Gly mutation

Example 3

Adding Amino Acid with Novel Reactivity to the Genetic Code of Eukaryotes

A site-specific, fast, reliable, and irreversible method of bioconjugation to proteins based on a [3+2] cycloaddition is demonstrated. There is a considerable need for chemical reactions that modify proteins under physiological conditions in a highly selective fashion. See, e.g., Lemineux, & Bertozzi, (1996) *TIBTECH*, 16:506-513. Most reactions currently used for the selective modification of proteins involve covalent bond formation between nucleophilic and electrophilic reaction partners, e.g. the reaction of α-haloketones with histidine or cysteine side chains. Selectivity in these cases is determined by the number and accessibility of the nucleophilic residues in the protein. In the case of synthetic or semisynthetic proteins, other more selective reactions can be used such as the reaction of an unnatural keto-amino acid with hydrazides or aminooxy compounds. See, e.g., Cornish, et al., (1996) *Am. Chem. Soc.*, 118:8150-8151; and, Mahal, et al., (1997) *Science*, 276:1125-1128. Recently, it has been possible to genetically encode unnatural amino acids (see, e.g., Wang, et al., (2001) *Science* 292:498-500; Chin, et al., (2002) *Am. Chem. Soc.* 124:9026-9027; and, Chin, et al., (2002) *Proc. Natl. Acad. Sci.*, 99:11020-11024), including ketone containing amino acids (see, e.g., Wang, et al., (2003) *Proc. Natl. Acad. Sci.*, 100:56-61; Zhang, et al., (2003) *Biochemistry*, 42:6735-6746; and, Chin, et al., (2003) *Science*, in press), in bacteria and yeast using orthogonal tRNA-synthetase pairs with altered amino acid specificities. This methodology has made possible the selective labeling of virtually any protein with a host of reagents including fluorophores, crosslinking agents and cytotoxic molecules.

A highly efficient method for the selective modification of proteins is described, which involves the genetic incorporation of azide or acetylene containing unnatural amino acids into proteins in response to, e.g., the amber nonsense codon, TAG. These amino acid side chains can then be modified by a Huisgen [3+2] cycloaddition reaction (see, e.g., Padwa, A. in *Comprehensive Organic Synthesis, Vol. 4*, (1991) Ed. Trost, B. M., Pergamon, Oxford, p. 1069-1109; and, Huisgen, R. in *1,3-Dipolar Cycloaddition Chemistry*, (1984) Ed. Padwa, A., Wiley, New York, p. 1-176) with alkynyl (acetylene) or azide derivatives, respectively.

Because this method involves a cycloaddition rather than a nucleophilic substitution, proteins can be modified with extremely high selectivity (another method that can be used is the ligand exchange on a bisarsenic compound with a tetracysteine motif, see, e.g., Griffin, et al., (1998) *Science* 281:269-272). This reaction can be carried out at room temperature in aqueous conditions with excellent regioselectivity (1.4>1.5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599. Indeed, Finn and coworkers have shown that this azide-alkyne [3+2] cycloaddition can be conducted on the surface of an intact cowpea mosaic virus. See, e.g., Wang, et al., (2003) *J. Am. Chem. Soc.*, 125:3192-3193. For another recent example of the electrophilic introduction of an azido group into a protein and a subsequent [3+2] cycloaddition, see, e.g., Speers, et al., (2003) *J. Am. Chem. Soc.*, 125:4686-4687.

Figure 11:
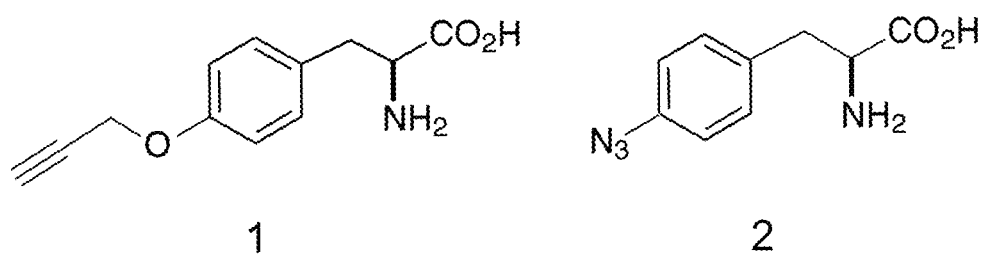
FIG. 11 illustrates examples of two unnatural amino acids (1) para-propargyloxyophenylalanine and (2) para-azidophenylalanine.

In order to selectively introduce either the alkynyl (acetylene) or azide functional group into eukaryotic proteins at unique sites, evolved orthogonal TyrRS/tRNA$_{CUA}$ pairs were generated in yeast that genetically encode the acetylene and azido amino acids, FIGS. 11, 1 and 2, respectively. The resulting proteins can be efficiently and selectively labeled with fluorophores in a subsequent cycloaddition reaction under physiological conditions.

Previously, an *E. coli* tyrosyl tRNA-tRNA synthetase pair was demonstrated as being orthogonal in yeast, i.e., neither the tRNA nor the synthetase cross react with the endogenous yeast tRNA or synthetases. See, e.g., Chin, et al., (2003) *Chem. Biol.*, 10:511-519. This orthogonal tRNA-synthetase pair has been used to selectively and efficiently incorporate a number of unnatural amino acids in yeast in response to the TAG codon (e.g., Chin, et al., (2003) *Science*, in press). In order to alter the amino acid specificity of the *E. coli* tyrosyl-tRNA synthetase to accept amino acid 1 or 2 of FIG. 11, a library of ~10$^7$ mutants was generated by randomizing the codons for Tyr$^{37}$, Asn$^{126}$, Asp$^{182}$, Phe$^{183}$, and Leu$^{186}$. These five residues were chosen based on a crystal structure of the homologous synthetase from *B. stearothermophilus*. To obtain a synthetase for which the particular amino acid serves as a substrate, a selection scheme was used in which the codons for Thr$^{44}$ and Arg$^{110}$ of the gene for the transcriptional activator GAL4 were converted to amber nonsense codons (TAG). See, e.g., Chin, et al., (2003) *Chem. Biol.*, 10:511-519. Suppression of these amber codons in the MaV203:pGADGAL4(2TAG) yeast strain leads to production of full length GAL4 (see, e.g., Keegan, et al., (1986) *Science,* 231:699-704; and, Ptashne, (1988) *Nature,* 335: 683-689) which in turn drives expression of the HIS3 and URA3 reporter genes. The latter gene products complement histidine and uracil auxotrophy allowing clones harboring active synthetase mutants to be selected in the presence of 1 or 2 of FIG. 11. Synthetases that load endogenous amino acids are removed by growth on medium lacking 1 or 2 of FIG. 11 but containing 5-fluoroorotic acid, which is converted into a toxic product by URA3. By passing the library through three rounds of selection (positive, negative, positive), we identified synthetases selective for 1 of FIG. 11 (pPR-EcRS1-5) and for 2 of FIG. 11 (pAZ-EcRS1-6) as shown in Table 8.

Figure 14:
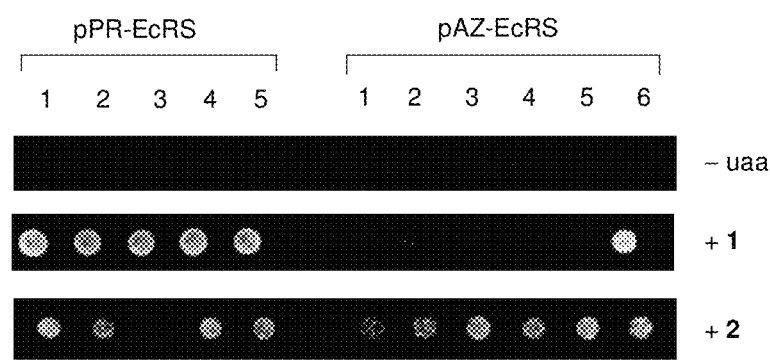
FIG. 14 illustrates growth of eukaryotic cells, e.g., *S. cerevisiae* cells, transformed with synthetase mutants in the absence or presence of 1 or 2 as indicated in FIG. 11 on SD media lacking uracil.

All synthetases show a strong sequence similarity, including a conserved Asn$^{126}$, suggesting an important functional role for this residue. Surprisingly, the synthetases pPR-EcRS-2 and pAZ-EcRS-6, evolved to bind 1 and 2 of FIG. 11 respectively, converged to the same sequence (Tyr37→Thr$^{37}$, Asn$^{126}$→Asn$^{126}$, Asp$^{182}$→Ser$^{82}$, and Phe$^{183}$→Ala$^{183}$, Leu$^{186}$→Leu$^{186}$). Both hydrogen bonds between the phenolic hydroxy group of bound tyrosine and Tyr$^{37}$ and Asp$^{182}$ are disrupted by mutations to Thr and Ser, respectively. Phe$^{183}$ is converted to Ala, possibly providing more space for the accommodation of the unnatural amino acid. To confirm the ability of this synthetase (and the other synthetases) to accept either amino acid as a substrate selection strains harboring the synthetase plasmids were grown on media lacking uracil (the same results were obtained for media lacking histidine) but supplemented with either 1 or 2 of FIG. 11. Growth results revealed that four of the five alkyne synthetases were able to load both unnatural amino acids onto its tRNA. The azido synthetases seem to be more selective, since only pAZ-EcRS-6 (which is identical with pPR-EcRS-2) was able to amino acylate its tRNA with both 1 and 2 of FIG. 11. The fact that no growth was detected in the absence of 1 or 2 of FIG. 11 suggests that the synthetases do not accept any of the 20 common amino acids as a substrate. See FIG. 14.

For all further experiments pPR-EcRS-2 (pAZ-EcRS-6) was used, allowing one to control which unnatural amino acid is incorporated simply by adding either 1 or 2 of FIG. 11 to media containing the expression strain. For protein production the codon for the permissive residue Trp$^{33}$ of human superoxide dismutase-1 (SOD) fused to a C-terminal 6×His tag was mutated to TAG. For example, human superoxide dismutase (Trp$^{33}$ TAG) HIS was cloned between the GAL1 promoter and CYC1 terminator from pYES2.1 (Invitrogen, Carlsbad, Calif. USA). Mutant synthetase and tRNA genes on pECTyrRS-tRNA$_{CUA}$ derived plasmids were co-transformed with pYES2.1 SOD(Trp$^{33}$ TAG) HIS into the strain InvSc (Invitrogen). For protein expression, cells were grown in SD –trp, –ura+raffinose and expression was induced at an OD$_{660}$ of 0.5 by the addition of galactose. Protein was expressed in the presence or absence of 1 mM 1 or 2 of FIG. 11 and purified by Ni-NTA chromatography (Qiagen, Valencia, Calif., USA).

Figure 12:
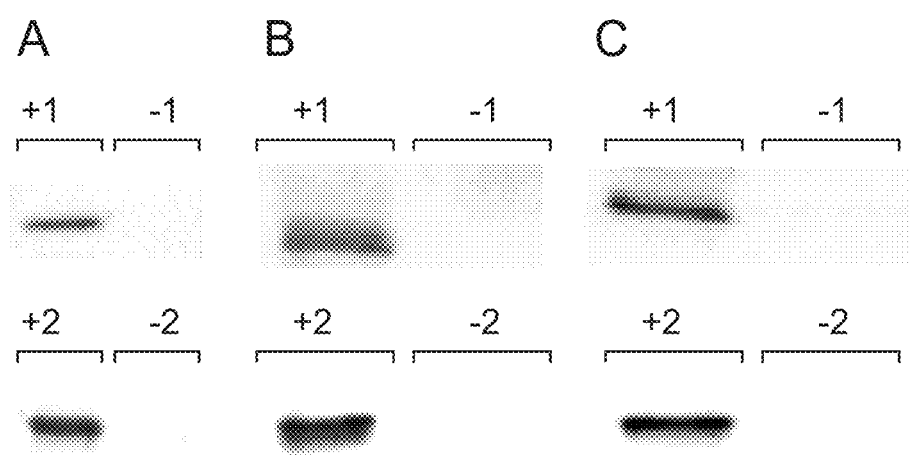
FIG. 12, Panels A, B and C illustrate SOD expression in the presence or absence of unnatural amino acids 1 and 2 indicated in FIG. 11.

Analysis by SDS-PAGE and Western blot revealed unnatural amino acid dependent protein expression with a fidelity of >99% as judged by densitometry comparisons to protein expression in absence of 1 or 2 of FIG. 11. See FIG. 12. To further confirm the identity of the amino acid incorporated, a tryptic digest was subjected to liquid chromatography and tandem mass spectrometry.

Figure 15A:
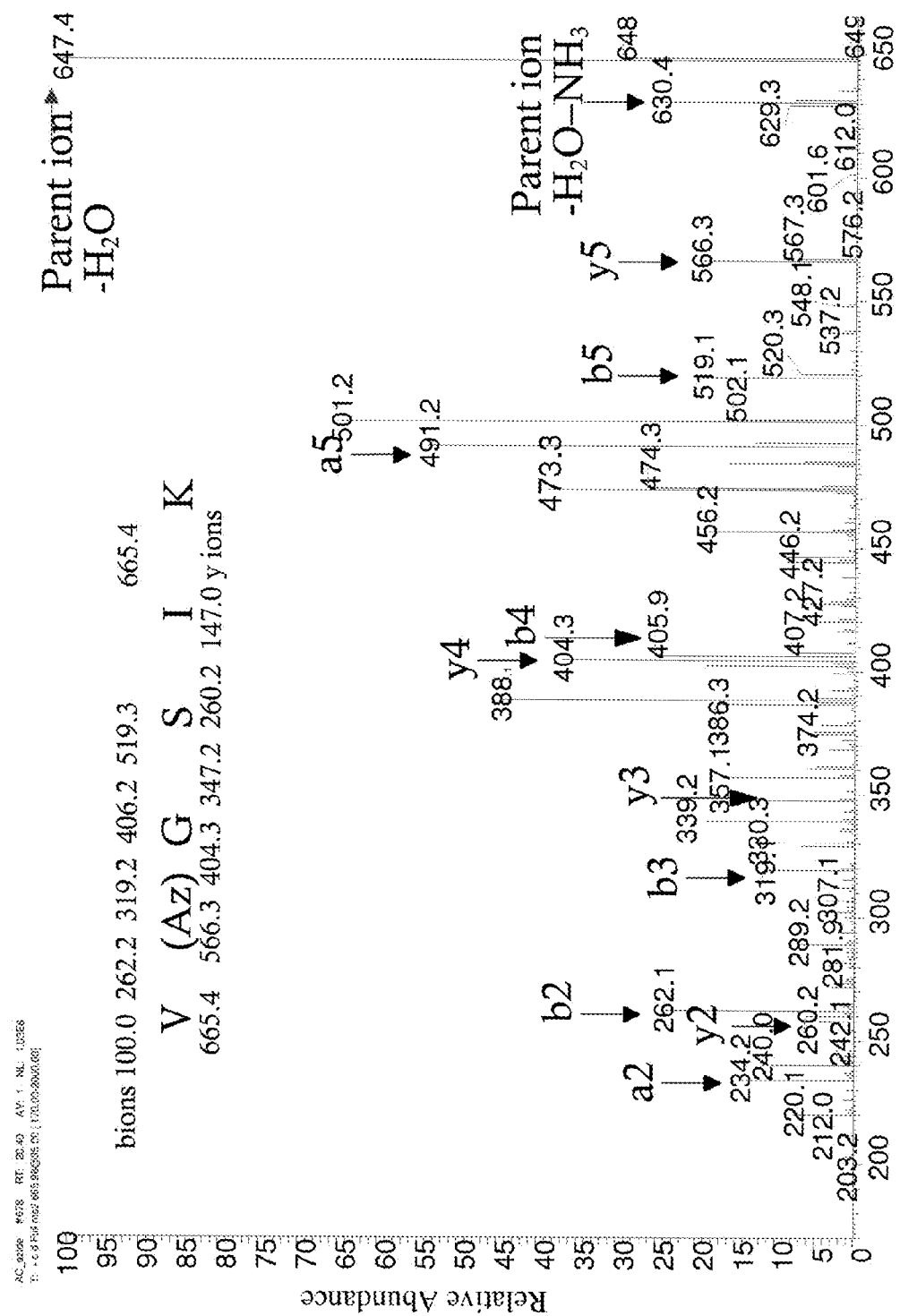
FIG. 15, Panels A and B, illustrate tandem mass spectrum of the tryptic peptide VY*GSIK (SEQ ID NO:87) containing the azide (Az) (FIG. 15, Panel A) or alkyne (Al) (FIG. 15, Panel B) unnatural amino acids in position Y* are shown with their expected fragment ion masses. Arrow indicates observed b (blue) and y (red) ions series for each peptide.
Figure 15B:
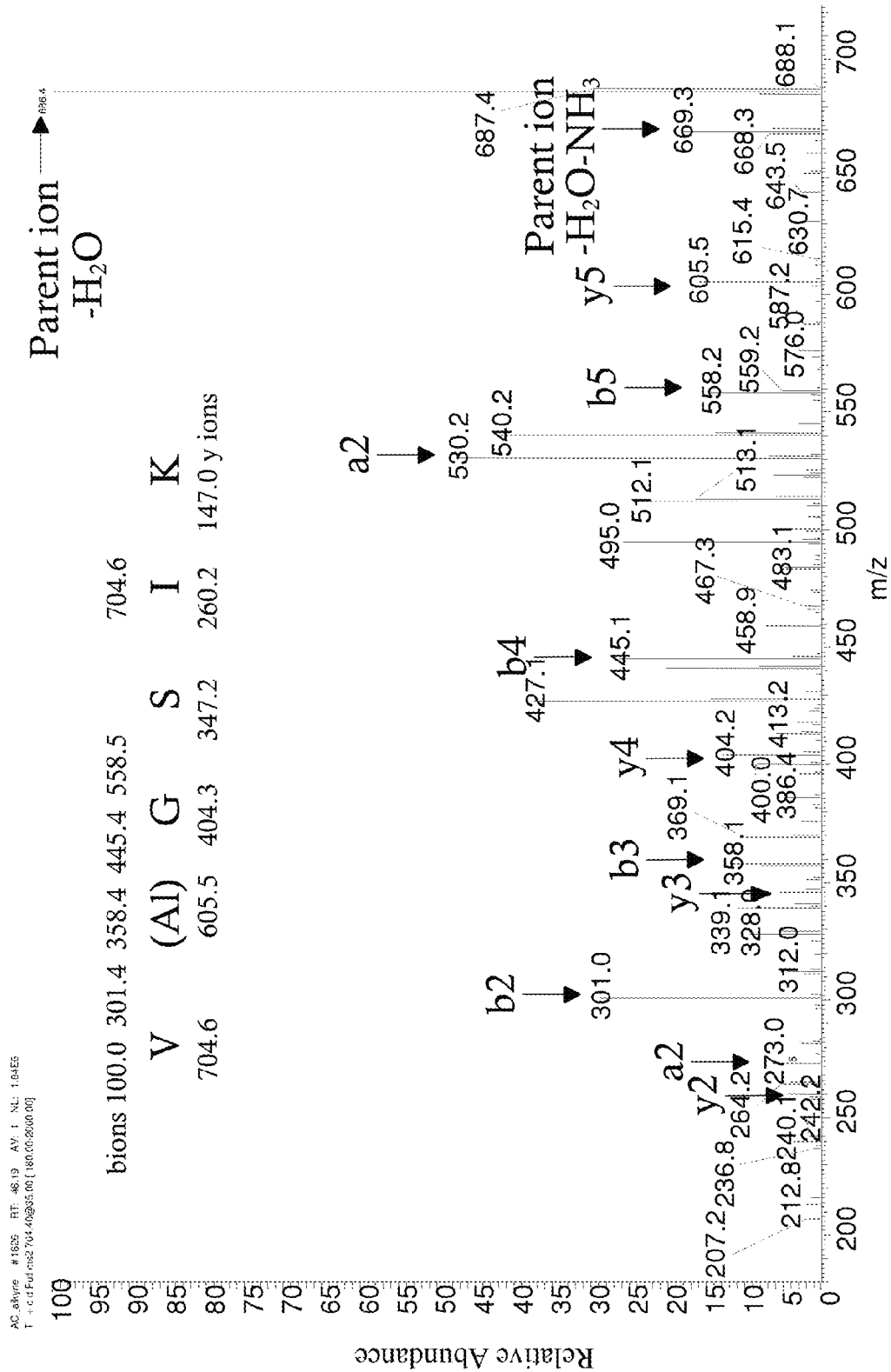
Figure 16:
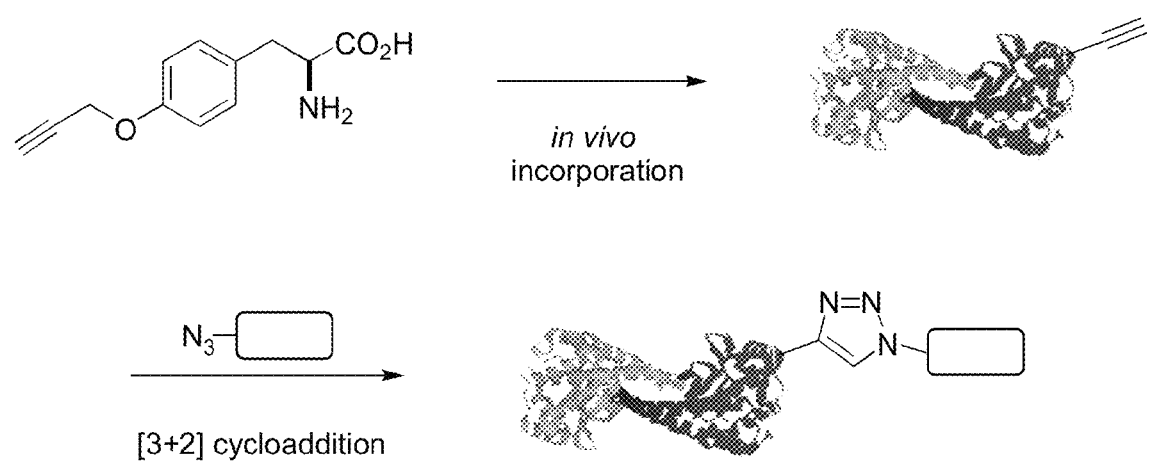
FIG. 16 schematically illustrates the in vivo incorporation of an unnatural amino acid, e.g., para-propargyloxyophenylalanine, into a growing polypeptide chain and the bioconjugation with small organic molecules by a [3+2]-cycloaddition reaction through this unnatural amino acid.

For example, the wild-type and mutant hSOD were purified using nickel affinity column and protein bands were visualized by colloidal Coomassie stain. Gels bands corresponding to wild-type and mutant SOD were excised from polyacrylamide gels, sliced into 1.5-mm cubes, reduced and alkylated, then subjected to trypsin hydrolysis essentially as described. See, e.g., Shevchenko, A et al., (1996) *Anal. Chem.* 68:850-858. Tryptic peptides containing the unnatural amino acid were analyzed by nanoflow reversed-phase HPLC/µESI/MS with an LCQ ion trap mass spectrometer. See, FIG. 15, Panel A and B. Liquid chromatography tandem mass spectrometry (LC-MS/MS) analysis was performed on a Finnigan LCQ Deca ion trap mass spectrometer (Thermo Finnigan) fitted with a Nanospray HPLC (Agilent 1100 series).

The precursor ions corresponding to the singly and doubly charged precursor ions of the peptide VY*GSIK (SEQ ID NO:87) containing the unnatural amino acid (denoted Y*) were separated and fragmented with an ion trap mass spectrometer. The fragment ion masses could be unambiguously assigned, confirming the site-specific incorporation of each unnatural amino acid. LC MS/MS did not indicate incorporation of any natural amino acid at this position. The signal-to-noise of the peptide for all mutants were >1000 suggesting fidelity of incorporation better than 99.8%. See, FIG. 15, Panel A and B.

Figure 13C:
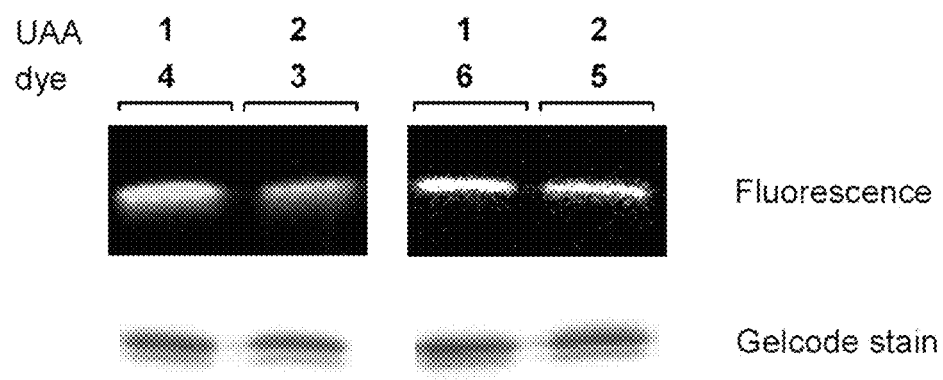

To demonstrate that small organic molecules can be conjugated to proteins by an azide-alkyne [3+2] cycloaddition reaction, the dyes 3-6 indicated in FIG. 13, Panel A, which contain either an acetylenic or an azido group and bear a dansyl or fluoresceine fluorophore, were synthesized (see Example 5 herein). The cycloaddition itself was carried out with 0.01 mM protein in phosphate buffer (PB), pH 8, in the presence of 2 mM 3-6 indicated in FIG. 13, Panel A, 1 mM $CuSO_4$, and ~1 mg Cu-wire for 4 hours at 37° C. (see FIG. 13, Panel B).

For example, to 45 µL of protein in PB buffer (pH=8) was added 1 µL of $CuSO_4$ (50 mM in $H_2O$), 2 µL of dye (50 mM in EtOH), 2 µL of tris(1-benzyl-1H-[1,2,3]triazol-4-ylmethyl)amine (50 mM in DMSO), and Cu wire. After 4 hours at room temperature or 37° C. or overnight at 4° C., 450 µL $H_2O$ were added and the mixture was spun through a dialysis membrane (10 kDa cut off). After washing the supernatant with 2×500 µL by centrifugation, the solution was brought to a volume of 50 mL. A sample of 20 mL was analyzed by SDS-PAGE. Occasionally remaining dye could be removed from the gel by soaking in $H_2O$/MeOH/AcOH (5:5:1) overnight. The use of tris(carboxyethyl)phosphine as the reducing agent generally led to less efficient labeling. In contrast to earlier observations (e.g., Wang, Q. et al., (2003) *J. Am. Chem. Soc.* 125:3192-3193), the presence or absence of the tris(triazolyl)amine ligand did not have a substantial influence on the outcome of the reaction.

After dialysis the labeled proteins were then analyzed by SDS-PAGE and in-gel imaged using a densitometer in case of the dansyl dyes 3-4 indicated in FIG. 13, Panel A ($\lambda_{ex}$=337 nm, $\lambda_{em}$=506 nm) or a phosphorimager in the case of the fluoresceine dyes 5-6 indicated in FIG. 13, Panel A ($\lambda_{ex}$=483 nm, $\lambda_{em}$=516 nm). See, e.g., Blake, (2001) *Curr. Opin. Pharmacol.*, 1:533-539; Wouters, et al., (2001) *Trends in Cell Biology* 11:203-211; and, Zacharias, et al., (2000) *Curr. Opin. Neurobiol.*, 10:416-421. The labeled proteins were characterized by LC MS/MS analysis of tryptic digests showing site-specific attachment of the fluorophores and the conversion was 75% on average (e.g., as determined by comparison of $A_{280}/A_{495}$ values for SOD labeled with 5 or 6 indicated in FIG. 13, Panel A). The selectivity of this bioconjugation is verified by the fact that there was no observable reaction between 3 indicated in FIG. 13, Panel A and alkyne protein or 4 indicated in FIG. 13, Panel A and azido protein.

TABLE 8

EVOLVED SYNTHETASES.
pPR-EcRS selected for 1 and pAZ-EcRS selected
for 2 (as indicated in FIG. 11)

| synthetase | 37 | 126 | 182 | 183 | 186 |
|---|---|---|---|---|---|
| wild type | Tyr | Asn | Asp | Phe | Leu |
| pPR-EcRS-1 | Gly | Asn | Ser | Met | Leu |
| pPR-EcRS-2 | Thr | Asn | Ser | Ala | Leu |
| pPR-EcRS-3 | Ser | Asn | Thr | Met | Val |
| pPR-EcRS-4 | Ala | Asn | Ser | Tyr | Leu |
| pPR-EcRS-5 | Ala | Asn | Thr | Met | Cys |
| pAZ-EcRS-1 | Leu | Asn | Ser | Met | Ala |
| pAZ-EcRS-2 | Val | Asn | Ser | Ala | Ala |
| pAZ-EcRS-3 | Leu | Asn | Ser | Ala | Ala |
| pAZ-EcRS-4 | Val | Asn | Ser | Ala | Val |
| pAZ-EcRS-5 | Ile | Asp | Asn | Phe | Val |
| pAZ-EcRS-6 | Thr | Asn | Ser | Ala | Leu |

Example 4

Synthesis of an Alkyne Amino Acid

In one aspect of the invention, the invention provides alkynyl amino acids. An example of a structure of the alkynyl amino acid is illustrated by Formula IV:

IV

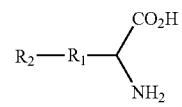

An alkyne amino acid is typically any structure having Formula IV, where $R_1$ is a substituent used in one of the twenty natural amino acids and $R_2$ is an alkynyl substituent. For example, 1 in FIG. 11 illustrates the structure of para-propargyloxyphenylalanine. p-Propargyloxyphenylalanine can be synthesized, e.g., as outline below. In this embodiment, the synthesis of p-propargyloxyphenylalanine can be completed in three steps starting from the commercially available N-Boc-tyrosine.

For example, N-tert-butoxycarbonyl-tyrosine (2 g, 7 mmol, 1 equiv.) and $K_2CO_3$ (3 g, 21 mmol, 3 equiv.) were suspended in anhydrous DMF (15 mL). Propargyl bromide (2.1 mL, 21 mmol, 3 equiv., 80% solution in toluene) was slowly added and the reaction mixture was stirred for 18 hours at room temperature. Water (75 mL) and $Et_2O$ (50 mL) were added, the layers were separated and the aqueous phase was extracted with $Et_2O$ (2×50 mL). The combined organic layers were dried ($MgSO_4$) and the solvent was removed under reduced pressure. The product was obtained as a yellow oil (2.3 g, 91%) and used in the next step without further purification. The Boc-protected product is illustrated below as chemical structure 8:

8

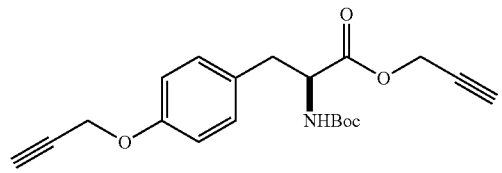

2-tert-Butoxycarbonylamino-3-[4-(prop-2-ynyloxy)phenyl]-propionic acid propargyl ester Acetyl chloride (7 mL) was added carefully to methanol (60 mL) at 0° C. to give a 5 M solution of anhydrous HCl in MeOH. The product of the previous step (2 g, 5.6 mmol) was added and the reaction was stirred for 4 hours while it was allowed to warm to ambient temperature. After removing the volatiles under reduced pressure, a yellowish solid (1.6 g, 98%) (see chemical structure 9) was obtained which was directly used in the next step.

9

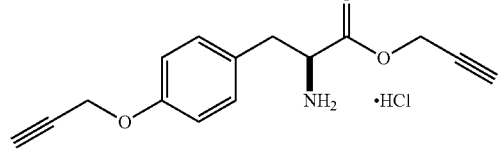

2-Amino-3-[4-(prop-2-ynyloxy)phenyl]-propionic acid propargyl ester

The propargyl ester (1.6 g, 5.5 mmol) from the previous step was dissolved in a mixture of aqueous 2 N NaOH (14 mL) and MeOH (10 mL). After stirring for 1.5 h at room temperature, the pH was adjusted to 7 by adding conc. HCl. Water (20 mL) was added and the mixture was kept at 4° C. overnight. The precipitate was filtered, washed with ice-cold H₂O, and dried under vacuum yielding, 1.23 g (90%) of 1 in FIG. 11 (2-Amino-3-phenylpropionic acid (1) (also known as p-propargyloxyphenylalanine) as a white solid. ¹H NMR (400 MHz, D₂O) (as the potassium salt in D₂O) δ 7.20 (d, J=8.8 Hz, 2 H), 6.99 (d, J=8.8 Hz, 2H), 4.75 (s, 2 H), 3.50 (dd, J=5.6, 7.2 Hz, 1 H), 2.95 (dd, J=5.6, 13.6 Hz, 1 H), 2.82 (dd, J=7.2, 13.6 Hz, 1 H); ¹³C NMR (100 MHz, D₂O) δ 181.3, 164.9, 155.6, 131.4, 130.7, 115.3, 57.3, 56.1, 39.3; HRMS (CI) m/z 220.0969 [C₁₂H₁₃NO₃ (M+1) requires 220.0968].

Example 5

Addition of Molecules to Proteins with an Unnatural Amino Acid Through a [3+2] Cycloaddition In one aspect, the invention provides methods and related compositions of proteins comprising unnatural amino acids coupled to additional substituent molecules. For example, additional substituents can be added to an unnatural amino acid through a [3+2] cycloaddition. See, e.g., FIG. 16. For example, the [3+2] cycloaddition of a desired molecule (e.g., that include a second reactive group, such as an alkyne triple bond or azido group) to a protein with an unnatural amino acid (e.g., having a first reactive group, such as azido group or triple bond) can be done following published conditions for the [3+2] cycloaddition reaction. For example, a protein comprising the unnatural amino acid in PB buffer (pH=8) is added to CuSO₄, the desired molecule, and Cu wire. After the mixture is incubated (e.g., about 4 hours at room temperature or 37° C., or overnight at 4° C.), H₂O is added and the mixture is filtered through a dialysis membrane. The sample can be analyzed for the addition, e.g., by gel analysis.

Examples of such molecules include, but are not limited to, e.g., a molecule having a triple bond or azido group, such as molecules have the structure of Formula 3, 4, 5, and 6 of FIG. 13, Panel A and the like. Furthermore, triple bonds or azido groups can be incorporated into the structures of other molecules of interest, such as polymers (e.g., poly(ethylene glycol) and derivatives), crosslinking agents, additional dyes, photocrosslinkers, cytotoxic compounds, affinity labesl, biotin, saccharides, resins, beads, a second protein or polypeptide, metal chelators, cofactors, fatty acids, carbohydrates, polynucleotides (e.g., DNA, RNA, etc.), and the like, which then can also be used in [3+2] cycloadditions.

In one aspect of the invention, molecules having the Formula 3, 4, 5, or 6 of FIG. 13, Panel A can be synthesized as described below. For example, an alkyne dye as shown in 3 of FIG. 13, Panel A and in chemical structure 3 below was synthesized by adding propargylamine (250 µL, 3.71 mmol, 3 equiv.) to a solution of dansyl chloride (500 mg, 1.85 mmol, 1 equiv.) and triethylamine (258 µL, 1.85 mmol, 1 equiv.) in CH₂Cl₂ (10 mL) at 0° C. After stirring for 1 hour, the reaction mixture was warmed to room temperature and stirred for an additional hour. The volatiles were removed in vacuo and the crude product was purified by chromatography on silica gel (Et₂O/hexanes=1:1) yielding 3 of FIG. 13, Panel A (418 mg, 78%) as a yellow solid. The analytical data are identical with those reported in the literature. See, for example, Bolletta, F et al., (1996) *Organometallics* 15:2415-17. An example of a structure of an alkyne dye that can be used in the invention is shown in chemical structure 3:

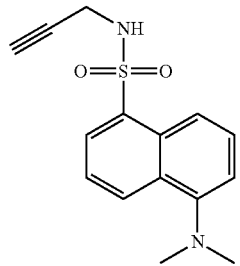

3

An azido dye as shown as shown in 4 of FIG. 13, Panel A and in chemical structure 4 below was synthesized by adding 3-azidopropylamine (e.g., as described by Carboni, B et al., (1993) *J. Org. Chem.* 58:3736-3741) (371 mg, 3.71 mmol, 3 equiv.) to a solution of dansyl chloride (500 mg, 1.85 mmol, 1 equiv.) and triethylamine (258 µL, 1.85 mmol, 1 equiv.) in CH₂Cl₂ (10 mL) at 0° C. After stirring for 1 hour, the reaction mixture was warmed to room temperature and stirred for an additional hour. The volatiles were removed in vacuo and the crude product was purified by chromatography on silica gel (Et₂O/hexanes=1:1) yielding 4 of FIG. 13, Panel A (548 mg, 89%) as a yellow oil. ¹H NMR (400 MHz, CDCl₃) δ 8.55 (d, J=8.4 Hz, 1 H), 8.29 (d, J=8.8 Hz, 1 H), 8.23 (dd, J=1.2, 7.2 Hz, 1 H), 7.56-7.49 (comp, 2 H), 7.18 (d, J=7.6 Hz, 1 H), 5.24 (br s, 1 H), 3.21 (t, J=6.4 Hz, 2 H), 2.95 (dt, J=6.4 Hz, 2 H), 2.89 (s, 6 H), 1.62 (quin, J=6.4 Hz, 2 H); ¹³C NMR (100 MHz, CDCl₃) δ 134.3, 130.4, 129.7, 129.4, 128.4, 123.3, 118.8, 115.3, 48.6, 45.4, 40.6, 28.7 (not all signals of quaternary carbon atoms are visible in the ¹³C NMR spectrum); HRMS (CI) m/z 334.1336 [C₁₅H₂₀N₅O₂S (M+1) requires 334.1332]. An example of a structure of an azido dye is shown in chemical structure 4:

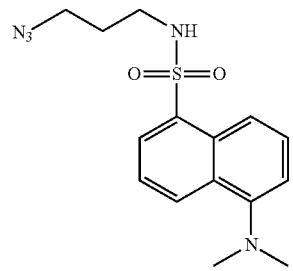

4

An alkyne dye as shown in 5 of FIG. 13, Panel A and in chemical structure 5 below was synthesized by adding EDCI (1-ethyl-3-(3-dimethylaminopropyl)carbodiimide hydrochloride) (83 mg, 0.43 mmol, 1 equiv.) to a solution of fluoresceinamine (150 mg, 0.43 mmol, 1 equiv.) and 10-undecynoic acid (79 mg, 0.43, 1 equiv.) in pyridine (2 mL) at room temperature. The suspension was stirred overnight and the reaction mixture was poured into H₂O (15 mL). The solution was acidified (pH<2) by adding conc. HCl. After stirring for 1 h, the precipitate was filtered off, washed with H₂O (5 mL) and dissolved in small amount of EtOAc. Addition of hexanes led to the precipitation of 5 of FIG. 13, Panel A as orange crystals, which were collected and dried under vacuum (138 mg, 63%). The analytical data are identical with those reported in the literature. See, e.g., Crisp, G. T.; & Gore, J. (1997) *Tetrahedron* 53:1505-1522. An example of a structure of an alkyne dye is shown in chemical structure 5:

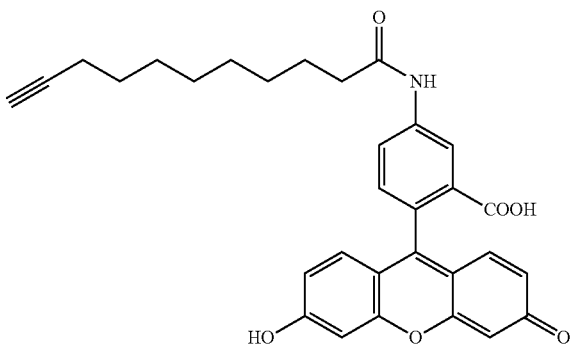

An azido dye as shown in 6 of FIG. 13, Panel A and in chemical structure 6 below was synthesized by adding EDCI (83 mg, 0.43 mmol, 1 equiv.) to a solution of fluorescein-amine (150 mg, 0.43 mmol, 1 equiv.) and 4-(3-azidopropylcarbamoyl)-butyric acid (e.g., synthesized by reacting 3-azidopropylamine with glutaric acid anhydride) (92 mg, 0.43, 1 equiv.) in pyridine (2 mL) at room temperature. The suspension was stirred over night and the reaction mixture was poured in H$_2$O (15 mL). The solution was acidified (pH<2) by adding conc. HCl. After stirring for 1 hour, the precipitate was filtered off, washed with 1 N HCl (3×3 mL) and was dissolved in a small amount of EtOAc. Addition of hexanes led to the precipitation of 6 of FIG. 13, Panel A as orange crystals, which were collected and dried under vacuum (200 mg, 86%). $^1$H NMR (400 MHz, CD$_3$OD) δ 8.65 (s, 1 H), 8.15 (d, J=8.4 Hz, 1 H), 7.61-7.51 (comp, 2 H), 7.40 (d, J=8.4 Hz, 1 H), 7.35 (br s, 2 H), 7.22-7.14 (comp, 2 H), 6.85-6.56 (comp, 3 H), 3.40-3.24 (comp, 4 H), 2.54 (t, J=7.2 Hz, 2 H), 2.39-2.30 (comp, 2 H), 2.10-1.99 (comp, 2 H), 1.82-1.72 (comp, 2 H); $^{13}$C NMR (100 MHz, CD$_3$OD) δ 175.7, 174.4, 172.4, 167.9, 160.8, 143.0, 134.3, 132.9, 131.8, 129.6, 124.4, 123.3, 121.1, 118.5 103.5, 50.2, 38.0, 37.2, 36.2, 29.8, 22.9 (not all signals of quaternary carbon atoms are visible in the $^{13}$C NMR spectrum); HRMS (CI) m/z 544.1835 [C$_{28}$H$_{25}$N$_5$O$_7$ (M+1) requires 544.1827]. An example of a structure of an azido dye is shown in chemical structure 6:

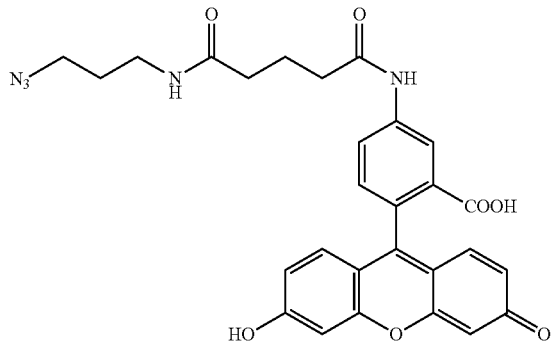

Figure 17A:
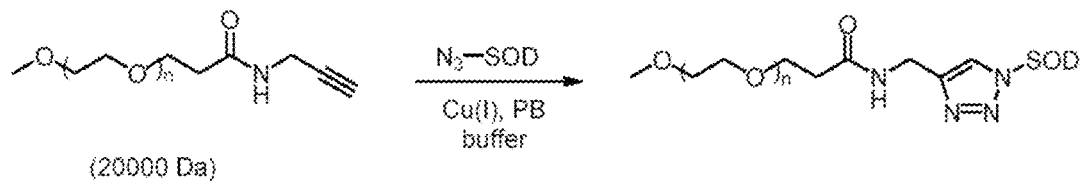
FIG. 17, Panels A, B and C illustrate PEGylation of a protein comprising an unnatural amino acid using a [3+2] cycloaddition.
Figure 17B:
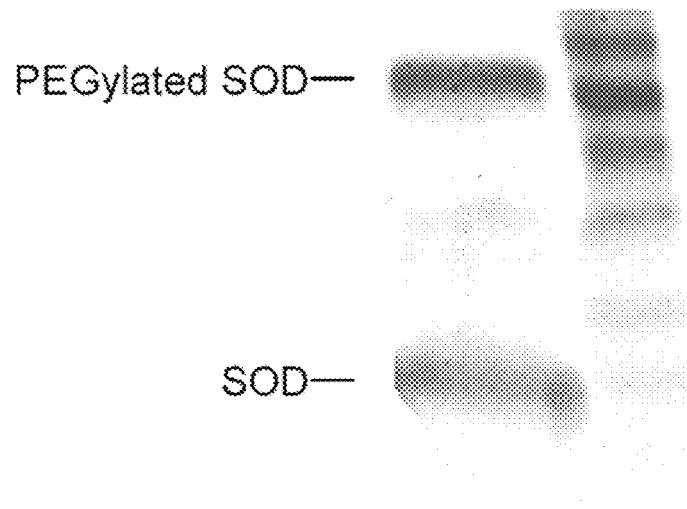
Figure 17C:
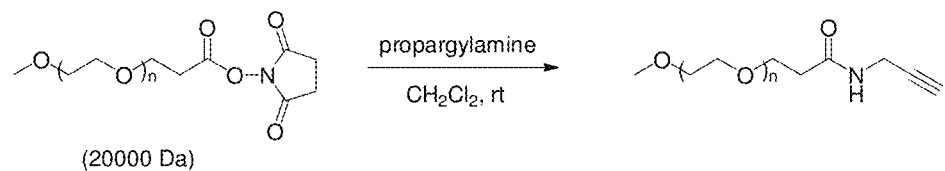

In one embodiment, a PEG molecule can also be added to a protein with an unnatural amino acid, e.g., an azido amino acid or a propargyl amino acid. For example, a propargyl amide PEG (e.g., illustrated in FIG. 17, Panel A) can be added to a protein with an azido amino acid through a [3+2] cycloaddition. See e.g., FIG. 17, Panel A. FIG. 17, Panel B illustrates a gel analysis of a protein with an added PEG substituent.

In one aspect of the invention, a propargyl amide PEG (e.g., illustrated in FIG. 17, Panel A) can be synthesized as described below. For example, a solution of propargylamine (30 μL) in CH$_2$Cl$_2$ (1 mL) was added to the 20 kDa PEG-hydroxysuccinimide ester (120 mg, purchased from Nektar). The reaction was stirred for 4 hours at room temperature. Then Et$_2$O (10 mL) was added, the precipitate was filtered off, and was twice recrystallized from MeOH (1 mL) by addition of Et$_2$O (10 mL). The product was dried under vacuum furnishing a white solid (105 mg, 88% yield). See, e.g., FIG. 17, Panel C.

Example 6

Exemplary O-RSs and O-tRNAs

An exemplary O-tRNA comprises SEQ ID NO.:65 (See, Table 5). Example O-RSs include SEQ ID NOs.: 36-63, 86 (See, Table 5). Examples of polynucleotides that encode O-RSs or portions thereof (e.g., the active site) include SEQ ID NOs.: 3-35. In addition, exemplary amino acid changes of O-RSs are indicated in Table 6.

TABLE 6

Evolved EcTyrRS Variants

| | Residue # | | | | | |
|---|---|---|---|---|---|---|
| | 37 | 126 | 182 | 183 | 186 | Representation |
| Ec TyrRS | Tyr | Asn | Asp | Phe | Leu | |
| p-iodoPheRS-1 | Val | Asn | Ser | Tyr | Leu | 1/8 |
| p-iodoPheRS-2 | Ile | Asn | Ser | Met | Leu | 1/8 |
| p-iodoPheRS-3 | Val | Asn | Ser | Met | Ala | 6/8 |
| OMeTyrRS-1 | Val | Asn | Ser | Met | Leu | 5/13 |
| OMeTyrRS-2 | Thr | Asn | Thr | Met | Leu | 1/13 |
| OMeTyrRS-3 | Thr | Asn | Thr | Tyr | Leu | 1/13 |
| OMeTyrRS-4 | Leu | Asn | Ser | Met | Ser | 1/13 |
| OMeTyrRS-5 | Leu | Asn | Ser | Met | Ala | 1/13 |
| OMeTyrRS-6 | Thr | Asn | Arg | Met | Leu | 4/13 |
| p-acetylPheRS-1 | Ile | Asn | Gly | Met | Ala | 4/4 |
| p-acetylPheRS-1$^a$ | Ile | Asn | Gly | Met | Ala | 10/10 |
| p-benzoylPheRS-1 | Gly | Asn | Gly | Phe | Ala | 1/2 |
| p-benzoylPheRS-2 | Gly | Asn | Gly | Tyr | Met | 1/2 |
| p-azidoPheRS-1 | Leu | Asn | Ser | Met | Ala | 1/6 |
| p-azidoPheRS-2 | Val | Asn | Ser | Ala | Ala | 1/6 |
| p-azidoPheRS-3 | Leu | Asn | Ser | Ala | Ala | 1/6 |
| p-azidoPheRS-4 | Val | Asn | Ser | Ala | Val | 1/6 |
| p-azidoPheRS-5 | Ile | Asp | Asn | Phe | Val | 1/6 |
| p-azidoPheRS-6 | Thr | Asn | Ser | Ala | Leu | 1/6 |
| p-PR-EcRS-1 | Gly | Asn | Ser | Met | Ala | 1/10 |
| p-PR-EcRS-2 | Thr | Asn | Ser | Ala | Leu | 1/10 |
| p-PR-EcRS-3 | Ser | Asn | Thr | Met | Val | 1/10 |
| p-PR-EcRS-4 | Ala | Asn | Ser | Tyr | Leu | 1/10 |
| p-PR-EcRS-5 | Ala | Asn | Thr | Met | Cys | 1/10 |
| p-PR-EcRS-6 | Thr | Asn | Thr | Phe | Met | 1/10 |
| p-PR-EcRS-7 | Thr | Asn | Ser | Val | Leu | 1/10 |
| p-PR-EcRS-8 | Val | Asn | Ser | Met | Thr | 1/10 |
| p-PR-EcRS-9 | Ser | Asn | Ser | Phe | Leu | 1/10 |
| p-PR-EcRS-10 | Thr | Asn | Thr | Phe | Thr | 1/10 |

$^a$These clones also contain a Asp165Gly mutation

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described herein can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 5

| SEQ ID NO.: | Label | SEQUENCE |
|---|---|---|
| SEQ ID NO.: 1 | E. coli wild-type TyrRS (synthetase) polynucleotide | ATGGCAAGCAGTAACTTGATTAAACAATTGCAAGAGCGGGGGCTGGTA GCCCAGGTGACGGACGAGGAAGCGTTAGCAGAGCGACTGGCGCAAGG CCCGATCGCGCTCTATTGCGGCTTCGATCCTACCGCTGACAGCTTGCAT TTGGGGCATCTTGTTCCATTGTTATGCCTGAAACGCTTCCAGCAGGCGG GCCACAAGCCGGTTGCGCTGGTAGGCGGCGCGACGGGTCTGATTGGCG ACCCGAGCTTCAAAGCTGCCGAGCGTAAGCTGAACACCGAAGAAACTG TTCAGGAGTGGGTGGACAAAATCCGTAAGCAGGTTGCCCCGTTCCTCG ATTTCGACTGTGGAGAAAACTCTGCTATCGCGGCGAACAACTATGACT GGTTCGGCAATATGAATGTGCTGACCTTCCTGCGCGATATTGGCAAACA CTTCTCCGTTAACCAGATGATCAACAAAGAAGCGGTTAAGCAGCGTCT CAACCGTGAAGATCAGGGGATTTCGTTCACTGAGTTTTCCTACAACCTG TTGCAGGGTTATGACTTCGCCTGTCTGAACAAACAGTACGGTGTGGTGC TGCAAATTGGTGGTTCTGACCAGTGGGGTAACATCACTTCTGGTATCGA CCTGACCCGTCGTCTGCATCAGAATCAGGTGTTTGGCCTGACCGTTCCG CTGATCACTAAAGCAGATGGCACCAAATTTGGTAAAACTGAAGGCGGC GCAGTCTGGTTGGATCCGAAGAAAACCAGCCCGTACAAATTCTACCAG TTCTGGATCAACACTGCGGATGCCGACGTTTACCGCTTCCTGAAGTTCT TCACCTTTATGAGCATTGAAGAGATCAACGCCCTGGAAGAAGAAGATA AAAACAGCGGTAAAGCACCGCGCGCCCAGTATGTACTGGCGGAGCAG GTGACTCGTCTGGTTCACGGTGAAGAAGGTTTACAGGCGGCAAAACGT ATTACCGAATGCCTGTTCAGCGGTTCTTTGAGTGCGCTGAGTGAAGCGG ACTTCGAACAGCTGGCGCAGGACGGCGTACCGATGGTTGAGATGGAAA AGGGCGCAGACCTGATGCAGGCACTGGTCGATTCTGAACTGCAACCTT CCCGTGGTCAGGCACGTAAAACTATCGCCTCCAATGCCATCACCATTAA CGGTGAAAAACAGTCCGATCCTGAATACTTCTTTAAAGAAGAAGATCG TCTGTTTGGTCGTTTTACCTTACTGCGTCGCGGTAAAAAGAATTACTGT CTGATTTGCTGGAAATAA |
| SEQ ID NO.: 2 | E. coli wild-type TyrRS (synthetase) Amino acid (aa) | MASSNLIKQLQERGLVAQVTDEEALAERLAQGPIALYCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYDFACLNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFLQLAQDGVPMVEM EKGADLMQALVDSELQPSRGQARKTIASNAITINGEKQSDPEYFEKEEDRLF GRFTLLRRGKKNYCLICWK |
| SEQ ID NO.: 3 | pOMe-1 Synthetase polynucleotide | ATGGCAAGCAGTAACTTGATTAAACAATTGCAAGAGCGGGGGCTGGTA GCCCAGGTGACGGACGAGGAAGCGTTAGCAGAGCGACTGGCGCAAGGC CCGATCGCACTCGTGTGTGGCTTCGATCCTACCGCTGACAGCTTGCATTT GGGGCATCTTGTTCCATTGTTATGCCTGAAACGCTTCCAGCAGGCGGGC CACAAGCCGGTTGCGCTGGTAGGCGGCGCGACGGGTCTGATTGGCGAC CCGAGCTTCAAAGCTGCCGAGCGTAAGCTGAACACCGAAGAAACTGTT CAGGAGTGGGTGGACAAAATCCGTAAGCAGGTTGCCCCGTTCCTCGATT TCGACTGTGGAGAAAACTCTGCTATCGCGGCCAATAATTATGACTGGTT CGGCAATATGAATGTGCTGACCTTCCTGCGCGATATTGGCAAACACTTC TCCGTTAACCAGATGATCAACAAAGAAGCGGTTAAGCAGCGTCTCAAC CGTGAAGATCAGGGGATTTCGTTCACTGAGTTTTCCTACAACCTGCTGC AGGGTTATAGTATGGCCTGTTTGAACAAACAGATACGGTGTGGTGCTGCA AATTGGTGGTTCTGACCAGTGGGGTAACATCACTTCTGGTATCGACCTG ACCCGTCGTCTGCATCAGAATCAGGTGTTTGGCCTGACCGTTCCGCTGA TCACTAAAGCAGATGGCACCAAATTTGGTAAAACTGAAGGCGGCGCAG TCTGGTTGGATCCGAAGAAAACCAGCCCGTACAAATTCTACCAGTTCTG GATCAACACTGCGGATGCCGACGTTTACCGCTTCCTGAAGTTCTTCACC TTTATGAGCATTGAAGAGATCAACGCCCTGGAAGAAGAAGATAAAAAC AGCGGTAAAGCACCGCGCGCCCAGTATGTACTGGCGGAGCAGGTGACT CGTCTGGTTCACGGTGAAGAAGGTTTACAGGCGGCAAAACGTATTACC GAATGCCTGTTCAGCGGTTCTTTGAGTGCGCTGAGTGAAGCGGACTTCG AACAGCTGGCGCAGGACGGCGTACCGATGGTTGAGATGGAAAAGGGCG CAGACCTGATGCAGGCACTGGTCGATTCTGAACTGCAACCTTCCcGTGG TCAGGCACGTAAAACTATCGCCTCCAATGCCATCACCATTAACGGTGAA AAACAGTCCGATCCTGAATACTTCTTTAAAGAAGAAGATCGTCTGTTTG GTCGTTTTACCTTACTGCGTCGCGGTAAAAAGAATTACTGTCTGATTTGC TGGAAATAA |

TABLE 5-continued

| SEQ ID NO.: | Label | SEQUENCE |
| --- | --- | --- |
| SEQ ID NO.: 4 | pOMe-2 Synthetase polynucleotide | ATGGCAAGCAGTAACTTGATTAAACAATTGCAAGAGCGGGGGCTGGTA<br>gCCCAGGTGACGGACGAGGAAGCGTTAGCAGAGCGACTGGCGCAAGGC<br>CCGATCGCACTCACTTGTGGCTTCGATCCTACCGCTGACAGCTTGCATTT<br>GGGGCATCTTGTTCCATTGTTATGCCTGAAACGCTTCCAGCAGGCGGGC<br>CACAAGCCGGTTGCGCTGGTAGGCGGCGCGACGGGTCTGATTGGCGAC<br>CCGAGCTTCAAAGCTGCCGAGCGTAAGCTGAACACCGAAGAAACTGTT<br>CAGGAGTGGGTGGACAAAATCCGTAAGCAGGTTGCCCCGTTCCTCGATT<br>TCGACTGTGGAGAAAACTCTGCTATCGCGGCCAATAATTATGACTGGTT<br>CAGCAATATGAATGTGCTGACCTTCCTGCGCGATATTGGCAAACACTTC<br>TCCGTTAACCAGATGATCAACAAAGAAGCGGTTAAGCAGCGTCTCAAC<br>CGTGAAGATCAGGGGATTTCGTTCACTGAGTTTTCCTACAACCTGCTGC<br>AGGGTTATACGTATGCCTGTCTGAACAAACAGTACGGTGTGGTGCTGCA<br>AATTGGTGGTTCTGACCAGTGGGGTAACATCACTTCTGGTATCGACCTG<br>ACCCGTCGTCTGCATCAGAATCAGGTGTTTGGCCTGACCGTTCCGCTGA<br>TCACTAAAGCAGATGGCACCAAATTTGGTAAAACTGAAGGCGGCGCAG<br>TCTGGTTGGATCCGAAGAAAACCAGCCCGTACAAATTCTACCAGTTCTG<br>GATCAACACTGCGGATGCCGACGTTTACCGCTTCCTGAAGTTCTTCACC<br>TTTATGAGCATTGAAGAGATCAACGCCCTGGAAGAAGAAGATAAAAAC<br>AGCGGTAAAGCACCGCGCGCCCAGTATGTACTGGCGGAGCAGGTGACT<br>CGTCTGGTTCACGGTGAAGAAGGTTTACAGGCGGCAAAACGTATTACC<br>GAATGCCTGTTCAGCGGTTCTTTGAGTGCGCTGAGTGAAGCGGACTTCG<br>AACAGCTGGCGCAGGACGGCGTACCGATGGTTGAGATGGAAAAGGGCG<br>CAGACCTGATGCAGGCACTGGTCGATTCTGAACTGCAACCTTCCCGTGG<br>TCAGGCACGTAAAACTATCGCCTCCAATGCCATCACCATTAACGGTGAA<br>AAACAGTCCGATCCTGAATACTTCTTTAAAGAAGAAGATCGTCTGTTTG<br>GTCGTTTTACCTTACTGCGTCGCGGTAAAAAGAATTACTGTCTGATTTGC<br>TGGAAATAA |
| SEQ ID NO.: 5 | pOMe-3 Synthetase polynucleotide | ATGGCAAGCAGTAACTTGATTAAACAATTGCAAGAGCGGGGGCTGGTA<br>GCCCAGGTGACGGACGAGGAAGCGTTAGCAGAGCGACTGGCGCAAGGC<br>CCGATCGCACTCGTGTGTGGCTTCGATCCTACCGCTGACAGCTTGCATTT<br>GGGGCATCTTGTTCCATTGTTATGCCTGAAACGCTTCCAGCAGGCGGGC<br>CACAAGCCGGTTGCGCTGGTAGGCGGCGCGACGGGTCTGATTGGCGAC<br>CCGAGCTTCAAAGCTGCCGAGCGTAAGCTGAACACCGAAGAAACTGTT<br>CAGGAGTGGGTGGACAAAATCCGTAAGCAGGTTGCCCCGTTCCTCGATT<br>TCGACTGTGGAGAAAACTCTGCTATCGCGGCCAATAATTATGACTGGTT<br>CGGCAATATGAATGTGCTGACCTTCCTGCGCGATATTGGCAAACACTTC<br>TCCGTTAACCAGATGATCAACAAAGAAGCGGTTAAGCAGCGTCTCAAC<br>CGTGAAGATCAGGGGATTTCGTTCACTGAGTTTTCCTACAACCTGCTGC<br>AGGGTTATAGTATGGCCTGTTTGAACAAACAGTACGGTGTGGTGCTGCA<br>AATTGGTGGTTCTGACCAGTGGGGTAACATCACTTCTGGTATCGACCTG<br>ACCCGTCGTCTGCATCAGAATCAGGTGTTTGGCCTGACCGTTCCGCTGA<br>TCACTAAAGCAGATGGCACCAAATTTGGTAAAACTGAAGGCGGCGCAG<br>TCTGGTTGGATCCGAAGAAAACCAGCCCGTACAAATTCTACCAGTTCTG<br>GATCAACACTGCGGATGCCGACGTTTACCGCTTCCTGAAGTTCTTCACC<br>TTTATGAGCATTGAAGAGATCAACGCCCTGGAAGAAGAAGATAAAAAC<br>AGCGGTAAAGCACCGCGCGCCCAGTATGTACTGGCGGAGCAGGTGACT<br>CGTCTGGTTCACGGTGAAGAAGGTTTACAGGCGGCAAAACGTATTACC<br>GAATGCCTGTTCAGCGGTTCTTTGAGTGCGCTGAGTGAAGCGGACTTCG<br>AACAGCTGGCGCAGGACGGCGTACCGATGGTTGAGATGGAAAAGGGCG<br>CAGACCTGATGCAGGCACTGGTCGATTCTGAACTGCAACCTTCCCGTGG<br>TCAGGCACGTAAAACTATCGCCTCCAATGCCATCACCATTAACGGTGAA<br>AAACAGTCCGATCCTGAATACTTCTTTAAAGAAGAAGATCGTCTGTTTG<br>GTCGTTTTACCTTACTGCGTCGCGGTAAAAAGAATTACTGTCTGATTTGC<br>TGGAAATAA |
| SEQ ID NO.: 6 | pOMe-4 Synthetase polynucleotide | ATGGCAAGCAGTAACTTGATTAAACAATTGCAAGAgCGGGGGCTGGTA<br>GCCCAGGTGACGGACGAGGAAGCGTTAGCAGAGCGACTGGCGCAAGGC<br>CCGATCGCACTCGTGTGTGGCTTCGATCCTACCGCTGACAGCTTGCATTT<br>GGGGCATCTTGTTCCATTGTTATGCCTGAAACGCTTCCAGCAGGCGGGC<br>CACAAGCCGGTTGCGCTGGTAGGCGGCGCGACGGGTCTGATTGGCGAC<br>CCGAGCTTCAAAGCTGCCGAGCGTAAGCTGAACACCGAAGAAACTGTT<br>CAGGAGTGGGTGGACAAAATCCGTAAGCAGGTTGCCCCGTTCCTCGATT<br>TCGACTGTGGAGAAAACTCTGCTATCGCGGCCAATAATTATGACTGGTT<br>CGGCAATATGAATGTGCTGACCTTCCTGCGCGATATTGGCAAACACTTC<br>TCCGTTAACCAGATGATCAACAAAGAAGCGGTTAAGCAGCGTCTCAAC<br>CGTGAAGATCAGGGGATTTCGTTCACTGAGTTTTCCTACAACCTGCTGC<br>AGGGTTATAGTATGGCCTGTTTGAACAAACAGTACGGTGTGGTGCTGCA<br>AATTGGTGGTTCTGACCAGTGGGGTAACATCACTTCTGGTATCGACCTG<br>ACCCGTCGTCTGCATCAGAATCAGGTGTTTGGCCTGACCGTTCCGCTGA<br>TCACTAAAGCAGATGGCACCAAATTTGGTAAAACTGAAGGCGGCGCAG<br>TCTGGTTGGATCCGAAGAAAACCAGCCCGTACAAATTCTACCAGTTCTG<br>GATCAACACTGCGGATGCCGACGTTTACCGCTTCCTGAAGTTCTTCACC<br>TTTATGAGCATTGAAGAGATCAACGCCCTGGAAGAAGAAGATAAAAAC<br>AGCGGTAAAGCACCGCGCGCCCAGTATGTACTGGCGGAGCAGGTGACT<br>CGTCTGGTTCACGGTGAAGAAGGTTTACAGGCGGCAAAACGTATTACC<br>GAATGCCTGTTCAGCGGTTCTTTGAGTGCGCTGAGTGAAgCGGACTTCG |

TABLE 5-continued

| SEQ ID NO.: | Label | SEQUENCE |
|---|---|---|
| | | AACAGCTGGCGCAGGACGGCGTACCGATGGTTGAGATGGAAAAGGGCG<br>CAGACCTGATGCAGGCACTGGTCGATTCTGAACTGCAACCTTCCCGTGG<br>TCAGGCACGTAAAACTATCGCCTCCAATGCCATCACCATTAACGGTGAA<br>AAACAGTCCGATCCTGAATACTTCTTTAAAGAAGAAGATCGTCTGTTTG<br>GTCGTTTTACCTTACTGCGTCGCGGTAAAAAGAATTACTGTCTGATTTGC<br>TGGAAATAA |
| SEQ ID NO.: 7 | pOMe-5<br>Synthetase<br>polynucleotide | ATGGCAAGCAGTAACTTGATTAAACAATTGCAAGAGCGGGGCTGGTA<br>gCCCAGGTGACGGACGAGGAAGCGTTAGCAGAGCGACTGGCGCAAGGC<br>CCGATCGCACTCACGTGTGGCTTCGATCCTACCGCTGACAGCTTGCATT<br>TGGGGCATCTTGTTCCATTGTTATGCCTGAAACGCTTCCAGCAGGCGGG<br>CCACAAGCCGGTTGCGCTGGTAGGCGGCGCGACGGGTCTGATTGGCGA<br>CCCGAGCTTCAAAGCTGCCGAGCGTAAGCTGAACACCGAAGAAACTGT<br>TCAGGAGTGGGTGGACAAAATCCGTAAGCAGGTTGCCCCGTTCCTCGAT<br>TTCGACTGTGGAGAAAACTCTGCTATCGCGGCCAATAATTATGACTGGT<br>TCGGCAATATGAATGTGCTGACCTTCCTGCGCGATATTGGCAAACACTT<br>CTCCGTTAACCAGATGATCAACAAAGAAGCGGTTAAGCAGCGTCTCAA<br>CCGTGAAGATCAGGGGATTTCGTTCACTGAGTTTTCCTACAGCCTGCTG<br>CAGGGTTATACGATGGCCTGTCTGAACAAACAGTACGGTGTGGTGCTGC<br>AAATTGGTGGTTCTGACCAGTGGGGTAACATCACTTCTGGTATCGACCT<br>GACCCGTCGTCTGCATCAGAATCAGGTGTTTGGCCTGACCGTTCCGCTG<br>ATCACTAAAGCAGATGGCACCCAAATTTGGTAAAACTGAAGGCGGCGCA<br>GTCTGGTTGGATCCGAAGAAAACCAGCCCGTACAAATTCTACCAGTTCT<br>GGATCAACACTGCGGATGCCGACGTTTACCGCTTCCTGAAGTTCTTCAC<br>CTTTATGAGCATTGAAGAGATCAACGCCCTGGAAGAAGAAGATAAAAA<br>CAGCGGTAAAGCACCGCGCGCCCAGTATGTACTGGCGGAGCAGGTGAC<br>TCGTCTGGTTCACGGTGAAGAAGGTTTACAGGCGGCAAAACGTATTACC<br>GAATGCCTGTTCAGCGGTTCTTTGAGTGCGCTGAGTGAAGCGGACTTCG<br>AACAGCTGGCGCAGGACGGCGTACCGATGGTTGAGATGGAAAAGGGCG<br>CAGACCTGATGCAGGCACTGGTCGATTCTGAACTGCAACCTTCCCGTGG<br>TCAGGCACGTAAAACTATCGCCTCCAATGCCATCACCATTAACGGTGAA<br>AAACAGTCCGATCCTGAATACTTCTTTAAAGAAGAAGATCGTCTGTTTG<br>GTCGTTTTACCTTACTGCGTCGCGGTAAAAAGAATTACTGTCTGATTTGC<br>TGGAAATAA |
| SEQ ID NO.: 8 | pOMe-6<br>(active site)<br>Synthetase<br>polynucleotide | CGGGGGCTGGTAGCCCAGGTGACGGACGAGGAAGCGTTAGCAGAGCGA<br>CTGGCGCAAGGCCCGATCGCACTCACTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCAGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGTATGCCTGTCTGAACAAACAGTACG<br>GTGTG |
| SEQ ID NO.: 9 | pOMe-7<br>(active site)<br>Synthetase<br>polynucleotide | CGGGGGCTGGTACCCCAGGTGACGGACGAGGAAGCGTTAGCAGAGCGA<br>CTGGCGCAAGGCCCGATCGCACTCACTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCAGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGTATGCCTGTCTGAACAAACAGTACG<br>GTGTG |
| SEQ ID NO.: 10 | pOMe-8<br>(active site)<br>Synthetase<br>polynucleotide | CGGGGGCTGGTAGCCCAGGTGACGGACGAGGAAGCGTTAGCAGAGCGA<br>CTGGCGCAAGGCCCGATCGCACTCACTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCAGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGTATGCCTGTCTGAACAAACAGTACG<br>GTGTG |

TABLE 5-continued

| SEQ ID NO.: | Label | SEQUENCE |
|---|---|---|
| SEQ ID NO.: 11 | pOMe-9 (active site) Synthetase polynucleotide | CGGGGGCTGGTAGCCCAGGTGACGGACGAGGAAGCGTTAGCAGAGCGA<br>CTGGCGCAAGGCCCGATCGCACTCACTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATTCGTATGCCTGTGCGAACAAACAGTACG<br>GTGTG |
| SEQ ID NO.: 12 | pOMe-10 (active site) Synthetase polynucleotide | CGGGGGCTGGTAGCCCAGGTGACGGACGAGGAAGCGTTAGCAGAGCGA<br>CTGGCGCAAGGCCCGATCGCACTCACTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCAGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGTATGCCTGTCTGAACAAACAGTACG<br>GTGTG |
| SEQ ID NO.: 13 | pOMe-11 (active site) Synthetase polynucleotide | CGGGGGCTGGTACCcCAGGTGACGGACGAGGAAGCGTTAGCAGAGCGA<br>CTGGCGCAAGGCCCGATCGCACTCCTTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATTCTATTGCCTGTTCGAACAAACAGTACG<br>GTGTG |
| SEQ ID NO.: 14 | pOMe-12 (active site) Synthetase polynucleotide | CGGGGGCTGGTAGCCCAGGTGACGGACGAGGAAGCGTTAGCAGAGCGA<br>CTGGCGCAAGGCCCGATCGCACTCGTGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATAGTATTGCCTGTTTGAACAAACAGTACG<br>GTGTG |
| SEQ ID NO.: 15 | pOMe-13 (active site) Synthetase polynucleotide | CGGGGGCTGGTACCCCAGGTGACGGACGAGGAAGCGTTAGCAGAGCGA<br>CTGGCGCAAGGCCCGATCGCACTCGTGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATAGTATTGCCTGTTTGAACAAACAGTACG<br>GTGTG |
| SEQ ID NO.: 16 | pOMe-14 (active site) Synthetase polynucleotide | CGGGGGCTGGTAGCCCAGGTGACGGACGAGGAAGCGTTAGCAGAGCGA<br>CTGGCGCAAGGCCCGATCGCACTCTGGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATT<br>GTTATGACTGGTTCGGCAATATGAATGTGCTGACCTTCCTGCGCGATAT |

TABLE 5-continued

| SEQ ID NO.: | Label | SEQUENCE |
|---|---|---|
| | | TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATATGCGTGCCTGTGAGAACAAACAGTACG<br>GTGTG |
| SEQ ID NO.: 17 | p-acetylPhe-1 (active site) Synthetase polynucleotide | CGGGGGCTGGTAGCCCAGGTGACGGACGAGGAAGCGTTAGCAGAGCGA<br>CTGGCGCAAGGCCCGATCGCACTCATTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGGTCAGGGGATTTCGTTCACTGAGTTTTCC<br>TACAACCTGCTGCAGGGTTATGGTATGGCCTGTGCTAACAAACAGTACG<br>GTGTGGTGCTGCAAATTGGTGGTTCTGACCAATGGGGTAACATCACTTC<br>TGGTATCGACCTGACCCGTCGTCTGCATCAGAATCAGGTG |
| SEQ ID NO.: 18 | pBenzophenon-1 (active site) Synthetase polynucleotide | CAGGTGACGGACGAGGAAGCGTTAGCAGAGCGACTGGCGCAAGGCCCG<br>ATCGCACTCGGTTGTGGCTTCGATCCTACCGCTGACAGCTTGCATTTGG<br>GGCATCTTGTTCCATTGTTATGCCTGAAACGCTTCCAGCAGGCGGGCCA<br>CAAGCCGGTTGCGCTGGTAGGCGGCGCGACGGGTCTGATTGGCGACCC<br>GAGCTTCAAAGCTGCCGAGCGTAAGCTGAACACCGAAGAAACTGTTCA<br>GGAGTGGGTGGACAAAATCCGTAAGCAGGTTGCCCCGTTCCTCGATTTC<br>GACTGTGGAGAAAACTCTGCTATCGCGGCCAATAATTATGACTGGTTCG<br>GCAATATGAATGTGCTGACCTTCCTGCGCGATATTGGCAAACACTTCTC<br>CGTTAACCAGATGATCAACAAAGAAGCGGTTAAGCAGCGTCTCAACCG<br>TGAAGATCAGGGGATTTCGTTCACTGAGTTTTCCTACAACCTGCTGCAG<br>GGTTATGGTTTTGCCTGTTTGAACAAACAGTACGGTGTGGTGCTGCAAA<br>TTGGTGGTTCTGACCAGTGGGGTAACATCACTTCTGGTATCGACCTGAC<br>CCGTCGTCTGCATCAGAATCAGGTG |
| SEQ ID NO.: 19 | pBenzophenone-2 (active site) Synthetase polynulceotide | GCGTTAGCAGAGCGACTGGCGCAAGGCCCGATCGCACTCGGGTGTGGC<br>TTCGATCCTACCGCTGACAGCTTGCATTTGGGGCATCTTGTTCCATTGTT<br>ATGCCTGAAACGCTTCCAGCAGGCGGGCCACAAGCCGGTTGCGCTGGT<br>AGGCGGCGCGACGGGTCTGATTGGCGACCCGAGCTTCAAAGCTGCCGA<br>GCGTAAGCTGAACACCGAAGAAACTGTTCAGGAGTGGGTGGACAAAAT<br>CCGTAAGCAGGTTGCCCCGTTCCTCGATTTCGACTGTGGAGAAAACTCT<br>GCTATCGCGGCCAATAATTATGACTGGTTCGGCAATATGAATGTGCTGA<br>CCTTCCTGCGCGATATTGGCAAACACTTCTCCGTTAACCAGATGATCAA<br>CAAAGAAGCGGTTAAGCAGCGTCTCAACCGTGAAGATCAGGGGATTTC<br>GTTCACTGAGTTTTCCTACAACCTGCTGCAGGGTTATGGTTATGCCTGTA<br>TGAACAAACAGTACGGTGTGGTGCTGCAAATTGGTGGTTCTGACCAGTG<br>GGGTAACATCACTTCTGGTATCGACCTGACCCGTCGTCTGCATCAGAAT<br>CAGGTG |
| SEQ ID NO.: 20 | pAzidoPhe-1 (active site) Synthetase polynucleotide | GGGCTGGTAGCCCAGGTGACGGACGNAGAAGCGTTAGCAGAGCGACTG<br>GCGCAAGGCCCGATCGCACTCCTTTGTGGCTTCGATCCTACCGCTGACA<br>GCTTGCATTTGGGGCATCTTGTTCCATTGTTATGCCTGAAACGCTTCCAG<br>CAGGCGGGCCACAAGCCGGTTGCGCTGGTAGGCGGCGCGACGGGTCTG<br>ATTGGCGACCCGAGCTTCAAAGCTGCCGAGCGTAAGCTGAACACCGAA<br>GAAACTGTTCAGGAGTGGGTGGACAAAATCCGTAAGCAGGTTGCCCCG<br>TTCCTCGATTTCGACTGTGGAGAAAACTCTGCTATCGCGGCCAATAATT<br>ATGACTGGTTCGGCAATATGAATGTGCTGACCTTCCTGCGCGATATTGG<br>CAAACACTTCTCCGTTAACCAGATGATCAACAAAGAAGCGGTTAAGCA<br>GCGTCTCAACCGTGAAGATCAGGGGATTTCGTTCACTGAGTTTTCCTAC<br>AACCTGCTGCAGGGTTATTCTATGGCCTGTGCGAACAAACAGTACGGTG<br>TGGTGCTGCAAATTGGTGGTTCTGACCAGTGGGGTAACATCACTTCTGG<br>TATCGACCTGACCCGTCGTCTGCATCANAATCANGTG |
| SEQ ID NO.: 21 | pAzidoPhe-2 (active site) Synthetase polynucleotide | TTAGCAGAGCGACTGGCGCAAGGCCCGATCGCACTCGTTTGTGGCTTCG<br>ATCCTACCGCTGACAGCTTGCATTTGGGGCATCTTGTTCCATTGTTATGC<br>CTGAAACGCTTCCAGCAGGCGGGCCACAAGCCGGTTGCGCTGGTAGGC<br>GGCGCGACGGGTCTGATTGGCGACCCGAGCTTCAAAGCTGCCGAGCGT<br>AAGCTGAACACCGAAGAAACTGTTCAGGAGTGGGTGGACAAAATCCGT<br>AAGCAGGTTGCCCCGTTCCTCGATTTCGACTGTGGAGAAAACTCTGCTA<br>TCGCGGCCAATAATTATGACTGGTTCGGCAATATGAATGTGCTGACCTT<br>CCTGCGCGATATTGGCAAACACTTCTCCGTTAACCAGATGATCAACAAA<br>GAAGCGGTTAAGCAGCGTCTCAACCGTGAAGATCAGGGGATTTCGTTC<br>ACTGAGTTTTCCTACAACCTGCTGCAGGGTTATTCTGCGGCCTGTGCGA<br>ACAAACAGTACGGTGTGGTGCTGCAAATTGGTGGTTCTGACCAGTGGG<br>GTAACATCACTTCTGGTATCGACCTGACCCGTCGTCTGCATCAGAATCA<br>GGTG |

TABLE 5-continued

| SEQ ID NO.: | Label | SEQUENCE |
|---|---|---|
| SEQ ID NO.: 22 | pAzidoPhe-3 (active site) Synthetase polynucleotide | GACGAGGAAGCGTTAGCAGAGCGACTGGCGCAAGGCCCGATCGCACTC CTGTGTGGCTTCGATCCTACCGCTGACAGCTTGCATTTGGGGCATCTTGT TCCATTGTTATGCCTGAAACGCTTCCAGCAGGCGGGCCACAAGCCGGTT GCGCTGGTAGGCGGCGCGACGGGTCTGATTGGCGACCCGAGCTTCAAA GCTGCCGAGCGTAAGCTGAACACCGAAGAAACTGTTCAGGAGTGGGTG GACAAAATCCGTAAGCAGGTTGCCCCGTTCCTCGATTTCGACTGTGGAG AAAACTCTGCTATCGCGGCCAATAATTATGACTGGTTCGGCAATATGAA TGTGCTGACCTTCCTGCGCGATATTGGCAAACACTTCTCCGTTAACCAG ATGATCAACAAANAAGCGGTTAAGCAGCGTCTCAACCGTGAAGATCAG GGGATTTCGTTCACTGAGTTTTCCTACAACCTGCTGCAGGGTTATTCGGC TGCCTGTGCGAACAAACAGTACGGNGNGGNGCTGCAAATTGGNGGTTC TGACCAGGGGGGTAACATCACTTCTGGTATCGACCTGACCCGTCGTCTG CATCAAAATCAGGTG |
| SEQ ID NO.: 23 | pAzidoPhe-4 (active site) Synthetase polynucleotide | GCGTTAGCAGAGCGACTGGCGCAAGGCCCGATCGCACTCGTTTGTGGCT TCGATCCTACCGCTGACAGCTTGCATTTGGGGCATCTTGTTCCATTGTTG TGCCTGAAACGCTTCCAGCAGGCGGGCCACAAGCCGGTTGCGCTGGTA GGCGGCGCGACGGGTCTGATTGGCGACCCGAGCTTCAAAGCTGCCGAG CGTAAGCTGAACACCGAAGAAACTGTTCAGGAGTGGGTGGACAAAATC CGTAAGCAGGTTGCCCCGTTCCTCGATTTCGACTGTGGAGAAAACTCTG CTATCGCGGCCAATAATTATGACTGGTTCGGCAATATGAATGTGCTGAC CTTCCTGCGCGATATTGGCAAACACTTCTCCGTTAACCAGATGATCAAC AAAGAAGCGGTTAAGCAGCGTCTCAACCGTGAAGATCAGGGGATTTCG TTCACTGAGTTTTCCTACAACCTGCTGCAGGGTTATAGTGCGGCCTGTGT TAACAAACAGTACGGTGTGGTGCTGCAAATTGGTGGTTCTGACCAGTGG GGTAACATCACTTCTGGTATCGACCTGACCCGTCGTCTGCATCAGAATC ANGTG |
| SEQ ID NO.: 24 | pAzidoPhe-5 (active site) Synthetase polynucleotide | GACGAGGAAGCGTTAGCAGAGCGACTGGCGCAAGGCCCGATCGCACTC ATTTGTGGCTTCGATCCTACCGCTGACAGCTTGCATTTGGGGCATCTTGT TCCATTGTTATGCCTGAAACGCTTCCAGCAGGCGGGCCACAAGCCGGTT GCGCTGGTAGGCGGCGCGACGGGTCTGATTGGCGACCCGAGCTTCAAA GCTGCCGAGCGTAAGCTGAACACCGAAGAAACTGTTCAGGAGTGGGTG GACAAAATCCGTAAGCAGGTTGCCCCGTTCCTCGATTTCGACTGTGGAG AAAACTCTGCTATCGCGGCCAATGATTATGACTGGTTCGGCAATATGAA TGTGCTGACCTTCCTGCGCGATATTGGCAAACACTTCTCCGTTAACCAG ATGATCAACAAAGAAGCGGTTAAGCAGCGTCTCAACCGTGAAGATCAG GGGATTTCGTTCACTGAGTTTTCCTACAACCTGCTGCAGGGTTATAATTT TGCCTGTGTGAACAAACAGTACGGTGTGGTGCTGCAAATTGGTGGTTCT GACCAGTGGGGTAACATCACTTCTGGTATCGACCTGACCCGTCGTCTGC ATCAGAATCAGGTG |
| SEQ ID NO.: 25 | pAzidoPhe-6 (active site) Synthetase polynucleotide | CGACTGGCGCAAGGCCCGATCGCACTCACGTGTGGCTTCGATCCTACCG CTGACAGCTTGCATTTGGGGCATCTTGTTCCATTGTTATGCCTGAAACGC TTCCAGCAGGCGGGCCACAAGCCGGTTGCGCTGGTAGGCGGCGCGACG GGTCTGATTGGCGACCCGAGCTTCAAAGCTGCCGAGCGTAAGCTGAAC ACCGAAGAAACTGTTCAGGAGTGGGTGGACAAAATCCGTAAGCAGGTT GCCCCGTTCCTCGATTTCGACTGTGGAGAAAACTCTGCTATCGCGGCCA ATAATTATGACTGGTTCGGCAATATGAATGTGCTGACCTTCCTGCGCGA TATTGGCAAACACTTCTCCGTTAACCAGATGATCAACAAAGAAGCGGTT AAGCAGCGTCTCAACCGTGAAGATCAGGGGATTTCGTTCACTGAGTTTT CCTACAATCTGCTGCAGGGTTATTCGGCTGCCTGTCTTAACAAACAGTA CGGTGTGGTGCTGCAAATTGGTGGTTCTGACCAGTGGGGTAACATCACT TCTGGTATCGACCTGACCCGTCGTCTGCATCAGAATCAGGTG |
| SEQ ID NO.: 26 | pPR-EcRS-1 (propargyloxy phenylalanine synthetase) (active site) Synthetase polynucleotide | CGGGGGCTGGTANCCCAGGTGACGGACGAGGAAGCGTTAGCAGAGCGA CTGGCGCAAGGCCCGATCGCACTCGGGTGTGGCTTCGATCCTACCGCTG ACAGCTTGCATTTGGGGCATCTTGTTCCATTGTTATGCCTGAAACGCTTC CAGCAGGCGGGCCACAAGCCGGTTGCGCTGGTAGGCGGCGCGACGGGT CTGATTGGCGACCCGAGCTTCAAAGCTGCCGAGCGTAAGCTGAACACC GAAGAAACTGTTCAGGAGTGGGTGGACAAAATCCGTAAGCAGGTTGCC CCGTTCCTCGATTTCGACTGTGGAGAAAACTCTGCTATCGCGGCCAATA ATTATGACTGGTTCGGCAATATGAATGTGCTGACCTTCCTGCGCGATAT TGGCAAACACTTCTCCGTTAACCAGATGATCAACAAAGAAGCGGTTAA GCAGCGTCTCAACCGTGAAGATCAGGGGATTTCGTTCACTGAGTTTTCC TACAACCTGCTGCAGGGTTATTCTATGGCCTGTTTGAACAAACAGTACG GTGTGGTGCTGCAAATTGGTGGTTCTGACCAGTGGGGTAACATCACTTC TGGTATCGACCTGANCCGTCGTCTGCATCAGAATCAGGTG |
| SEQ ID NO.: 27 | pPR-EcRS-2 (active site) Synthetase polynucleotide | CGGGGGCTGGTAGCCCAGGTGACGGACGAGGAAGCGTTAGCAGAGCGA CTGGCGCAAGGCCCGATCGCACTCACGTGTGGCTTCGATCCTACCGCTG ACAGCTTGCATTTGGGGCATCTTGTTCCATTGTTATGCCTGAAACGCTTC CAGCAGGCGGGCCACAAGCCGGTTGCGCTGGTAGGCGGCGCGACGGGT CTGATTGGCGACCCGAGCTTCAAAGCTGCCGAGCGTAAGCTGAACACC GAAGAAACTGTTCAGGAGTGGGTGGACAAAATCCGTAAGCAGGTTGCC CCGTTCCTCGATTTCGACTGTGGAGAAAACTCTGCTATCGCGGCCAATA |

TABLE 5-continued

| SEQ ID NO.: | Label | SEQUENCE |
|---|---|---|
| | | ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAATCTGCTGCAGGGTTATTCGGCTGCCTGTCTTAACAAACAGTACG<br>GTGTGGTGCTGCAAATTGGTGGTTCTGACCAGTGGGGTAACATCACTTC<br>TGGTATCGAACCTGANCCGTCGTCTGCATCAAAATCAAGTG |
| SEQ ID NO.: 28 | pPR-EcRS-3 (active site) Synthetase polynucleotide | CGGGGGCTGGTACCCCAAGTGACGGACGAGGAAACGTTAGCAGAGCGA<br>CTGGCGCAAGGCCCGATCGCACTCTCTTGTGGCTTCGATCCTACCGCTG<br>ACAGCTTGCATTTGGGGCATCTTGTTCCATTGTTATGCCTGAAACGCTTC<br>CAGCAGGCAGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGATGGCCTGTGTGAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 29 | pPR-EcRS-4 (active site) Synthetase polynucleotide | CGGGGGCTGGTAGCCCAGGTGACGGACGAGGAAGCGTTAGCAGAGCGA<br>CTGGCGCAAGGCCCGATCGCACTCGCGTGCGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAGGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATTCTTATGCCTGTCTTAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 30 | pPR-EcRS-5 (active site) Synthetase polynucleotide | CGGGGGCTGGTAGCCCAGGTGACGGACGAGGAAGCGTTAGCAGAGCGA<br>CTGGCGCAAGGCCCGATCGCACTCGCGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGATGGCCTGTTGTAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 31 | pPR-EcRS-6 (active site) Synthetase polynucleotide | CGGGGGCTGGTACCCCAAGTGACGGACGAGGAAGCGTTAGCAGAGCGA<br>CTGGCGCAAGGCCCGATCGCACTCGCGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCGCTGAGTTTTCC<br>TACAACCTGCTGCAGGGTTATACGTTTGCCTGTATGAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 32 | pPR-EcRS-7 (active site) Synthetase polynucleotide | GTGACGGACGAGGAAGCGTTAGCAGAGCGACTGGCGCAAGGCCCGATC<br>GCACTCACGTGTGGCTTCGATCCTACCGCTGACAGCTTGCATTTGGGGC<br>ATCTTGTTCCATTGTTATGCCTGAAACGCTTCCAGCAGGCGGGCCACAA<br>GCCGGTTGCGCTGGTAGGCGGCGCGACGGGTCTGATTGGCGACCCGAG<br>CTTCAAAGCTGCCGAGCGTAAGCTGAACACCGAAGAAACTGTTCAGGA<br>GTGGGTGGACAAAATCCGTAAGCAGGTTGCCCCGTTCCTCGATTTCGAC<br>TGTGGAGAAAACTCTGCTATCGCGGCCAATAATTATGACTGGTTCGGCA<br>ATATGAATGTGCTGACCTTCCTGCGCGATATTGGCAAACACTTCTCCGT<br>TAACCAGATGATCAACAAAGAAGCGGTTAAGCAGCGTCTCAACCGTGA<br>AGATCAGGGGATTTCGTTCACTGAGTTTTCCTACAATCTGCTGCAGGGT<br>TATTCGGCTGCCTGTCTTAACAAACAGTACGGTGTGGTGCTGCAAATTG<br>GTGGTTCTGACCAGTGGGGTAACATCACTTCTGGTATCGACCTGACCCG<br>TCGTCTGCATCAGAATCAGGTG |

TABLE 5-continued

| SEQ ID NO.: | Label | SEQUENCE |
|---|---|---|
| SEQ ID NO.: 33 | pPR-EcRS-8 (active site) Synthetase polynucleotide | CGGGGGCTGGTAGCCCAGGTGACGGACGAGGAAGCGTTAGCAGAGCGA<br>CTGGCGCAAGGCCCGATCGCACTCGTTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATTCGATGGCCTGTACGAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 34 | pPR-EcRS-9 (active site) Synthetase polynucleotide | CGGGGGCTGGTANCCCAAGTGACGGACGGGGAAGCGTTAGCAGAGCGA<br>CTGGCGCAAGGCCCGATCGCACTCAGTTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATCTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATAGTTTTGCCTGTCTGAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 35 | pPR-EcRS-10 (active site) Synthetase polynucleotide | CGGGGGCTGGTAGCCCAGGTGACGGACGAGGAAGCGTTAGCAGAGCGA<br>CTGGCGCAAGGCCCGATCGCACTCGTGTGGCTTCGATCCTACCGCTG<br>ACAGCTTGCATTTGGGGCATCTTGTTCCATTGTTATGCCTGAAACGCTTC<br>CAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACC<br>GAAGAAACTGTTCAGGAGTGGGTGGACAAAATCCGTAAGCAGGTTGCC<br>CCGTTCCTCGATTTCGACTGTGGAGAAAACTCTGCTATCGCGGCCAATA<br>ATTATGACTGGTTCGGCAATATGAATGTGCTGACCTTCCTGCGCGATAT<br>TGGCAAACACTTCTCCGTTAACCAGATGATCAACAAAGAAGCGGTTAA<br>GCAGCGTCTCAACCGTGAAGATCAGGGGATTTCGTTCACTGAGTTTTCC<br>TACAACCTGCTGCAGGGTTATACGTTTGCCTGTACTAACAAACAGTACG<br>GTGTGGTGCTGCAAATTGGTGGTTCTGACCAGTGGGGTAACATCACTTC<br>TGGTATCGACCTGACCCGTCGTCTGCATCAGAATCAGGTG |
| SEQ ID NO.: 36 | p-iodoPheRS-1 Synthetase Amino acid (aa) | MASSNLIKQLQERGLVAQVTDEEALAERLAQGPIALVCGFDPTADSLHLGH<br>LVPLLCLKRFQQAGHKPVALVGGATGLIGDPSFKAAERKLNTEETVQEWV<br>DKIRKQVAPFLDFDCGENSAIAANNYDWFGNMNVLTFLRDIGKHFSVNQM<br>INKEAVKQRLNREDQGISFTEFSYNLLQGYSYACLNKQYGVVLQIGGSDQ<br>WGNITSGIDLTRRLHQNQVFGLTVPLITKADGTKFGKTEGGAVWLDPKKTS<br>PYKFYQFWINTADADVYRFLKFFTFMSIEEINALEEEDKNSGKAPRAQYVL<br>AEQVIRLVHGEEGLQAAKRITECLFSGSLSALSEADFEQLAQDGVPMVEM<br>EKGADLMQALVDSELQPSRGQARKTIASNAITINGEKQSDPEYFEKEEDRLF<br>GRFTLLRRGKKNYCLICWK |
| SEQ ID NO.: 37 | p-iodoPheRS-2 Synthetase Amino acid (aa) | MASSNLIKQLQERGLVAQVTDEEALAERLAQGPIALICGFDPTADSLHLGH<br>LVPLLCLKRFQQAGHKPVALVGGATGLIGDPSFKAAERKLNTEETVQEWV<br>DKIRKQVAPFLDFDCGENSAIAANNYDWFGNMNVLTFLRDIGKHFSVNQM<br>INKEAVKQRLNREDQGISFTEFSYNLLQGYSMACLNKQYGVVLQIGGSDQ<br>WGNITSGIDLTRRLHQNQVFGLTVPLITKADGTKFGKTEGGAVWLDPKKTS<br>PYKFYQFWINTADADVYRFLKFFTFMSIEEINALEEEDKNSGKAPRAQYVL<br>AEQVIRLVHGEEGLQAAKRITECLFSGSLSALSEADFEQLAQDGVPMVEM<br>EKGADLMQALVDSELQPSRGQARKTIASNAITINGEKQSDPEYFEKEEDRLF<br>GRFTLLRRGKKNYCLICWK |
| SEQ ID NO.: 38 | p-iodoPheRS-3 Synthetase Amino acid (aa) | MASSNLIKQLQERGLVAQVTDEEALAERLAQGPIALVCGFDPTADSLHLGH<br>LVPLLCLKRFQQAGHKPVALVGGATGLIGDPSFKAAERKLNTEETVQEWV<br>DKIRKQVAPFLDFDCGENSAIAANNYDWFGNMNVLTFLRDIGKHFSVNQM<br>INKEAVKQRLNREDQGISFTEFSYNLLQGYSMACANKQYGVVLQIGGSDQ<br>WGNITSGIDLTRRLHQNQVFGLTVPLITKADGTKFGKTEGGAVWLDPKKTS<br>PYKFYQFWINTADADVYRFLKFFTFMSIEEINALEEEDKNSGKAPRAQYVL<br>AEQVIRLVHGEEGLQAAKRITECLFSGSLSALSEADFEQLAQDGVPMVEM<br>EKGADLMQALVDSELQPSRGQARKTIASNAITINGEKQSDPEYFEKEEDRLF<br>GRFTLLRRGKKNYCLICWK |
| SEQ ID NO.: 39 | OMeTyrRS-1 Synthetase Amino acid (aa) | MASSNLIKQLQERGLVAQVTDEEALAERLAQGPIALVCGFDPTADSLHLGH<br>LVPLLCLKRFQQAGHKPVALVGGATGLIGDPSFKAAERKLNTEETVQEWV<br>DKIRKQVAPFLDFDCGENSAIAANNYDWFGNMNVLTFLRDIGKHFSVNQM<br>INKEAVKQRLNREDQGISFTEFSYNLLQGYSMACLNKQYGVVLQIGGSDQ<br>WGNITSGIDLTRRLHQNQVFGLTVPLITKADGTKFGKTEGGAVWLDPKKTS |

TABLE 5-continued

| SEQ ID NO.: | Label | SEQUENCE |
|---|---|---|
| | | PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 40 | OMeTyrRS-2 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTMACLNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 41 | OMeTyrRS-3 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTYACLNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 42 | OMeTyrRS-4 Synthetase Amino acid (aa) | MASSNLIKQLQERGLVAQVTDEEALAERLAQGPIALLCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSMACSNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 43 | OMeTyrRS-5 Synthetase Amino acid (aa) | MASSNLIKQLQERGLVAQVTDEEALAERLAQGPIALLCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSMACANKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 44 | OMeTyrRS-6 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYRMACLNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 45 | p-acetylPheRS-1 Synthetase Amino acid (aa) | MASSNLIKQLQERGLVAQVTDEEALAERLAQGPIALICGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYGMACNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 46 | p-benzoylPheRS-1 Synthetase Amino acid (aa) | MASSNLIKQLQERGLVAQVTDEEALAERLAQGPIALGCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYGFACANKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |

TABLE 5-continued

| SEQ ID NO.: | Label | SEQUENCE |
|---|---|---|
| SEQ ID NO.: 47 | p-benzoylPheRS-2 Synthetase Amino acid (aa) | MASSNLIKQLQERGLVAQVTDEEALAERLAQGPIALGCFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYGYACMNKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 48 | p-azidoPheRS-1 Synthetase Amino acid (aa) | MASSNLIKQLQERGLVAQVTDEEALAERLAQGPIALLCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSMACANKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 49 | p-azidoPheRS-2 Synthetase Amino acid (aa) | MASSNLIKQLQERGLVAQVTDEEALAERLAQGPIALVCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSAACANKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 50 | p-azidoPheRS-3 Synthetase Amino acid (aa) | MASSNLIKQLQERGLVAQVTDEEALAERLAQGPIALLCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSAACANKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 51 | p-azidoPheRS-4 Synthetase Amino acid (aa) | MASSNLIKQLQERGLVAQVTDEEALAERLAQGPIALVCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSAACVNKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 52 | p-azidoPheRS-5 Synthetase Amino acid (aa) | MASSNLIKQLQERGLVAQVTDEEALAERLAQGPIALICGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYNFACVNKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 53 | p-azidoPheRS-6 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSAACLNKQYGVVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 54 | pPR-EcRS-1 Synthetase Amino acid (aa) | MASSNLIKQLQERGLVAQVTDEEALAERLAQGPIALGCFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSMACLNKQYGVVVLQIGGSDQ |

TABLE 5-continued

| SEQ ID NO.: | Label | SEQUENCE |
|---|---|---|
| | p-propargyloxy-phenylalanine synthetase | WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVTRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 55 | pPR-EcRS-2 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSAACLNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 56 | pPR-EcRS-3 Synthetase Amino acid (aa) | MASSNLIKQLQERGLVAQVTDEEALAERLAQGPIALSCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTMACVNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 57 | pPR-EcRS-4 Synthetase Amino acid (aa) | MASSNLIKQLQERGLVAQVTDEEALAERLAQGPIALACGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSYACLNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 58 | pPR-EcRS-5 Synthetase Amino acid (aa) | MASSNLIKQLQERGLVAQVTDEEALAERLAQGPIALACGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTMACCNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 59 | pPR-EcRS-6 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTFACMNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 60 | pPR-EcRS-7 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSVACLNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |
| SEQ ID NO.: 61 | pPR-EcRS-8 Synthetase Amino acid (aa) | MASSNLIKQLQERGLVAQVTDEEALAERLAQGPIALVCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSMACTNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |

TABLE 5-continued

| SEQ ID NO.: | Label | SEQUENCE |
|---|---|---|
| SEQ ID NO.: 62 | pPR-EcRS-9 Synthetase Amino acid (aa) | MASSNLIKQLQERGLVAQVTDEEALAERLAQGPIALSCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYSFACLNKQYGVVLQIGGSDQW GNITSGIDLTRRLHQNQVFGLTVPLITKADGTICFGKTEGGAVWLDPKKTSP YKFYQFWINTADADVYRFLKFFTFMSIEEINALEEEDKNSGKAPRAQYVLA EQVTRLVHGEEGLQAAKRITECLFSGSLSALSEADFEQLAQDGVPMVEME KGADLMQALVDSELQPSRGQARKTIASNAITINGEKQSDPEYFFKEEDRLF GRFTLLRRGKKNYCLICWK |
| SEQ ID NO.: 63 | pPR-EcRS-10 Synthetase Amino acid (aa) | MASSNLIKQLQERGLVAQVTDEEALAERLAQGPIALTCGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREDQGISFTEFSYNLLQGYTFACTNKQYGVVLQIGGSDQ WGNITSGIDLTRRLHQNQVFGLTVPLITKADGTKEGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFLQLAQDGVPMVEM EKGADLMQALVDSELQPSRGQARKTIASNAITINGEKQSDPEYFEKEEDRLF GRFTLLRRGKKNYCLICWK |
| SEQ ID NO.: 64 | tRNA/Tyr polynucleotide | AGCTTCCCGATAAGGGAGCAGGCCAGTAAAAAGCATTACCCCGTGGTG GGGTTCCCGAGCGGCCAAAGGGAGCAGACTCTAAATCTGCCGTCATCG ACCTCGAAGGTTCGAATCCTTCCCCCACCACCA |
| SEQ ID NO.: 65 | tRNA/Tyr | AGCUUCCCGAUAAGGGAGCAGGCCAGUAAAAAGCAUUACCCCGUGGU GGGGUUCCCGAGCGGCCAAAGGGAGCAGACUCUAAAUCUGCCGUCAU CGACCUCGAAGGUUCGAAUCCUUCCCCCACCACCA |
| SEQ ID NO.: 66 | Amber Mutants L3TAG | 5'-ATGAAGTAGCTGTCTTCTATCGAACAAGCATGCG-3' |
| SEQ ID NO.: 67 | Amber Mutants I13TAG | 5'-CGAACAAGCATGCGATTAGTGCCGACTTAAAAAG-3' |
| SEQ ID NO.: 68 | Amber Mutants T44TAG | 5'-CGCTACTCTCCCCAAATAGAAAAGGTCTCCGCTG-3' |
| SEQ ID NO.: 69 | Amber Mutants F68TAG | 5'-CTGGAACAGCTATAGCTACTGATTTTTCCTCG-3' |
| SEQ ID NO.: 70 | Amber Mutants R110TAG | 5'-GCCGTCACAGATTAGTTGGCTTCAGTGGAGACTG-3' |
| SEQ ID NO.: 71 | Amber Mutants V114TAG | 5'-GATTGGCTTCATAGGAGACTGATATGCTCTAAC-3' |
| SEQ ID NO.: 72 | Amber Mutants T121TAG | 5'-GCCTCTATAGTTGAGACAGCATAGAATAATGCG-3' |
| SEQ ID NO.: 73 | Amber Mutants I127TAG | 5'-GAGACAGCATAGATAGAGTGCGACATCATCATCGG-3' |
| SEQ ID NO.: 74 | Amber Mutants S131TAG | 5'-GAATAAGTGCGACATAGTCATCGGAAGAGAGTAGTAG-3' |
| SEQ ID NO.: 75 | Amber Mutants T145TAG | 5'-GGTCAAAGACAGTTGTAGGTATCGATTGACTCGGC-3' |
| SEQ ID NO.: 76 | Permissive Site Mutants T44F | 5'-CGCTACTCTCCCCAAATTTAAAAGGTCTCCGCTG-3' |
| SEQ ID NO.: 77 | Permissive Site Mutants T44Y | 5'-CGCTACTCTCCCCAAATATAAAAGGTCTCCGCTG-3' |

TABLE 5-continued

| SEQ ID NO.: | Label | SEQUENCE |
|---|---|---|
| SEQ ID NO.: 78 | Permissive Site Mutants T44W | 5'-CGCTACTCTCCCCAAATGGAAAAGGTCTCCGCTG-3' |
| SEQ ID NO.: 79 | Permissive Site Mutants T44D | 5'-CGCTACTCTCCCCAAAGATAAAAGGTCTCCGCTG-3' |
| SEQ ID NO.: 80 | Permissive Site Mutants T44K | 5'-CGCTACTCTCCCCAAAAAAAAAAGGTCTCCGCTG-3' |
| SEQ ID NO.: 81 | Permissive Site Mutants R110F | 5'-GCCGTCACAGATTTTTTGGCTTCAGTGGAGACTG-3' |
| SEQ ID NO.: 82 | Permissive Site Mutants R110Y | 5'-GCCGTCACAGATTATTTGGCTTCAGTGGAGACTG-3' |
| SEQ ID NO.: 83 | Permissive Site Mutants R110W | 5'-GCCGTCACAGATTGGTTGGCTTCAGTGGAGACTG-3' |
| SEQ ID NO.: 84 | Permissive Site Mutants R110D | 5'-GCCGTCACAGATGATTTGGCTTCAGTGGAGACTG-3' |
| SEQ ID NO.: 85 | Permissive Site Mutants R110K | 5'-GCCGTCACAGATAAATTGGCTTCAGTGGAGACTG-3' |
| SEQ ID NO.: 86 | p-acetylPheRS-1 Synthetase Amino acid (aa)[a] | MASSNLIKQLQERGLVAQVTDEEALAERLAQGPIALICGFDPTADSLHLGH LVPLLCLKRFQQAGHKPVALVGGATGLIGDPSFKAAERKLNTEETVQEWV DKIRKQVAPFLDFDCGENSAIAANNYDWFGNMNVLTFLRDIGKHFSVNQM INKEAVKQRLNREGQGISFTEFSYNLLQGYGMACANKQYGVVLQIGGSDQ WGNITSGIDLTRRLHQNQVFGLTVPLITKADGTKFGKTEGGAVWLDPKKTS PYKFYQFWINTADADVYRFLKFFTFMSIEEINALEEEDKNSGKAPRAQYVL AEQVIRLVHGEEGLQAAKRITECLFSGSLSALSEADFEQLAQDGVPMVEM EKGADLMQALVDSELQPSRGQARKTIASNAITINGEKQSDPEYFEKEEDRLF GRFTLLRRGKKNYCLICWK |

[a]These clones also contain a Asp165Gly mutation

What is claimed is:

1. A composition comprising a protein, antibody, or antibody fragment, wherein the protein, antibody or antibody fragment comprises at least one unnatural amino acid comprising a first reactive group and at least one post-translational modification, wherein the at least one post-translational modification comprises attachment of a molecule comprising a second reactive group by a cycloaddition reaction to the at least one unnatural amino acid comprising the first reactive group;
    wherein the unnatural amino acid comprising the first reactive group was incorporated into the protein, antibody or antibody fragment using an orthogonal translation system.

2. The composition of claim 1, wherein the first reactive group is an alkynyl or azido moiety and the second reactive group is an azido or alkynyl moiety.

3. The composition of claim 2, wherein the first reactive group is the alkynyl moiety and the second reactive group is the azido moiety.

4. The composition of claim 2, wherein the first reactive group is the azido moiety and the second reactive group is the alkynyl moiety.

5. The composition of claim 1, wherein the at least one post-translational modification is made in vivo in a eukaryotic cell.

6. The composition of claim 1, further comprising a eukaryotic cell containing the protein, antibody, or antibody fragment.

7. The composition of claim 1, wherein the unnatural amino acid is a p-azido-L-phenylalanine or a p-propargyloxyphenylalanine.

8. The composition of claim 1, wherein the molecule is a dye, a polymer, a derivative of polyethylene glycol, a photocrosslinker, a cytotoxic compound, an affinity label, a derivative of biotin, a resin, a second protein or polypeptide, a metal chelator, a cofactor, a fatty acid, a carbohydrate, or a polynucleotide.

9. The composition of claim 1, wherein the at least one unnatural amino acid was incorporated into the protein, antibody, or antibody fragment using an orthogonal synthetase comprising a polypeptide sequence selected from the group consisting of any one of SEQ ID NOs.: 48 to 63.

* * * * *

UNITED STATES PATENT AND TRADEMARK OFFICE
CERTIFICATE OF CORRECTION

PATENT NO. : 9,797,908 B2
APPLICATION NO. : 14/338113
DATED : October 24, 2017
INVENTOR(S) : Deiters et al.

Page 1 of 1

It is certified that error appears in the above-identified patent and that said Letters Patent is hereby corrected as shown below:

In the Specification

Column 1, Lines 24-32, the paragraph STATEMENT AS TO RIGHTS TO INVENTIONS MADE UNDER FEDERALLY SPONSORED RESEARCH AND DEVELOPMENT should be changed to:

-- STATEMENT OF GOVERNMENT LICENSE RIGHTS
This invention was made with government support under grant number GM062159 awarded by the National Institutes of Health and under grant number DE-FG03-00ER45812 awarded by the United States Department of Energy. The government has certain rights in the invention. --

Signed and Sealed this
Ninth Day of June, 2020

Andrei Iancu
*Director of the United States Patent and Trademark Office*